United States Patent
Zhang et al.

(10) Patent No.: US 12,275,788 B2
(45) Date of Patent: *Apr. 15, 2025

(54) SINGLE-DOMAIN ANTIBODIES AGAINST CD33 AND CONSTRUCTS THEREOF

(71) Applicant: Legend Biotech Ireland Limited, Dublin (IE)

(72) Inventors: Yafeng Zhang, Jiangsu (CN); Tailan Zhan, Jiangsu (CN); Fei Sun, Jiangsu (CN); Jian Liu, Jiangsu (CN); Qing Zhang, Jiangsu (CN); Shu Wu, Jiangsu (CN)

(73) Assignee: Legend Biotech Ireland Limited, Dublin (IE)

( * ) Notice: Subject to any disclaimer, the term of this patent is extended or adjusted under 35 U.S.C. 154(b) by 1066 days.

This patent is subject to a terminal disclaimer.

(21) Appl. No.: 17/274,458

(22) PCT Filed: Sep. 10, 2019

(86) PCT No.: PCT/CN2019/105059
§ 371 (c)(1),
(2) Date: Mar. 9, 2021

(87) PCT Pub. No.: WO2020/052543
PCT Pub. Date: Mar. 19, 2020

(65) Prior Publication Data
US 2021/0275590 A1   Sep. 9, 2021

(30) Foreign Application Priority Data

Sep. 10, 2018  (WO) ............... PCT/CN2018/104882
Sep. 10, 2018  (WO) ............... PCT/CN2018/104883

(51) Int. Cl.
| | |
|---|---|
| A61P 35/00 | (2006.01) |
| A61K 35/17 | (2015.01) |
| A61K 40/11 | (2025.01) |
| A61K 40/31 | (2025.01) |
| A61K 40/42 | (2025.01) |
| C07K 14/705 | (2006.01) |
| C07K 14/725 | (2006.01) |
| C07K 16/28 | (2006.01) |
| C12N 5/0783 | (2010.01) |
| A61K 39/00 | (2006.01) |

(52) U.S. Cl.
CPC .......... *C07K 16/2803* (2013.01); *A61K 35/17* (2013.01); *A61K 40/11* (2025.01); *A61K 40/31* (2025.01); *A61K 40/4202* (2025.01); *A61K 40/4204* (2025.01); *A61K 40/421* (2025.01); *A61K 40/4221* (2025.01); *A61K 40/4224* (2025.01); *A61P 35/00* (2018.01); *C07K 14/7051* (2013.01); *C07K 14/70578* (2013.01); *C07K 16/2851* (2013.01); *C07K 16/2866* (2013.01); *C12N 5/0636* (2013.01); *A61K 2039/505* (2013.01); *A61K 2239/29* (2023.05); *A61K 2239/31* (2023.05); *A61K 2239/38* (2023.05); *A61K 2239/48* (2023.05); *C07K 2317/31* (2013.01); *C07K 2317/565* (2013.01); *C07K 2317/569* (2013.01); *C07K 2317/92* (2013.01); *C07K 2319/02* (2013.01); *C07K 2319/03* (2013.01); *C12N 2510/00* (2013.01)

(58) Field of Classification Search
None
See application file for complete search history.

(56) References Cited

U.S. PATENT DOCUMENTS

| | | |
|---|---|---|
| 4,676,980 A | 6/1987 | Segal |
| 4,737,456 A | 4/1988 | Weng |
| 4,816,567 A | 3/1989 | Cabilly |
| 5,208,020 A | 5/1993 | Chari |
| 5,225,539 A | 7/1993 | Winter |
| 5,416,064 A | 5/1995 | Chari |
| 5,500,362 A | 3/1996 | Robinson |
| 5,545,806 A | 8/1996 | Lonberg |
| 5,545,807 A | 8/1996 | Surani |
| 5,569,825 A | 10/1996 | Lonberg |
| 5,571,894 A | 11/1996 | Wels |
| 5,587,458 A | 12/1996 | King |
| 5,591,828 A | 1/1997 | Bosslet |

(Continued)

FOREIGN PATENT DOCUMENTS

| | | |
|---|---|---|
| CA | 2424602 C | 9/2012 |
| CN | 101210048 A | 7/2008 |

(Continued)

OTHER PUBLICATIONS

MacCallum et al., Antibody-antigen interactions: contact analysis and binding site topography; 1996, J. Mol. Biol., 262: 732-745. (Year: 1996).*

(Continued)

*Primary Examiner* — Daniel E Kolker
*Assistant Examiner* — James Ryland Melchior
(74) *Attorney, Agent, or Firm* — Fish & Richardson P.C.

(57) ABSTRACT

The present application provides single-domain antibodies targeting CD33 and constructs thereof, including chimeric receptors, immune effector cell engagers and immunoconjugates. Further provided are engineered immune cells (such as T cells) comprising an anti-CD33 chimeric receptor and optionally a second chimeric receptor targeting a second antigen or epitope. Pharmaceutical compositions, kits and methods of treating cancer are also provided.

18 Claims, 16 Drawing Sheets
Specification includes a Sequence Listing.

(56) References Cited

U.S. PATENT DOCUMENTS

| | | | |
|---|---|---|---|
| 5,624,821 A | 4/1997 | Winter | |
| 5,625,126 A | 4/1997 | Lonberg | |
| 5,633,425 A | 5/1997 | Lonberg | |
| 5,635,483 A | 6/1997 | Pettit | |
| 5,641,870 A | 6/1997 | Rinderknecht | |
| 5,648,260 A | 7/1997 | Winter | |
| 5,661,016 A | 8/1997 | Lonberg | |
| 5,712,374 A | 1/1998 | Kuntsmann | |
| 5,714,586 A | 2/1998 | Kunstmann | |
| 5,731,168 A | 3/1998 | Carter | |
| 5,739,116 A | 4/1998 | Hamann | |
| 5,750,373 A | 5/1998 | Garrard | |
| 5,767,285 A | 6/1998 | Hamann | |
| 5,770,429 A | 6/1998 | Lonberg et al. | |
| 5,770,701 A | 6/1998 | Mcgahren | |
| 5,770,710 A | 6/1998 | Mcgahren | |
| 5,773,001 A | 6/1998 | Hamann | |
| 5,780,588 A | 7/1998 | Pettit | |
| 5,821,337 A | 10/1998 | Carter | |
| 5,858,358 A | 1/1999 | June et al. | |
| 5,869,046 A | 2/1999 | Presta | |
| 5,877,296 A | 3/1999 | Hamann | |
| 5,883,223 A | 3/1999 | Gray | |
| 6,075,181 A | 6/2000 | Kucherlapati | |
| 6,150,584 A | 11/2000 | Kucherlapati | |
| 6,194,551 B1 | 2/2001 | Idusogie | |
| 6,352,694 B1 | 3/2002 | June | |
| 6,534,055 B1 | 3/2003 | June | |
| 6,602,684 B1 | 8/2003 | Umana | |
| 6,630,579 B2 | 10/2003 | Chari | |
| 6,692,964 B1 | 2/2004 | June | |
| 6,737,056 B1 | 5/2004 | Presta | |
| 6,797,514 B2 | 9/2004 | Berenson | |
| 6,867,041 B2 | 3/2005 | Berenson | |
| 6,887,466 B2 | 5/2005 | June | |
| 6,905,680 B2 | 6/2005 | June | |
| 6,905,681 B1 | 6/2005 | June | |
| 6,905,874 B2 | 6/2005 | Berenson | |
| 6,982,321 B2 | 1/2006 | Winter | |
| 7,041,870 B2 | 5/2006 | Tomizuka | |
| 7,052,906 B1 | 5/2006 | Lawson et al. | |
| 7,067,318 B2 | 6/2006 | June | |
| 7,087,409 B2 | 8/2006 | Barbas, III | |
| 7,144,575 B2 | 12/2006 | June | |
| 7,172,869 B2 | 2/2007 | June | |
| 7,175,843 B2 | 2/2007 | June | |
| 7,189,826 B2 | 3/2007 | Rodman | |
| 7,232,566 B2 | 6/2007 | June | |
| 7,332,581 B2 | 2/2008 | Presta | |
| 7,371,826 B2 | 5/2008 | Presta | |
| 7,371,849 B2 | 5/2008 | Honda | |
| 7,498,298 B2 | 3/2009 | Doronina | |
| 7,521,541 B2 | 4/2009 | Eigenbrot | |
| 7,527,791 B2 | 5/2009 | Adams | |
| 7,718,175 B2 | 5/2010 | Hanai et al. | |
| 8,313,913 B2 | 11/2012 | Nakamura | |
| 8,754,287 B2 | 6/2014 | Macdonald | |
| 8,945,867 B2 | 2/2015 | Ogawa | |
| 12,097,219 B2 * | 9/2024 | Zhang | A61K 39/464404 |
| 2002/0164328 A1 | 11/2002 | Shinkawa | |
| 2003/0115614 A1 | 6/2003 | Kanda | |
| 2003/0157108 A1 | 8/2003 | Presta | |
| 2004/0093621 A1 | 5/2004 | Shitara | |
| 2004/0101519 A1 | 5/2004 | June et al. | |
| 2004/0109865 A1 | 6/2004 | Niwa | |
| 2004/0110282 A1 | 6/2004 | Kanda | |
| 2004/0110704 A1 | 6/2004 | Yamane | |
| 2004/0132140 A1 | 7/2004 | Satoh | |
| 2005/0014934 A1 | 1/2005 | Hinton | |
| 2005/0031613 A1 | 2/2005 | Nakamura | |
| 2005/0079574 A1 | 4/2005 | Bond | |
| 2005/0119455 A1 | 6/2005 | Fuh | |
| 2005/0123546 A1 | 6/2005 | Umana | |
| 2005/0266000 A1 | 12/2005 | Bond | |
| 2006/0025576 A1 | 2/2006 | Miller | |
| 2006/0034810 A1 | 2/2006 | Riley et al. | |
| 2006/0121005 A1 | 6/2006 | Berenson | |
| 2006/0270045 A1 | 11/2006 | Cregg | |
| 2007/0061900 A1 | 3/2007 | Murphy | |
| 2007/0117126 A1 | 5/2007 | Sidhu | |
| 2007/0134759 A1 | 6/2007 | Nishiya | |
| 2007/0160598 A1 | 7/2007 | Dennis | |
| 2007/0237764 A1 | 10/2007 | Birtalan | |
| 2007/0292936 A1 | 12/2007 | Barthelemy | |
| 2008/0241884 A1 | 10/2008 | Shitara | |
| 2009/0002360 A1 | 1/2009 | Chen | |
| 2009/0307787 A1 | 12/2009 | Grosveld | |
| 2010/0122358 A1 | 5/2010 | Brueggemann | |
| 2011/0028695 A1 | 2/2011 | Revets | |
| 2012/0135110 A1 | 5/2012 | Chiba | |
| 2014/0287509 A1 | 9/2014 | Sharei | |
| 2015/0289489 A1 | 10/2015 | Macdonald | |
| 2016/0096892 A1 | 4/2016 | Brogdon et al. | |
| 2016/0368994 A1 | 12/2016 | Kelley et al. | |
| 2017/0088617 A1 | 3/2017 | Konopitzky et al. | |
| 2018/0086831 A1 | 3/2018 | Pule et al. | |
| 2018/0230225 A1 | 8/2018 | Fan et al. | |
| 2021/0277126 A1 | 9/2021 | Zhang et al. | |

FOREIGN PATENT DOCUMENTS

| | | |
|---|---|---|
| CN | 105384825 A | 3/2016 |
| CN | 106928368 A | 7/2017 |
| CN | 107001465 A | 8/2017 |
| CN | 107109420 A | 8/2017 |
| CN | 108047333 A | 5/2018 |
| CN | 108290955 A | 7/2018 |
| EP | 0404097 B1 | 9/1996 |
| EP | 0425235 B1 | 9/1996 |
| EP | 3191520 A1 | 7/2017 |
| TW | 201619379 A | 6/2016 |
| TW | 201619380 A | 6/2016 |
| TW | 201718647 A | 6/2017 |
| TW | 201741339 A | 12/2017 |
| WO | 198704462 A1 | 7/1987 |
| WO | 199110741 A1 | 7/1991 |
| WO | 199301161 A1 | 1/1993 |
| WO | 199308829 A1 | 5/1993 |
| WO | 199311161 A1 | 6/1993 |
| WO | 199316185 A3 | 9/1993 |
| WO | 199411026 A3 | 8/1994 |
| WO | 199429351 A3 | 2/1995 |
| WO | 199633735 A1 | 10/1996 |
| WO | 199634096 A1 | 10/1996 |
| WO | 199634103 A1 | 10/1996 |
| WO | 199730087 A1 | 8/1997 |
| WO | 199824893 A3 | 8/1998 |
| WO | 199858964 A1 | 12/1998 |
| WO | 199922764 A1 | 5/1999 |
| WO | 199951642 A1 | 10/1999 |
| WO | 2000032776 A2 | 6/2000 |
| WO | 200061739 A1 | 10/2000 |
| WO | 2001029246 A1 | 4/2001 |
| WO | 2002085945 A3 | 3/2003 |
| WO | 2003035694 A3 | 10/2003 |
| WO | 2003084570 A1 | 10/2003 |
| WO | 2003085107 A1 | 10/2003 |
| WO | 2003085119 A1 | 10/2003 |
| WO | 2003101878 A1 | 11/2003 |
| WO | 2004049794 A3 | 12/2004 |
| WO | 2004106380 A2 | 12/2004 |
| WO | 2004106381 A1 | 12/2004 |
| WO | 2005035586 A1 | 4/2005 |
| WO | 2004056312 A3 | 5/2005 |
| WO | 2005053742 A1 | 6/2005 |
| WO | 2005100402 A1 | 10/2005 |
| WO | 2006008548 A3 | 6/2006 |
| WO | 2006029879 A3 | 9/2006 |
| WO | 2005035778 A1 | 12/2006 |
| WO | 2007042261 A3 | 12/2007 |
| WO | 2008077546 A1 | 7/2008 |
| WO | 2008119567 A3 | 1/2009 |
| WO | 2009089004 A1 | 7/2009 |
| WO | 2010037838 A3 | 7/2010 |

(56) References Cited

FOREIGN PATENT DOCUMENTS

| WO | | 2010150918 | A1 | 12/2010 | | |
|---|---|---|---|---|---|---|
| WO | | 2002031140 | A1 | 9/2012 | | |
| WO | WO | 2013169625 | A1 | 11/2013 | | |
| WO | WO | 2016014535 | A1 | 1/2016 | | |
| WO | WO | 2016014576 | A1 | 1/2016 | | |
| WO | WO | 2016168766 | A1 | 10/2016 | | |
| WO | | 2016180982 | A1 | 11/2016 | | |
| WO | | 2016201389 | A2 | 12/2016 | | |
| WO | WO | 2017125897 | A1 | 7/2017 | | |
| WO | | 2017133175 | A1 | 8/2017 | | |
| WO | | 2017133633 | A1 | 8/2017 | | |
| WO | WO | 2017132279 | A1 | 8/2017 | | |
| WO | WO | 2018068201 | A1 | 4/2018 | | |
| WO | | WO-2022272033 | A2 | * | 12/2022 | ............ A61K 47/64 |

OTHER PUBLICATIONS

Dondelinger et al., Understanding the significance and implications of antibody numbering and antigen-binding surface/residue definition; 2018, Front. Immunol., 9: 2278. (Year: 2018).*

Chen et al., Generation and analysis of random point mutations in an antibody CDR2 sequence: many mutated antibodies lose their ability to bind antigen; 1992, J. Exp. Med., 176: 855-866. (Year: 1992).*

Kenderian et al., "Targeting CLEC12A with Chimeric Antigen Receptor T Cells Can Overcome the Chemotherapy Refractoriness of Leukemia Stem Cells," Transplantation and Cellular Therapy, Mar. 2017, 23(3):S247-S248.

Laborda et al., "Development of A Chimeric Antigen Receptor Targeting C-Type Lectin-Like Molecule-1 for Human Acute Myeloid Leukemia," International Journal of Molecular Sciences, Oct. 27, 2017, 18(11):2259.

Alarcon, B. (1991). "The CD3-γ and CD3-δ Subunits Of The T Cell Antigen Receptor Can Be Expressed Within Distinct Functional TCR/CD3 Complexes," EMBO J. 10(4):903-912.

Almagro, J. et al. (Jan. 1, 2008). "Humanization of Antibodies," Frontiers in Bioscience 13:1619-1633.

Anasetti, C. et al. (Dec. 1990). "Induction of Specific Nonresponsiveness in Unprimed Human T Cells by Anti-CD3 Antibody and Alloantigen," J. Exp. Med. 172:1691-1700.

Aronovich, E.L., et al. (2011, e.pub. Apr. 1, 2011). "The Sleeping Beauty Transposon System: A Non-Viral Vector For Gene Therapy," Human Molecular Genetics 20(1):R14-R20.

Baca, M. et al. (Apr. 18, 1997). "Antibody Humanization Using Monovalent Phage Display," J. Biol. Chem. 272(16):10678-10684.

Bahram, S. et al. (Oct. 2005, e-pub. Aug. 8, 2005). "MIC And Other NKG2D Ligands: From None To Too Many," Curr Opin Immunol. 17(5):505-509.

Barbas III, C.F. et al. (Apr. 1994). "In Vitro Evolution Of A Neutralizing Human Antibody To Human Immunodeficiency Virus Type 1 To Enhance Affinity and Broaden Strain Cross-Reactivity," Proc Nat. Acad. Sci. USA 91:3809-3813.

Berg, I.J.M. et al. (Dec. 1998). "Selective Expansion Of A Peripheral Blood CD8+ Memory T Cell Subset Expressing Both Granzyme B And L-Selectin During Primary Viral Infection In Renal Allograft Recipients," Transplant Proc. 30(8):3975-3977.

Beverley, P. C. et al. (Apr. 1981). "Distinctive Functional Characteristics Of Human "T" Lymphocytes Defined By E Rosetting Or A Monoclonal Anti-T Cell Antibody," Eur. J. Immunol. 11(4):329-334.

Boerner, P. et al. (Jul. 1, 1991). "Production of a Antigen-Specific Human Monoclonal Antibodies from In Vitro-Primed Human Splenocytes," J. Immunol. 147(1):86-95.

Brennan, M. et al. (Jul. 5, 1985). "Preparation of Bispecific Antibodies by Chemical Recombination of Monoclonal Immunoglobulin G1 Fragments," Science 229:81-83.

Brüggemann, M. et al. (1993). "Designer Mice: The Production of Human Antibody Repertoires in Transgenic Animals," Year in Immuno. 7:33-40.

Brüggemann, M. et al. (Nov. 1, 1987). "Comparison of the Effector Functions of Human Immunoglobulins Using a Matched Set of Chimeric Antibodies," J. Exp. Med. 166:1351-1361.

Carpenter, P.A. et al. (Apr. 15, 2002). "A Humanized Non-FcR-Binding Anti-CD3 Antibody, Visilizumab, For Treatment Of Steroid-Refractory Acute Graft-Versus-Host Disease," Blood 99(8):2712-2719.

Carter, P. et al. (May 1992). "Humanization of an Anti-p185HER2 Antibody for Human Cancer Therapy," Proc. Natl. Acad. Sci. USA 89:4285-4289.

Chari, R.V.J. et al. (Jan. 1, 1992). "Immunoconjugates Containing Novel Maytansinoids: Promising Anticancer Drugs," Cancer Res. 52:127-131.

Chen, X. J. et al. (2007). "Construction, Expression And Functional Characterization Of Single Chain Variable Fragments (Scfv) Against Human CD33 Antigen," Chinese Journal of Cellular and Molecular Immunology 23(12):1147-1149.

Chen, Y. et al. (1999). "Selection and Analysis of an Optimized Anti-VEGF Antibody: Crystal Structure of an Affinity-Matured Fab In Complex With Antigen," J. Mol. Biol 293:865-881.

Chothia, C. et al. (Aug. 20, 1987). "Canonical Structures for the Hypervariable Regions of Immunoglobulins," J. Mol. Biol. 196(4):901-917.

Chothia, C. et al. (Dec. 5, 1985). "Domain Association In Immunoglobulin Molecules. The Packing Of Variable Domains," J. Mol. Biol. 186(3):651-663.

Chowdhury, P.S. (2008). "Engineering Hot Spots for Affinity Enhancement of Antibodies," Methods Mol. Biol. 207:179-196.

Clackson, T. et al. (Aug. 15, 1991). "Making Antibody Fragments Using Phage Display Libraries," Nature 352:624-628.

Clynes, R. et al. (Jan. 1998). "Fc Receptors are Required in Passive and Active Immunity to Melanoma," Proc. Natl. Acad. Sci. U.S.A. 95:652-656.

Cole, S.P.C et al. (1985). "The EBV-Hybridoma Technique and Its Application to Human Lung Cancer," in Monoclonal Antibodies and Cancer Therapy, Alan R. Liss, p. 77-96.

Conrad, M.L. et al. (2007, e-pub. Jul. 25, 2007). "TCR and CD3 Antibody Cross-Reactivity in 44 Species," Cytometry Part A 71A:925-933.

Conrath, K.E. et al. (Mar. 9, 2001). "Camel Single-domain Antibodies as Modular Building Units in Bispecific and Bivalent Antibody Constructs" J. Biol. Chem. 276(10):7346-7350.

Cragg, M.S. et al. (Apr. 1, 2004). "Antibody Specificity Controls In Vivo Effector Mechanisms Of Anti-CD20 Reagents," Blood 103(7):2738-2743.

Cragg, M.S. et al. (Feb. 1, 2003). "Complement-Mediated Lysis By Anti-CD20 Mab Correlates With Segregation Into Lipid Rafts," Blood 101(3):1045-1052.

Cunningham, B.C. et al. (Jun. 2, 1989). "High-Resolution Epitope Mapping of hGH-Receptor Interactions by Alanine-Scanning Mutagenesis," Science 244:1081-1085.

Dall'acqua, W.F. et al. (2005). "Antibody Humanization by Framework Shuffling," Methods 36:43-60.

Dubowchik, G.M. et al. (2002). "Doxorubicin Immunoconjugates Containing Bivalent, Lysosomally-Cleavable Dipeptide Linkages," Bioorganic & Medicinal Chemistry Letters 12:1529-1532.

Duncan, A.R. et al. (Apr. 21, 1988). "The Binding Site for C1q on IgG," Nature 322:738-740.

Endo, Y. et al. (2003). "High-Throughput, Genome-Scale Protein Production Method Based On The Wheat Germ Cell-Free Expression System," Biotechnol. Adv. 21:695-713.

Fellouse, F.A. et al. (Aug. 24, 2004). "Synthetic Antibodies from a Four-Amino-Acid Code: A Dominant Role for Tyrosine in Antigen Recognition," Proc. Natl. Acad. Sci. USA 101(34): 12467-12472.

Fishwild, D.M. et al. (Jul. 1996). "High-Avidity Human IgGK Monoclonal Antibodies from a Novel Strain of Minilocus Transgenic Mice," Nature Biotechnol. 14:845-851.

Foote, J. et al. (1992). "Antibody Framework Residues Affecting the Conformation of the Hypervariable Loops," J Mol Biol. 224(2): 487-499.

Frankel, A. E. et al. (Jul. 17, 2014, e-pub. May 23, 2014). "Activity Of SL-401, A Targeted Therapy Directed To Interleukin-3 Receptor,

(56) References Cited

OTHER PUBLICATIONS

In Blastic Plasmacytoid Dendritic Cell Neoplasm Patients," Blood, The Journal of the American Society of Hematology 124(3):385-392.

Garland, R.J. et al. (Jul. 1999). "The Use Of Teflon Cell Culture Bags To Expand Functionally Active CD8+ Cytotoxic T Lymphocytes," J. Immunol Meth. 227(1-2):53-63.

Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.

Greenberg, A.S. et al. (Mar. 9, 1995). "A New Antigen Receptor Gene Family That Undergoes Rearrangement And Extensive Somatic Diversification In Sharks" Nature 374(6518):168-173.

Griffiths, A.D. et al. (1993). "Human Anti-Self Antibodies with High Specificity from Phage Display Libraries," EMBO J. 12(2):725-734.

Gruber, M. et al. (1994). "Efficient Tumor Cell Lysis Mediated by a Bispecific Single Chain Antibody Expressed in *Escherichia coli*," J. Immunol. 152:5368-5374.

Guyer, R.L. et al. (Aug. 1976). "Immunoglobulin Binding By Mouse Intestinal Epithelial Cell Receptors," J. Immunol. 117(2):587-593.

Haanen, J.B. et al. (Nov. 1, 1999). "Selective Expansion Of Cross-Reactive CD8+ Memory T Cells By Viral Variants." The Journal of Experimental Medicine 190(9):1319-1328.

Hamers-Casterman, C. et al. (Jun. 3, 1993). "Naturally Occurring Antibodies Devoid of Light Chains," Nature 363:446-448.

Harris, W.J. (1995). "Production of Humanized Monoclonal and Antibodies for in vivo Imaging and Therapy," Biochem. Soc. Transactions 23:1035-1038.

Hassanzadeh-Ghassabeh, G. et al. (2013, e-pub. Jun. 4, 2013). "Nanobodies and their Potential Applications," Nanomedicine (Lond) 8(6):1013-1026.

Hawkins, R.E. et al. (1992). "Selection of Phage Antibodies by Binding Affinity: Mimicking Affinity Maturations," J. Mol. Biol. 226:889-896.

Hellstrom, I. et al. (Mar. 1985). "Strong Antitumor Activities of IgG3 Antibodies to a Human Melanoma-associated Ganglioside," Proc. Natl. Acad. Sci. USA 82:1499-1502.

Hellstrom, I. et al. (Sep. 1986). "Antitumor Effects of L6, an IgG2a Antibody That Reacts With Most Human Carcinomas," Proc. Natl. Acad. Sci. USA 83:7059-7063.

Herold, K. C. et al. (Feb. 1, 2003). "Activation Of Human T Cells By FcR Nonbinding Anti-CD3 mAb, hOKT3γ1(Ala-Ala)," J. Clin. Invest. 111(3):409-418.

Hinman, L.M. et al. (Jul. 15, 1993). "Preparation and Characterization of Monoclonal Antibody Conjugates of the Calicheamicins: A Novel and Potent Family of Antitumor Antibiotics," Cancer Research 53:3336-3342.

Hirsch, R. et al. (Jun. 1, 1988). "Effects Of In Vivo Administration Of Anti-T3 Monoclonal Antibody On T Cell Function In Mice. I. Immunosuppression Of Transplantation Responses," J. Immunol. 140(11):3766-3772.

Hollinger, P. et al. (Jul. 1993). "Diabodies": Small Bivalent And Bispecific Antibody Fragments, Proc. Natl. Acad. Sci. USA 90:6444-6448.

Hongo, J.A.S. et al. (1995). "Development and Characterization of Murine Monoclonal Antibodies to the Latency-Associated Peptide of Transforming Growth Factor Beta1," Hybridoma, 14(3):253-260.

Hoogenboom, H.R. et al. (Sep. 20, 1992). "By-Passing Immunisation Human Antibodies From Synthetic Repertoires Of Germline VH Gene Segments Rearranged In Vitro," J. Mol. Biol. 227(2):381-388.

Hudson, P.J. et al. (Jan. 2003). "Engineered Antibodies," Nat. Med. 9(1):129-134.

Hurle, M.R. et al. (1994). "Protein Engineering Techniques for Antibody Humanization," Curr. Op. Biotech. 5(4):428-433.

Idusogie, E.E. et al. (2000). "Mapping of the C1q Binding Site on Rituxan, a Chimeric Antibody With a Human IgG1 Fc," J. Immunol. 164:4178-4184.

International Preliminary Report on Patentability issued Mar. 9, 2021, for Patent Application No. PCT/CN2019/105059 filed on Sep. 10, 2019, 7 pages.

International Search Report and Written Opinion from the International Searching Authority mailed Jan. 9, 2020, for Patent Application No. PCT/CN2019/105059, filed Sep. 10, 2019, 14 pages.

Jackson, J.R. et al. (Apr. 1, 1995). "In Vitro Antibody Maturation. Improvement Of A High Affinity, Neutralizing Antibody Against IL-1 Beta," J. Immunol. 154(7):3310-3319.

Jakobovits, A. et al. (Mar. 18, 1993). "Germ-Line Transmission and Expression of a Human-Derived Yeast Artificial Chromosome," Nature 362:255-258.

Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90(6):2551-2555.

Janssens, R. et al. (Oct. 10, 2006). "Generation Of Heavy-Chain-Only Antibodies In Mice," Proc. Natl. Acad. Sci. USA 103(41):15130-15135.

Jeffrey, S.C. et al. (2006, e-pub. Nov. 3, 2005). "Dipeptide-based Highly Potent Doxorubicin Antibody Conjugates," Bioorganic Medicinal Chemistry Letters 16:358-362.

Jones, P.T. et al. (May 29, 1986). "Replacing The Complementarity-Determining Regions In A Human Antibody With Those From A Mouse," Nature 321:522-525.

Jordan, C. T. et al. (Oct. 2000). "The Interleukin-3 Receptor Alpha Chain Is A Unique Marker For Human Acute Myelogenous Leukemia Stem Cells," Leukemia 14(10):1777-1784.

Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.

Kashmiri, S.V. et al. (2005). "SDR grafting-A New Approach to Antibody Humanization," Methods 36:25-34.

Kim, J-K. et al. (1994). "Localization of the Site of the Murine IgG1 Molecule That is Involved in Binding to the Murine Intestinal Fc Receptor," Eur. J. Immunol. 24:2429-2434.

King, H.D. et al. (2002, e-pub. Aug. 14, 2002). "Monoclonal Antibody Conjugates of Doxorubicin with Branched Peptide Linkers: Inhibition of Aggregation by Methoxytriethyleneglycol Chains," J. Med. Chem. 45(19):4336-4343.

Klimka, A. et al. (2000). "Human Anti-CD30 Recombinant Antibodies by Guided Phage Antibody Selection Using Cell Panning," Br. J. Cancer 83(2):252-260.

Kohler, G. et al. (Aug. 7, 1975) "Continuous Cultures Of Fused Cells Secreting Antibody Of Predefined Specificity," Nature 256:495-497.

Kostelny, S.A. et al. (Mar. 1, 1992). "Formation of a Bispecific Antibody By The Use of Leucine Zippers," J. Immunol. 148(5):1547-1553.

Kozbor, D. (Dec. 1984). "A Human Hybrid Myeloma for Production of Human Monoclonal Antibodies," J. Immunol. 133(6):3001-3005.

Kratz, F. et al. (2006). "Prodrugs of Anthracyclines in Cancer Chemotherapy," Current Medicinal Chemistry 13(5):477-523.

Le Bert, N. et al. (2014, e-pub. Jan. 21, 2014). Advances In NKG2D Ligand Recognition And Responses By NK Cells, Immunology And Cell Biology 92(3):230-236.

Lee, C.V. et al. (2004). "Bivalent Antibody Phage Display Mimics Natural Immunoglobulin," .J. Immunol. Methods 284(1-2):119-132.

Lee, C.V. et al. (2004). "High-Affinity Human Antibodies From Phage-Displayed Synthetic Fab Libraries With A Single Framework Scaffold," J. Mol. Biol. 340:1073-1093.

Li, J. et al. (Mar. 7, 2006). "Human Antibodies for Immunotherapy Development Generated via a Human B Cell Hybridoma Technology," Proc. Natl. Acad. Sci. USA 103(10):3557-3562.

Liu, Y-J. et al. (Feb. 12, 2015) "Confinement And Low Adhesion Induce Fast Amoeboid Migration Of Slow Mesenchymal Cells," Cell 160(4):659-672.

Lode, H.N. et al. (Jul. 15, 1998). "Targeted Therapy with a Novel Enediyene Antibiotic Calicheamicin θ11 Effectively Suppresses Growth and Dissemination of Liver Metastases in a Syngeneic Model of Murine Neuroblastoma," Cancer Res. 58:2925-2928.

(56) References Cited

OTHER PUBLICATIONS

Lonberg, N. (Sep. 2005). "Human Antibodies From Transgenic Animals," Nat. Biotech. 23(9):1117-1125.
Lonberg, N. et al. (1995, e-pub. Jul. 10, 2009). "Human Antibodies From Transgenic Mice," Int. Rev. Immunol. 13(1):65-93.
Lonberg, N. et al. (2008, e-pub. Jul. 21, 2008). "Fully Human Antibodies From Transgenic Mouse and Phage Display Platforms," Curr. Opin. Immunol. 20:450-459.
Lonberg, N. et al. (Apr. 28, 1994). "Antigen-Specific Human Antibodies From Mice Comprising Four Distinct Genetic Modifications," Nature 368(6474):856-859.
Lu, H. et al. (Sep. 8, 2014). "Targeting Human C-Type Lectin-Like Molecule-1 (CLL1) With A Bispecific Antibody For Immunotherapy Of Acute Myeloid Leukemia," Angewandte Chemie 53(37):9841-9845.
Marks, J.D. et al. (1991). "By-Passing Immunization Human Antibodies from V-gene Libraries Displayed on Phage," J. Mol. Biol. 222:581-597.
Marks, J.D. et al. (Jul. 1992). "By-Passing Immunization: Building High Affinity Human Antibodies by Chain Shuffling," Bio/Technology 10:779-783.
McCafferty, J. et al. (Dec. 6, 1990). "Phage Antibodies: Filamentous Phage Displaying Antibody Variable Domains," Nature 348:552-554.
Milone, M. C. et al. (Aug. 2009, e-pub. Apr. 21, 2009). "Chimeric Receptors Containing CD137 Signal Transduction Domains Mediate Enhanced Survival Of T Cells And Increased Antileukemic Efficacy In Vivo," Molecular Therapy 17(8):1453-1464.
Milstein, C. et al. (Oct. 6, 1983). "Hybrid Hybridomas and Their Use in Immunohistochemistry," Nature 305:537-539.
Morea, V. et al. (Mar. 2000). "Antibody Modeling: Implications for Engineering and Design," Methods 20(3):267-279.
Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.
Morrison, S.L. (Apr. 28, 1994). "Success in Specification," Nature 368:812-813.
Munoz, L. et al. (Dec. 2001). "Interleukin-3 Receptor Alpha Chain (CD123) Is Widely Expressed In Hematologic Malignancies," Haematologica 86(12):1261-1269.
Nagy, A. et al. (Jan. 18, 2000). "Stability of Cytotoxic Luteinizing Hormone-Releasing Hormone Conjugate (AN-152) Containing Doxorubicin 14-O-Hemiglutarate in Mouse and Human Serum in Vitro: Implications for the Design of Preclinical Studies," Proc. Nat'l. Acad. Sci. 97(2):829-834.
Neuberger, M. (Jul. 1996). "Generating High-Avidity Human Mabs in Mice," Nature Biotechnology 14:826.
Ni, J. (Oct. 23, 2006). "Research Progress and Future Perspectives in Antibodmics and Antibodomic Drugs," J. General Review 26(4):265-268, 3 pages.
Okazaki, A. et al. (Mar. 5, 2004). "Fucose Depletion From Human IgG1 Oligosaccharide Enhances Binding Enthalpy And Association Rate Between IgG1 and FcγRIIIa," J. Mol. Biol. 336(5):1239-1249.
Osbourn, J. et al. (2005). "From Rodent Regents to Human Therapeutics Using Antibody Guided Selection," Methods 36:61-68.
O'hear, C. et al. (2015). "Anti-CD33 Chimeric Antigen Receptor Targeting Of Acute Myeloid Leukemia," Haematologica 100(3):336-344.
Padlan, E.D. (1991). "A Possible Procedure for Reducing the Immunogenicity of Antibody Variable Domains While Preserving Their Ligand-Binding Properties," Mol. Immunol. 28(4/5):489-498.
Pardon, E. et al. (Mar. 2014, e-pub. Feb. 27, 2014). "A General Protocol for the Generation of Nanobodies for Structural Biology," Nature Protocol 9(3):674-693, 40 pages.
Pessano, S. et al. (1985). "The T3/T Cell Receptor Complex: Antigenic Distinction Between The Two 20-kd T3 (T3-δ and T3-ε) Subunits," The EMBO Journal 4(2):337-344.
Petkova, S.B. et al. (2006, e-pub. Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.
Presta, L.G. (1992). "Antibody Engineering," Current Opinion in Structural Biology 2:593-596.
Presta, L.G. et al. (Sep. 1, 1993). "Humanization of an Antibody Directed Against IgE," J. Immunol. 151(5):2623-2632.
Queen, C. et al. (Dec. 1989). "A Humanized Antibody That Binds to the Interleukin 2 Receptor," Proc. Natl Acad. Sci. USA 86:10029-10033.
Rabinovich, P.M. et al. (Oct. 2006). "Synthetic Messenger RNA As A Tool For Gene Therapy." Human Gene Therapy 17(10):1027-1035.
Ravetch, J.V. et al. (1991). "Fc Receptors," Annu. Rev. Immunol. 9:457-492.
Reichmann, L. et al. (Mar. 1988). "Reshaping Human Antibodies for Therapy," Nature 332:323-327.
Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.
Rosenberg, S.A. et al. (Dec. 22, 1988). "Use of Tumor-Infiltrating Lymphocytes and Interleukin-2 in the Immunotherapy of Patients with Metastatic Melanoma-A preliminary Report," The New England Journal of Medicine 319:1676-1680.
Rosok, M.J. et al. (Sep. 13, 1996). "A Combinatorial Library Strategy for the Rapid Humanization of Anticarcinoma BR96 Fab," J. Biol. Chem. 271(37):22611-22618.
Salmeron A. et al. (Nov. 1, 1991). "A Conformational Epitope Expressed Upon Association Of CD3-Epsilon With Either CD3-Delta Or CD3-Gamma Is The Main Target For Recognition By Anti-CD3 Monoclonal Antibodies," J. Immunol. 147(9):3047-3052.
Sato, N., et al. (Aug. 1, 1993). "Expression and factor-dependent modulation of the interleukin-3 receptor subunits on human hematopoietic cells," Blood 82(3):752-761.
Schier, R. et al. (1995). "Identification of Functional and Structural Amino-Acid Residues by Parsimonious Mutagenesis," Gene 169:147-155.
Sentman, C. L. et al. (2014, e-pub. Mar. 1, 2015). "NKG2D Cars As Cell Therapy For Cancer," Cancer Journal 20(2):156-159, 9 pages.
Sheriff, S. et al. (Sep. 1996). "Redefining the Minimal Antigen-Binding Fragment," Nature Struct. Biol. 3(9):733-736.
Shields, R.L. et al. (Mar. 2, 2001). "High Resolution Mapping of the Binding Site on Human IgG1 for FcγRI, FcγRII. FcγRIII, and FcRn and Design of IgG1 Variants With Improved Binding to the FcγR," J. Biol.Chem. 276(9):6591-6604.
Shinkawa, T. et al. (Jan. 31, 2003). "The Absence Of Fucose But Not The Presence Of Galactose Or Bisecting N-Acetylglucosamine Of Human Lgg1 Complex-Type Oligosaccharides Shows The Critical Role Of Enhancing Antibody-Dependent Cellular Cytotoxicity," Journal of Biological Chemistry 278(5):3466-3473.
Sidhu, S.S. et al. (2004). "Phage-Displayed Antibody Libraries of Synthetic Heavy Chain Complementarity Determining Regions," J. Mol. Biol. 338(2):299-310.
Sims, M.J. et al. (Aug. 15, 1993). "A Humanized CD18 Antibody Can Block Function Without Cell Destruction," J. Immunol. 151(4):2296-2308.
Sitaraman, K. et al. (2009). "High-Throughput Protein Expression Using Cell-Free System," Methods Mol. Biol. 498:229-244.
Spirin, A.S. (Oct. 2004). "High-Throughput Cell-Free Systems For Synthesis Of Functionally Active Proteins," Trends Biotechnol. 22(10):538-545.
Torgov, M.Y. et al. (2005; e-published on Apr. 27, 2005). "Generation of an Intensely Potent Anthracycline by a Monoclonal Antibody-ß-Galactosidase Conjugate," Bioconjugate Chem. 16:717-721.
Traunecker, A. et al. (1991). "Bispecific Single Chain Molecules (Janusins) Target Cytotoxic Lymphocytes on HIV Infected Cells," EMBO J. 10(12):3655-3659.
Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.

(56) References Cited

OTHER PUBLICATIONS

Ui-Tel, K. et al. (2000). "Sensitive Assay of RNA Interference in *Drosophila* and Chinese Hamster Cultured Cells Using Firefly Luciferase Gene As Target," FEBS Letters 479:79-82.

Van Der Linden, R. et al. (2000). "Induction Of Immune Responses And Molecular Cloning Of The Heavy Chain Antibody Repertoire Of Lama Glama," Journal Of Immunological Methods 240(1-2):185-195.

Van Dijk, M.A. et al. (Aug. 2001). "Human Antibodies as Next Generation Therapeutics," Curr. Opin. Che. Biology 5(4):368-374.

Vaswani, S.K. et al. (Aug. 1998) "Humanized Antibodies as Potential Therapeutic Drugs," Annals of Allergy, Asthma, & Immunology 81:105-115.

Vitetta, E.S. et al. (Nov. 20, 1987). "Redesigning Nature's Poisons to Create Anti-Tumor Reagents," Science 238:1098-1104.

Vollmers, H.P. et al. (2005). "Death By Stress: Natural IgM-Induced Apoptosis," Methods and Findings in Experimental and Clinical Pharmacology 27(3):185-191.

Vollmers, H.P. et al. (2005). "The 'Early Birds': Natural IgM Antibodies and Immune Surveillance," Histology and Histopathology, 20(3):927-937.

Wang, J. et al. (Jan. 10, 2018). "CAR-T Cells Targeting CLL-1 As An Approach To Treat Acute Myeloid Leukemia," Journal Of Hematology & Oncology 11(1):1-13.

Winter, G. el al. (1994). "Making Antibodies by Phage Display Technology," Ann. Rev. Immunol. 12:433-455.

Wright, A. et al. (Jan. 1997). "Effect of Glycosylation on Antibody Function: Implications for Genetics Engineering," Trends Biotechnol. 15:26-32.

Yamane-Ohnuki, N. et al. (Sep. 5, 2004, e-pub Aug. 6, 2004). "Establishment Of FUT8 Knockout Chinese Hamster Ovary Cells: An Ideal Host Cell Line For Producing Completely Defucosylated Antibodies With Enhanced Antibody-Dependent Cellular Cytotoxicity," Biotechnology and Bioengineering 87(5):614-622.

Yang, S.Y. et al. (Aug. 1986). "A Common Pathway For T Lymphocyte Activation Involving Both The CD3-Ti Complex And CD2 Sheep Erythrocyte Receptor Determinants," J. Immunol. 137(4):1097-1100.

Yelton, D.E. et al. (1995). "Affinity Maturation of the BR96 Anti-Carcinoma Antibody by Codon-Based Mutagenesis," J. Immunol. 155:1994-2004.

Yin, H. et al. (Aug. 2014). "Non-Viral Vectors for Gene-Based Therapy," Nature Reviews Genetics 15:541-555.

Yoshino, N. et al. (2000). "Upgrading Of Flow Cytometric Analysis For Absolute Counts, Cytokines AndOther Antigenic Molecules Of Cynomolgus Monkeys (Macaca Fascicularis) By Using Anti-Human Cross-Reactive Antibodies," Experimental Animals 49(2):97-110.

Zapata, G. et al. (1995). "Engineering Linear F(ab')2 Fragments For Efficient Production In *Escherichia coli* And Enhanced Antiproliferative Activity," Protein Engineering 8(10):1057-1062.

Zhao, S. et al.(2016). "Piggybac Transposon Vectors: The Tools Of The Human Gene Editing," Transl. Lung Cancer Res. 5(1):120-125.

Zhao, X. et al. (2010). "Targeting C-Type Lectin-Like Molecule-1 For Antibody-Mediated Immunotherapy In Acute Myeloid Leukemia," Haematologica 95(1):71-78.

\* cited by examiner

| sdAb | Human CD33 | | | | Cyno CD33 | | | |
| --- | --- | --- | --- | --- | --- | --- | --- | --- |
| | Ka | Kd | KD | cell | Ka | Kd | KD | cell |
| AS49175 | 1.4E+05 | 3.0E-04 | 2.2E-09 | +++ | 3.2E+05 | 2.8E-03 | 8.7E-09 | + |
| AS49226 | 2.1E+05 | 5.1E-02 | 2.4E-07 | + | 3.0E+05 | 7.1E-02 | 2.4E-07 | + |
| AS49264 | 1.4E+05 | 6.9E-04 | 4.9E-09 | +++ | 2.6E+05 | 1.6E-03 | 5.9E-09 | + |
| AS49814 | 1.3E+05 | 1.8E-03 | 1.4E-08 | + | 2.3E+05 | 2.4E-03 | 1.1E-08 | + |
| AS49873 | 1.4E+05 | 4.6E-03 | 3.3E-08 | ++ | 2.9E+05 | 8.1E-03 | 2.8E-08 | ++ |
| AS49889 | 1.3E+05 | 1.5E-04 | 1.2E-09 | ++ | 2.2E+05 | 3.5E-04 | 1.6E-09 | ++ |
| AS49902 | 1.3E+05 | 3.1E-04 | 2.4E-09 | ++ | 3.0E+05 | 2.7E-03 | 9.2E-09 | ++ |
| AS50073 | 1.4E+05 | 2.3E-03 | 1.7E-08 | ++ | 8.3E+05 | 3.8E-02 | 4.6E-08 | +++ |
| AS50502 | 1.5E+05 | 1.8E-03 | 1.3E-08 | ++ | 3.0E+05 | 4.8E-04 | 1.6E-09 | +++ |
| AS66873 | 1.1E+05 | 4.6E-03 | 4.2E-08 | ++ | 5.6E+05 | 3.7E-03 | 6.5E-09 | ++ |
| AS60399 | 1.6E+04 | 6.6E-05 | 4.0E-09 | +++ | 8.7E+04 | 5.3E-05 | 6.2E-10 | ++ |
| AS59101 | 6.6E+05 | 1.1E-02 | 1.7E-08 | +++ | 2.7E+06 | 1.1E-02 | 4.0E-09 | +++ |
| AS58930 | 6.9E+04 | 1.3E-05 | 2.0E-10 | +++ | 1.3E+05 | 1.3E-05 | 9.5E-11 | +++ |
| AS67190 | 2.5E+05 | 1.2E-03 | 4.9E-09 | ++ | 5.4E+05 | 2.0E-03 | 3.8E-09 | + |
| AS67147 | 8.7E+04 | 7.6E-04 | 8.7E-09 | + | 1.0E+05 | 3.0E-03 | 3.0E-08 | + |

FIG. 2

| CAR | %CAR-T positive rate | CAR-T cells induced THP-1 cell lysis | | CAR-T cells induced MV-4-11 cell lysis | |
|---|---|---|---|---|---|
| | | ET=1:1 | ET=3:1 | ET=1:1 | ET=3:1 |
| AS49175 | 63.7% | 46.7% | 101.3% | 59.4% | 108.9% |
| AS49226 | 60.2% | 44.3% | 104.2% | 69.4% | 94.6% |
| AS49264 | 37.3% | 42.5% | 84.3% | 71.8% | 97.1% |
| AS49814 | 64.9% | 54.3% | 104.0% | 76.5% | 89.1% |
| AS49873 | 56.3% | 48% | 87% | 66% | 81% |
| AS49889 | 65.3% | 58% | 96% | 53% | 75% |
| AS49902 | 63.0% | 78% | 86% | 68% | 103% |
| AS50073 | 62.1% | 64% | 102% | 44% | 82% |
| AS50502 | 72.3% | 58% | 96% | 66% | 85% |
| AS66873 | 55.2% | 62% | 91% | 63% | 66% |
| AS60399 | 53.0% | 54% | 82% | 48% | 76% |
| AS59101 | 40.3% | 50% | 80% | 76% | 83% |
| AS58930 | 44.8% | 48% | 78% | 60% | 78% |
| AS67190 | 35.5% | 51% | 83% | 58% | 94% |
| AS67147 | 56.3% | 60% | 93% | 57% | 88% |
| CD33 Benchmark CAR (BM CAR) | 20.6% | 55% | 81% | 50% | 75% |
| Untransduced T cell (UnT) | 0.5% | -36% | -4% | -18% | -11% |

FIG. 3

SINGLE-DOMAIN ANTIBODIES AGAINST CD33 AND CONSTRUCTS THEREOF

CROSS REFERENCE TO RELATED APPLICATIONS

This application is a national stage application under 35 U.S.C. § 371 of International Patent Application No. PCT/CN2019/105059, filed Sep. 10, 2019, which claims priority benefits of International Patent Application No. PCT/CN2018/104882 filed Sep. 10, 2018, and International Patent Application No. PCT/CN2018/104883 filed Sep. 10, 2018, the contents of each of which are incorporated herein by reference in their entirety.

SUBMISSION OF SEQUENCE LISTING ON ASCII TEXT FILE

The contents of the following submission on ASCII text file are incorporated herein by reference in their entirety: a computer readable form (CRF) of the Sequence Listing (file name: 761422002900SEQLISTING.txt, date recorded: Mar. 8, 2021, size: 211 KB).

FIELD OF THE PRESENT APPLICATION

The present invention relates to single-domain antibodies, chimeric receptors and engineered immune cells that target CD33, and methods of use thereof.

BACKGROUND OF THE PRESENT APPLICATION

With the development of tumor immunotherapy and clinical technology, chimeric antigen receptor T cell (CAR-T) immunotherapy is now one of the most promising tumor immunotherapy approaches. Generally, a chimeric antigen receptor (CAR) comprises an extracellular domain, a transmembrane domain and an intracellular signaling domain. The extracellular domain may comprise a single chain variable fragment (scFv) targeting an identified tumor antigen. CARs can be expressed on the surface of T cells using gene transfection techniques. Upon binding to the target tumor antigen, the CARs can activate the T cells to launch specific anti-tumor response in an antigen-dependent manner without being limited by the availability of major histocompatibility complexes (MHC) specific to the target tumor antigen.

Single-domain antibodies (sdAbs) are different from conventional 4-chain antibodies by having a single monomeric antibody variable domain. For example, camelids and sharks produce sdAbs named heavy chain-only antibodies (HcAbs), which naturally lack light chains. The antigen-binding fragment in each arm of the camelid heavy-chain only antibodies has a single heavy chain variable domain ($V_HH$), which can have high affinity to an antigen without the aid of a light chain. Camelid $V_HH$ is known as the smallest functional antigen-binding fragment with a molecular weight of approximately 15 kD.

Acute myeloid leukemia (AML) is a cancer of the myeloid line of blood cells, characterized by the rapid growth of immature blood cells ("blasts") that build up in the bone marrow and blood and interfere with normal blood cells. AML may spread to other organs, such as the liver, spleen, and brain. Clinical symptoms of AML include feeling tired, shortness of breath, easy bruising and bleeding, and increased risk of infection. Without treatment, AML progresses rapidly and is typically fatal within weeks or months. AML has several subtypes for which treatments and outcomes may vary. Typically, AML is initially treated with chemotherapy, sometimes along with a targeted therapy drug. Patients may then go on to receive a stem cell transplant, additional chemotherapy, surgery, or radiation therapy. AML most commonly occurs in older adults, some of whom are not healthy enough to receive intensive chemotherapy and thus have poor clinical outcome. Although current therapies for AML often lead to remissions, almost all patients eventually relapse. There is a need for an effective immunotherapeutic agent to treat AML.

The disclosures of all publications, patents, patent applications and published patent applications referred to herein are hereby incorporated herein by reference in their entirety.

BRIEF SUMMARY OF THE PRESENT APPLICATION

The present application provides anti-CD33 single-domain antibodies (sdAb) and constructs thereof, including chimeric receptors, immune effector cell engagers, and immunoconjugates, engineered immune cells, and methods of use thereof in cancer immunotherapy.

One aspect of the present application provides an anti-CD33 construct comprising an single domain antibody ("sdAb") moiety that specifically binds to CD33, wherein the sdAb moiety (e.g., $V_HH$) comprises a CDR1 comprising the amino acid sequence of any one of SEQ ID NOs: 4, 11, 18, 25, 32, 39, 46, 53, 60, 67, 74, 81, 88, 95, and 102, or a variant thereof comprising up to about 3 amino acid substitutions in the CDR1; a CDR2 comprising the amino acid sequence of any one of SEQ ID NOs: 6, 13, 20, 27, 34, 41, 48, 55, 62, 69, 76, 83, 90, 97, and 104, or a variant thereof comprising up to about 3 amino acid substitutions in the CDR2; and a CDR3 comprising the amino acid sequence of any one of SEQ ID NOs: 8, 15, 22, 29, 36, 43, 50, 57, 64, 71, 78, 85, 92, 99, and 106, or a variant thereof comprising up to about 3 amino acid substitutions in the CDR3. In some embodiments, the sdAb moiety comprises: (1) a CDR1 comprising the amino acid sequence of SEQ ID NO: 4, a CDR2 comprising the amino acid sequence of SEQ ID NO: 6, and a CDR3 comprising the amino acid sequence of SEQ ID NO: 8, or a variant thereof comprising up to about 5 amino acid substitutions in the CDRs; (2) a CDR1 comprising the amino acid sequence of SEQ ID NO: 11, a CDR2 comprising the amino acid sequence of SEQ ID NO: 13, and a CDR3 comprising the amino acid sequence of SEQ ID NO: 15, or a variant thereof comprising up to about 5 amino acid substitutions in the CDRs; (3) a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22, or a variant thereof comprising up to about 5 amino acid substitutions in the CDRs; (4) a CDR1 comprising the amino acid sequence of SEQ ID NO: 25, a CDR2 comprising the amino acid sequence of SEQ ID NO: 27, and a CDR3 comprising the amino acid sequence of SEQ ID NO: 29, or a variant thereof comprising up to about 5 amino acid substitutions in the CDRs; (5) a CDR1 comprising the amino acid sequence of SEQ ID NO: 32, a CDR2 comprising the amino acid sequence of SEQ ID NO: 34, and a CDR3 comprising the amino acid sequence of SEQ ID NO: 36, or a variant thereof comprising up to about 5 amino acid substitutions in the CDRs; (6) a CDR1 comprising the amino acid sequence of SEQ ID NO: 39, a CDR2 comprising the amino acid sequence of SEQ ID NO: 41, and a CDR3 comprising the amino acid sequence of SEQ ID NO: 43, or a variant thereof comprising up to about 5 amino acid substitutions in the CDRs; (7) a CDR1 comprising the amino acid sequence of SEQ ID NO: 46, a CDR2 comprising the amino acid sequence of SEQ ID NO: 48, and a CDR3 comprising the amino acid sequence of SEQ ID NO: 50, or a variant thereof comprising up to about 5 amino acid substitutions in the CDRs; (8) a CDR1 comprising the amino acid sequence of SEQ ID NO: 53, a CDR2 comprising the amino acid sequence of SEQ ID NO: 55, and a CDR3 comprising the amino acid sequence of SEQ ID NO: 57, or a variant thereof comprising up to about 5 amino acid substitutions in the CDRs; (9) a CDR1 comprising the amino acid sequence of SEQ ID NO: 60, a CDR2 comprising the amino acid sequence of SEQ ID NO: 62, and a CDR3 comprising the amino acid sequence of SEQ ID NO: 64, or a variant thereof comprising up to about 5 amino acid substitutions in the CDRs; (10) a CDR1 comprising the amino acid sequence of SEQ ID NO: 67, a CDR2 comprising the amino acid sequence of SEQ ID NO: 69, and a CDR3 comprising the amino acid sequence of SEQ ID NO: 71, or a variant thereof comprising up to about 5 amino acid substitutions in the CDRs; (11) a CDR1 comprising the amino acid sequence of SEQ ID NO: 74, a CDR2 comprising the amino acid sequence of SEQ ID NO: 76, and a CDR3 comprising the amino acid sequence of SEQ ID NO: 78, or a variant thereof comprising up to about 5 amino acid substitutions in the CDRs; (12) a CDR1 comprising the amino acid sequence of SEQ ID NO: 81, a CDR2 comprising the amino acid sequence of SEQ ID NO: 83, and a CDR3 comprising the amino acid sequence of SEQ ID NO: 85, or a variant thereof comprising up to about 5 amino acid substitutions in the CDRs; (13) a CDR1 comprising the amino acid sequence of SEQ ID NO: 88, a CDR2 comprising the amino acid sequence of SEQ ID NO: 90, and a CDR3 comprising the amino acid sequence of SEQ ID NO: 92, or a variant thereof comprising up to about 5 amino acid substitutions in the CDRs; (14) a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99, or a variant thereof comprising up to about 5 amino acid substitutions in the CDRs; or (15) a CDR1 comprising the amino acid sequence of SEQ ID NO: 102, a CDR2 comprising the amino acid sequence of SEQ ID NO: 104, and a CDR3 comprising the amino acid sequence of SEQ ID NO: 106, or a variant thereof comprising up to about 5 amino acid substitutions in the CDRs.

In some embodiments, there is provided an anti-CD33 construct comprising an sdAb moiety that specifically binds to CD33, wherein the sdAb moiety comprises a CDR1, a CDR2, and a CDR3 of an sdAb comprising the amino acid sequence of any one of SEQ ID NOs: 108-122.

In some embodiments according to any one of the anti-CD33 constructs described herein, the sdAb moiety comprises an amino acid sequence having at least about 95% (e.g., about 96%, 97%, 98%, 99% or 100%) sequence identity to the amino acid sequence of any one of SEQ ID NOs: 108-122. In some embodiments, the sdAb moiety comprises the amino acid sequence of any one of SEQ ID NOs: 108-122.

Also provided are CD33 epitopes that any one of the anti-CD33 sdAb moieties described above specifically bind to, and anti-CD33 antibodies (such as anti-CD33 sdAbs) that compete with any one of the anti-CD33 sdAb moieties described above.

In some embodiments according to any one of the anti-CD33 constructs described above, the sdAb moiety is a camelid antibody. In some embodiments, the sdAb moiety is a chimeric antibody. In some embodiments, the sdAb moiety is humanized. In some embodiments, the sdAb moiety is a $V_HH$ fragment.

In some embodiments, the anti-CD33 construct is a chimeric receptor (also referred herein as "anti-CD33 chimeric receptor") comprising an extracellular domain comprising the sdAb moiety (e.g., $V_HH$), a transmembrane domain, and an intracellular signaling domain comprising a primary intracellular signaling sequence of an immune effector cell (e.g., T cell). In some embodiments, the primary intracellular signaling sequence is derived from CD3ζ, FcRγ, FcRβ, CD3γ, CD3δ, CD3ε, CD5, CD22, CD79a, CD79b, or CD66d. In some embodiments, the primary intracellular signaling sequence is a CD3ζ intracellular signaling sequence. In some embodiments, the intracellular signaling domain further comprises an intracellular co-stimulatory sequence. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB. In some embodiments, the extracellular domain of the anti-CD33 construct further comprises a second binding moiety that specifically binds to a second antigen or epitope. In some embodiments, the second binding moiety is an sdAb (e.g., $V_HH$) or an scFv. In some embodiments, the second binding moiety is an extracellular domain of a receptor. In some embodiments, the second binding moiety specifically binds to CLL1, CD123 or an NKG2D ligand. In some embodiments, the second binding moiety is an anti-CLL1 sdAb or an anti-CD123 sdAb. In some embodiments, the second binding moiety is an extracellular domain (ECD) of NKG2D.

In some embodiments, the anti-CD33 construct is a chimeric receptor (also referred herein as "anti-CD33 chimeric receptor") comprising an extracellular domain comprising the sdAb moiety (e.g., $V_HH$), a transmembrane domain, and an intracellular signaling domain comprising an intracellular co-stimulatory sequence. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB. In some embodiments, the extracellular domain of the anti-CD33 construct further comprises a second binding moiety that specifically binds to a second antigen or epitope. In some embodiments, the second binding moiety is an sdAb or an scFv. In some embodiments, the second binding moiety is an extracellular domain of a receptor. In some embodiments, the second binding moiety specifically binds to CLL1, CD123 or an NKG2D ligand. In some embodiments, the second binding moiety is an sdAb or scFv that specifically binds to CLL1 or CD123. In some embodiments, the second binding moiety is an ECD of NKG2D.

One aspect of the present application provides an anti-CD33 chimeric receptor comprising an extracellular domain comprising an anti-CD33 sdAb moiety, a transmembrane domain, and an intracellular signaling domain, wherein the anti-CD33 sdAb moiety comprises: a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22. In some embodiments, the intracellular signaling domain comprises a primary intracellular signaling sequence of an immune effector cell (e.g., T cell). In some embodiments, the primary intracellular signaling sequence is derived from CD3ζ, FcRγ, FcRβ, CD3γ, CD3δ, CD3ε, CD5, CD22, CD79a, CD79b, or CD66d. In some embodiments, the primary intracellular signaling sequence is a CD3ζ intracellular signaling sequence. In some embodiments, the intracellular signaling domain further comprises an intracellular co-stimulatory sequence. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB.

One aspect of the present application provides a multi-specific chimeric receptor comprising an extracellular domain comprising an extracellular domain comprising an anti-CD33 sdAb moiety and an anti-CLL1 sdAb moiety, a transmembrane domain, and an intracellular signaling domain, wherein the anti-CD33 sdAb moiety comprises: a CDR1 comprising the amino acid sequence of SEQ ID NO: 11, a CDR2 comprising the amino acid sequence of SEQ ID NO: 13, and a CDR3 comprising the amino acid sequence of SEQ ID NO: 15; and wherein the anti-CLL1 sdAb moiety comprises: a CDR1 comprising the amino acid sequence of SEQ ID NO: 189, a CDR2 comprising the amino acid sequence of SEQ ID NO: 191, and a CDR3 comprising the amino acid sequence of SEQ ID NO: 193. In some embodiments, the intracellular signaling domain comprises a primary intracellular signaling sequence of an immune effector cell (e.g., T cell). In some embodiments, the primary intracellular signaling sequence is derived from CD3ζ, FcRγ, FcRβ, CD3γ, CD3δ, CD3ε, CD5, CD22, CD79a, CD79b, or CD66d. In some embodiments, the primary intracellular signaling sequence is a CD3ζ intracellular signaling sequence. In some embodiments, the intracellular signaling domain further comprises an intracellular co-stimulatory sequence. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB.

One aspect of the present application provides an anti-CD33 chimeric receptor comprising the amino acid sequence of any one of SEQ ID NOs: 108-122, 155-169, and 170-181.

One aspect of the present application provides an engineered immune cell comprising any one of the anti-CD33 chimeric receptors described above, or a nucleic acid encoding the anti-CD33 chimeric receptor. In some embodiments, the engineered immune cell further comprises a second chimeric receptor. In some embodiments, the second chimeric receptor comprises an extracellular domain comprising a second binding moiety that specifically binds to a second antigen or epitope, a transmembrane domain, and an intracellular signaling domain comprising a primary intracellular signaling sequence of an immune effector cell (e.g., T cell). In some embodiments, the primary intracellular signaling sequence is derived from CD3ζ, FcRγ, FcRβ, CD3γ, CD3δ, CD3ε, CD5, CD22, CD79a, CD79b, or CD66d. In some embodiments, the primary intracellular signaling sequence is a CD3ζ intracellular signaling sequence. In some embodiments, the intracellular signaling domain further comprises an intracellular co-stimulatory sequence. In some embodiments, the second chimeric receptor comprises an extracellular domain comprising a second binding moiety that specifically binds to a second antigen or epitope, a transmembrane domain, and an intracellular signaling domain comprising an intracellular co-stimulatory sequence. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB. In some embodiments, the second binding moiety is an extracellular domain of a receptor. In some embodiments, the second binding moiety specifically binds to CLL1, CD123 or an NKG2D ligand. In some embodiments, the second binding moiety is an sdAb or scFv that specifically binds to CLL1 or CD123. In some embodiments, the second binding moiety is an ECD of NKG2D.

One aspect of the present application provides a dual chimeric receptor system comprising: (a) a first chimeric receptor comprising an extracellular domain comprising an anti-CD33 sdAb, a transmembrane, and an intracellular signaling domain, wherein the anti-CD33 sdAb comprises: (1) a CDR1 comprising the amino acid sequence of SEQ ID NO: 25, a CDR2 comprising the amino acid sequence of SEQ ID NO: 27, and a CDR3 comprising the amino acid sequence of SEQ ID NO: 29; (2) a CDR1 comprising the amino acid sequence of SEQ ID NO: 53, a CDR2 comprising the amino acid sequence of SEQ ID NO: 55, and a CDR3 comprising the amino acid sequence of SEQ ID NO: 57; or (3) a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99; and (b) a second chimeric receptor comprising an extracellular domain comprising an anti-CLL1 sdAb, a transmembrane domain, and an intracellular signaling domain, wherein the anti-CLL1 sdAb comprises: (1) a CDR1 comprising the amino acid sequence of SEQ ID NO: 196, a CDR2 comprising the amino acid sequence of SEQ ID NO: 198, and a CDR3 comprising the amino acid sequence of SEQ ID NO: 200; or (2) a CDR1 comprising the amino acid sequence of SEQ ID NO: 203, a CDR2 comprising the amino acid sequence of SEQ ID NO: 205, and a CDR3 comprising the amino acid sequence of SEQ ID NO: 207. In some embodiments, the intracellular signaling domain of the first chimeric receptor and/or the second chimeric receptor comprises a primary intracellular signaling sequence of an immune effector cell (e.g., T cell). In some embodiments, the primary intracellular signaling sequence is derived from CD3ζ, FcRγ, FcRβ, CD3γ, CD3δ, CD3ε, CD5, CD22, CD79a, CD79b, or CD66d. In some embodiments, the primary intracellular signaling sequence is a CD3ζ intracellular signaling sequence. In some embodiments, the intracellular signaling domain of the first chimeric receptor and/or the second chimeric receptor further comprises an intracellular co-stimulatory sequence. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB. In some embodiments, the intracellular co-stimulatory sequence of the first chimeric receptor comprises an intracellular co-stimulatory sequence derived from 4-1BB. In some embodiments, the intracellular co-stimulatory sequence of the second chimeric receptor comprises an intracellular co-stimulatory sequence derived from CD28.

Also provided is a dual chimeric receptor construct comprising the amino acid sequence of any one of SEQ ID NOs: 183-185.

In some embodiments, there is provided an engineered immune cell comprising any one of the dual chimeric receptor systems or dual chimeric receptor constructs described above.

In some embodiments according to any one of the engineered immune cells described above, the immune cell is a T cell, an NK cell, a peripheral blood mononuclear cell (PBMC), a hematopoietic stem cell, a pluripotent stem cell, or an embryonic stem cell. In some embodiments, the immune cell is a T cell, such as a cytotoxic T cell, a helper T cell, a natural killer T cell, or a γδT cell. In some embodiments, the engineered immune cell expresses a safety-switch antigen or epitope, such as CD52, EGFR, CD20 or an epitope thereof.

In some embodiments, the anti-CD33 construct is a monospecific molecule. In some embodiments, the anti-CD33 construct is a multispecific molecule, such as a bispecific molecule. In some embodiments, the anti-CD33 construct is a secreted molecule. In some embodiments, the anti-CD33 construct comprises the sdAb moiety (e.g., V$_H$H) linked to a second binding moiety that specifically binds to a second antigen or epitope. In some embodiments, the second binding moiety is an sdAb or an scFv. In some embodiments, the sdAb moiety is linked to the second binding moiety via a peptide linker.

In some embodiments, the anti-CD33 construct is an immune effector cell engager, wherein the second binding moiety specifically binds to an antigen on the surface of an immune cell. In some embodiments, the anti-CD33 construct comprises a second binding moiety that specifically binds to an antigen on the surface of a T cell. In some embodiments, the second binding moiety specifically binds to an antigen is selected from the group consisting of CD3γ, CD3δ, CD3ε, CD3ζ, CD28, OX40, GITR, 4-1BB, CD27, CD40L, and HVEM.

In some embodiments, the anti-CD33 construct is an immunoconjugate comprising the sdAb moiety and an effector molecule. In some embodiments, the effector molecule is a therapeutic agent selected from the group consisting of a drug, a toxin, a radioisotope, a protein, a peptide, and a nucleic acid. In some embodiments, the effector molecule is a drug or a toxin. In some embodiments, the effector molecule is a label.

One aspect of the present application provides an isolated nucleic acid comprising a nucleic acid sequence encoding any one of the anti-CD33 constructs (including anti-CD33 sdAbs, anti-CD33 chimeric receptors, immune effector cell engagers and anti-CD33 immunoconjugates) described above. In some embodiments, the nucleic acid sequence is selected from the group consisting of SEQ ID NOs: 123-137.

In some embodiments, there is provided an isolated nucleic acid comprising a nucleic acid sequence encoding any one of the anti-CD33 chimeric receptors described above. In some embodiments, the isolated nucleic acid comprises a first nucleic acid sequence encoding the anti-CD33 chimeric receptor, and a second nucleic acid sequence encoding a second chimeric receptor (e.g., anti-CLL1, anti-CD123, or NKG2D chimeric receptor), wherein the second nucleic acid sequence is operably linked to the first nucleic acid sequence via a third nucleic acid sequence encoding a self-cleaving peptide, such as a T2A, P2A, or F2A peptide. In some embodiments, the isolated nucleic acid further comprises a nucleic acid sequence encoding a safety-switch antigen or epitope, such as CD52, CD20, EGFR or an epitope thereof.

One aspect of the present application provides a vector comprising any one of the isolated nucleic acids described above. In some embodiments, the vector is an expression vector. In some embodiments, the vector is a viral vector, such as a lentiviral vector. In some embodiments, the vector is a non-viral vector.

One aspect of the present application provides a pharmaceutical composition comprising any one of the anti-CD33 chimeric receptors described above, or any one of the engineered immune cells described above, and a pharmaceutically acceptable carrier. Further provided is a method of treating a disease (such as cancer) in an individual, comprising administering to the individual an effective amount of any one of the pharmaceutical compositions described above. In some embodiments, the engineered immune cell is autologous. In some embodiments, the engineered immune cell is allogenic. In some embodiments, the disease is cancer. In some embodiments, the cancer is a liquid cancer. In some embodiments, the cancer is acute myeloid leukemia (AML). In some embodiments, the cancer is chronic myelogenous leukemia (CML). In some embodiments, the cancer is myelodysplastic syndromes (MDS). In some embodiments, wherein the immune cell expresses a safety-switch antigen or epitope, the method further comprises subsequently administering an effective amount of antibody that specifically binds to the safety-switch antigen or epitope.

One aspect of the present application provides a pharmaceutical composition comprising any one of the anti-CD33 constructs described above and a pharmaceutically acceptable carrier. In some embodiments, there is provided a method of treating a disease (such as cancer) in an individual, comprising administering to the individual an effective amount of the pharmaceutical composition. In some embodiments, there is provided a method of treating a cancer in an individual, comprising administering to the individual an effective amount of the anti-CD33 construct according to any one of the anti-CD33 constructs described above. In some embodiments, the cancer is acute myeloid leukemia (AML). In some embodiments, the cancer is chronic myelogenous leukemia (CML). In some embodiments, the cancer is myelodysplastic syndromes (MDS).

Also provided are methods of use, kits, and articles of manufacture comprising any one of the anti-CD33 sdAbs, chimeric receptors, immune effector cell engagers, immunoconjugates, engineered immune cells, isolated nucleic acids, or vectors described above.

BRIEF DESCRIPTION OF THE DRAWINGS

FIG. 2 shows in vitro binding properties of exemplary anti-CD33 sdAbs.

FIG. 3 shows in vitro cytotoxicity of exemplary chimeric receptor constructs assayed by LDH method. Un-transduced T (UnT) cells were used as negative control, and BM CAR-T cells were used as positive control.

FIG. 4B shows in vitro cytotoxicity of T cells transduced with exemplary chimeric receptor constructs against THP-1 cells at effector cell:target cell (E:T) ratio of 1:1 or 3:1 as assayed by LDH method. UnT cells were used as negative control, and BM CAR-T cells were used as positive control.

FIG. 10A shows an exemplary anti-CD33 CAR comprising a CD33 binding domain, a transmembrane domain, a CD28 or 4-1BB intracellular co-stimulatory sequence, and an intracellular signaling domain comprising a CD3ζ intracellular signaling sequence.

FIG. 10B shows an exemplary tandem CAR comprising an extracellular domain comprising a CD33 binding domain and a second antigen binding domain, a transmembrane domain, and an intracellular signaling domain comprising a CD28 or 4-1BB intracellular co-stimulatory sequence and a CD3ζ intracellular signaling sequence.

FIG. 10C shows a dual CAR system comprising: (a) a first chimeric receptor comprising a CD33 binding domain, a transmembrane domain, a CD28 or 4-1BB intracellular co-stimulatory sequence, and an intracellular signaling domain comprising a CD3ζ intracellular signaling sequence; and (b) a second chimeric receptor comprising a CLL1 binding domain or an extracellular domain (ECD) of NKG2D ("NKG2D ECD"), a transmembrane domain, and an intracellular signaling domain comprising a CD28 or 4-1BB intracellular co-stimulatory sequence and a CD3ζ intracellular signaling sequence.

FIG. 10D shows a split CAR system comprising: (a) a first chimeric receptor comprising a CD33 binding domain, a transmembrane domain, and an intracellular signaling domain comprising a CD3ζ intracellular signaling sequence; and (b) a second chimeric receptor comprising a CLL1 binding domain or NKG2D ECD, a transmembrane domain, and an intracellular signaling domain comprising a CD28 or 4-1BB intracellular co-stimulatory sequence.

FIG. 10E shows a split CAR system comprising: (a) a first chimeric receptor comprising a CLL1 binding domain or NKG2D ECD, a transmembrane domain, and an intracellular signaling domain comprising a CD3ζ intracellular signaling sequence; and (b) a second chimeric receptor comprising a CD33 binding domain, a transmembrane domain, and an intracellular signaling domain comprising a CD28 or 4-1BB intracellular co-stimulatory sequence.

In FIGS. 10A-10E, the CD33 binding domain may be any one of the anti-CD33 sdAbs described herein. The second antigen binding domain may be NKG2D ECD or a CLL1 binding domain (e.g., anti-CLL1 sdAb).

FIG. 12A shows cytotoxicity of CAR-T cells at various time points (2, 5, 7, 9, and 12 days after co-culture) as determined by FACS analysis. FIG. 12B shows T cell proliferation rates at various time points (2, 5, 7, and 9 days after co-culture).

FIG. 13A shows levels of IFN-γ secreted by CLL1/CD33 tandem CAR-T cells at various time points (3, 6, and 9 days after co-culture). FIG. 13B shows levels of GM-CSF secreted by CLL1/CD33 tandem CAR-T cells at various time points (2, 5, 7, 9 and days after co-culture).

Luc xenograft mouse model. FIGS. 15A and 15C show the schematic of in vivo efficacy study. FIGS. 15B and 15D shows the curve of tumor growth in the HL-60-Luc xenograft mouse model after CAR-T cells treatment.

DETAILED DESCRIPTION OF THE PRESENT APPLICATION

Figure 1A:
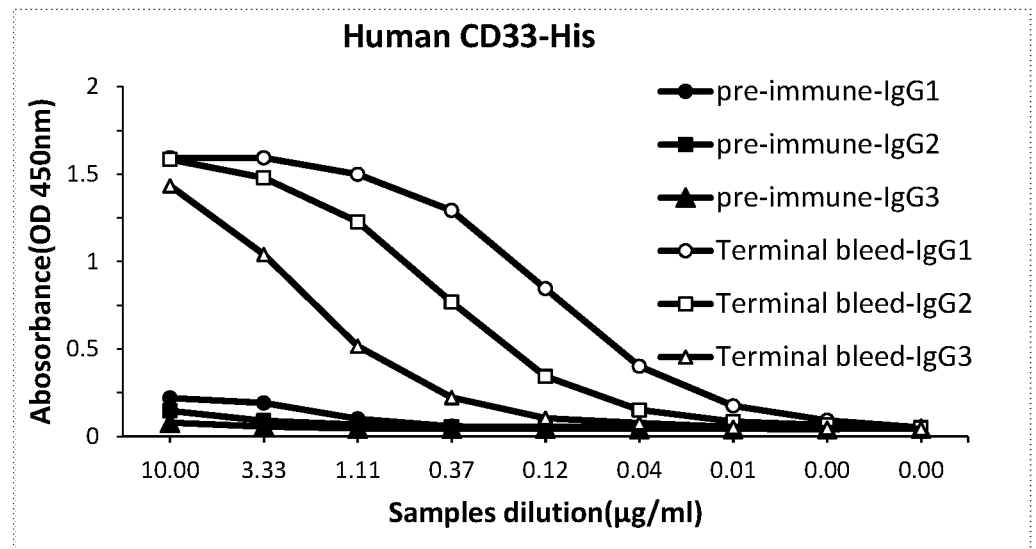
FIG. 1A shows immune response of immunized camel against recombinant human CD33 protein.

The present application provides anti-CD33 single-domain antibodies (sdAbs) and constructs thereof, such as chimeric receptors, immune effector cell engagers, and immunoconjugates. Multivalent and multispecific chimeric receptors, dual chimeric receptor systems, and split chimeric receptor systems are also provided. The anti-CD33 sdAbs, chimeric receptors, and engineered immune cells expressing the chimeric receptors described herein are useful agents for cancer treatment.

Accordingly, one aspect of the present application provides an anti-CD33 construct comprising a single domain antibody ("sdAb") moiety that specifically binds to CD33 (e.g., the extracellular domain of CD33).

In another aspect, there is provided an anti-CD33 chimeric receptor comprising an extracellular domain comprising an anti-CD33 sdAb (e.g., $V_HH$), a transmembrane domain, and an intracellular signaling domain (e.g., an intracellular co-stimulatory sequence and/or a primary intracellular signaling sequence of an immune effector cell, e.g., CD3ζ intracellular signaling sequence).

In another aspect, there is provided a multispecific chimeric receptor comprising an extracellular domain comprising an anti-CD33 sdAb (e.g., $V_HH$) and a second antigen binding domain that specifically binds to a second antigen or epitope (e.g., an anti-CLL1 sdAb, an anti-CD123 sdAb, or an extracellular domain of NKG2D), a transmembrane domain, and an intracellular signaling domain comprising an intracellular co-stimulatory sequence and a primary intracellular signaling sequence of an immune effector cell (e.g., CD3ζ intracellular signaling sequence).

In another aspect, there is provide a split chimeric receptor system comprising a first chimeric receptor comprising an anti-CD33 sdAb (e.g., $V_HH$), a transmembrane domain, and an intracellular signaling domain comprising a primary intracellular signaling sequence of an immune effector cell (e.g., CD3ζ intracellular signaling sequence); and a second chimeric receptor comprising a second antigen binding domain that specifically binds to a second antigen or epitope (e.g., an anti-CLL1 sdAb, an anti-CD123 sdAb, or an extracellular domain of NKG2D), a transmembrane domain, and an intracellular signaling domain comprising an intracellular co-stimulatory sequence.

In another aspect, there is provide a split chimeric receptor system comprising a first chimeric receptor comprising an anti-CD33 sdAb (e.g., $V_HH$), a transmembrane domain, and an intracellular co-stimulatory sequence; and a second chimeric receptor comprising a second antigen binding domain that specifically binds to a second antigen or epitope (e.g., an anti-CLL1 sdAb, an anti-CD123 sdAb, or an extracellular domain of NKG2D), a transmembrane domain, and an intracellular signaling domain comprising a primary intracellular signaling sequence of an immune effector cell (e.g., CD3ζ intracellular signaling sequence).

Nucleic acids encoding the anti-CD33 constructs, engineered immune cells (such as T cells) comprising the chimeric receptors or chimeric receptor systems, pharmaceutical compositions, kits, articles of manufacture and methods of treatment are also described herein.

I. Definitions

The term "antigen" refers to any molecule capable of inducing an immune response in a host cell, or any molecule capable of binding to an antigen-specific receptor.

The term "antibody" or "antibody moiety" includes monoclonal antibodies (including full length 4-chain antibodies or full length heavy-chain only antibodies which have an immunoglobulin Fc region), antibody compositions with polyepitopic specificity, multispecific antibodies (e.g., bispecific antibodies, diabodies, and single-chain molecules), as well as antibody fragments (e.g., Fab, F(ab')$_2$, and Fv). The term "immunoglobulin" (Ig) is used interchangeably with "antibody" herein. Antibodies contemplated herein include single-domain antibodies, such as heavy chain only antibodies.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1 and IgA2.

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

The term "single-domain antibody," "single-domain antibody moiety," "sdAb" or "sdAb moiety" refers to a single antigen-binding polypeptide having three complementary determining regions (CDRs), including full-length antibodies (e.g., HCAbs) and antigen-binding fragments thereof (e.g., $V_H H$). The sdAb alone is capable of binding to the antigen without pairing with a corresponding CDR-containing polypeptide. In some cases, single-domain antibodies are engineered from camelid HCAbs, and their heavy chain variable domains are referred herein as "$V_H Hs$". Some $V_H Hs$ may also be known as Nanobodies. Camelid sdAb is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic $V_H H$ has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

An "isolated" antibody is one that has been identified, separated and/or recovered from a component of its production environment (e.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or nonproteinaceous solutes. In preferred embodiments, the polypeptide will be purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. Heavy-chain only antibodies from the Camelid species have a single heavy chain variable region, which is referred to as "$V_H H$". $V_H H$ is thus a special type of $V_H$.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture or recombinantly, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present application may be made by a variety of techniques, including, for example, the hybridoma method (e.g., Kohler and Milstein., *Nature*, 256: 495-97 (1975); Hongo et al., *Hybridoma*, 14 (3): 253-260 (1995), Harlow et al., *Antibodies: A Laboratory Manual*, (Cold Spring Harbor Laboratory Press, $2^{nd}$ ed. 1988); Hamerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); *Neuberger, Nature Biotechnol.* 14: 826 (1996); and Lonberg and Huszar, *Intern. Rev. Immunol.* 13: 65-93 (1995).

The terms "full-length antibody," "intact antibody" or "whole antibody" are used interchangeably to refer to an antibody in its substantially intact form, as opposed to an antibody fragment. Specifically, full-length 4-chain antibodies include those with heavy and light chains including an Fc region. Full-length heavy-chain only antibodies include the heavy chain (such as $V_H H$) and an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., Protein Eng. 8(10): 1057-1062 [1995]); single-chain antibody molecules; single-domain antibodies (such as V$_H$H), and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain (V$_H$), and the first constant domain of one heavy chain (C$_H$1). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the C$_H$1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the V$_H$ and V$_L$ antibody domains connected into a single polypeptide chain. Preferably, the sFv polypeptide further comprises a polypeptide linker between the V$_H$ and V$_L$ domains which enables the sFv to form the desired structure for antigen binding. For a review of the sFv, see Pluckthun in The Pharmacology of Monoclonal Antibodies, vol. 113, Rosenburg and Moore eds., Springer-Verlag, New York, pp. 269-315 (1994).

"Functional fragments" of the antibodies described herein comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the V$_H$ and V$_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the V$_H$ and V$_L$ domains of the two antibodies are present on different polypeptide chains. Diabodies are described in greater detail in, for example, EP 404,097; WO 93/11161; Hollinger et al., Proc. Natl. Acad. Sci. USA 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). Chimeric antibodies of interest herein include PRIMATTZFD® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., camelid) antibodies are chimeric antibodies that contain minimal sequence derived from non-human immunoglobulin. In some embodiments, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J. Mol. Biol.,* 222:581 (1991). Also available for the preparation of human monoclonal antibodies are methods described in Cole et al., *Monoclonal Antibodies and Cancer Therapy,* Alan R. Liss, p. 77 (1985); Boerner et al., *J. Immunol.,* 147(1):86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, sdAbs comprise three HVRs (or CDRs): HVR1 (or CDR1), HVR2 (or CDR2), and HVR3 (or CDR3). HVR3 displays the most diversity of the three HVRs, and is believed to play a unique role in conferring fine specificity to antibodies. See, e.g., Hamers-Casterman et al., *Nature* 363:446-448 (1993); Sheriff et al., *Nature Struct. Biol.* 3:733-736 (1996).

The term "Complementarity Determining Region" or "CDR" are used to refer to hypervariable regions as defined by the Kabat system. See Kabat et al., *Sequences of Proteins of Immunological Interest,* 5th Ed. Public Health Service, National Institutes of Health, Bethesda, Md. (1991)

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below in Table 1.

TABLE 1

HVR delineations.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The amino acid residues of an sdAb (such as $V_HH$) are numbered according to the general numbering for $V_H$ domains given by Kabat et al. ("Sequence of proteins of immunological interest", US Public Health Services, NIH Bethesda, Md., Publication No. 91), as applied to $V_HH$ domains from Camelids in the article of Riechmann and Muyldermans, J. Immunol. Methods 2000 Jun. 23; 240 (1-2): 185-195. According to this numbering, FR1 of a $V_HH$ comprises the amino acid residues at positions 1-30, CDR1 of a $V_HH$ comprises the amino acid residues at positions 31-35, FR2 of a $V_HH$ comprises the amino acids at positions 36-49, CDR2 of a $V_HH$ comprises the amino acid residues at positions 50-65, FR3 of a $V_HH$ comprises the amino acid residues at positions 66-94, CDR3 of a $V_HH$ comprises the amino acid residues at positions 95-102, and FR4 of a $V_HH$ comprises the amino acid residues at positions 103-113. In this respect, it should be noted that—as is well known in the art for $V_H$ domains and for $V_HH$ domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering).

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest,* 5th Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the VH, the subgroup may be subgroup I, subgroup II, or subgroup III as in Kabat et al. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain preexisting amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In some embodiments, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically binds," "specifically recognizes," or is "specific for" refers to measurable and reproducible interactions such as binding between a target and an antigen binding protein (such as a chimeric receptor or an sdAb), which is determinative of the presence of the target in the presence of a heterogeneous population of molecules including biological molecules. For example, an antigen binding protein that specifically binds a target (which can be an epitope) is an antigen binding protein that binds this target with greater affinity, avidity, more readily, and/or with greater duration than it binds other targets. In some embodiments, the extent of binding of an antigen binding protein to an unrelated target is less than about 10% of the binding of the antigen binding protein to the target as measured, e.g., by a radioimmunoassay (RIA). In some embodiments, an antigen binding protein that specifically binds a target has a dissociation constant (Kd) of ≤1 μM, ≤100 nM, ≤10 nM, ≤1 nM, or ≤0.1 nM. In some embodiments, an antigen binding protein specifically binds an epitope on a protein that is conserved among the protein from different species. In some embodiments, specific binding can include, but does not require exclusive binding.

The term "specificity" refers to selective recognition of an antigen binding protein (such as a chimeric receptor or an antibody construct) for a particular epitope of an antigen. Natural antibodies, for example, are monospecific. The term "multispecific" as used herein denotes that an antigen binding protein has two or more antigen-binding sites of which at least two bind different antigens or epitopes. "Bispecific" as used herein denotes that an antigen binding protein has two different antigen-binding specificities. The term "monospecific" as used herein denotes an antigen binding protein that has one or more binding sites each of which bind the same antigen or epitope.

The term "valent" as used herein denotes the presence of a specified number of binding sites in an antigen binding protein. A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein.

"Antibody effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody—dependent cell-mediated cytotoxicity (ADCC); phagocytosis; down regulation of cell surface receptors (e.g., B cell receptors); and B cell activation. "Reduced or minimized" antibody effector function means that which is reduced by at least 50% (alternatively 60%, 65%, 70%, 75%, 80%, 85%, 90%, 95%, 96%, 97%, 98%, 99%) from the wild type or unmodified antibody. The determination of antibody effector function is readily determinable and measurable by one of ordinary skill in the art. In a preferred embodiment, the antibody effector functions of complement binding, complement dependent cytotoxicity and antibody dependent cytotoxicity are affected. In some embodiments, effector function is eliminated through a mutation in the constant region that eliminated glycosylation, e.g., "effectorless mutation." In one aspect, the effector-less mutation is an N297A or DANA mutation (D265A+N297A) in the $C_H2$ region. Shields et al., *J. Biol. Chem.* 276 (9): 6591-6604 (2001). Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., *E. coli.*) or in which result in an altered glycosylation pattern that is ineffective or less effective at promoting effector function (e.g., Shinkawa et al., *J. Biol. Chem.* 278(5): 3466-3473 (2003).

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998).

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Binding affinity" generally refers to the strength of the sum total of non-covalent interactions between a single binding site of a molecule (e.g., an antibody or a CAR) and its binding partner (e.g., an antigen). Unless indicated otherwise, as used herein, "binding affinity" refers to intrinsic binding affinity that reflects a 1:1 interaction between members of a binding pair (e.g., antibody and antigen, or CAR and antigen). The affinity of a molecule X for its partner Y can generally be represented by the dissociation constant (Kd) Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present application. Specific illustrative and exemplary embodiments for measuring binding affinity are described in the following.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

"Chimeric receptor," "chimeric antigen receptor" or "CAR" as used herein refers to genetically engineered receptors, which can be used to graft one or more antigen specificity onto immune cells, such as T cells. Some chimeric receptors are also known as "artificial T-cell receptors," "chimeric T cell receptors," or "chimeric immune receptors." In some embodiments, the chimeric receptor comprises an extracellular domain specific for one or more antigens (such as tumor antigens) or epitopes, a transmembrane domain, and an intracellular signaling domain of a T cell and/or co-stimulatory receptors. "CAR-T" refers to a T cell that expresses a CAR. "Anti-CD33 CAR" refers to a CAR having an extracellular binding domain specific for CD33.

An "isolated" nucleic acid molecule encoding a chimeric receptor or an anti-CD33 construct described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, the term "autologous" is meant to refer to any material derived from the same individual to whom it is later to be re-introduced into the individual.

"Allogeneic" refers to a graft derived from a different individual of the same species.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

As used herein, the expressions "cell", "cell line", and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence(s) of cancer. The methods of the present application contemplate any one or more of these aspects of treatment.

As used herein, an "individual" or a "subject" refers to a mammal, including, but not limited to, human, bovine, horse, feline, canine, rodent, or primate. In some embodiments, the individual is a human.

The term "effective amount" used herein refers to an amount of an agent, such as an anti-CD33 construct, an engineered immune cell, or a pharmaceutical composition thereof, sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile. A "sterile" formulation is aseptic or free from all living microorganisms and their spores.

It is understood that embodiments of the present application described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "an" and "the" include plural referents unless the context clearly dictates otherwise.

II. Anti-CD33 Constructs in one aspect, the present application provides an anti-CD33 constructs comprising an anti-CD33 sdAb moiety. Any one of the anti-CD33 sdAbs described herein or antigen-binding fragments thereof (e.g., $V_HH$) may be used in the anti-CD33 construct. Anti-CD33 sdAbs are described in Section "A. Anti-CD33 single-domain antibodies" below.

In some embodiments, there is provided an anti-CD33 construct comprising an sdAb moiety that specifically binds to CD33, wherein the sdAb moiety comprises a CDR1 comprising the amino acid sequence of SEQ ID NO: 4, a CDR2 comprising the amino acid sequence of SEQ ID NO: 6, and a CDR3 comprising the amino acid sequence of SEQ ID NO: 8, or a variant thereof comprising up to about 5 amino acid substitutions in the CDRs. In some embodiments, the sdAb moiety comprises the amino acid sequence of SEQ ID NO: 108, or a variant thereof comprising an amino acid sequence having at least about 95% sequence identity to the amino acid sequence of SED ID NO: 108.

In some embodiments, there is provided an anti-CD33 construct comprising an sdAb moiety that specifically binds to CD33, wherein the sdAb moiety comprises a CDR1 comprising the amino acid sequence of SEQ ID NO: 11, a CDR2 comprising the amino acid sequence of SEQ ID NO: 13, and a CDR3 comprising the amino acid sequence of SEQ ID NO: 15, or a variant thereof comprising up to about 5 amino acid substitutions in the CDRs. In some embodiments, the sdAb moiety comprises the amino acid sequence of SEQ ID NO: 109, or a variant thereof comprising an amino acid sequence having at least about 95% sequence identity to the amino acid sequence of SED ID NO: 109.

In some embodiments, there is provided an anti-CD33 construct comprising an sdAb moiety that specifically binds to CD33, wherein the sdAb moiety comprises a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22, or a variant thereof comprising up to about 5 amino acid substitutions in the CDRs. In some embodiments, the sdAb moiety comprises the amino acid sequence of SEQ ID NO: 110, or a variant thereof comprising an amino acid sequence having at least about 95% sequence identity to the amino acid sequence of SED ID NO: 110.

In some embodiments, there is provided an anti-CD33 construct comprising an sdAb moiety that specifically binds to CD33, wherein the sdAb moiety comprises a CDR1 comprising the amino acid sequence of SEQ ID NO: 25, a CDR2 comprising the amino acid sequence of SEQ ID NO: 27, and a CDR3 comprising the amino acid sequence of SEQ ID NO: 29, or a variant thereof comprising up to about 5 amino acid substitutions in the CDRs. In some embodiments, the sdAb moiety comprises the amino acid sequence of SEQ ID NO: 111, or a variant thereof comprising an amino acid sequence having at least about 95% sequence identity to the amino acid sequence of SED ID NO: 111.

In some embodiments, there is provided an anti-CD33 construct comprising an sdAb moiety that specifically binds to CD33, wherein the sdAb moiety comprises a CDR1 comprising the amino acid sequence of SEQ ID NO: 32, a CDR2 comprising the amino acid sequence of SEQ ID NO: 34, and a CDR3 comprising the amino acid sequence of SEQ ID NO: 36, or a variant thereof comprising up to about 5 amino acid substitutions in the CDRs. In some embodiments, the sdAb moiety comprises the amino acid sequence of SEQ ID NO: 112, or a variant thereof comprising an amino acid sequence having at least about 95% sequence identity to the amino acid sequence of SED ID NO: 112.

In some embodiments, there is provided an anti-CD33 construct comprising an sdAb moiety that specifically binds to CD33, wherein the sdAb moiety comprises a CDR1 comprising the amino acid sequence of SEQ ID NO: 39, a CDR2 comprising the amino acid sequence of SEQ ID NO: 41, and a CDR3 comprising the amino acid sequence of SEQ ID NO: 43, or a variant thereof comprising up to about 5 amino acid substitutions in the CDRs. In some embodiments, the sdAb moiety comprises the amino acid sequence of SEQ ID NO: 113, or a variant thereof comprising an amino acid sequence having at least about 95% sequence identity to the amino acid sequence of SED ID NO: 113.

In some embodiments, there is provided an anti-CD33 construct comprising an sdAb moiety that specifically binds to CD33, wherein the sdAb moiety comprises a CDR1 comprising the amino acid sequence of SEQ ID NO: 46, a CDR2 comprising the amino acid sequence of SEQ ID NO: 48, and a CDR3 comprising the amino acid sequence of SEQ ID NO: 50, or a variant thereof comprising up to about 5 amino acid substitutions in the CDRs. In some embodiments, the sdAb moiety comprises the amino acid sequence of SEQ ID NO: 114, or a variant thereof comprising an amino acid sequence having at least about 95% sequence identity to the amino acid sequence of SED ID NO: 114.

In some embodiments, there is provided an anti-CD33 construct comprising an sdAb moiety that specifically binds to CD33, wherein the sdAb moiety comprises a CDR1 comprising the amino acid sequence of SEQ ID NO: 53, a CDR2 comprising the amino acid sequence of SEQ ID NO: 55, and a CDR3 comprising the amino acid sequence of SEQ ID NO: 57, or a variant thereof comprising up to about 5 amino acid substitutions in the CDRs. In some embodiments, the sdAb moiety comprises the amino acid sequence of SEQ ID NO: 115, or a variant thereof comprising an amino acid sequence having at least about 95% sequence identity to the amino acid sequence of SED ID NO: 115.

In some embodiments, there is provided an anti-CD33 construct comprising an sdAb moiety that specifically binds to CD33, wherein the sdAb moiety comprises a CDR1 comprising the amino acid sequence of SEQ ID NO: 60, a CDR2 comprising the amino acid sequence of SEQ ID NO: 62, and a CDR3 comprising the amino acid sequence of SEQ ID NO: 64, or a variant thereof comprising up to about 5 amino acid substitutions in the CDRs. In some embodiments, the sdAb moiety comprises the amino acid sequence of SEQ ID NO: 116, or a variant thereof comprising an amino acid sequence having at least about 95% sequence identity to the amino acid sequence of SED ID NO: 116.

In some embodiments, there is provided an anti-CD33 construct comprising an sdAb moiety that specifically binds to CD33, wherein the sdAb moiety comprises a CDR1 comprising the amino acid sequence of SEQ ID NO: 67, a CDR2 comprising the amino acid sequence of SEQ ID NO: 69, and a CDR3 comprising the amino acid sequence of SEQ ID NO: 71, or a variant thereof comprising up to about 5 amino acid substitutions in the CDRs. In some embodiments, the sdAb moiety comprises the amino acid sequence of SEQ ID NO: 117, or a variant thereof comprising an amino acid sequence having at least about 95% sequence identity to the amino acid sequence of SED ID NO: 117.

In some embodiments, there is provided an anti-CD33 construct comprising an sdAb moiety that specifically binds to CD33, wherein the sdAb moiety comprises a CDR1 comprising the amino acid sequence of SEQ ID NO: 74, a CDR2 comprising the amino acid sequence of SEQ ID NO: 76, and a CDR3 comprising the amino acid sequence of SEQ ID NO: 78, or a variant thereof comprising up to about 5 amino acid substitutions in the CDRs. In some embodiments, the sdAb moiety comprises the amino acid sequence of SEQ ID NO: 118, or a variant thereof comprising an amino acid sequence having at least about 95% sequence identity to the amino acid sequence of SED ID NO: 118.

In some embodiments, there is provided an anti-CD33 construct comprising an sdAb moiety; that specifically binds to CD33, wherein the sdAb moiety comprises a CDR1 comprising the amino acid sequence of SEQ ID NO: 81, a CDR2 comprising the amino acid sequence of SEQ ID NO: 83, and a CDR3 comprising the amino acid sequence of SEQ ID NO: 85, or a variant thereof comprising up to about 5 amino acid substitutions in the CDRs. In some embodiments, the sdAb moiety comprises the amino acid sequence of SEQ ID NO: 119, or a variant thereof comprising an amino acid sequence having at least about 95% sequence identity to the amino acid sequence of SED ID NO: 119.

In some embodiments, there is provided an anti-CD33 construct comprising an sdAb moiety that specifically binds to CD33, wherein the sdAb moiety comprises a CDR1 comprising a CDR1 comprising the amino acid sequence of SEQ ID NO: 88, a CDR2 comprising the amino acid sequence of SEQ ID NO: 90, and a CDR3 comprising the amino acid sequence of SEQ ID NO: 92, or a variant thereof comprising up to about 5 amino acid substitutions in the CDRs. In some embodiments, the sdAb moiety comprises the amino acid sequence of SEQ ID NO: 120, or a variant thereof comprising an amino acid sequence having at least about 95% sequence identity to the amino acid sequence of SED ID NO: 120.

In some embodiments, there is provided an anti-CD33 construct comprising an sdAb moiety that specifically binds to CD33, wherein the sdAb moiety comprises a CDR1 comprising a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99, or a variant thereof comprising up to about 5 amino acid substitutions in the CDRs. In some embodiments, the sdAb moiety comprises the amino acid sequence of SEQ ID NO: 121, or a variant thereof comprising an amino acid sequence having at least about 95% sequence identity to the amino acid sequence of SED ID NO: 121.

In some embodiments, there is provided an anti-CD33 construct comprising an sdAb moiety that specifically binds to CD33, wherein the sdAb moiety comprises a CDR1 comprising a CDR1 comprising the amino acid sequence of SEQ ID NO: 102, a CDR2 comprising the amino acid sequence of SEQ ID NO: 104, and a CDR3 comprising the amino acid sequence of SEQ ID NO: 106, or a variant thereof comprising up to about 5 amino acid substitutions in the CDRs. In some embodiments, the sdAb moiety comprises the amino acid sequence of SEQ ID NO: 122, or a variant thereof comprising an amino acid sequence having at least about 95% sequence identity to the amino acid sequence of SED ID NO: 122.

In some embodiments, the anti-CD33 construct is a transmembrane molecule. In some embodiments, the anti-CD33 construct is a secreted molecule.

In some embodiments, the anti-CD33 construct is a monoclonal antibody comprising any one of the anti-CD33 sdAbs described herein, including a camelid, chimeric, humanized or human antibody. In some embodiments, the anti-CD33 construct is an antibody fragment, e.g., a $V_HH$ fragment. In some embodiments, the anti-CD33 construct is a full-length heavy chain only antibody comprising an Fc region of any antibody class or isotype, such as IgG1 or IgG4. In some embodiments, the Fc region has reduced or minimized effector function.

In some embodiments, the anti-CD33 construct is a chimeric receptor comprising an extracellular domain comprising any one of the anti-CD33 sdAbs described herein, a transmembrane domain, and an intracellular signaling domain. In some embodiments, the intracellular signaling domain comprises a primary intracellular signaling sequence of an immune effector cell (e.g., CD3ζ intracellular signaling sequence). In some embodiments, the intracellular signaling domain comprises an intracellular co-stimulatory sequence. In some embodiments, the intracellular signaling domain comprises both a primary intracellular signaling sequence of an immune effector cell (e.g., CD3ζ intracellular signaling sequence) and an intracellular co-stimulatory sequence. Anti-CD33 chimeric receptors and chimeric receptor systems are further described in Section "B. Chimeric receptors". Engineered immune cells comprising the anti-CD33 chimeric receptors or chimeric receptor systems are described in Section IV.

In some embodiments, the anti-CD33 construct is a monospecific molecule. In some embodiments, the anti-CD33 construct is a multispecific molecule. In some embodiments, the anti-CD33 construct is a bispecific molecule.

In some embodiments, the anti-CD33 construct is a multispecific antigen binding protein comprising an anti-CD33 sdAb (such as any one of the anti-CD33 sdAbs described herein) and a second binding moiety that specifically binds to a second antigen or epitope. In some embodiments, the second binding moiety is an sdAb or an scFv. In some embodiments, the second binding moiety specifically binds to a different epitope on CD33. In some embodiments, the second binding moiety specifically binds to a second antigen, such as a tumor antigen, or an antigen on the surface of an immune cell. In some embodiments, the anti-CD33 sdAb is linked to the second binding moiety via a peptide linker.

In some embodiments, the anti-CD33 construct is an immune effector cell engager comprising any one of the anti-CD33 sdAbs described herein and a second binding moiety that specifically binds to an antigen on the surface of an immune cell, such as T cell. In some embodiments, the second binding moiety specifically binds to an antigen selected from the group consisting of CD3γ, CD3δ, CD3ε, CD3ζ, CD28, OX40, GITR, 4-1BB, CD27, CD40L, and HVEM Immune effector cell engagers are further described in Section "C. Immune effector cell engagers" below.

In some embodiments, the anti-CD33 construct is an immunoconjugate comprising any one of the anti-CD33 sdAbs described herein and an effector molecule. In some embodiments, the effector molecule is a therapeutic agent selected from the group consisting of a drug, a toxin, a radioisotope, a protein, a peptide, and a nucleic acid. In some embodiments, the effector molecule is a drug or a toxin. In some embodiments, the effector molecule is a label. Immunoconjugates are further described in Section "D. Immunoconjugates" below.

A. Anti-CD33 Single-Domain Antibodies

One aspect of the present application provides isolated single-domain antibodies (referred herein as "anti-CD33 sdAbs") that specifically bind to CD33. In some embodiments, the anti-CD33 sdAb modulates CD33 activity. In some embodiments, the anti-CD33 sdAb is an antagonist antibody. Further provided are antigen-binding fragments (e.g., $V_HH$) derived from any one of the anti-CD33 sdAbs described herein, and constructs comprising any one of the anti-CD33 sdAbs described herein. Exemplary anti-CD33 sdAbs are listed in Table 2 below. The anti-CD33 constructs described herein comprise one or more anti-CD33 sdAb moieties.

TABLE 2

Exemplary anti-CD33 sdAbs.

| sdAb/ SEQ ID (AA/NA) | FR1/ SEQ ID NO | CDR1/ SEQ ID | FR2/ SEQ ID | CDR2/ SEQ ID | FR3/ SEQ ID NO | CDR3/ SEQ ID | FR4/ SEQ ID |
|---|---|---|---|---|---|---|---|
| AS49175 108/123 | EVQLAESGGGLV QAGGSLRLSCTA S 3 | GFTFDDY VMG 4 | WFRQAP GKEREG VS 5 | CISWSGD TTYYADS VKG 6 | RFTASRDNAKNTL YLQMNSLKPEDT AMYYCAA 7 | DQGKCSL ASAEPDD MDY 8 | WGRGT LVTVSS 9 |
| AS49226 109/124 | EVQLAESGGGSV QAGGSLRLSCAA S 10 | GVTFSST SVA 11 | WFRQAP GKEREG VA 12 | YIYTGDS STYYADS VKG 13 | RFTIAQDNAKNAV YLQMNSLKPEDT AMYYCAA 14 | DGFLLNH RSYQY 15 | WGQGT QVTVS S 16 |
| AS49264 110/125 | EVQLVESGGGSV QAGGSLRLSCAA S 17 | GYTYSIN CMG 18 | WFRQAP GKEREG VA 19 | VISTGGG RTDYRDS VKG 20 | RFTISQDNAKNTV YLQMNSLKPEDT AMYYCAG 21 | KTTYPGY GCGLGRS AYNY 22 | WGQGT QVTVS S 23 |
| AS49814 111/126 | QIQLVESGGGSV QAGGSLRLSCVA S 24 | GYIGGHY YMG 25 | WFRQAP GKEREG VA 26 | AIDIDSD GRTRYA GSVQG 27 | RFTISQDNAKNTL HLQMSSLKPEDTG MYYCAV 28 | GVGWVP ARLTPQA VSY 29 | WGKGT LVTVSS 30 |
| AS49873 112/127 | EVQLVESGGGSV QAGGSLRLSCVA S 31 | GYTYGIN CMG 32 | WFRQAP GKEREGI A 33 | AISTGGG TTGVADS VKG 34 | RFTISQDNAKNTV YLQMNSLKPEDT AMYYCAA 35 | RSTYSGY ACVYSEV NGYNY 36 | RGQGT QVTVS S 37 |
| AS49889 113/128 | EVQLVESGGGSV QAGGSLRLSCVA S 38 | GYTWCR YDMS 39 | WYRQAP GKEREFV S 40 | GFDNDG TTSYADS VKG 41 | RFTISQDNDKNTV YLQMNSLKPEDT AMYYCKE 42 | DRSRGSL DGRVCPL SYDN 43 | WGQGT QVTVS S 44 |
| AS49902 114/129 | EVQLVESGGGLV QAGGSLRLSCTA S 45 | GFTFDDY VMG 46 | WFRQAP GKEREG VS 47 | CISWSGD TTYYADS VKG 48 | RFTVSRDNAKNTL YLQMNSLKPEDT AMYYCAA 49 | DQSLCSL APPYNYA Y 50 | WGQGT QVTVS S 51 |
| AS50073 115/130 | QVQLVESGGGLV QAGGSLRLSCTA S 52 | GFTFDNY VMG 53 | WFRQAP GKEREG VS 54 | CIGWSGD STYYADS VKG 55 | RFTISRDNAKNTL YLQMNSLKPEDT AMYYCAA 56 | DQKCSL GSAGAD DMDY 57 | WGRGT LVTVSS 58 |
| AS50502 116/131 | EVQLVESGGGSV QAGGSLRLSCAA P 59 | GYTYCT YDMM 60 | WYRQAL GKEREFV S 61 | AVYTDG STLYADS VKG 62 | RFTISQDNAKNTL YLQMNSLKPEDT AMYYCKT 63 | ETAVTYD KPCDF 64 | WGQGT QVTVS S 65 |
| AS66873 117/132 | QVQLVESGGGLV QPGGSLRLSCAA S 66 | GSIFSITA MG 67 | WYRQAP GKQREL VA 68 | TVTSGGS TKYVESV KG 69 | RFTSNDNAKNTV YLQMNSLKPEDT AVYYCWA 70 | DIVARWN SDYNVY DDY 71 | WGQGT QVTVS S 72 |
| AS60399 118/133 | QVKLEESGGGLV QEGGSLRLSCAA S 73 | GTIYTDS TIY 74 | WYRQAP GKQREL VA 75 | SITRGGD TKYVDS VKG 76 | RFAISSDNAKNTV YLQMNSLKPEDT AVYYCNL 77 | YYRTGPS SYYRND 78 | WGQGT QVTVS S 79 |
| AS59101 119/134 | AVQLVESGGGLV QPGGSLRLSCAV S 80 | GIYYSINL MG 81 | WYRQAP GKPRELA A 82 | SITDSGIT NYADSV KG 83 | RFTISRDNAKNTV HLQMNNLKPEDT AVYYCKP 84 | MGVN 85 | WGQGI QVTVS S 86 |
| AS58930 120/135 | AVQLVESGGGLV QAGGSLRLSCTA S 87 | GSILRTY EMG 88 | WYRQAP GSQRELV A 89 | SITSDGD TNYVDS VKG 90 | RFTISRDNGKNMV YLQMNSLKPDDT AVYYCNA 91 | VILSPSYS MRTSH 92 | WGQGT QVTVS S 93 |
| AS67190 121/136 | QVQLVESGGGLV QAGGSLRLSCAA S 94 | GNVFRFN IMG 95 | WYRQAP GNQREL VA 96 | SIDDGGD RSYADSV EG 97 | RFTISRENGKKIM YLQMNSLKPEDT AVYYCAA 98 | GLGTYLN GRVSMA TNY 99 | WGQGT QVTVS S 100 |

TABLE 2-continued

Exemplary anti-CD33 sdAbs.

| sdAb/ SEQ ID (AA/NA) | FR1/ SEQ ID NO | CDR1/ SEQ ID | FR2/ SEQ ID | CDR2/ SEQ ID | FR3/ SEQ ID NO | CDR3/ SEQ ID | FR4/ SEQ ID |
|---|---|---|---|---|---|---|---|
| AS67147 122/137 | EVQLVESGGGLV QAGGSLRLSCAA S 101 | GDTFSFA AMG 102 | WYRQAP GKQREL VA 103 | SISFSGGE STVYANS V 104 | RGRFTISGDNAKN RVSLEMNNLKPED TAVYYCTA 105 | KRGPYLP GPEY 106 | WGQGT QVTVS S 107 |

AS49175 sdAb amino acid sequence; CDRs are underlined
SEQ ID NO: 108
EVQLAESGGGLVQAGGSLRLSCTAS<u>GFTFDDYVMG</u>WFRQAPGKEREGVS<u>CISWSGDTTYYADSVKG</u>RETA
SRDNAKNTLYLQMNSLKPEDTAMYYCAA<u>DQGKCSLASAEPDDMDY</u>WGRGTLVTVSS AS49226 sdAb amino acid sequence; CDRs are underlined
SEQ ID NO: 109
EVQLAESGGGSVQAGGSLRLSCAAS<u>GVTFSSTSVA</u>WFRQAPGKEREGVA<u>YIYTGDSSTYYADSVKG</u>RFTI
AQDNAKNAVYLQMNSLKPEDTAMYYCAA<u>DGFLLNHRSYQY</u>WGQGTQVTVSS AS49264 sdAb amino acid sequence; CDRs are underlined
SEQ ID NO: 110
EVQLVESGGGSVQAGGSLRLSCAAS<u>GYTYSINCMG</u>WFRQAPGKEREGVA<u>VISTGGGRTDYRDSVKG</u>RFTI
SQDNAKNTVYLQMNSLKPEDTAMYYCAG<u>KTTYPGYGCGLGRSAYNY</u>WGQGTQVTVSS AS49814 sdAb amino acid sequence; CDRs are underlined
SEQ ID NO: 111
QIQLVESGGGSVQAGGSLRLSCVAS<u>GYIGGHYYMG</u>WFRQAPGKEREGVA<u>AIDIDSDGRTRYAGSVQG</u>RFT
ISQDNAKNTLHLQMSSLKPEDIGMYYCAV<u>GVGWVPARLTPQAVSY</u>WGKGTLVTVSS AS49873 sdAb amino acid sequence; CDRs are underlined
SEQ ID NO: 112
EVQLVESGGGSVQAGGSLRLSCVAS<u>GYTYGINCMG</u>WFRQAPGKEREGIA<u>AISTGGGTTGVADSVKG</u>RFTI
SQDNAKNTVYLQMNSLKPEDTAMYYCAA<u>RSTYSGYACVYSEVNGYNY</u>RGQGTQVTVSS AS49889 sdAb amino acid sequence; CDRs are underlined
SEQ ID NO: 113
EVQLVESGGGSVQAGGSLRLSCVAS<u>GYTWCRYDMS</u>WYRQAPGKEREFVS<u>GFDNDGTTSYADSVKG</u>RFTIS
QDNDKNTVYLQMNSLKPEDTAMYYCE<u>DRSRGSLDGRVCPLSYDN</u>WGQGTQVTVSS AS49902 sdAb amino acid sequence; CDRs are underlined
SEQ ID NO: 114
EVQLVESGGGLVQAGGSLRLSCTAS<u>GFTEDDYVMG</u>WFRQAPGKEREGVS<u>CISWSGDTTYYADSVKG</u>RFTV
SRDNAKNTLYLQMNSLKPEDTAMYYCAA<u>DQSLCSLAPPYNYAY</u>WGQGTQVTVSS AS50073 sdAb amino acid sequence; CDRs are underlined
SEQ ID NO: 115
QVQLVESGGGLVQAGGSLRLSCTAS<u>GFTFDNYVMG</u>WFRQAPGKEREGVS<u>CIGWSGGSTYYADSVKG</u>RFTI
SRDNAKNTLYLQMNSLKPEDTAMYYCAA<u>DQGKCSLGSAGADDMDY</u>WGRGTLVTVSS AS50502 sdAb amino acid sequence; CDRs are underlined
SEQ ID NO: 116
EVQLVESGGGSVQAGGSLRLSCAAP<u>GYTYCTYDMM</u>WYRQALGKEREFVS<u>AVYTDGSTLYADSVKG</u>RFTIS
QDNAKNTLYLQMNSLKPEDTAMYYCKT<u>ETAVTYDKPCDF</u>WGQGTQVTVSS AS66873 sdAb amino acid sequence; CDRs are underlined
SEQ ID NO: 117
QVQLVESGGGLVQPGGSLRLSCAAS<u>GSIFSITAMG</u>WYRQAPGKQRELVA<u>TVTSGGSTKYVESVKG</u>RATIS
NDNAKNTVYLQMNSLKPEDTAVYYCWA<u>DIVARWNSDYNVYDDY</u>WGQGTQVTVSS AS60399 sdAb amino acid sequence; CDRs are underlined
SEQ ID NO: 118
QVKLEESGGGLVQEGGSLRLSCAAS<u>GTIYTDSTIY</u>WYRQAPGKQRELVAS<u>ITRGGDTKYVDSVKG</u>RFAIS
SDNAKNTVYLQMNSLKPEDTAVYYCNL<u>YYRTGPSSYYRND</u>WGQGTQVTVSS AS59101 sdAb amino acid sequence; CDRs are underlined
SEQ ID NO: 119
AVQLVESGGGLVQPGGSLRLSCAVS<u>GIYYSINLMG</u>WYRQAPGKPRELAAS<u>ITDSGITNYADSVKG</u>RFTIS
RDNAKNTVHLQMNNLKPEDTAVYYCK<u>PMGVN</u>WGQGIQVTVSS AS58930C sdAb amino acid sequence; CDRs are underlined
SEQ ID NO: 120
AVQLVESGGGLVQAGGSLRLSCTAS<u>GSILRTYEMG</u>WYRQAPGSQRELVAS<u>ITSDGDTNYVDSVKG</u>RFTIS
RDNGKNMVYLQMNSLKPDDTAVYYCNA<u>VILSPSYSMRTSH</u>WGQGTQVTVSS AS67190 sdAb amino acid sequence; CDRs are underlined
SEQ ID NO: 121
QVQLVESGGGLVQAGGSLRLSCAASGNVFRENIMGWYRQAPGNQRELVASIDDGGDRSYADSVEGRETIS
RENGKKIMYLQMNSLKPEDTAVYYCAAGLGTYLNGRVSMATNYWGQGTQVTVSS AS67147 sdAb amino acid sequence; CDRs are underlined
SEQ ID NO: 122
EVQLVESGGGLVQAGGSLRLSCAASGDTFSFAAMGWYRQAPGKQRELVASISFSGGESTVYANSVRGRFT
ISGDNAKNRVSLEMNNLKPEDTAVYYCTAKRGPYLPGPEYWGQGTQVTVSS AS49175 sdAb nucleic acid sequence
SEQ ID NO: 123
GAGGTGCAGCTGGCGGAGTCTGGGGGAGGCTTGGTGCAGGCAGGGGGGTCTCTGAGACTCTCCTGTACAG
CCTCTGGATTCACTTTTGATGATTATGTCATGGGCTGGTTCCGCCAGGCCCCAGGGAAGGAGCGCGAGGG
GGTCTCATGTATTAGCTGGAGTGGTGACACCACATACTATGCAGACTCCGTGAAGGGCCGATTCACCGCC
TCCAGAGACAACGCCAAGAACACGCTGTATCTGCAAATGAACAGCCTGAAACCTGAGGACACGGCCATGT
ATTATTGTGCGGCAGATCAAGGTAAATGCTCCCTTGCGAGCGCGGAACCGGACGACATGGACTACTGGGG
CAGAGGGACCCTGGTCACCGTCTCCTCA AS49226 sdAb nucleic acid sequence
SEQ ID NO: 124
GAGGTGCAACTGGCGGAGTCTGGGGGAGGCTCGGTGCAGGCTGGAGGGTCTCTGAGACTCTCCTGTGCAG
CCTCTGGAGTCACCTTTAGTAGCACGTCCGTGGCCTGGTTCCGCCAGGCTCCAGGGAAGGAGCGCGAGGG
GGTCGCATATATTTATACTGGTGATAGTAGCACATACTATGCCGACTCCGTGAAGGGCCGATTCACCATC
GCCCAAGACAACGCCAAGAACGCGGTGTATCTGCAAATGAACAGCCTGAAACCTGAGGACACTGCCATGT
ACTACTGTGCGGCAGATGGTTTTTACTGAATCACCGCTCATACCAATACTGGGGCCAGGGGACCCAGGT
CACCGTCTCCTCA AS49264 sdAb nucleic acid sequence
SEQ ID NO: 125
GAGGTGCAACTGGTGGAGTCTGGGGGAGGCTCGGTGCAGGCTGGAGGGTCTCTGAGACTCTCCTGTGCAG
CCTCTGGATACACCTACAGTATCAACTGCATGGGCTGGTTCCGCCAGGCTCCAGGGAAGGAGCGCGAGGG
GGTCGCGGTTATTAGTACTGGTGGTGGACGCACAGACTATCGCGACTCCGTGAAGGGCCGATTCACCATC
TCCCAAGACAACGCCAAGAACACGGTGTATCTGCAAATGAACAGCCTGAAACCTGAGGACACTGCCATGT
ACTACTGTGCGGGTAAAACGACCTATCCAGGGTATGGCTGCGGACTTGGGAGATCGGCCTATAACTACTG
GGGCCAGGGGACCCAGGTCACCGTCTCCTCA AS49814 sdAb nucleic acid sequence
SEQ ID NO: 126
CAGATTCAGCTGGTGGAGTCTGGGGGAGGCTCGGTGCAGGCTGGAGGGTCTCTGAGGCTCTCCTGTGTAG
CCTCTGGATACATCGGCGGTCACTACTACATGGGGTGGTTCCGCCAGGCTCCAGGGAAGGAGCGCGAGGG
GGTCGCAGCTATAGATATTGATAGTGATGGTAGGACAAGGTACGCAGGCTCCGTGCAGGGCCGATTCACC
ATCTCCCAAGACAACGCCAAGAACACTCTGCATCTGCAAATGAGCAGCCTGAAACCTGAGGACACTGGCA
TGTACTACTGTGCGGTTGGTGTGGGTTGGGTCCCCGCGAGACTTACACCCCAAGCCGTGAGCTACTGGGG
CAAAGGAACCCTGGTCACCGTCTCCTCA AS49873 sdAb nucleic acid sequence
SEQ ID NO: 127
GAGGTGCAACTGGTGGAGTCTGGGGGAGGCTCGGTGCAGGCTGGAGGGTCTCTGAGACTCTCCTGTGTAG
CCTCTGGATACACCTACGGTATCAACTGCATGGGCTGGTTCCGCCAGGCTCCAGGGAAGGAGCGCGAGGG
GATCGCAGCTATTAGCACTGGTGGTGGTACCACAGGCGTTCGCGACTCCGTGAAGGGCCGATTCACCATC
TCCCAAGACAACGCCAAGAACACGGTGTATCTGCAAATGAACAGCCTGAAACCGGAGGACACTGCCATGT
ACTACTGTGCGGCGAGATCGACTTATAGCGGCTATGCGTGCGTGTACTCGGAAGTGAATGGGTATAACTA
CCGGGGGCCAGGGGACCCAGGTCACCGTCTCCTCA AS49889 sdAb nucleic acid sequence
SEQ ID NO: 128
GAGGTGCAACTGGTGGAGTCTGGGGGAGGCTCGGTGCAGGCTGGAGGATCTCTGAGACTCTCCTGTGTAG
CCTCTGGATACACCTGGTGTAGGTACGACATGAGCTGGTACCGCCAGGAAGGAGGAGCGCGAGTT
CGTCTCAGGTTTTGATAATGATGGTACCACAAGTTACGCTGACTCCGTGAAGGGCCGATTCACCATCTCC
CAAGACAACGACAAGAACACGGTGTATCTGCAAATGAACAGCCTGAAACCTGAGGACACGGCCATGTATT
ACTGTAAAGAAGATCGTTCCCGGGGTAGCTTGGACGGACGCGTATGTCCATTGTCTTATGACAACTGGGG
CCAGGGGACCCAGGTCACCGTCTCCTCA AS49902 sdAb nucleic acid sequence
SEQ ID NO: 129
GAGGTGCAGCTGGTGGAGTCTGGGGGAGGCTTGGTGCAGGCAGGGGGGTCTCTGAGACTCTCCTGTACAG
CCTCTGGATTCACTTTTGATGATTATGTCATGGGCTGGTTCCGCCAGGCCCCAGGGAAGGAGCGCGAGGG
GGTCTCATGTATTAGCTGGAGTGGTGATACCACATACTATGCAGACTCCGTGAAGGGCCGATTCACCGTC
TCCAGAGACAACGCCAAGAACACGCTGTATCTGCAAATGAACAGCCTGAAACCTGAGGACACGGCCATGT
ATTACTGTGCGGCAGATCAGAGTCTTTGCTCTCTAGCACCCCCCTACAATTATGCCTACTGGGGCCAGGG
GACCCAGGTCACCGTCTCCTCA AS50073 sdAb nucleic acid sequence
SEQ ID NO: 130
CAGGTGCAGCTGGTGGAGTCTGGGGGAGGCTTGGTGCAGGCAGGGGGGTCTCTGAGACTCTCCTGTACAG
CCTCTGGATTCACTTTTGATAATTATGTCATGGGCTGGTTCCGCCAGGCTCCAGGGAAGGAGCGCGAGGG
GGTCTCATGTATTGCTGGAGTGGTGGTAGCACATACTATGCAGACTCCGTGAAGGGCCGATTCACCATC
TCCAGAGACAACGCCAAGAACACGCTGTATCTGCAAATGAACAGCCTGAAACCTGAGGACACGGCCATGT
ATTACTGTGCGGCAGATCAAGGTAAATGCTCCCTTGGGAGCGCGGGTGCGGACGACATGGACTACTGGGG
CAGAGGGACCCTGGTCACCGTCTCCTCA

```
AS50502 sdAb nucleic acid sequence
                                                        SEQ ID NO: 131
GAGGTGCAGCTGGTGGAGTCTGGGGGAGGCTCGGTGCAGGCTGGCGGGTCTCTGAGACTCTCCTGTGCTG
CCCCTGGATACACCTACTGTACTTACGACATGATGTGGTACCGCCAGGCTCTAGGGAAAGAGCGCGAGTT
CGTCTCAGCTGTTTATACTGATGGTAGCACTCTCTACGCAGACTCCGTGAAGGGCCGATTCACCATCTCC
CAAGACAACGCCAAGAACACGCTGTATCTGCAAATGAACAGCCTGAAACCTGAGGACACGGCCATGTATT
ACTGTAAAACAGAAACGGCCGTGACCTATGACAAGCCTTGCGACTTTTGGGGCCAGGGGACCCAGGTCAC
CGTCTCCTCA AS66873 sdAb nucleic acid sequence
                                                        SEQ ID NO: 132
CAGGTGCAGCTGGTGGAGTCTGGGGGAGGCTTGGTGCAGCCTGGGGGGTCTCTGAGACTCTCCTGTGCAG
CCTCTGGAAGCATCTTCAGTATCACTGCCATGGGCTGGTACCGCCAGGCTCCAGGGAAGCAGCGCGAGTT
GGTCGCAACCGTTACGAGTGGTGGTAGTACAAAGTATGTAGAGTCCGTGAAGGGCCGATTCACCATCTCC
AACGACAACGCCAAGAACACGGTGTATCTGCAAATGAACAGCCTGAAACCTGAGGACACGGCCGTCTATT
ACTGTTGGGCAGATATCGTAGCTCGGTGGAATAGCGACTATAATGTTTACGATGACTACTGGGGCCAGGG
GACCCAGGTCACCGTCTCCTCA AS60399 sdAb nucleic acid sequence
                                                        SEQ ID NO: 133
CAGGTAAAGCTGGAGGAGTCTGGGGGAGGCTTGGTGCAGGAGGGGGGTCTCTGAGACTCTCCTGTGCGG
CCTCTGGAACCATCTATACGGACAGTACCATATACTGGTACCGGCAGGCTCCAGGGAAGCAGCGCGAGTT
GGTCGCTAGTATTACGCGTGGTGGTGATACAAAGTATGTAGACTCCGTGAAGGGCCGATTCGCCATCTCC
AGCGACAACGCCAAGAACACGGTGTATCTTCAAATGAACAGCCTGAAACCTGAGGACACAGCCGTCTATT
ATTGTAATCTATATTATCGCACAGGCCCTTCTTCTTACTACAGGAATGACTGGGGCCAGGGGACCCAGGT
CACTGTCTCCTCG AS59101 sdAb nucleic acid sequence
                                                        SEQ ID NO: 134
GCGGTGCAGCTGGTGGAGTCTGGGGGAGGCTTGGTGCAGCCTGGGGGGTCTCTGAGACTCTCCTGTGCAG
TCTCTGGAATCTATTACAGTATCAATCTCATGGGCTGGTACCGCCAGGCTCCCGGGAAGCGCGCGAGTT
GGCAGCATCGATTACTGATAGTGGTATCACAAACTATGCAGACTCCGTGAAGGGCCGATTCACCATCTCC
AGAGACAACGCCAAGAACACGGTGCATCTGCAAATGAACAACCTGAAACCTGAGGACACGGCCGTCTATT
ACTGTAAACCGATGGGTGTAAACTGGGGCCAGGGGATCCAGGTCACCGTCTCCTCA AS58930C sdAb nucleic acid sequence
                                                        SEQ ID NO: 135
GCGGTGCAGCTAGTGGAGTCTGGGGGAGGCTTGGTGCAGGCTGGGGGGTCTCTGAGACTCTCCTGTACAG
CCTCTGGAAGCATCCTCAGAACATATGAGATGGGCTGGTACCGCCAGGCTCCAGGGAGCCAGCGCGAGTT
GGTCGCAAGTATTACTAGTGATGGCGATACAAACTATGTCGACTCCGTGAAGGGCCGATTCACCATCTCC
AGAGACAACGGCAAGAATATGGTATATCTGCAAATGAACAGCCTGAAACCTGACGACACAGCCGTCTATT
ACTGTAATGCAGTCATTTTATCTCCTTCCTATTCTATGAGAACTTCCCACTGGGCCAGGGGACCCAGGT
CACCGTCTCCTCA AS67190 sdAb nucleic acid sequence
                                                        SEQ ID NO: 136
CAGGTGCAGCTGGTGGAGTCTGGGGGAGGCTTGGTGCAGGCTGGGGCTCTCTGAGACTCTCCTGTGCAG
CCTCTGGAAACGTCTTTCGTTTCAATATTATGGGGTGGTACCGCCAGGCTCCAGGGAACCAGCGCGAATT
GGTCGCATCAATAGACGATGGTGGTGACCGAAGCTATGCAGACTCCGTGGAGGGCCGATTCACCATCTCC
AGAGAGAACGGCAAGAAAATAATGTATCTGCAAATGAATAGCCTGAAACCCGAGGACACAGCCGTCTATT
ACTGTGCAGCGGGCCTGGGAACATATCTGAATGGACGTGTTTCCATGGCGACTAACTACTGGGGCCAGGG
GACCCAGGTCACCGTCTCCTCA AS67147 sdAb nucleic acid sequence
                                                        SEQ ID NO: 137
GAGGTGCAGCTGGTGGAGTCTGGGGGAGGCTTGGTGCAGGCTGGGGGTCTCTGAGACTCTCCTGTGCAG
CCTCTGGAGACACCTTCAGTTTCGCTGCCATGGGCTGGTACCGCCAGGCTCCAGGGAAGCAGCGCGAATT
GGTCGCAAGTATTAGTTTTAGTGGTGGTGAAAGTACAGTATATGCAAACTCCGTGAGGGGCCGTTTCACC
ATCTCCGGAGACAACGCCAAGAACAGAGTGTCTCTCGAAATGAACAACTTGAAACCTGAGGACACGGCCG
TGTATTACTGTACGGCAAAAGGGGACCCTATCTTCCTGGCCGGAGTACTGGGGCCAGGGGACGCAGGT
CACCGTCTCCTCA
```

CD33, also known as Siglec-3 (sialic acid binding Ig-like lectin 3), gp67, or p67, is a transmembrane receptor expressed on cells of myeloid lineage. CD33 is the target of gemtuzumab ozogamicin (MYLOTARG®), an antibody-drug conjugate, which has been approved for treatment of patients with acute myeloid leukemia.

In some embodiments, the anti-CD33 sdAb specifically binds to human CD33. In some embodiments, the anti-CD33 sdAb specifically binds to cynomolgus monkey CD33. In some embodiments, the anti-CD33 sdAb specifically binds to the extracellular domain of CD33. In some embodiments, the anti-CD33 sdAb specifically binds to the amino acid sequence of SEQ ID NO: 1 or 2. In some embodiments, the anti-CD33 sdAb specifically recognizes an epitope within human CD33. In some embodiments, the anti-CD33 sdAb cross-reacts with CD33 from species other than human. In some embodiments, the anti-CD33 sdAb is completely specific for human CD33 and does not exhibit species or other types of non-human cross-reactivity.

In some embodiments, the anti-CD33 sdAb cross-reacts with at least one allelic variant of the CD33 protein (or fragments thereof). In some embodiments, the allelic variant has up to about 30 (such as about any of 1, 2, 3, 4, 5, 6, 7, 8, 9, 10, 15, 20, 25, or 30) amino acid substitutions (such as a conservative substitution) when compared to the naturally occurring CD33 (or fragments thereof). In some embodiments, the anti-CD33 sdAb does not cross-react with any allelic variant of the CD33 protein (or fragments thereof).

In some embodiments, there is provided an anti-CD33 sdAb comprising one, two, or all three CDRs of the amino acid sequence of SEQ ID NO: 108. In some embodiments, there is provided an anti-CD33 sdAb comprising one, two, or all three CDRs of the amino acid sequence of SEQ ID NO: 109, in some embodiments, there is provided an anti-CD33 sdAb comprising one, two, or all three CDRs of the amino acid sequence of SEQ ID NO: 110. In some embodiments, there is provided an anti-CD33 sdAb comprising one, two, or all three CDRs of the amino acid sequence of SEQ ID NO: 111. In some embodiments, there is provided an anti-CD33 sdAb comprising one, two, or all three CDRs of the amino acid sequence of SEQ ID NO: 112. In some embodiments, there is provided an anti-CD33 sdAb comprising one, two, or all three CDRs of the amino acid sequence of SEQ ID NO: 113. In some embodiments, there is provided an anti-CD33 sdAb comprising one, two, or all three CDRs of the amino acid sequence of SEQ ID NO: 114. In some embodiments, there is provided an anti-CD33 sdAb comprising one, two, or all three CDRs of the amino acid sequence of SEQ ID NO: 115. In some embodiments, there is provided an anti-CD33 sdAb comprising one, two, or all three CDRs of the amino acid sequence of SEQ ID NO: 116. In some embodiments, there is provided an anti-CD33 sdAb comprising one, two, or all three CDRs of the amino acid sequence of SEQ ID NO: 117. In some embodiments, there is provided an anti-CD33 sdAb comprising one, two, or all three CDRs of the amino acid sequence of SEQ ID NO: 118. In some embodiments, there is provided an anti-CD33 sdAb comprising one, two, or all three CDRs of the amino acid sequence of SEQ ID NO: 119. In some embodiments, there is provided an anti-CD33 sdAb comprising one, two, or all three CDRs of the amino acid sequence of SEQ ID NO: 120. In some embodiments, there is provided an anti-CD33 sdAb comprising one, two, or all three CDRs of the amino acid sequence of SEQ ID NO: 121. In some embodiments, there is provided an anti-CD33 sdAb comprising one, two, or all three CDRs of the amino acid sequence of SEQ ID NO: 122.

In some embodiments, there is provided an anti-CD33 sdAb comprising at least one, at least two, or all three CDRs selected from: (a) a CDR1 comprising the amino acid sequence of any one of SEQ ID NOs: 4, 11, 18, 25, 32, 39, 46, 53, 60, 67, 74, 81, 88, 95, and 102; (b) a CDR2 comprising the amino acid sequence of any one of SEQ ID NOs: 6, 13, 20, 27, 34, 41, 48, 55, 62, 69, 76, 83, 90, 97, and 104; and (c) a CDR3 comprising the amino acid sequence of any one of SEQ ID NOs: 8, 15, 22, 29, 36, 43, 50, 57, 64, 71, 78, 85, 92, 99, and 106.

In some embodiments, there is provided an anti-CD33 sdAb comprising: (a) a CDR1 having at least about any one of 85%, 86%, 87%, 88%, 89%, 90%, 91%, 92%, 93%, 94%, 95%, 96%, 97%, 98%, 99%, or 100% sequence identity to the amino acid sequence of any one of SEQ ID NOs: 4, 11, 18, 25, 32, 39, 46, 53, 60, 67, 74, 81, 88, 95, and 102; (b) a CDR2 having at least about any one of 85%, 86%, 87%, 88%, 89%, 90%, 91%, 92%, 93%, 94%, 95%, 96%, 97%, 98%, 99%, or 100% sequence identity to the amino acid sequence of any one of SEQ ID NOs: 6, 13, 20, 27, 34, 41, 48, 55, 62, 69, 76, 83, 90, 97, and 104; and (c) a CDR3 having at least about any one of 85%, 86%, 87%, 88%, 89%, 90%, 91%, 92%, 93%, 94%, 95%, 96%, 97%, 98%, 99%, or 100% sequence identity to the amino acid sequence of any one of SEQ ID NOs: 8, 15, 22, 29, 36, 43, 50, 57, 64, 71, 78, 85, 92, 99, and 106, In some embodiments, a CDR having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-CD33 sdAb comprising that sequence retains the ability to bind to CD33. In some embodiments, there is provided an anti-CD33 sdAb comprising: (a) a CDR1 having about any one of 1, 2, or 3 amino acid substitutions (e.g., conservative substitutions), insertions, or deletions to the amino acid sequence of any one of SEQ ID NOs: 4, 11, 18, 25, 32, 39, 46, 53, 60, 67, 74, 81, 88, 95, and 102; (h) a CDR2 having about any one of 1, 2, or 3 amino acid substitutions (e.g., conservative substitutions), insertions, or deletions to the amino acid sequence of any one of SEQ ID NOs: 6, 13, 20, 27, 34, 41, 48, 55, 62, 69, 76, 83, 90, 97, and 104; and (c) a CDR3 having about any one of 1, 2, or 3 amino acid substitutions (e.g., conservative substitutions), insertions, or deletions to the amino acid sequence of any one of SEQ ID NOs: 8, 15, 22, 29, 36, 43, 50, 57, 64, 71, 78, 85, 92, 99, and 106.

In some embodiments, there is provided an anti-CD33 sdAb comprising: (a) a CDR1 comprising the amino acid sequence of SEQ ID NO: 4, or a variant thereof comprising up to about 3 (e.g., 1, 2, or 3) amino acid substitutions in the CDR1; (b) a CDR2 comprising the amino acid sequence of SEQ ID NO: 6, or a variant thereof comprising up to about 3 (e.g., 1, 2, or 3) amino acid substitutions in the CDR2; and (c) a CDR3 comprising the amino acid sequence of SEQ ID NO: 8, or a variant thereof comprising up to about 3 (e.g., 1, 2, or 3) amino acid substitutions in the CDR3. In some embodiments, there is provided an anti-CD33 sdAb comprising: (a) a CDR1 comprising the amino acid sequence of SEQ ID NO: 4; (b) a CDR2 comprising the amino acid sequence of SEQ ID NO: 6; and (c) a CDR3 comprising the amino acid sequence of SEQ ID NO: 8, or a variant thereof comprising up to about 5 (e.g., 1, 2, 3, 4, or 5) amino acid substitutions in the CDRs. In some embodiments, there is provided an anti-CD33 sdAb comprising: (a) a CDR1 comprising the amino acid sequence of SEQ ID NO: 4; (b) a CDR2 comprising the amino acid sequence of SEQ ID NO: 6; and (c) a CDR3 comprising the amino acid sequence of SEQ ID NO: 8. In some embodiments, there is provided a polypeptide comprising the amino acid sequences of SEQ ID NOs: 4, 6 and 8.

In some embodiments, there is provided an anti-CD33 sdAb comprising: (a) a CDR1 comprising the amino acid sequence of SEQ ID NO: 11, or a variant thereof comprising up to about 3 (e.g., 1, 2, or 3) amino acid substitutions in the CDR1; (b) a CDR2 comprising the amino acid sequence of SEQ ID NO: 13, or a variant thereof comprising up to about 3 (e.g., 1, 2, or 3) amino acid substitutions in the CDR2; and (c) a CDR3 comprising the amino acid sequence of SEQ ID NO: 15, or a variant thereof comprising up to about 3 (e.g., 1, 2, or 3) amino acid substitutions in the CDR3, in some embodiments, there is provided an anti-CD33 sdAb comprising: (a) a CDR1 comprising the amino acid sequence of SEQ ID NO: 1 (b) a CDR2 comprising the amino acid sequence of SEQ ID NO: 13; and (c) a CDR3 comprising the amino acid sequence of SEQ ID NO: 15, or a variant thereof comprising up to about 5 (e.g., 1, 2, 3, 4, or 5) amino acid substitutions in the CDRs. In some embodiments, there is provided an anti-CD33 sdAb comprising: (a) a CDR1 comprising the amino acid sequence of SEQ ID NO: 11; (b) a CDR2 comprising the amino acid sequence of SEQ ID NO: 13, and (c) a CDR3 comprising the amino acid sequence of SEQ ID NO: 15. In some embodiments, there is provided a polypeptide comprising the amino acid sequences of SEQ ID NOs: 11, 13 and 15.

In some embodiments, there is provided an anti-CD33 sdAb comprising: (a) a CDR1 comprising the amino acid sequence of SEQ ID NO: 18, or a variant thereof comprising up to about 3 (e.g., 1, 2, or 3) amino acid substitutions in the CDR1; (b) a CDR2 comprising the amino acid sequence of SEQ ID NO: 20, or a variant thereof comprising up to about 3 (e.g., 1, 2, or 3) amino acid substitutions in the CDR2; and (c) a CDR3 comprising the amino acid sequence of SEQ ID NO: 22, or a variant thereof comprising up to about 3 (e.g., 1, 2, or 3) amino acid substitutions in the CDR3. In some embodiments, there is provided an anti-CD33 sdAb comprising: (a) a CDR1 comprising the amino acid sequence of SEQ 11) NO: 18, (b) a CDR2 comprising the amino acid sequence of SEQ ID NO: 20; and (c) a CDR3 comprising the amino acid sequence of SEQ ID NO: 22, or a variant thereof comprising up to about 5 (e.g., 1, 2, 3, 4, or 5) amino acid substitutions in the CDRs. In some embodiments, there is provided an anti-CD33 sdAb comprising: (a) a CDR1 comprising the amino acid sequence of SEQ ID NO: 18; (b) a CDR2 comprising the amino acid sequence of SEQ ID NO; 20; and (c) a CDR3 comprising the amino acid sequence of SEQ ID NO: 22. In some embodiments, there is provided a polypeptide comprising the amino acid sequences of SEQ ID NOs: 18, 20 and 22.

In some embodiments, there is provided an anti-CD33 sdAb comprising: (a) a CDR1 comprising the amino acid sequence of SEQ ID NO: 25, or a variant thereof comprising up to about 3 (e.g., 1, 2, or 3) amino acid substitutions in the CDR1; (h) a CDR2 comprising the amino acid sequence of SEQ ID NO: 27, or a variant thereof comprising up to about 3 (e.g., 1, 2, or 3) amino acid substitutions in the CDR2; and (c) a CDR3 comprising the amino acid sequence of SEQ ID NO: 29, or a variant thereof comprising up to about 3 (e.g., 1, 2, or 3) amino acid substitutions in the CDR3. In some embodiments, there is provided an anti-CD33 sdAb comprising: (a) a CDR1 comprising the amino acid sequence of SEQ ID NO: 25; (h) a CDR2 comprising the amino acid sequence of SEQ ID NO: 27; and (c) a CDR3 comprising the amino acid sequence of SEQ ID NO: 29, or a variant thereof comprising up to about 5 (e.g., 1, 2, 3, 4, or 5) amino acid substitutions in the CDRs. In some embodiments, there is provided an anti-CD33 sdAb comprising: (a) a CDR1 comprising the amino acid sequence of SEQ ID NO: 25; (b) a CDR2 comprising the amino acid sequence of SEQ ID NO; 27; and (c) a CDR3 comprising the amino acid sequence of SEQ ID NO: 29. In some embodiments, there is provided a polypeptide comprising the amino acid sequences of SEQ NOs: 25, 2.7 and 29.

In some embodiments, there is provided an anti-CD33 sdAb comprising: (a) a CDR1 comprising the amino acid sequence of SEQ ID NO: 32, or a variant thereof comprising up to about 3 (e.g., 1, 2, or 3) amino acid substitutions in the CDR1; (h) a CDR2 comprising the amino acid sequence of SEQ ID NO: 34, or a variant thereof comprising up to about 3 (e.g., 1, 2, or 3) amino acid substitutions in the CDR2; and (c) a CDR3 comprising the amino acid sequence of SEQ ID NO: 36, or a variant thereof comprising up to about 3 (e.g., 1, 2, or 3) amino acid substitutions in the CDR3. In some embodiments, there is provided an anti-CD33 sdAb comprising: (a) a CDR1 comprising the amino acid sequence of SEQ ID NO: 32; (h) a CDR2 comprising the amino acid sequence of SEQ ID NO: 34; and (c) a CDR3 comprising the amino acid sequence of SEQ ID NO: 36, or a variant thereof comprising up to about 5 (e.g., 1, 2, 3, 4, or 5) amino acid substitutions in the CDRs. In some embodiments, there is provided an anti-CD33 sdAb comprising: (a) a CDR1 comprising the amino acid sequence of SEQ ID NO: 32; (b) a CDR2 comprising the amino acid sequence of SEQ ID NO: 34; and (c) a CDR3 comprising the amino acid sequence of SEQ ID NO: 36. In some embodiments, there is provided a polypeptide comprising the amino acid sequences of SEQ NOs: 32, 34 and 36.

In some embodiments, there is provided an anti-CD33 sdAb comprising: (a) a CDR1 comprising the amino acid sequence of SEQ ID NO: 39, or a variant thereof comprising up to about 3 (e.g., 1, 2, or 3) amino acid substitutions in the CDR1; (b) a CDR2 comprising the amino acid sequence of SEQ ID NO: 41, or a variant thereof comprising up to about 3 (e.g., 1, 2, or 3) amino acid substitutions in the CDR2, and (c) a CDR3 comprising the amino acid sequence of SEQ ID NO: 43, or a variant thereof comprising up to about 3 (e.g., 1, 2, or 3) amino acid substitutions in the CDR3. In some embodiments, there is provided an anti-CD33 sdAb comprising: (a) a CDR1 comprising the amino acid sequence of SEQ ID NO: 39; (b) a CDR2 comprising the amino acid sequence of SEQ ID NO: 41; and (c) a CDR3 comprising the amino acid sequence of SEQ ID NO: 43, or a variant thereof comprising up to about 5 (e.g., 1, 2, 3, 4, or 5) amino acid substitutions in the CDRs. In some embodiments, there is provided an anti-CD33 sdAb comprising: (a) a CDR1 comprising the amino acid sequence of SEQ ID NO: 39; (b) a CDR2 comprising the amino acid sequence of SEQ ID NO: 41; and (c) a CDR3 comprising the amino acid sequence of SEQ ID NO: 43. In some embodiments, there is provided a polypeptide comprising the amino acid sequences of SEQ ID NOs: 39, 41 and 43.

In some embodiments, there is provided an anti-CD33 sdAb comprising: (a) a CDR1 comprising the amino acid sequence of SEQ ID NO: 46, or a variant thereof comprising up to about 3 (e.g., 1, 2, or 3) amino acid substitutions in the CDR1; (b) a CDR2 comprising the amino acid sequence of SEQ ID NO: 48, or a variant thereof comprising up to about 3 (e.g., 1, 2, or 3) amino acid substitutions in the CDR2; and (c) a CDR3 comprising the amino acid sequence of SEQ ID NO: 50, or a variant thereof comprising up to about 3 (e.g., 1, 2, or 3) amino acid substitutions in the CDR3, in some embodiments, there is provided an anti-CD33 sdAb comprising: (a) a CDR1 comprising the amino acid sequence of SEQ ID NO: 46; (b) a CDR2 comprising the amino acid sequence of SEQ ID NO: 48; and (c) a CDR3 comprising the amino acid sequence of SEQ ID NO: 50, or a variant thereof comprising up to about 5 (e.g., 1, 2, 3, 4, or 5) amino acid substitutions in the CDRs. In some embodiments, there is provided an anti-CD33 sdAb comprising: (a) a CDR1 comprising the amino acid sequence of SEQ ID NO: 46; (b) a CDR2 comprising the amino acid sequence of SEQ ID NO: 48; and (c) a CDR3 comprising the amino acid sequence of SEQ ID NO: 50. In some embodiments, there is provided a polypeptide comprising the amino acid sequences of SEQ ID NOs: 46, 48 and 50.

In some embodiments, there is provided an anti-CD33 sdAb comprising: (a) a CDR1 comprising the amino acid sequence of SEQ ID NO: 53, or a variant thereof comprising up to about 3 (e.g., 1, 2, or 3) amino acid substitutions in the CDR1; (b) a CDR2 comprising the amino acid sequence of SEQ ID NO: 55, or a variant thereof comprising up to about 3 (e.g., 1, 2, or 3) amino acid substitutions in the CDR2; and (c) a CDR3 comprising the amino acid sequence of SEQ ID NO: 57, or a variant thereof comprising up to about 3 (e.g., 1, 2, or 3) amino acid substitutions in the CDR3, in some embodiments, there is provided an anti-CD33 sdAb comprising: (a) a CDR1 comprising the amino acid sequence of SEQ ID NO: 53; (b) a CDR2 comprising the amino acid sequence of SEQ ID NO: 55; and (c) a CDR3 comprising the amino acid sequence of SEQ ID NO: 57, or a variant thereof comprising up to about 5 (e.g., 1, 2, 3, 4, or 5) amino acid substitutions in the CDRs. In some embodiments, there is provided an anti-CD33 sdAb comprising: (a) a CDR1 comprising the amino acid sequence of SEQ ID NO: 53; (b) a CDR2 comprising the amino acid sequence of SEQ ID NO: 55; and (c) a CDR3 comprising the amino acid sequence of SEQ ID NO: 57. In some embodiments, there is provided a polypeptide comprising the amino acid sequences of SEQ ID NOs: 53, 55 and 57.

In some embodiments, there is provided an anti-CD33 sdAb comprising: (a) a CDR comprising the amino acid sequence of SEQ ID NO: 60, or a variant thereof comprising up to about 3 (e.g., 1, 2, or 3) amino acid substitutions in the CDR1; (b) a CDR2 comprising the amino acid sequence of SEQ ID NO: 62, or a variant thereof comprising up to about 3 (e.g., 1, 2, or 3) amino acid substitutions in the CDR2; and (c) a CDR3 comprising the amino acid sequence of SEQ ID NO: 64, or a variant thereof comprising up to about 3 (e.g., 1, 2, or 3) amino acid substitutions in the CDR3. In some embodiments, there is provided an anti-CD33 sdAb comprising: (a) a CDR1 comprising the amino acid sequence of SEQ ID NO: 60; (b) a CDR2 comprising the amino acid sequence of SEQ ID NO: 62; and (c) a CDR3 comprising the amino acid sequence of SEQ ID NO: 64, or a variant thereof comprising up to about 5 (e.g., 1, 2, 3, 4, or 5) amino acid substitutions in the CDRs. In some embodiments, there is provided an anti-CD33 sdAb comprising: (a) a CDR1 comprising the amino acid sequence of SEQ ID NO: 60; (b) a CDR2 comprising the amino acid sequence of SEQ ID NO: 62; and (c) a CDR3 comprising the amino acid sequence of SEQ ID NO: 64. In some embodiments, there is provided a polypeptide comprising the amino acid sequences of SEQ ID NOs: 60, 62 and 64.

In some embodiments, there is provided an anti-CD33 sdAb comprising: (a) a CDR comprising the amino acid sequence of SEQ ID NO: 67, or a variant thereof comprising up to about 3 (e.g., 1, 2, or 3) amino acid substitutions in the CDR1; (b) a CDR2 comprising the amino acid sequence of SEQ ID NO: 69, or a variant thereof comprising up to about 3 (e.g., 1, 2, or 3) amino acid substitutions in the CDR2; and (c) a CDR3 comprising the amino acid sequence of SEQ ID NO: 71, or a variant thereof comprising up to about 3 (e.g., 1, 2, or 3) amino acid substitutions in the CDR3. In some embodiments, there is provided an anti-CD33 sdAb comprising: (a) a CDR1 comprising the amino acid sequence of SEQ ID NO: 67; (b) a CDR2 comprising the amino acid sequence of SEQ ID NO: 69; and (c) a CDR3 comprising the amino acid sequence of SEQ ID NO: 71, or a variant thereof comprising up to about 5 (e.g., 1, 2, 3, 4, or 5) amino acid substitutions in the CDRs. In some embodiments, there is provided an anti-CD33 sdAb comprising: (a) a CDR1 comprising the amino acid sequence of SEQ ID NO: 67; (b) a CDR2 comprising the amino acid sequence of SEQ ID NO: 69; and (c) a CDR3 comprising the amino acid sequence of SEQ ID NO: 71. In some embodiments, there is provided a polypeptide comprising the amino acid sequences of SEQ ID NOs: 67, 69 and 71.

In some embodiments, there is provided an anti-CD33 sdAb comprising: (a) a CDR1 comprising the amino acid sequence of SEQ ID NO: 74, or a variant thereof comprising up to about 3 (e.g., 1, 2, or 3) amino acid substitutions in the CDR1; (b) a CDR2 comprising the amino acid sequence of SEQ ID NO: 76, or a variant thereof comprising up to about 3 (e.g., 1, 2, or 3) amino acid substitutions in the CDR2; and (c) a CDR3 comprising the amino acid sequence of SEQ ID NO: 78, or a variant thereof comprising up to about 3 (e.g., 1, 2, or 3) amino acid substitutions in the CDR3. In some embodiments, there is provided an anti-CD33 sdAb comprising: (a) a CDR1 comprising the amino acid sequence of SEQ ID NO: 74; (b) a CDR2 comprising the amino acid sequence of SEQ ID NO: 76; and (c) a CDR3 comprising the amino acid sequence of SEQ ID NO: 78, or a variant thereof comprising up to about 5 (e.g., 1, 2, 3, 4, or 5) amino acid substitutions in the CDRs. In some embodiments, there is provided an anti-CD33 sdAb comprising: (a) a CDR1 comprising the amino acid sequence of SEQ ID NO: 74; (b) a CDR2 comprising the amino add sequence of SEQ ID NO: 76; and (c) a CDR3 comprising the amino acid sequence of SEQ ID NO: 78, in some embodiments, there is provided a poly/peptide comprising the amino acid sequences of SEQ ID NOs: 74, 76 and 78.

In some embodiments, there is provided an anti-CD33 sdAb comprising: (a) a CDR1 comprising the amino acid sequence of SEQ ID NO: 81, or a variant thereof comprising up to about 3 (e.g., 1, 2, or 3) amino acid substitutions in the CDR1; (b) a CDR2 comprising the amino acid sequence of SEQ ID NO: 83, or a variant thereof comprising up to about 3 (e.g., 1, 2, or 3) amino acid substitutions in the CDR2; and (c) a CDR3 comprising the amino acid sequence of SEQ ID NO: 85, or a variant thereof comprising up to about 3 (e.g., 1, 2, or 3) amino acid substitutions in the CDR3. In some embodiments, there is provided an anti-CD33 sdAb comprising: (a) a CDR1 comprising the amino acid sequence of SEQ ID NO: 81; (b) a CDR2 comprising the amino acid sequence of SEQ ID NO: 83; and (c) a CDR3 comprising the amino acid sequence of SEQ ID NO: 85, or a variant thereof comprising up to about 5 (e.g., 1, 2, 3, 4, or 5) amino acid substitutions in the CDRs. In some embodiments, there is provided an anti-CD33 sdAb comprising: (a) a CDR1 comprising the amino acid sequence of SEQ ID NO: 81; (b) a CDR2 comprising the amino add sequence of SEQ ID NO: 83; and (c) a CDR3 comprising the amino acid sequence of SEQ ID NO: 85, in some embodiments, there is provided a poly/peptide comprising the amino acid sequences of SEQ ID NOs: 81, 83 and 85.

In some embodiments, there is provided an anti-CD33 sdAb comprising: (a) a CDR1 comprising the amino acid sequence of SEQ ID NO: 88, or a variant thereof comprising up to about 3 (e.g., 1, 2, or 3) amino acid substitutions in the CDR1; (b) a CDR2 comprising the amino acid sequence of SEQ ID NO: 90, or a variant thereof comprising up to about 3 (e.g., 1, 2, or 3) amino acid substitutions in the CDR2; and (c) a CDR3 comprising the amino acid sequence of SEQ ID NO: 92, or a variant thereof comprising up to about 3 (e.g., 1, 2, or 3) amino acid substitutions in the CDR3. In some embodiments; there is provided an anti-CD33 sdAb comprising: (a) a CDR1 comprising the amino acid sequence of SEQ ID NO: 88; (b) a CDR2 comprising the amino acid sequence of SEQ ID NO: 90; and (c) a CDR3 comprising the amino acid sequence of SEQ ID NO: 92, or a variant thereof comprising up to about 5 (e.g., 1, 2, 3, 4, or 5) amino acid substitutions in the CDRs. In some embodiments, there is provided an anti-CD33 sdAb comprising: (a) a CDR1 comprising the amino acid sequence of SEQ ID NO: 88; (b) a CDR2 comprising the amino acid sequence of SEQ ID NO: 90; and (c) a CDR3 comprising the amino acid sequence of SEQ ID NO: 92. In some embodiments, there is provided a polypeptide comprising the amino acid sequences of SEQ ID NOs: 88, 90 and 92.

In some embodiments, there is provided an anti-CD33 sdAb comprising: (a) a CDR1 comprising the amino acid sequence of SEQ ID NO: 95, or a variant thereof comprising up to about 3 (e.g., 1, 2, or 3) amino acid substitutions in the CDR1; (b) a CDR2 comprising the amino acid sequence of SEQ ID NO: 97, or a variant thereof comprising up to about 3 (e.g., 1, 2, or 3) amino acid substitutions in the CDR2; and (c) a CDR3 comprising the amino acid sequence of SEQ ID NO: 99, or a variant thereof comprising up to about 3 (e.g., 1, 2, or 3) amino acid substitutions in the CDR3. In some embodiments; there is provided an anti-CD33 sdAb comprising: (a) a CDR1 comprising the amino acid sequence of SEQ ID NO: 95; (b) a CDR2 comprising the amino acid sequence of SEQ ID NO: 97; and (c) a CDR3 comprising the amino acid sequence of SEQ ID NO: 99, or a variant thereof comprising up to about 5 (e.g., 1, 2, 3, 4, or 5) amino acid substitutions in the CDRs. In some embodiments, there is provided an anti-CD33 sdAb comprising: (a) a CDR1 comprising the amino acid sequence of SEQ ID NO: 95; (b) a CDR2 comprising the amino acid sequence of SEQ ID NO: 97; and (c) a CDR3 comprising the amino acid sequence of SEQ ID NO: 99, in some embodiments, there is provided a polypeptide comprising the amino acid sequences of SEQ ID NOs: 95, 97 and 99.

In some embodiments, there is provided an anti-CD33 sdAb comprising: (a) a CDR1 comprising the amino acid sequence of SEQ ID NO: 102, or a variant thereof comprising up to about 3 (e.g., 1, 2, or 3) amino acid substitutions in the CDR1; (b) a CDR2 comprising the amino acid sequence of SEQ ID NO: 104, or a variant thereof comprising up to about 3 (e.g., 1, 2, or 3) amino acid substitutions in the CDR2; and (c) a CDR3 comprising the amino acid sequence of SEQ ID NO: 106, or a variant thereof comprising up to about 3 (e.g., 1, 2, or 3) amino acid substitutions in the CDR3. In some embodiments, there is provided an anti-CD33 sdAb comprising: (a) a CDR1 comprising the amino acid sequence of SEQ ID NO: 102; (b) a CDR2 comprising the amino acid sequence of SEQ ID NO: 104; and (c) a CDR3 comprising the amino acid sequence of SEQ ID NO: 106, or a variant thereof comprising up to about 5 (e.g., 1, 2, 3, 4, or 5) amino acid substitutions in the CDRs, in some embodiments, there is provided an anti-CD33 sdAb comprising: (a) a CDR1 comprising the amino acid sequence of SEQ ID NO: 102; (b) a CDR2 comprising the amino acid sequence of SEQ ID NO: 104; and (c) a CDR3 comprising the amino acid sequence of SEQ ID NO: 106. In some embodiments, there is provided a polypeptide comprising the amino acid sequences of SEQ ID NOs: 102, 104 and 106.

In some embodiments, the anti-CD33 sdAb, including any of the embodiments described above (i.e., anti-CD33 sdAb comprising specific CDR1, CDR2, and/or CDR3) comprises a $V_HH$ domain having at least about any one of 85%, 86%, 87%, 88%, 89%, 90%, 91%, 92%, 93%, 94%, 95%, 96%, 97%, 98%, 99%, or 100% sequence identity to the amino acid sequence of any one of SEQ ID NOs: 108-122. In some embodiments, a $V_HH$ sequence having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-CD33 sdAb comprising that sequence retains the ability to bind to CD33. In some embodiments, a total of 1 to 10 amino acids have been substituted, inserted and/or deleted in the amino acid sequence of any one of SEQ ID NOs: 108-122. In some embodiments, substitutions, insertions, or deletions occur in regions outside the CDRs (i.e., in the ERs). In some embodiments, the anti-CD33 sdAb comprises the amino acid sequence of any one of SEQ ID NOs: 108-122, optionally including post-translational modifications of that sequence.

In some embodiments, there is provided an isolated anti-CD33 sdAb comprising the amino acid sequence SEQ ID NO: 108. In some embodiments, there is provided a polypeptide comprising the amino acid sequence of SEQ ID NO: 108. In some embodiments, there is provided an isolated anti-CD33 sdAb comprising the amino acid sequence SEQ ID NO: 109. In some embodiments, there is provided a polypeptide comprising the amino acid sequence of SEQ ID NO: 109. In some embodiments, there is provided an isolated anti-CD33 sdAb comprising the amino acid sequence SEQ ID NO: 110. In some embodiments, there is provided a polypeptide comprising the amino acid sequence of SEQ ID NO: 110. In some embodiments, there is provided an isolated anti-CD33 sdAb comprising the amino acid sequence SEQ ID NO: 111. In some embodiments, there is provided a polypeptide comprising the amino acid sequence of SEQ ID NO: 111. In some embodiments, there is provided an isolated anti-CD33 sdAb comprising the amino acid sequence SEQ ID NO: 112. In some embodiments, there is provided a polypeptide comprising the amino acid sequence of SEQ ID NO: 112, in some embodiments, there is provided an isolated anti-CD33 sdAb comprising the amino acid sequence SEQ ID NO: 113. In some embodiments, there is provided a polypeptide comprising the amino acid sequence of SEQ ID NO: 113. In some embodiments, there is provided an isolated anti-CD33 sdAb comprising the amino acid sequence SEQ ID NO: 114. In some embodiments, there is provided a polypeptide comprising the amino acid sequence of SEQ ID NO: 114. In some embodiments, there is provided an isolated anti-CD33 sdAb comprising the amino acid sequence SEQ ID NO: 115. In some embodiments, there is provided a polypeptide comprising the amino acid sequence of SEQ ID NO: 115. In some embodiments, there is provided an isolated anti-CD33 sdAb comprising the amino acid sequence SEQ ID NO: 116. In some embodiments, there is provided a polypeptide comprising the amino acid sequence of SEQ ID NO: 116. In some embodiments, there is provided an isolated anti-CD33 sdAb comprising the amino acid sequence SEQ ID NO: 117. In some embodiments, there is provided a polypeptide comprising the amino acid sequence of SEQ ID NO: 117. In some embodiments, there is provided an isolated anti-CD33 sdAb comprising the amino acid sequence SEQ ID NO: 118. In some embodiments, there is provided a polypeptide comprising the amino acid sequence of SEQ ID NO: 118, in some embodiments, there is provided an isolated anti-CD33 sdAb comprising the amino acid sequence SEQ ID NO: 119. In some embodiments, there is provided a polypeptide comprising the amino acid sequence of SEQ ID NO: 119. In some embodiments, there is provided an isolated anti-CD33 sdAb comprising the amino acid sequence SEQ ID NO: 120. In some embodiments, there is provided a polypeptide comprising the amino acid sequence of SEQ ID NO: 120. In some embodiments, there is provided an isolated anti-CD33 sdAb comprising the amino acid sequence SEQ ID NO: 121. In some embodiments, there is provided a polypeptide comprising the amino acid sequence of SEQ ID NO: 121. In some embodiments, there is provided an isolated anti-CD33 sdAb comprising the amino acid sequence SEQ ID NO: 122. In some embodiments, there is provided a polypeptide comprising the amino acid sequence of SEQ ID NO: 122.

In some embodiments, functional epitopes can be mapped by combinatorial alanine scanning. In this process, a combinatorial alanine-scanning strategy can be used to identify amino acids in the CD33 protein that are necessary for interaction with anti-CD33 sdAbs. In some embodiments, the epitope is conformational and crystal structure of anti-CD33 sdAb bound to CD33 may be employed to identify the epitopes.

In some embodiments, the present application provides antibodies (e.g., sdAbs) which compete with any one of the anti-CD33 sdAbs described herein for binding to CD33. In some embodiments, the present application provides antibodies (e.g., sdAbs) which compete with any one of the anti-CD33 sdAbs provided herein for binding to an epitope on the CD33. In some embodiments, an anti-CD33 antibody (e.g., sdAb) is provided that binds to the same epitope as an anti-CD33 sdAb comprising the amino acid sequence of any one of SEQ ID NOs: 108-122, In some embodiments, an anti-CD33 antibody (e.g., sdAbs) is provided that specifically binds to CD33 competitively with an anti-CD33 sdAb comprising the amino acid sequence of any one of SEQ ID NOs: 108-122.

In some embodiments, competition assays may be used to identify a monoclonal antibody that competes with an anti-CD33 sdAb described herein for binding to CD33. Competition assays can be used to determine whether two antibodies bind the same epitope by recognizing identical or sterically overlapping epitopes or one antibody competitively inhibits binding of another antibody to the antigen. In certain embodiments, such a competing antibody binds to the same epitope that is bound by an antibody described herein. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). In some embodiments, two antibodies are said to bind to the same epitope if each blocks binding of the other by 50% or more. In some embodiments, the antibody that competes with an anti-CD33 sdAb described herein is a camelid, chimeric, humanized or human antibody. In some embodiments, the present application provides an antibody that competes with a camelid, chimeric, humanized, or human anti-CD33 sdAb as described herein.

B. Chimeric Receptors and Chimeric Receptor Systems

One aspect of the present application provides a chimeric receptor comprising an extracellular domain comprising one or more anti-CD33 sdAbs (e.g., $V_H$Hs), a transmembrane domain, and an intracellular signaling domain. Also provided is a chimeric receptor system comprising: (a) a first chimeric receptor comprising an extracellular domain comprising an anti-CD33 sdAb (e.g., $V_H$H), a transmembrane domain, and an intracellular signaling domain; and (b) a second chimeric receptor comprising an extracellular domain comprising a binding moiety that specifically binds to a second antigen or epitope. Any one of the anti-CD33 sdAbs described in Section A can be used in the chimeric receptors or chimeric receptor systems described herein. Exemplary structures of chimeric receptors and chimeric receptor systems are shown in FIGS. 10A-10E.

In some embodiments, there is provided a chimeric receptor targeting CD33 (also referred herein as "anti-CD33 chimeric receptor" or "anti-CD33 CAR") comprising: (a) an extracellular domain comprising an anti-CD33 sdAb (such as any one of the anti-CD33 sdAbs described herein); (b) a transmembrane domain; and (c) an intracellular signaling domain. In some embodiments, the anti-CD33 sdAb comprises any one of the following: (1) a CDR1 comprising the amino acid sequence of SEQ ID NO: 4, a CDR2 comprising the amino acid sequence of SEQ ID NO: 6, and a CDR3 comprising the amino acid sequence of SEQ ID NO: 8, or a variant thereof comprising up to about 5 amino acid substitutions in the CDRs; (2) a CDR1 comprising the amino acid sequence of SEQ ID NO: 11, a CDR2 comprising the amino acid sequence of SEQ ID NO: 13, and a CDR3 comprising the amino acid sequence of SEQ ID NO: 15, or a variant thereof comprising up to about 5 amino acid substitutions in the CDRs; (3) a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22, or a variant thereof comprising up to about 5 amino acid substitutions in the CDRs; (4) a CDR1 comprising the amino acid sequence of SEQ ID NO: 25, a CDR2 comprising the amino acid sequence of SEQ ID NO: 27, and a CDR3 comprising the amino acid sequence of SEQ ID NO: 29, or a variant thereof comprising up to about 5 amino acid substitutions in the CDRs; (5) a CDR1 comprising the amino acid sequence of SEQ ID NO: 32, a CDR2 comprising the amino acid sequence of SEQ ID NO: 34, and a CDR3 comprising the amino acid sequence of SEQ ID NO: 36, or a variant thereof comprising up to about 5 amino acid substitutions in the CDRs; (6) a CDR1 comprising the amino acid sequence of SEQ ID NO: 39, a CDR2 comprising the amino acid sequence of SEQ ID NO: 41, and a CDR3 comprising the amino acid sequence of SEQ ID NO: 43, or a variant thereof comprising up to about 5 amino acid substitutions in the CDRs; (7) a CDR1 comprising the amino acid sequence of SEQ ID NO: 46, a CDR2 comprising the amino acid sequence of SEQ ID NO: 48, and a CDR3 comprising the amino acid sequence of SEQ ID NO: 50, or a variant thereof comprising up to about 5 amino acid substitutions in the CDRs; (8) a CDR1 comprising the amino acid sequence of SEQ ID NO: 53, a CDR2 comprising the amino acid sequence of SEQ ID NO: 55, and a CDR3 comprising the amino acid sequence of SEQ ID NO: 57, or a variant thereof comprising up to about 5 amino acid substitutions in the CDRs; (9) a CDR1 comprising the amino acid sequence of SEQ ID NO: 60, a CDR2 comprising the amino acid sequence of SEQ ID NO: 62, and a CDR3 comprising the amino acid sequence of SEQ ID NO: 64, or a variant thereof comprising up to about 5 amino acid substitutions in the CDRs; (10) a CDR1 comprising the amino acid sequence of SEQ ID NO: 67, a CDR2 comprising the amino acid sequence of SEQ ID NO: 69, and a CDR3 comprising the amino acid sequence of SEQ ID NO: 71, or a variant thereof comprising up to about 5 amino acid substitutions in the CDRs; (11) a CDR1 comprising the amino acid sequence of SEQ ID NO: 74, a CDR2 comprising the amino acid sequence of SEQ ID NO: 76, and a CDR3 comprising the amino acid sequence of SEQ ID NO: 78, or a variant thereof comprising up to about 5 amino acid substitutions in the CDRs; (12) a CDR1 comprising the amino acid sequence of SEQ ID NO: 81, a CDR2 comprising the amino acid sequence of SEQ ID NO: 83, and a CDR3 comprising the amino acid sequence of SEQ ID NO: 85, or a variant thereof comprising up to about 5 amino acid substitutions in the CDRs; (13) a CDR1 comprising the amino acid sequence of SEQ ID NO: 88, a CDR2 comprising the amino acid sequence of SEQ ID NO: 90, and a CDR3 comprising the amino acid sequence of SEQ ID NO: 92, or a variant thereof comprising up to about 5 amino acid substitutions in the CDRs; (14) a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99, or a variant thereof comprising up to about 5 amino acid substitutions in the CDRs; or (15) a CDR1 comprising the amino acid sequence of SEQ ID NO: 102, a CDR2 comprising the amino acid sequence of SEQ ID NO: 104, and a CDR3 comprising the amino acid sequence of SEQ ID NO: 106, or a variant thereof comprising up to about 5 amino acid substitutions in the CDRs. In some embodiments, the anti-CD33 sdAb moiety comprises a V$_H$H domain comprising the amino acid sequence of any one of SEQ ID NOs: 108-122, or a variant thereof comprising an amino acid sequence having at least about 95% sequence identity to the amino acid sequence of any one of SEQ ID NOs: 108-122. In some embodiments, the anti-CD33 sdAb moiety is camelid, chimeric, human, or humanized. In some embodiments, the intracellular signaling domain comprises a primary intracellular signaling sequence of an immune effector cell (such as T cell). In some embodiments, the primary intracellular signaling sequence is derived from CD3ζ, FcRγ, FcRβ, CD3γ, CD3δ, CD3ε, CD5, CD22, CD79a, CD79b, or CD66d. In some embodiments, the primary intracellular signaling sequence is derived from CD3ζ (i.e., "a CD3ζ intracellular signaling sequence"). In some embodiments, the intracellular signaling domain comprises an intracellular co-stimulatory sequence. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB. In some embodiments, the intracellular signaling domain comprises both a primary intracellular signaling sequence (e.g., a CD3ζ intracellular signaling sequence) and an intracellular co-stimulatory sequence. In some embodiments, the intracellular signaling domain comprises a primary intracellular signaling sequence but does not comprise an intracellular co-stimulatory sequence. In some embodiments, the intracellular signaling domain comprises an intracellular co-stimulatory sequence but does not comprise a primary intracellular signaling sequence. In some embodiments, the anti-CD33 chimeric receptor further comprises a hinge domain (e.g., a CD8 hinge domain) located between the C-terminus of the extracellular domain and the N-terminus of the transmembrane domain. In some embodiments, the anti-CD33 chimeric receptor further comprises a signal peptide (such as a CD8 signal peptide). In some embodiments, the anti-CD33 chimeric receptor comprises a polypeptide comprising from the N-terminus to the C-terminus: a CD8 signal peptide, the anti-CD33 sdAb moiety, a CD8 hinge domain, a CD8 transmembrane domain, and an intracellular signaling domain comprising an intracellular co-stimulatory sequence derived from 4-1BB or CD28 and a CD3ζ intracellular signaling sequence. In some embodiments, the anti-CD33 chimeric receptor comprises a polypeptide comprising from the N-terminus to the C-terminus: a CD8 signal peptide, the anti-CD33 sdAb moiety, a CD8 hinge domain, a CD8 transmembrane domain, and an intracellular signaling domain comprising a CD3ζ intracellular signaling sequence. In some embodiments, the anti-CD33 chimeric receptor comprises a polypeptide comprising from the N-terminus to the C-terminus: a CD8 signal peptide, the anti-CD33 sdAb moiety, a CD8 hinge domain, a CD8 transmembrane domain, and an intracellular signaling domain comprising an intracellular co-stimulatory sequence derived from 4-1BB or CD28.

In some embodiments, there is provided an anti-CD33 chimeric receptor comprising a polypeptide having at least about any one of 85%, 86%, 87%, 88%, 89%, 90%, 91%, 92%, 93%, 94%, 95%, 96%, 97%, 98%, 99%, or 100% sequence identity to the amino acid sequence of any one of SEQ ID NOs: 155-169. In some embodiments, there is provided an anti-CD33 chimeric receptor comprising a polypeptide comprising the amino acid sequence of any one of SEQ ID NOs: 155-169. Also provided is a polypeptide comprising the amino acid sequence of any one of SEQ ID NOs: 155-169.

In some embodiments, there is provided a chimeric receptor targeting CLL1 comprising: (a) an extracellular domain comprising an anti-CD33 sdAb comprising a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22, or a variant thereof comprising up to about 5 amino acid substitutions in the CDRs; (b) a transmembrane domain; and (c) an intracellular signaling domain. In some embodiments, the anti-CD33 sdAb moiety comprises a V$_H$H domain comprising the amino acid sequence of SEQ ID NO: 110, or a variant thereof comprising an amino acid sequence having at least about 95% sequence identity to the amino acid sequence of SEQ ID NO: 110. In some embodiments, the primary intracellular signaling sequence is derived from CD3ζ. In some embodiments, the intracellular signaling domain comprises an intracellular co-stimulatory sequence. In some embodiments, the anti-CD33 chimeric receptor further comprises a hinge domain (e.g., a CD8 hinge domain) located between the C-terminus of the extracellular domain and the N-terminus of the transmembrane domain. In some embodiments, the anti-CD33 chimeric receptor further comprises a signal peptide (such as a CD8 signal peptide). In some embodiments, the anti-CD33 chimeric receptor comprises a polypeptide comprising from the N-terminus to the C-terminus: a CD8 signal peptide, the anti-CD33 sdAb moiety, a CD8 hinge domain, a CD8 transmembrane domain, and an intracellular signaling domain comprising an intracellular co-stimulatory sequence derived from 4-1BB and a CD3ζ intracellular signaling sequence. In some embodiments, the anti-CD33 chimeric receptor comprises a polypeptide comprising from the N-terminus to the C-terminus: a CD8 signal peptide, the anti-CLL1 sdAb moiety, a CD28 hinge domain, a CD28 transmembrane domain, and an intracellular signaling domain comprising an intracellular co-stimulatory sequence derived from CD28 and a CD3ζ intracellular signaling sequence. In some embodiments, the anti-CD33 chimeric receptor comprises a polypeptide comprising the amino acid sequence of SEQ ID NO: 157, or a variant thereof comprising an amino acid sequence having at least about 95% sequence identity to the amino acid sequence of SEQ ID NO: 157.

In some embodiments, there is provided a chimeric receptor targeting CLL1 comprising: (a) an extracellular domain comprising an anti-CD33 sdAb comprising a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99, or a variant thereof comprising up to about 5 amino acid substitutions in the CDRs; (b) a transmembrane domain; and (c) an intracellular signaling domain. In some embodiments, the anti-CD33 sdAb moiety comprises a V$_H$H domain comprising the amino acid sequence of SEQ ID NO: 121, or a variant thereof comprising an amino acid sequence having at least about 95% sequence identity to the amino acid sequence of SEQ ID NO: 121. In some embodiments, the primary intracellular signaling sequence is derived from CD3ζ. In some embodiments, the intracellular signaling domain comprises an intracellular co-stimulatory sequence.

In some embodiments, the anti-CD33 chimeric receptor further comprises a hinge domain (e.g., a CD8 hinge domain) located between the C-terminus of the extracellular domain and the N-terminus of the transmembrane domain. In some embodiments, the anti-CD33 chimeric receptor further comprises a signal peptide (such as a CD8 signal peptide). In some embodiments, the anti-CD33 chimeric receptor comprises a polypeptide comprising from the N-terminus to the C-terminus: a CD8 signal peptide, the anti-CD33 sdAb moiety, a CD8 hinge domain, a CD8 transmembrane domain, and an intracellular signaling domain comprising an intracellular co-stimulatory sequence derived from 4-1BB and a CD3ζ intracellular signaling sequence. In some embodiments, the anti-CD33 chimeric receptor comprises a polypeptide comprising from the N-terminus to the C-terminus: a CD8 signal peptide, the anti-CLL1 sdAb moiety, a CD28 hinge domain, a CD28 transmembrane domain, and an intracellular signaling domain comprising an intracellular co-stimulatory sequence derived from CD28 and a CD3ζ intracellular signaling sequence. In some embodiments, the anti-CD33 chimeric receptor comprises a polypeptide comprising the amino acid sequence of SEQ ID NO: 168, or a variant thereof comprising an amino acid sequence having at least about 95% sequence identity to the amino acid sequence of SEQ ID NO: 168.

In some embodiments, there is provided a chimeric receptor targeting CLL1 comprising: (a) an extracellular domain comprising an anti-CD33 sdAb comprising a CDR1 comprising the amino acid sequence of SEQ ID NO: 4, a CDR2 comprising the amino acid sequence of SEQ ID NO: 6, and a CDR3 comprising the amino acid sequence of SEQ ID NO: 8, or a variant thereof comprising up to about 5 amino acid substitutions in the CDRs; (b) a transmembrane domain; and (c) an intracellular signaling domain. In some embodiments, the anti-CD33 sdAb moiety comprises a $V_HH$ domain comprising the amino acid sequence of SEQ ID NO: 108, or a variant thereof comprising an amino acid sequence having at least about 95% sequence identity to the amino acid sequence of SEQ ID NO: 108. In some embodiments, the primary intracellular signaling sequence is derived from CD3ζ. In some embodiments, the intracellular signaling domain comprises an intracellular co-stimulatory sequence. In some embodiments, the anti-CD33 chimeric receptor further comprises a hinge domain (e.g., a CD8 hinge domain) located between the C-terminus of the extracellular domain and the N-terminus of the transmembrane domain. In some embodiments, the anti-CD33 chimeric receptor further comprises a signal peptide (such as a CD8 signal peptide). In some embodiments, the anti-CD33 chimeric receptor comprises a polypeptide comprising from the N-terminus to the C-terminus: a CD8 signal peptide, the anti-CD33 sdAb moiety, a CD8 hinge domain, a CD8 transmembrane domain, and an intracellular signaling domain comprising an intracellular co-stimulatory sequence derived from 4-1BB and a CD3ζ intracellular signaling sequence. In some embodiments, the anti-CD33 chimeric receptor comprises a polypeptide comprising the amino acid sequence of SEQ ID NO: 155, or a variant thereof comprising an amino acid sequence having at least about 95% sequence identity to the amino acid sequence of SEQ ID NO: 155.

In some embodiments, there is provided a chimeric receptor targeting CLL1 comprising: (a) an extracellular domain comprising an anti-CD33 sdAb comprising a CDR1 comprising the amino acid sequence of SEQ ID NO: 11, a CDR2 comprising the amino acid sequence of SEQ ID NO: 13, and a CDR3 comprising the amino acid sequence of SEQ ID NO: 15, or a variant thereof comprising up to about 5 amino acid substitutions in the CDRs; (b) a transmembrane domain; and (c) an intracellular signaling domain. In some embodiments, the anti-CD33 sdAb moiety comprises a $V_HH$ domain comprising the amino acid sequence of SEQ ID NO: 109, or a variant thereof comprising an amino acid sequence having at least about 95% sequence identity to the amino acid sequence of SEQ ID NO: 109. In some embodiments, the primary intracellular signaling sequence is derived from CD3ζ. In some embodiments, the intracellular signaling domain comprises an intracellular co-stimulatory sequence. In some embodiments, the anti-CD33 chimeric receptor further comprises a hinge domain (e.g., a CD8 hinge domain) located between the C-terminus of the extracellular domain and the N-terminus of the transmembrane domain. In some embodiments, the anti-CD33 chimeric receptor further comprises a signal peptide (such as a CD8 signal peptide). In some embodiments, the anti-CD33 chimeric receptor comprises a polypeptide comprising from the N-terminus to the C-terminus: a CD8 signal peptide, the anti-CD33 sdAb moiety, a CD8 hinge domain, a CD8 transmembrane domain, and an intracellular signaling domain comprising an intracellular co-stimulatory sequence derived from 4-1BB and a CD3ζ intracellular signaling sequence. In some embodiments, the anti-CD33 chimeric receptor comprises a polypeptide comprising from the N-terminus to the C-terminus: a CD8 signal peptide, the anti-CLL1 sdAb moiety, a CD28 hinge domain, a CD28 transmembrane domain, and an intracellular signaling domain comprising an intracellular co-stimulatory sequence derived from CD28 and a CD3ζ intracellular signaling sequence. In some embodiments, the anti-CD33 chimeric receptor comprises a polypeptide comprising the amino acid sequence of SEQ ID NO: 156, or a variant thereof comprising an amino acid sequence having at least about 95% sequence identity to the amino acid sequence of SEQ ID NO: 156.

Exemplary anti-CD33 chimeric receptors are shown in Table 3 below.

TABLE 3

Exemplary anti-CD33 Chimeric Receptors.

| CAR SEQ ID NO. | SP | Extra-cellular. sdAb | Hinge | TM | Intracellular signaling Co-stimulatory | Primary signaling |
|---|---|---|---|---|---|---|
| 155 | CD8α | AS49175 | CD8α | CD8α | 4-1BB | CD3ζ |
| 156 | CD8α | AS49226 | CD8α | CD8α | 4-1BB | CD3ζ |
| 157 | CD8α | AS49264 | CD8α | CD8α | 4-1BB | CD3ζ |
| 158 | CD8α | AS49814 | CD8α | CD8α | 4-1BB | CD3ζ |
| 159 | CD8α | AS49873 | CD8α | CD8α | 4-1BB | CD3ζ |
| 160 | CD8α | AS49889 | CD8α | CD8α | 4-1BB | CD3ζ |
| 161 | CD8α | AS49902 | CD8α | CD8α | 4-1BB | CD3ζ |
| 162 | CD8α | AS50073 | CD8α | CD8α | 4-1BB | CD3ζ |
| 163 | CD8α | AS50502 | CD8α | CD8α | 4-1BB | CD3ζ |
| 164 | CD8α | AS66873 | CD8α | CD8α | 4-1BB | CD3ζ |
| 165 | CD8α | AS60399 | CD8α | CD8α | 4-1BB | CD3ζ |
| 166 | CD8α | AS59101 | CD8α | CD8α | 4-1BB | CD3ζ |
| 167 | CD8α | AS58930 | CD8α | CD8α | 4-1BB | CD3ζ |
| 168 | CD8α | AS67190 | CD8α | CD8α | 4-1BB | CD3ζ |
| 169 | CD8α | AS67147 | CD8α | CD8α | 4-1BB | CD3ζ |

(AS49175 CAR amino acid sequence)
SEQ ID NO: 155
MALPVTALLLPLALLLHAARPEVQLAESGGGLVQAGGSLRLSCTASGFTFDDYVMGWFRQAPG
KEREGVSCISWSGDTTYYADSVKGRFTASRDNAKNTLYLQMNSLKPEDTAMYYCAADQGKCSL
ASAEPDDMDYWGRGTLVTVSSTTTPAPRPPTPAPTIASQPLSLRPEACRPAAGGAVHTRGLDFAC
DIYIWAPLAGTCGVLLLSLVITLYCKRGRKKLLYIFKQPFMRPVQTTQEEDGCSCRFPEEEEGGCE
LRVKFSRSADAPAYKQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR (AS49226 CAR amino acid sequence)
SEQ ID NO: 156
MALPVTALLLPLALLLHAARPEVQLAESGGGSVQAGGSLRLSCAASGVTFSSTSVAWFRQAPGK
EREGVAYIYTGDSSTYYADSVKGRFTIAQDNAKNAVYLQMNSLKPEDTAMYYCAADGFLLNHR
SYQYWGQGTQVTVSSTTTPAPRPPTPAPTIASQPLSLRPEACRPAAGGAVHTRGLDFACDIYIWA
PLAGTCGVLLLSLVITLYCKRGRKKLLYIFKQPFMRPVQTTQEEDGCSCRFPEEEEGGCELRVKFS
RSADAPAYKQGQNQLYNELNLGRREEYDVLDKRRGRDPEMGGKPRRKNPQEGLYNELQKDKM
AEAYSEIGMKGERRRGKGHDGLYQGLSTATKDTYDALHMQALPPR (AS49264 CAR amino acid sequence)
SEQ ID NO: 157
MALPVTALLLPLALLLHAARPEVQLVESGGGSVQAGGSLRLSCAASGYTYSINCMGWFRQAPG
KEREGVAVISTGGGRTDYRDSVKGRFTISQDNAKNTVYLQMNSLKPEDTAMYYCAGKTTYPGY
GCGLGRSAYNYWGQGTQVTVSSTTTPAPRPPTPAPTIASQPLSLRPEACRPAAGGAVHTRGLDFA
CDIYIWAPLAGTCGVLLLSLVITLYCKRGRKKLLYIFKQPFMRPVQTTQEEDGCSCRFPEEEEGGC
ELRVKFSRSADAPAYKQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (AS49814 CAR amino acid sequence)
SEQ ID NO: 158
MALPVTALLLPLALLLHAARPQIQLVESGGGSVQAGGSLRLSCVASGYIGGHYYMGWFRQAPG
KEREGVAAIDIDSDGRTRYAGSVQGRFTISQDNAKNTLHLQMSSLKPEDTGMYYCAVGVGWVP
ARLTPQAVSYWGKGTLVTVSSTTTPAPRPPTPAPTIASQPLSLRPEACRPAAGGAVHTRGLDFAC
DIYIWAPLAGTCGVLLLSLVITLYCKRGRKKLLYIFKQPFMRPVQTTQEEDGCSCRFPEEEEGGCE
LRVKFSRSADAPAYKQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR (AS49873 CAR amino acid sequence)
SEQ ID NO: 159
MALPVTALLLPLALLLHAARPEVQLVESGGGSVQAGGSLRLSCVASGYTYGINCMGWFRQAPG
KEREGIAAISTGGGTTGVADSVKGRFTISQDNAKNTVYLQMNSLKPEDTAMYYCAARSTYSGYA
CVYSEVNGYNYRGQGTQVTVSSTTTPAPRPPTPAPTIASQPLSLRPEACRPAAGGAVHTRGLDFA
CDIYIWAPLAGTCGVLLLSLVITLYCKRGRKKLLYIFKQPFMRPVQTTQEEDGCSCRFPEEEEGGC
ELRVKFSRSADAPAYKQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (AS49889 CAR amino acid sequence)
SEQ ID NO: 160
MALPVTALLLPLALLLHAARPEVQLVESGGGSVQAGGSLRLSCVASGYTWCRYDMSWYRQAP
GKEREFVSGFDNDGTTSYADSVKGRFTISQDNDKNTVYLQMNSLKPEDTAMYYCKEDRSRGSL
DGRVCPLSYDNWGQGTQVTVSSTTTPAPRPPTPAPTIASQPLSLRPEACRPAAGGAVHTRGLDFA
CDIYIWAPLAGTCGVLLLSLVITLYCKRGRKKLLYIFKQPFMRPVQTTQEEDGCSCRFPEEEEGGC
ELRVKFSRSADAPAYKQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (AS49902 CAR amino acid sequence)
SEQ ID NO: 161
MALPVTALLLPLALLLHAARPEVQLVESGGGLVQAGGSLRLSCTASGFTFDDYVMGWFRQAPG
KEREGVSCISWSGDTTYYADSVKGRFTVSRDNAKNTLYLQMNSLKPEDTAMYYCAADQSLCSL
APPYNYAYWGQGTQVTVSSTTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSCRFPEEEEGGCEL
RVKFSRSADAPAYKQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR (AS50073 CAR amino acid sequence)
SEQ ID NO: 162
MALPVTALLLPLALLLHAARPQVQLVESGGGLVQAGGSLRLSCTASGFTFDNYVMGWFRQAPG
KEREGVSCIGWSGGSTYYADSVKGRFTISRDNAKNTLYLQMNSLKPEDTAMYYCAADQGKCSL
GSAGADDMDYWGRGTLVTVSSTTTPAPRPPTPAPTIASQPLSLRPEACRPAAGGAVHTRGLDFA
CDIYIWAPLAGTCGVLLLSLVITLYCKRGRKKLLYIFKQPFMRPVQTTQEEDGCSCRFPEEEEGGC
ELRVKFSRSADAPAYKQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (AS50502 CAR amino acid sequence)
SEQ ID NO: 163
MALPVTALLLPLALLLHAARPEVQLVESGGGSVQAGGSLRLSCAAPGYTYCTYDMMWYRQAL
GKEREFVSAVYTDGSTLYADSVKGRFTISQDNAKNTVYLQMNSLKPEDTAMYYCKTETAVTYD
KPCDFWGQGTQVTVSSTTTPAPRPPTPAPTIASQPLSLRPEACRPAAGGAVHTRGLDFACDIYIW
APLAGTCGVLLLSLVITLYCKRGRKKLLYIFKQPFMRPVQTTQEEDGCSCRFPEEEEGGCELRVK
FSRSADAPAYKQGQNQLYNELNLGRREEYDVLDKRRGRDPEMGGKPRRKNPQEGLYNELQKD
KMAEAYSEIGMKGERRRGKGHDGLYQGLSTATKDTYDALHMQALPPR

```
(AS66873 CAR amino acid sequence)
                                                  SEQ ID NO: 164
MALPVTALLLPLALLLHAARPQVQLVESGGGLVQPGGSLRLSCAASGSIFSITAMGWYRQAPGK
QRELVATVTSGGSTKYVESVKGRFTISNDNAKNTVYLQMNSLKPEDTAVYYCWADIVARWNSD
YNVYDDYWGQGTQVTVSSTTTPAPRPPTPAPTIASQPLSLRPEACRPAAGGAVHTRGLDFACDIY
IWAPLAGTCGVLLLSLVITLYCKRGRKKLLYIFKQPFMRPVQTTQEEDGCSCRFPEEEEGGCELR
VKFSRSADAPAYKQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPR (AS60399 CAR amino acid sequence)
                                                  SEQ ID NO: 165
MALPVTALLLPLALLLHAARPQVKLEESGGGLVQEGGSLRLSCAASGTIYTDSTIYWYRQAPGK
QRELVASITRGGDTKYVDSVKGRFAISSDNAKNTVYLQMNSLKPEDTAVYYCNLYYRTGPSSYY
RNDWGQGTQVTVSSTTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCCRFPEEEEGGCELRVKFS
RSADAPAYKQGQNQLYNELNLGRREEYDVLDKRRGRDPEMGGKPRRKNPQEGLYNELQKDKM
AEAYSEIGMKGERRRGKGHDGLYQGLSTATKDTYDALHMQALPPR (AS59101 CAR amino acid sequence)
                                                  SEQ ID NO: 166
MALPVTALLLPLALLLHAARPAVQLVESGGGLVQPGGSLRLSCAVSGIYYSINLMGWYRQAPGK
PRELAASITDSGITNYADSVKGRFTISRDNAKNTVHLQMNNLKPEDTAVYYCKPMGVNWGQGI
QVTVSSTTTPAPRPPTPAPTIASQPLSLRPEACRPAAGGAVHTRGLDFACDIYIWAPLAGTCGVLL
LSLVITLYCKRGRKKLLYIFKQPFMRPVQTTQEEDGCSCRFPEEEEGGCELRVKFSRSADAPAYK
QGQNQLYNELNLGRREEYDVLDKRRGRDPEMGGKPRRKNPQEGLYNELQKDKMAEAYSEIGM
KGERRRGKGHDGLYQGLSTATKDTYDALHMQALPPR (AS58930 CAR amino acid sequence)
                                                  SEQ ID NO: 167
MALPVTALLLPLALLLHAARPAVQLVESGGGLVQAGGSLRLSCTASGSILRTYEMGWYRQAPGS
QRELVASITSDGDTNYVDSVKGRFTISRDNGKNMVYLQMNSLKPDDTAVYYCNAVILSPSYSMR
TSHWGQGTQVTVSSTTTPAPRPPTPAPTIASQPLSLRPEACRPAAGGAVHTRGLDFACDIYIWAPL
AGTCGVLLLSLVITLYCKRGRKKLLYIFKQPFMRPVQTTQEEDGCSCRFPEEEEGGCELRVKFSRS
ADAPAYKQGQNQLYNELNLGRREEYDVLDKRRGRDPEMGGKPRRKNPQEGLYNELQKDKMA
EAYSEIGMKGERRRGKGHDGLYQGLSTATKDTYDALHMQALPPR (AS67190 CAR amino acid sequence)
                                                  SEQ ID NO: 168
MALPVTALLLPLALLLHAARPQVQLVESGGGLVQAGGSLRLSCAASGNVFRFNIMGWYRQAPG
NQRELVASIDDGGDRSYADSVEGRFTISRENGKKIMYLQMNSLKPEDTAVYYCAAGLGTYLNG
RVSMATNYWGQGTQVTVSSTTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSCRFPEEEEGGCEL
RVKFSRSADAPAYKQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR (AS67147 CAR amino acid sequence)
                                                  SEQ ID NO: 169
MALPVTALLLPLALLLHAARPEVQLVESGGGLVQAGGSLRLSCAASGDTFSFAAMGWYRQAPG
KQRELVASISFSGGESTVYANSVRGRFTISGDNAKNRVSLEMNNLKPEDTAVYYCTAKRGPYLP
GPEYWGQGTQVTVSSTTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEEEEGGCELRVKFS
RSADAPAYKQGQNQLYNELNLGRREEYDVLDKRRGRDPEMGGKPRRKNPQEGLYNELQKDKM
AEAYSEIGMKGERRRGKGHDGLYQGLSTATKDTYDALHMQALPPR
```

Multivalent Chimeric Receptors

The present application also provides multivalent anti-CD33 chimeric receptors that have two or more (such as about any one of 2, 3, 4, 5, 6, or more) binding moieties that specifically bind to CD33. In some embodiments, one or more of the binding moieties are antigen binding fragments. In some embodiments, one or more of the binding moieties comprise sdAbs. In some embodiments, one or more of the binding moieties are derived from camelid antibodies. In some embodiments, one or more of the binding moieties are derived from a four-chain antibody. In some embodiments, one or more of the binding moieties are scFvs. In some embodiments, one or more of the binding moieties are derived from human antibodies. In some embodiments, one or more of the binding moieties are extracellular domains of receptors, polypeptide ligands or other non-antibody polypeptides that specifically bind to CD33. In some embodiments, the multivalent chimeric receptor is monospecific, i.e., the multivalent chimeric receptor only targets CD33, and comprises two or more binding sites for CD33. In some embodiments, the multivalent chimeric receptor is multispecific, i.e., the multivalent chimeric receptor targets more than one antigen or epitope. The binding moieties specific for the same antigen may bind to the same epitope of the antigen (i.e., "mono-epitope chimeric receptor") or bind to different epitopes (i.e., "multi-epitope chimeric receptor" such as bi-epitope chimeric receptor or tri-epitope chimeric receptor) of the antigen. The binding sites specific for the same antigen may comprise the same or different sdAbs.

In some embodiments, the present application provides a multivalent (such as bivalent, trivalent, or of higher number of valencies) chimeric receptor comprising: (a) an extracellular domain comprising a plurality (such as at least about any one of 2, 3, 4, 5, 6, or more) of binding moieties specifically binding to CD33; (b) a transmembrane domain; and (c) an intracellular signaling domain.

In some embodiments, the present application provides a multivalent (such as bivalent, trivalent, or of higher number of valencies) chimeric receptor comprising: (a) an extracellular domain comprising a plurality (such as at least about any one of 2, 3, 4, 5, 6, or more) of anti-CD33 sdAb moieties; (b) a transmembrane domain; and (c) an intracellular signaling domain.

In some embodiments, the present application provides a multivalent (such as bivalent, trivalent, or of higher number of valencies) chimeric receptor comprising: (a) an extracellular domain comprising an sdAb moiety specifically binding to a first epitope of CD33, and a second binding moiety (e.g., sdAb or scFv) specifically binding to a second epitope of CD33; (b) a transmembrane domain; and (c) an intracellular signaling domain, wherein the first epitope and the second epitope are different. In some embodiments, the first anti-CD33 sdAb is located at the N-terminus of the second CD33 binding moiety (e.g., the second anti-CD33 sdAb). In some embodiments, the first anti-CD33 sdAb is located at the C-terminus of the second CD33 binding moiety (e.g., the second anti-CD33 sdAb). In some embodiments, the multivalent chimeric receptor specifically binds to two different epitopes on CD33. In some embodiments, the multivalent chimeric receptor specifically binds to three or more different epitopes on CD33.

In some embodiments, the binding moieties, such as sdAbs (including the plurality of sdAbs, or the first sdAb and/or the second sdAb) are camelid, chimeric, human, or humanized. In some embodiments, the binding moieties or sdAbs are fused to each other via peptide bonds or peptide linkers. In some embodiments, each peptide linker is no more than about 50 (such as no more than about any one of 35, 25, 20, 15, 10, or 5) amino acids long. In some embodiments, the transmembrane domain is selected from the group consisting of CD8α, CD4, CD28, 4-1BB, CD80, CD86, CD152 and PD1. In some embodiments, the intracellular signaling domain comprises a primary intracellular signaling sequence of an immune effector cell (such as T cell). In some embodiments, the primary intracellular signaling sequence is derived from CD3ζ, FcRγ, FcRβ, CD3γ, CD3δ, CD3ε, CD5, CD22, CD79a, CD79b, or CD66d. In some embodiments, the primary intracellular signaling sequence is derived from CD3ζ. In some embodiments, the intracellular signaling domain comprises an intracellular co-stimulatory sequence. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB. In some embodiments, the multivalent chimeric receptor further comprises a hinge domain (such as a CD8 hinge domain) located between the C-terminus of the extracellular domain and the N-terminus of the transmembrane domain. In some embodiments, the multivalent chimeric receptor further comprises a signal peptide (such as a CD8 signal peptide). In some embodiments, the anti-CD33 chimeric receptor comprises a polypeptide comprising from the N-terminus to the C-terminus: a CD8 signal peptide, the extracellular domain, a CD8 hinge domain, a CD8 transmembrane domain, and an intracellular signaling domain comprising an intracellular co-stimulatory sequence derived from 4-1BB or CD28 and a CD3ζ intracellular signaling sequence. In some embodiments, the multivalent chimeric receptor is monospecific. In some embodiments, the multivalent chimeric receptor is multispecific, such as bispecific.

The multivalent chimeric receptors describe herein may be specially suitable for targeting multimeric antigens via synergistic binding by the different antigen binding sites, or for enhancing binding affinity or avidity to the antigen. Any of the anti-CD33 sdAbs described herein may be used in the extracellular domain of the multivalent chimeric receptors described herein.

Multispecific Chimeric Receptor

The present application further provides multispecific chimeric receptors targeting two or more (such as about any one of 2, 3, 4, 5, 6, or more) different antigens. In some embodiments, the multispecific chimeric receptor has one antigen binding site for each antigen. In some embodiments, the multispecific chimeric receptor has more than two binding sites for at least one antigen. Each antigen binding site may comprise an sdAb. In some embodiments, the multispecific chimeric receptor is a bispecific chimeric receptor. In some embodiments, the multispecific chimeric receptor is a trispecific chimeric receptor.

In some embodiments, there is provided a multispecific (such as bispecific) chimeric receptor comprising: (a) an extracellular domain comprising an anti-CD33 sdAb (such as any one of the anti-CD33 sdAbs described herein) and a second binding domain that specifically binds to a second antigen or epitope; (b) a transmembrane domain; and (c) an intracellular signaling domain.

In some embodiments, there is provided a multispecific (such as bispecific) chimeric receptor comprising: (a) an extracellular domain comprising an anti-CD33 sdAb (such as any one of the anti-CD33 sdAbs described herein) and a second sdAb that specifically binds to a second antigen or epitope; (b) a transmembrane domain; and (c) an intracellular signaling domain.

In some embodiments, there is provided a multispecific (such as bispecific) chimeric receptor comprising: (a) an extracellular domain comprising an anti-CD33 sdAb (such as any one of the anti-CD33 sdAbs described herein) and an scFv that specifically binds to a second antigen; (b) a transmembrane domain; and (c) an intracellular signaling domain.

In some embodiments, there is provided a multispecific (such as bispecific) chimeric receptor comprising: (a) an extracellular domain comprising an anti-CD33 sdAb (such as any one of the anti-CD33 sdAbs described herein) and an extracellular domain of a receptor that specifically binds to a second antigen; (b) a transmembrane domain; and (c) an intracellular signaling domain.

In some embodiments, the second antigen is selected from the group consisting of NKG2D ligands, CLL1, WT1, CS1, CD123, Folate Receptor β, FLT3R, B7H6, TIM3, MUC1, c-kit, CD44v6, Lewis-Y, CD99, CD27 and CD70. In some embodiments, the anti-CD33 sdAb and/or the second binding moiety (including second sdAb, or scFv) is camelid, chimeric, human, or humanized. In some embodiments, the anti-CD33 sdAb and the second binding moiety (including second sdAb, scFv, or an extracellular domain of a receptor) are fused to each other via a peptide bond or a peptide linker. In some embodiments, the peptide linker is no more than about 50 (such as no more than about any one of 35, 25, 20, 15, 10, or 5) amino acids long. In some embodiments, the transmembrane domain is selected from the group consisting of CD8α, CD4, CD28, 4-1BB, CD80, CD86, CD152 and PD1. In some embodiments, the intracellular signaling domain comprises a primary intracellular signaling sequence of an immune effector cell (such as T cell). In some embodiments, the primary intracellular signaling sequence is derived from CD3ζ, FcRγ, FcRβ, CD3γ, CD3δ, CD3ε, CD5, CD22, CD79a, CD79b, or CD66d. In some embodiments, the primary intracellular signaling sequence is derived from CD3ζ. In some embodiments, the intracellular signaling domain comprises an intracellular co-stimulatory sequence. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB. In some embodiments, the multispecific chimeric receptor further comprises a hinge domain (such as a CD8 hinge domain) located between the C-terminus of the extracellular domain and the N-terminus of the transmembrane domain. In some embodiments, the multispecific chimeric receptor further comprises a signal peptide (such as a CD8 signal peptide). In some embodiments, the multispecific chimeric receptor comprises a polypeptide comprising from the N-terminus to the C-terminus: a CD8 signal peptide, the extracellular domain, a CD8 hinge domain, a CD8 transmembrane domain, and an intracellular signaling domain comprising an intracellular co-stimulatory sequence derived from 4-1BB or CD28 and a CD3ζ intracellular signaling sequence.

In some embodiments, there is provided a multispecific (e.g., bispecific) chimeric receptor comprising: (a) an extracellular domain comprising an anti-CD33 sdAb (such as any one of the anti-CD33 sdAbs described herein) and an anti-CLL1 sdAb or scFv; (b) a transmembrane domain, and (c) an intracellular domain comprising an intracellular co-stimulatory sequence derived from 4-1BB or CD28 and a CD3ζ intracellular signaling sequence.

In some embodiments, there is provided a multispecific (e.g., bispecific) chimeric receptor comprising: (a) an extracellular domain comprising an anti-CD33 sdAb and an anti-CLL1 sdAb; (b) a transmembrane domain (e.g., a CD28 transmembrane domain), and (c) an intracellular domain (e.g., an intracellular signaling domain comprising an intracellular co-stimulatory sequence derived from CD28 and a CD3ζ intracellular signaling sequence), wherein the anti-CD33 sdAb comprises: a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22, or a variant thereof comprising up to about 5 amino acid substitutions in the CDRs; and wherein the anti-CLL1 sdAb comprises: a CDR1 comprising the amino acid sequence of SEQ ID NO: 189, a CDR2 comprising the amino acid sequence of SEQ ID NO: 191, and a CDR3 comprising the amino acid sequence of SEQ ID NO: 193, or a variant thereof comprising up to about 5 amino acid substitutions in the CDRs. In some embodiments, the anti-CD33 sdAb is at the N-terminus of the anti-CLL1 sdAb. In some embodiments, the anti-CD33 sdAb is at the C-terminus of the anti-CLL1 sdAb. In some embodiments, the anti-CD33 sdAb moiety comprises a $V_HH$ domain comprising the amino acid sequence of SEQ ID NO: 110, or a variant thereof comprising an amino acid sequence having at least about 95% sequence identity to the amino acid sequence of SEQ ID NO: 110. In some embodiments, the anti-CLL1 sdAb moiety comprises a $V_HH$ domain comprising the amino acid sequence of SEQ ID NO: 209, or a variant thereof comprising an amino acid sequence having at least about 95% sequence identity to the amino acid sequence of SEQ ID NO: 209. In some embodiments, the multispecific chimeric receptor comprises a polypeptide comprising from the N-terminus to the C-terminus: a CD8 signal peptide, the extracellular domain, a CD28 hinge domain, a CD28 transmembrane domain, and an intracellular signaling domain comprising an intracellular co-stimulatory sequence derived from CD28 and a CD3ζ intracellular signaling sequence.

In some embodiments, there is provided a multispecific (e.g., bispecific) chimeric receptor comprising: (a) an extracellular domain comprising an anti-CD33 sdAb and an anti-CLL1 sdAb, wherein the C-terminus of the anti-CLL1 sdAb is fused to the N-terminus of the anti-CD33 sdAb via a peptide linker; (b) a transmembrane domain (e.g., a CD28 transmembrane domain), and (c) an intracellular domain (e.g., an intracellular domain comprising an intracellular co-stimulatory sequence derived from CD28 and a CD3ζ intracellular signaling sequence), wherein the anti-CD33 sdAb comprises: a CDR1 comprising the amino acid sequence of SEQ ID NO: 11, a CDR2 comprising the amino acid sequence of SEQ ID NO: 13, and a CDR3 comprising the amino acid sequence of SEQ ID NO: 15; and wherein the anti-CLL1 sdAb comprises: a CDR1 comprising the amino acid sequence of SEQ ID NO: 189, a CDR2 comprising the amino acid sequence of SEQ ID NO: 191, and a CDR3 comprising the amino acid sequence of SEQ ID NO: 193. In some embodiments, the peptide linker comprises the amino acid sequence of SEQ ID NO: 147. In some embodiments, the peptide linker comprises the amino acid sequence of SEQ ID NO: 149. In some embodiments, the peptide linker comprises the amino acid sequence of SEQ ID NO: 182. In some embodiments, the anti-CD33 sdAb moiety comprises a $V_HH$ domain comprising the amino acid sequence of SEQ ID NO: 109, or a variant thereof comprising an amino acid sequence having at least about 95% sequence identity to the amino acid sequence of SEQ ID NO: 109. In some embodiments, the anti-CLL1 sdAb moiety comprises a $V_HH$ domain comprising the amino acid sequence of SEQ ID NO: 209, or a variant thereof comprising an amino acid sequence having at least about 95% sequence identity to the amino acid sequence of SEQ ID NO: 209. In some embodiments, the multispecific chimeric receptor comprises a polypeptide comprising from the N-terminus to the C-terminus: a CD8 signal peptide, the extracellular domain, a CD28 hinge domain, a CD28 transmembrane domain, and an intracellular signaling domain comprising an intracellular co-stimulatory sequence derived from CD28 and a CD3ζ intracellular signaling sequence. In some embodiments, the multispecific chimeric receptor comprises an amino acid sequence having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 170. In some embodiments, the multispecific chimeric receptor comprises an amino acid sequence having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 171. In some embodiments, the multispecific chimeric receptor comprises an amino acid sequence having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 174.

In some embodiments, there is provided a multispecific (e.g., bispecific) chimeric receptor comprising a polypeptide having at least about any one of 85%, 86%, 87%, 88%, 89%, 90%, 91%, 92%, 93%, 94%, 95%, 96%, 97%, 98%, 99%, or 100% sequence identity to the amino acid sequence of any one of SEQ ID NOs: 170-181. In some embodiments, there is provided a multispecific (e.g., bispecific) chimeric receptor comprising a polypeptide comprising the amino acid sequence of any one of SEQ ID NOs: 170-181. Also provided is a polypeptide comprising the amino acid sequence of any one of SEQ ID NOs: 170-181.

Exemplary anti-CD33 tandem chimeric receptors are shown in Table 4 below.

TABLE 4

Exemplary anti-CD33 Tandem Chimeric Receptors.

| CAR SEQ ID NO. | SF | Extra-cellular.1 | Linker | Extra-cellular.2 | Hinge | TM | Intracellular signaling Co-stimulatory | Intracellular signaling Primary signaling |
|---|---|---|---|---|---|---|---|---|
| 170 | CD8α | AS82658 | Linker-1 | AS49264 | CD28 | CD28 | CD28 | CD3ζ |
| 171 | CD8α | AS82658 | Linker-2 | AS49264 | CD28 | CD28 | CD28 | CD3ζ |
| 172 | CD8α | AS82658 | Linker-3 | AS49264 | CD28 | CD28 | CD28 | CD3ζ |
| 173 | CD8α | AS82658 | Linker-4 | AS49264 | CD28 | CD28 | CD28 | CD3ζ |
| 174 | CD8α | AS82658 | Linker-5 | AS49264 | CD28 | CD28 | CD28 | CD3ζ |
| 175 | CD8α | AS82658 | Linker-6 | AS49264 | CD28 | CD28 | CD28 | CD3ζ |
| 176 | CD8α | AS49264 | Linker-1 | AS82658 | CD28 | CD28 | CD28 | CD3ζ |
| 177 | CD8α | AS49264 | Linker-2 | AS82658 | CD28 | CD28 | CD28 | CD3ζ |
| 178 | CD8α | AS49264 | Linker-3 | AS82658 | CD28 | CD28 | CD28 | CD3ζ |
| 179 | CD8α | AS49264 | Linker-4 | AS82658 | CD28 | CD28 | CD28 | CD3ζ |
| 180 | CD8α | AS49264 | Linker-5 | AS82658 | CD28 | CD28 | CD28 | CD3ζ |
| 181 | CD8α | AS49264 | Linker-6 | AS82658 | CD28 | CD28 | CD28 | CD3ζ |

Any suitable anti-CLL1 sdAb or scFv may be used for the multispecific chimeric receptor targeting CD33 and CLL1 described herein. Exemplary anti-CLL1 sdAbs have been described, for example, see, PCT/CN2018/104883. Sequences of exemplary anti-CLL1 sdAbs are shown in Table 5 below.

TABLE 5

Exemplary anti-CLL sdAbs.

| sdAb/ SEQ ID (AA) | FR1/ SEQ ID NO | CDR1/ SEQ ID | FR2/ SEQ ID | CDR2/ SEQ ID | FR3/ SEQ ID NO | CDR3/ SEQ ID | FR4/ SEQ ID |
|---|---|---|---|---|---|---|---|
| AS82658 209 | QVQLVESGGGSV QAGGALSLSCAA S 188 | GYTVRID YMG 189 | WYRQTP GKGREPV A 190 | TIASNGG TAYADS VEG 191 | RFTISQDNAKNSV YLQMNTLKPGDT AMYYCAA 192 | GTWPTLT Y 193 | FGQGT QVTVS S 194 |
| AS82472 210 | QVQLVESGGDLV RPGGSLRLSCAA S 195 | GFTFSIY DMN 196 | WVRQAP GKGLEW VA 197 | GISGNGY STSYAES VKG 198 | RFTISRDNAKNTV YLQLSSLKFEDTA MYYCVR 199 | DAERWD ENDLRR 200 | KGQGT QVTVS S 201 |
| AS82494 211 | QVQLVESGGGLV QPGGSLRLSCAA S 202 | GFTFSVY DMN 203 | WFRQAP GKGLEW VS 204 | GITGNGY TTSY ADS VKG 205 | RFTISRDNAKNTL YLQLNSLKSEDTA MYYCAK 206 | ETN 207 | RGQGT QVTVS S 208 |

(AS82658 sdAb amino acid sequence; CDRs are underlined)

SEQ ID NO: 209
QVQLVESGGGSVQAGGALSLSCAASGYTVRIDYMGWYRQTPGKGREPVA
TIASNGGTAYADSVEGRFTISQDNAKNSVYLQMNTLKPGDTAMYYCAAG
TWPTLTYFGQGTQVTVSS (AS82472 sdAb amino acid sequence; CDRs are underlined)

SEQ ID NO: 210
QVQLVESGGDLVRPGGSLRLSCAASGFTFSIYDMNWVRQAPGKGLEWVA
GISGNGYSTSYAESVKGRFTISRDNAKNTVYLQLSSLKFEDTAMYYCVR
DAERWDENDLRRKGQGTQVTVSS (AS82494 sdAb amino acid sequence; CDRs are underlined)

SEQ ID NO: 211
QVQLVESGGGLVQPGGSLRLSCAASGFTFSVYDMNWFRQAPGKGLEWVS
GITGNGYTTSYADSVKGRFTISRDNAKNTLYLQLNSLKSEDTAMYYCAK
ETNRGQGTQVTVSS

In some embodiments, there is provided a multispecific (e.g., bispecific) chimeric receptor comprising: (a) an extracellular domain comprising an anti-CD33 sdAb (such as any one of the anti-CD33 sdAbs described herein) and an anti-CD123 sdAb or scFv; (b) a transmembrane domain, and (c) an intracellular domain comprising an intracellular co-stimulatory sequence derived from 4-1BB or CD28 and a CD3ζ intracellular signaling sequence.

In some embodiments, there is provided a multispecific (e.g., bispecific) chimeric receptor comprising: (a) an extracellular domain comprising an anti-CD33 sdAb (such as any one of the anti-CD33 sdAbs described herein) and an extracellular domain of NKG2D; (b) a transmembrane domain, and (c) an intracellular domain comprising an intracellular co-stimulatory sequence derived from 4-1BB or CD28 and a CD3ζ intracellular signaling sequence.

Chimeric Receptor Systems

The present application further provides chimeric receptor systems comprising two or more chimeric receptors, including dual chimeric receptor systems and split chimeric receptors.

In some embodiments, there is provided a dual chimeric receptor system comprising: (a) a first chimeric receptor comprising an extracellular domain comprising an anti-CD33 sdAb (such as any one of the anti-CD33 sdAbs described herein), a transmembrane domain, and an intracellular signaling domain comprising a primary intracellular signaling sequence of an immune effector cell (e.g., T cell)

and an intracellular co-stimulatory sequence; (b) a second chimeric receptor comprising an extracellular domain comprising a second binding moiety (e.g., sdAb, scFv, or an extracellular domain of a receptor) that specifically binds to a second antigen or epitope, a transmembrane domain, and an intracellular signaling domain comprising a primary intracellular signaling sequence of an immune effector cell (e.g., T cell) and an intracellular co-stimulatory sequence. In some embodiments, the second antigen is selected from the group consisting of NKG2D ligands, CLL1, WT1, CS1, CD123, Folate Receptor β, FLT3R, B7H6, TIM3, MUC1, c-kit, CD44v6, Lewis-Y, CD99, CD27 and CD70. In some embodiments, the transmembrane domain is selected from the group consisting of CD8α, CD4, CD28, 4-1BB, CD80, CD86, CD152 and PD1. In some embodiments, the primary intracellular signaling sequence is derived from CD3ζ, FcRγ, FcRβ, CD3γ, CD3δ, CD3ε, CD5, CD22, CD79a, CD79b, or CD66d. In some embodiments, the primary intracellular signaling sequence is derived from CD3ζ. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB. In some embodiments, the first chimeric receptor and/or the second chimeric receptor further comprises a hinge domain (such as a CD8 hinge domain) located between the C-terminus of the extracellular domain and the N-terminus of the transmembrane domain. In some embodiments, the first chimeric receptor and/or the second chimeric receptor further comprises a signal peptide (such as a CD8 signal peptide). In some embodiments, the first chimeric receptor and the second chimeric receptor each comprises a polypeptide comprising from the N-terminus to the C-terminus: a CD8 signal peptide, the extracellular domain, a CD8 hinge domain, a CD8 transmembrane domain, and an intracellular signaling domain comprising an intracellular co-stimulatory sequence derived from 4-1BB or CD28 and a CD3ζ intracellular signaling sequence.

In some embodiments, there is provided a split chimeric receptor system comprising: (a) a first chimeric receptor comprising an extracellular domain comprising an anti-CD33 sdAb (such as any one of the anti-CD33 sdAbs described herein), a transmembrane domain, and an intracellular domain comprising a primary intracellular signaling sequence of an immune effector cell (e.g., T cell), wherein optionally the intracellular signaling domain does not comprise an intracellular co-stimulatory sequence; (b) a second chimeric receptor comprising an extracellular domain comprising a second binding moiety (e.g., sdAb, scFv, or an extracellular domain of a receptor) that specifically binds to a second antigen or epitope, a transmembrane domain, and an intracellular signaling domain comprising an intracellular co-stimulatory sequence, wherein optionally the intracellular signaling domain does not comprise a primary intracellular signaling sequence. In some embodiments, the second antigen is selected from the group consisting of NKG2D ligands, CLL1, WT1, CS1, CD123, Folate Receptor β, FLT3R, B7H6, TIM3, MUC1, c-kit, CD44v6, Lewis-Y, CD99, CD27 and CD70. In some embodiments, the transmembrane domain is selected from the group consisting of CD8α, CD4, CD28, 4-1BB, CD80, CD86, CD152 and PD1. In some embodiments, the primary intracellular signaling sequence is derived from CD3ζ, FcRγ, FcRβ, CD3γ, CD3δ, CD3ε, CD5, CD22, CD79a, CD79b, or CD66d. In some embodiments, the primary intracellular signaling sequence is derived from CD3ζ. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB. In some embodiments, the first chimeric receptor and/or the second chimeric receptor further comprises a hinge domain (such as a CD8 hinge domain) located between the C-terminus of the extracellular domain and the N-terminus of the transmembrane domain. In some embodiments, the first chimeric receptor and/or the second chimeric receptor further comprises a signal peptide (such as a CD8 signal peptide). In some embodiments, the first chimeric receptor comprises a polypeptide comprising from the N-terminus to the C-terminus: a CD8 signal peptide, the anti-CD33 sdAb, a CD8 hinge domain, a CD8 transmembrane domain, and an intracellular signaling domain comprising a CD3ζ intracellular signaling sequence. In some embodiments, the second chimeric receptor comprises a polypeptide comprising from the N-terminus to the C-terminus: a CD8 signal peptide, the second binding domain, a CD8 hinge domain, a CD8 transmembrane domain, and an intracellular signaling domain comprising an intracellular co-stimulatory sequence derived from 4-1BB or CD28.

In some embodiments, there is provided a split chimeric receptor system comprising: (a) a first chimeric receptor comprising an extracellular domain comprising an anti-CD33 sdAb (such as any one of the anti-CD33 sdAbs described herein), a transmembrane domain, and an intracellular domain comprising an intracellular signaling domain comprising an intracellular co-stimulatory sequence, wherein optionally the intracellular signaling domain does not comprise a primary intracellular signaling sequence; (b) a second chimeric receptor comprising an extracellular domain comprising a second binding moiety (e.g., sdAb, scFv, or an extracellular domain of a receptor) that specifically binds to a second antigen or epitope, a transmembrane domain, and an intracellular signaling domain comprising a primary intracellular signaling sequence of an immune effector cell (e.g., T cell), wherein optionally the intracellular signaling domain does not comprise an intracellular co-stimulatory sequence. In some embodiments, the second antigen is selected from the group consisting of NKG2D ligands, CLL1, WT1, CS1, CD123, Folate Receptor β, FLT3R, B7H6, TIM3, MUC1, c-kit, CD44v6, Lewis-Y, CD99, CD27 and CD70. In some embodiments, the transmembrane domain is selected from the group consisting of CD8α, CD4, CD28, 4-1BB, CD80, CD86, CD152 and PD1. In some embodiments, the primary intracellular signaling sequence is derived from CD3ζ, FcRγ, FcRβ, CD3γ, CD3δ, CD3ε, CD5, CD22, CD79a, CD79b, or CD66d. In some embodiments, the primary intracellular signaling sequence is derived from CD3ζ. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB. In some embodiments, the first chimeric receptor and/or the second chimeric receptor further comprises a hinge domain (such as a CD8 hinge domain) located between the C-terminus of the extracellular domain and the N-terminus of the transmembrane domain. In some embodiments, the first chimeric receptor and/or the second chimeric receptor further comprises a signal peptide (such as a CD8 signal peptide). In some embodiments, the first chimeric receptor comprises a polypeptide comprising from the N-terminus to the C-terminus: a CD8 signal peptide, the anti-CD33 sdAb, a CD8 hinge domain, a CD8 transmembrane domain, and an intracellular signaling domain comprising an intracellular co-stimulatory sequence derived from 4-1BB or CD28. In some embodiments, the second chimeric receptor comprises a polypeptide comprising from the N-terminus to the C-terminus: a CD8 signal peptide, the second binding domain, a CD8 hinge domain, a CD8 transmembrane domain, and an intracellular signaling domain comprising a CD3ζ intracellular signaling sequence.

In some embodiments, there is provided a dual chimeric receptor system comprising: (a) a first chimeric receptor comprising an extracellular domain comprising an anti-CD33 sdAb (such as any one of the anti-CD33 sdAbs described herein), a transmembrane domain, and an intracellular signaling domain comprising an intracellular co-stimulatory sequence derived from 4-1BB or CD28 and a CD3ζ intracellular signaling sequence; and (b) a second chimeric receptor comprising an extracellular domain comprising an anti-CLL1 sdAb or scFv, a transmembrane domain, and an intracellular signaling domain comprising an intracellular co-stimulatory sequence derived from 4-1BB or CD28 and a CD3ζ intracellular signaling sequence. In some embodiments, the transmembrane domain is selected from the group consisting of CD8α, CD4, CD28, 4-1BB, CD80, CD86, CD152 and PD1. In some embodiments, the primary intracellular signaling sequence is derived from CD3ζ. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the first chimeric receptor and/or the second chimeric receptor further comprises a hinge domain (such as a CD8 hinge domain) located between the C-terminus of the extracellular domain and the N-terminus of the transmembrane domain. In some embodiments, the first chimeric receptor and/or the second chimeric receptor further comprises a signal peptide (such as a CD8 signal peptide).

Any suitable anti-CLL1 sdAb or scFv may be used for the dual chimeric receptor systems targeting CD33 and CLL1 described herein. Exemplary anti-CLL1 sdAbs have been described, for example, see, PCT/CN2018/104883. Sequences of exemplary anti-CLL1 sdAbs are shown in Table 5.

In some embodiments, there is provided a dual chimeric receptor system comprising: (a) a first chimeric receptor comprising an extracellular domain comprising an anti-CD33 sdAb, a transmembrane domain (e.g., a CD8 transmembrane domain), and an intracellular signaling domain (e.g., an intracellular signaling domain comprising an intracellular co-stimulatory sequence derived from 4-1BB and a CD3ζ intracellular signaling sequence), wherein the anti-CD33 sdAb comprises: (1) a CDR1 comprising the amino acid sequence of SEQ ID NO: 25, a CDR2 comprising the amino acid sequence of SEQ ID NO: 27, and a CDR3 comprising the amino acid sequence of SEQ ID NO: 29, or a variant thereof comprising up to about 5 amino acid substitutions in the CDRs; (2) a CDR1 comprising the amino acid sequence of SEQ ID NO: 53, a CDR2 comprising the amino acid sequence of SEQ ID NO: 55, and a CDR3 comprising the amino acid sequence of SEQ ID NO: 57, or a variant thereof comprising up to about 5 amino acid substitutions in the CDRs; or (3) a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99, or a variant thereof comprising up to about 5 amino acid substitutions in the CDRs; and (b) a second chimeric receptor comprising an extracellular domain comprising an anti-CLL1 sdAb, a transmembrane domain (e.g., CD28 transmembrane domain), and an intracellular signaling domain (e.g., an intracellular signaling domain comprising an intracellular co-stimulatory sequence derived from CD28 and a CD3ζ intracellular signaling sequence), wherein the anti-CLL1 sdAb comprises: (1) a CDR1 comprising the amino acid sequence of SEQ ID NO: 196, a CDR2 comprising the amino acid sequence of SEQ ID NO: 198, and a CDR3 comprising the amino acid sequence of SEQ ID NO: 200, or a variant thereof comprising up to about 5 amino acid substitutions in the CDRs; or (2) a CDR1 comprising the amino acid sequence of SEQ ID NO: 203, a CDR2 comprising the amino acid sequence of SEQ ID NO: 205, and a CDR3 comprising the amino acid sequence of SEQ ID NO: 207, or a variant thereof comprising up to about 5 amino acid substitutions in the CDRs. In some embodiments, the anti-CD33 sdAb moiety comprises a $V_HH$ domain comprising the amino acid sequence of SEQ ID NO: 111, or a variant thereof comprising an amino acid sequence having at least about 95% sequence identity to the amino acid sequence of SEQ ID NO: 111. In some embodiments, the anti-CD33 sdAb moiety comprises a $V_HH$ domain comprising the amino acid sequence of SEQ ID NO: 115, or a variant thereof comprising an amino acid sequence having at least about 95% sequence identity to the amino acid sequence of SEQ ID NO: 115. In some embodiments, the anti-CD33 sdAb moiety comprises a $V_HH$ domain comprising the amino acid sequence of SEQ ID NO: 121, or a variant thereof comprising an amino acid sequence having at least about 95% sequence identity to the amino acid sequence of SEQ ID NO: 121. In some embodiments, the anti-CLL1 sdAb moiety comprises a $V_HH$ domain comprising the amino acid sequence of SEQ ID NO: 210, or a variant thereof comprising an amino acid sequence having at least about 95% sequence identity to the amino acid sequence of SEQ ID NO: 210. In some embodiments, the anti-CLL1 sdAb moiety comprises a $V_HH$ domain comprising the amino acid sequence of SEQ ID NO: 211, or a variant thereof comprising an amino acid sequence having at least about 95% sequence identity to the amino acid sequence of SEQ ID NO: 211. In some embodiments, the first chimeric receptor comprises a polypeptide comprising from the N-terminus to the C-terminus: a CD8 signal peptide, the extracellular domain, a CD8 hinge domain, a CD8 transmembrane domain, and an intracellular signaling domain comprising an intracellular co-stimulatory sequence derived from 4-1BB and a CD3ζ intracellular signaling sequence. In some embodiments, the second chimeric receptor comprises a polypeptide comprising from the N-terminus to the C-terminus: a CD8 signal peptide, the extracellular domain, a CD28 hinge domain, a CD28 transmembrane domain, and an intracellular signaling domain comprising an intracellular co-stimulatory sequence derived from CD28 and a CD3ζ intracellular signaling sequence.

In some embodiments, there is provided a dual chimeric receptor system comprising: (a) a first chimeric receptor comprising an extracellular domain comprising an anti-CD33 sdAb, a transmembrane domain (e.g., a CD8 transmembrane domain), and an intracellular signaling domain (e.g., an intracellular signaling domain comprising an intracellular co-stimulatory sequence derived from 4-1BB and a CD3ζ intracellular signaling sequence), wherein the anti-CD33 sdAb comprises a CDR1 comprising the amino acid sequence of SEQ ID NO: 25, a CDR2 comprising the amino acid sequence of SEQ ID NO: 27, and a CDR3 comprising the amino acid sequence of SEQ ID NO: 29; and (b) a second chimeric receptor comprising an extracellular domain comprising an anti-CLL1 sdAb, a transmembrane domain (e.g., CD28 transmembrane domain), and an intracellular signaling domain (e.g., an intracellular signaling domain comprising an intracellular co-stimulatory sequence derived from CD28 and a CD3ζ intracellular signaling sequence), wherein the anti-CLL1 sdAb comprises a CDR1 comprising the amino acid sequence of SEQ ID NO: 196, a CDR2 comprising the amino acid sequence of SEQ ID NO: 198, and a CDR3 comprising the amino acid sequence of SEQ ID NO: 200. In some embodiments, the anti-CD33 sdAb moiety comprises a $V_HH$ domain comprising the amino acid sequence of SEQ ID NO: 158, or a variant thereof comprising an amino acid sequence having at least about 95% sequence identity to the amino acid sequence of SEQ ID NO: 158. In some embodiments, the anti-CLL1 sdAb moiety comprises a $V_HH$ domain comprising the amino acid sequence of SEQ ID NO: 186, or a variant thereof comprising an amino acid sequence having at least about 95% sequence identity to the amino acid sequence of SEQ ID NO: 186. In some embodiments, the first chimeric receptor comprises a polypeptide comprising from the N-terminus to the C-terminus: a CD8 signal peptide, the extracellular domain, a CD8 hinge domain, a CD8 transmembrane domain, and an intracellular signaling domain comprising an intracellular co-stimulatory sequence derived from 4-1BB and a CD3ζ intracellular signaling sequence. In some embodiments, the second chimeric receptor comprises a polypeptide comprising from the N-terminus to the C-terminus: a CD8 signal peptide, the extracellular domain, a CD28 hinge domain, a CD28 transmembrane domain, and an intracellular signaling domain comprising an intracellular co-stimulatory sequence derived from CD28 and a CD3ζ intracellular signaling sequence.

In some embodiments, there is provided a dual chimeric receptor system comprising: (a) a first chimeric receptor comprising an extracellular domain comprising an anti-CD33 sdAb, a transmembrane domain (e.g., a CD8 transmembrane domain), and an intracellular signaling domain (e.g., an intracellular signaling domain comprising an intracellular co-stimulatory sequence derived from 4-1BB and a CD3ζ intracellular signaling sequence), wherein the anti-CD33 sdAb comprises a CDR1 comprising the amino acid sequence of SEQ ID NO: 53, a CDR2 comprising the amino acid sequence of SEQ ID NO: 55, and a CDR3 comprising the amino acid sequence of SEQ ID NO: 57; and (b) a second chimeric receptor comprising an extracellular domain comprising an anti-CLL1 sdAb, a transmembrane domain (e.g., CD28 transmembrane domain), and an intracellular signaling domain (e.g., an intracellular signaling domain comprising an intracellular co-stimulatory sequence derived from CD28 and a CD3ζ intracellular signaling sequence), wherein the anti-CLL1 sdAb comprises a CDR1 comprising the amino acid sequence of SEQ ID NO: 196, a CDR2 comprising the amino acid sequence of SEQ ID NO: 198, and a CDR3 comprising the amino acid sequence of SEQ ID NO: 200. In some embodiments, the anti-CD33 sdAb moiety comprises a $V_HH$ domain comprising the amino acid sequence of SEQ ID NO: 162, or a variant thereof comprising an amino acid sequence having at least about 95% sequence identity to the amino acid sequence of SEQ ID NO: 162. In some embodiments, the anti-CLL1 sdAb moiety comprises a $V_HH$ domain comprising the amino acid sequence of SEQ ID NO: 186, or a variant thereof comprising an amino acid sequence having at least about 95% sequence identity to the amino acid sequence of SEQ ID NO: 186. In some embodiments, the first chimeric receptor comprises a polypeptide comprising from the N-terminus to the C-terminus: a CD8 signal peptide, the extracellular domain, a CD8 hinge domain, a CD8 transmembrane domain, and an intracellular signaling domain comprising an intracellular co-stimulatory sequence derived from 4-1BB and a CD3ζ intracellular signaling sequence. In some embodiments, the second chimeric receptor comprises a polypeptide comprising from the N-terminus to the C-terminus: a CD8 signal peptide, the extracellular domain, a CD28 hinge domain, a CD28 transmembrane domain, and an intracellular signaling domain comprising an intracellular co-stimulatory sequence derived from CD28 and a CD3ζ intracellular signaling sequence.

In some embodiments, there is provided a dual chimeric receptor system comprising: (a) a first chimeric receptor comprising an extracellular domain comprising an anti-CD33 sdAb, a transmembrane domain (e.g., a CD8 transmembrane domain), and an intracellular signaling domain (e.g., an intracellular signaling domain comprising an intracellular co-stimulatory sequence derived from 4-1BB and a CD3ζ intracellular signaling sequence), wherein the anti-CD33 sdAb comprises a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99; and (b) a second chimeric receptor comprising an extracellular domain comprising an anti-CLL1 sdAb, a transmembrane domain (e.g., CD28 transmembrane domain), and an intracellular signaling domain (e.g., an intracellular signaling domain comprising an intracellular co-stimulatory sequence derived from CD28 and a CD3ζ intracellular signaling sequence), wherein the anti-CLL1 sdAb comprises a CDR1 comprising the amino acid sequence of SEQ ID NO: 203, a CDR2 comprising the amino acid sequence of SEQ ID NO: 205, and a CDR3 comprising the amino acid sequence of SEQ ID NO: 207. In some embodiments, the anti-CD33 sdAb moiety comprises a $V_HH$ domain comprising the amino acid sequence of SEQ ID NO: 168, or a variant thereof comprising an amino acid sequence having at least about 95% sequence identity to the amino acid sequence of SEQ ID NO: 168. In some embodiments, the anti-CLL1 sdAb moiety comprises a $V_HH$ domain comprising the amino acid sequence of SEQ ID NO: 187, or a variant thereof comprising an amino acid sequence having at least about 95% sequence identity to the amino acid sequence of SEQ ID NO: 187. In some embodiments, the first chimeric receptor comprises a polypeptide comprising from the N-terminus to the C-terminus: a CD8 signal peptide, the extracellular domain, a CD8 hinge domain, a CD8 transmembrane domain, and an intracellular signaling domain comprising an intracellular co-stimulatory sequence derived from 4-1BB and a CD3ζ intracellular signaling sequence. In some embodiments, the second chimeric receptor comprises a polypeptide comprising from the N-terminus to the C-terminus: a CD8 signal peptide, the extracellular domain, a CD28 hinge domain, a CD28 transmembrane domain, and an intracellular signaling domain comprising an intracellular co-stimulatory sequence derived from CD28 and a CD3ζ intracellular signaling sequence.

In some embodiments, there is provided a dual chimeric receptor system comprising: (a) a first chimeric receptor comprising a polypeptide having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 186 or 187; and (b) a second chimeric receptor comprising a polypeptide having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 158, 162 or 168. In some embodiments, there is provided a dual chimeric receptor system comprising: (a) a first chimeric receptor comprising a polypeptide comprising the amino acid sequence of SEQ ID NO: 186 or 187; and (b) a second chimeric receptor comprising a polypeptide comprising the amino acid sequence of SEQ ID NO: 158, 162 or 168. In some embodiments, there is provided a dual chimeric receptor system comprising: (a) a first chimeric receptor comprising a polypeptide comprising the amino acid sequence of SEQ ID NO: 186; and (b) a second chimeric receptor comprising a polypeptide comprising the amino acid sequence of SEQ ID NO: 158. In some embodiments, there is provided a dual chimeric receptor system comprising: (a) a first chimeric receptor comprising a polypeptide comprising the amino acid sequence of SEQ ID NO: 186; and (b) a second chimeric receptor comprising a polypeptide comprising the amino acid sequence of SEQ ID NO: 162. In some embodiments, there is provided a dual chimeric receptor system comprising: (a) a first chimeric receptor comprising a polypeptide comprising the amino acid sequence of SEQ ID NO: 187; and (b) a second chimeric receptor comprising a polypeptide comprising the amino acid sequence of SEQ ID NO: 168.

In some embodiments, there is provided a dual chimeric receptor construct comprising a first polypeptide comprising any one of the anti-CD33 chimeric receptor described herein and a second polypeptide comprising any one of the anti-CLL1 chimeric receptor described herein, wherein the first polypeptide and the second polypeptide are fused to each other via a self-cleaving peptide (e.g., P2A peptide). In some embodiments, the dual chimeric receptor construct comprises an amino acid sequence having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 183. In some embodiments, the dual chimeric receptor construct comprises an amino acid sequence having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 184. In some embodiments, the dual chimeric receptor construct comprises an amino acid sequence having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 185. In some embodiments, the dual chimeric receptor construct comprises the amino acid sequence of SEQ ID NO: 183, 184 or 185. Further provided are nucleic acid(s) encoding any one of the dual chimeric receptor constructs described herein. Also provided is a polypeptide comprising the amino acid sequence of any one of SEQ ID NOs: 183-185.

Exemplary anti-CD33 dual chimeric receptors are shown in Table 6 below.

TABLE 6

Exemplary anti-CD33 sdAb Dual Chimeric Receptors.

| Construct | SEQ ID NO. | CAR1 (CLL1) | CAR1 SEQ ID NO. | Linker | CAR2 (CD33) | CAR2 SEQ ID NO. |
|---|---|---|---|---|---|---|
| Dual 1 | 183 | AS82472-28z CAR | 186 | P2A | AS49814 CAR | 158 |
| Dual 2 | 184 | AS82472-28z CAR | 186 | P2A | AS50073 CAR | 162 |
| Dual 3 | 185 | AS82494-28z CAR | 187 | P2A | AS67190 CAR | 168 |

In some embodiments, there is provided a dual chimeric receptor system comprising: (a) a first chimeric receptor comprising an extracellular domain comprising an anti-CD33 sdAb (such as any one of the anti-CD33 sdAbs described herein), a transmembrane domain, and an intracellular signaling domain comprising an intracellular co-stimulatory sequence derived from 4-1BB or CD28 and a CD3ζ intracellular signaling sequence; and (b) a second chimeric receptor comprising an extracellular domain comprising an anti-CD123 sdAb or scFv, a transmembrane domain, and an intracellular signaling domain comprising an intracellular co-stimulatory sequence derived from 4-1BB or CD28 and a CD3ζ intracellular signaling sequence.

In some embodiments, there is provided a dual chimeric receptor system comprising: (a) a first chimeric receptor comprising an extracellular domain comprising an anti-CD33 sdAb (such as any one of the anti-CD33 sdAbs described herein), a transmembrane domain, and an intracellular signaling domain comprising an intracellular co-stimulatory sequence derived from 4-1BB or CD28 and a CD3ζ intracellular signaling sequence; and (b) a second chimeric receptor comprising an extracellular domain comprising an extracellular domain of NKG2D, a transmembrane domain, and an intracellular signaling domain comprising an intracellular co-stimulatory sequence derived from 4-1BB or CD28 and a CD3ζ intracellular signaling sequence.

In some embodiments, there is provided a split chimeric receptor system comprising: (a) a first chimeric receptor comprising an extracellular domain comprising an anti-CD33 sdAb (such as any one of the anti-CD33 sdAbs described herein), a transmembrane domain, and an intracellular signaling domain comprising a CD3ζ intracellular signaling sequence; and (b) a second chimeric receptor comprising an extracellular domain comprising an anti-CLL1 sdAb or scFv, a transmembrane domain, and an intracellular signaling domain comprising an intracellular co-stimulatory sequence derived from 4-1BB or CD28.

In some embodiments, there is provided a split chimeric receptor system comprising: (a) a first chimeric receptor comprising an extracellular domain comprising an anti-CD33 sdAb (such as any one of the anti-CD33 sdAbs described herein), a transmembrane domain, and an intracellular signaling domain comprising a CD3ζ intracellular signaling sequence; and (b) a second chimeric receptor comprising an extracellular domain comprising an anti-CD123 sdAb or scFv, a transmembrane domain, and an intracellular signaling domain comprising an intracellular co-stimulatory sequence derived from 4-1BB or CD28.

In some embodiments, there is provided a split chimeric receptor system comprising: (a) a first chimeric receptor comprising an extracellular domain comprising an anti-CD33 sdAb (such as any one of the anti-CD33 sdAbs described herein), a transmembrane domain, and an intracellular signaling domain comprising a CD3ζ intracellular signaling sequence; and (b) a second chimeric receptor comprising an extracellular domain comprising an extracellular domain of NKG2D, a transmembrane domain, and an intracellular signaling domain comprising an intracellular co-stimulatory sequence derived from 4-1BB or CD28.

In some embodiments, there is provided a split chimeric receptor system comprising: (a) a first chimeric receptor comprising an extracellular domain comprising an anti-CD33 sdAb (such as any one of the anti-CD33 sdAbs described herein), a transmembrane domain, and an intracellular signaling domain comprising an intracellular co-stimulatory sequence derived from 4-1BB or CD28; and (b) a second chimeric receptor comprising an extracellular domain comprising an anti-CLL1 sdAb or scFv, a transmembrane domain, and an intracellular signaling domain comprising a CD3ζ intracellular signaling sequence.

In some embodiments, there is provided a split chimeric receptor system comprising: (a) a first chimeric receptor comprising an extracellular domain comprising an anti-CD33 sdAb (such as any one of the anti-CD33 sdAbs described herein), a transmembrane domain, and an intracellular signaling domain comprising an intracellular co-stimulatory sequence derived from 4-1BB or CD28; and (b) a second chimeric receptor comprising an extracellular domain comprising an anti-CD123 sdAb or scFv, a transmembrane domain, and an intracellular signaling domain comprising a CD3ζ intracellular signaling sequence.

In some embodiments, there is provided a split chimeric receptor system comprising: (a) a first chimeric receptor comprising an extracellular domain comprising an anti-CD33 sdAb (such as any one of the anti-CD33 sdAbs described herein), a transmembrane domain, and an intracellular signaling domain comprising an intracellular co-stimulatory sequence derived from 4-1BB or CD28; and (b) a second chimeric receptor comprising an extracellular domain comprising an extracellular domain of NKG2D, a transmembrane domain, and an intracellular signaling domain comprising a CD3ζ intracellular signaling sequence.

Extracellular Domain

The extracellular domain of the chimeric receptors described herein comprises one or more (such as any one of 1, 2, 3, 4, 5, 6 or more) binding moieties, such as sdAbs. In some embodiments, the one or more binding moieties are antibodies or antigen-binding fragments thereof. In some embodiments, the one or more binding moieties are derived from four-chain antibodies. In some embodiments, the one or more binding moieties are derived from camelid antibodies. In some embodiments, the one or more binding moieties are derived from human antibodies. In some embodiments, the one or more binding moieties are non-antibody binding proteins, such as extracellular domains of receptors, polypeptide ligands or engineered proteins that bind to an antigen. The binding moieties can be fused to each other directly via peptide bonds, or via peptide linkers.

In some embodiments, the extracellular domain comprises a second binding moiety. The second binding moiety specifically binds to a cell surface molecule. The second binding moiety may be chosen to recognize an antigen that acts as a cell surface marker on target cells associated with a special disease state. The antigens targeted by the second binding moiety may be directly or indirectly involved in the diseases. In some embodiments, the antigen is a tumor antigen. In some embodiments, the tumor antigen is associated with an acute myeloid leukemia (AML). In some embodiments, the tumor antigen is associated with chronic myelogenous leukemia (CML). In some embodiments, the tumor antigen is associated with myelodysplastic syndromes (MDS).

Tumor antigens are proteins that are produced by tumor cells that can elicit an immune response, particularly T-cell mediated immune responses. The selection of the targeted antigen of the invention will depend on the particular type of cancer to be treated. Exemplary tumor antigens include, for example, a glioma-associated antigen, carcinoembryonic antigen (CEA), β-human chorionic gonadotropin, alphafetoprotein (AFP), lectin-reactive AFP, thyroglobulin, RAGE-1, MN-CAIX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, HER2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In some embodiments, the tumor antigen is a tumor-specific antigen (TSA) or a tumor-associated antigen (TAA). A TSA is unique to tumor cells and does not occur on other cells in the body. A TAA associated antigen is not unique to a tumor cell, and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development, when the immune system is immature, and unable to respond or they may be antigens that are normally present at extremely low levels on normal cells, but which are expressed at much higher levels on tumor cells.

Non-limiting examples of TSA or TAA antigens include the following: Differentiation antigens such as MART-1/MelanA (MART-I), gp 100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23HI, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS 1, SDCCAG16, TA-90\Mac-2 binding protein\cyclophilin C-associated protein, TAAL6, TAG72, TLP, and TPS.

The second binding moiety can be of any suitable format. In some embodiments, the second binding moiety is derived from an antibody, such as a four-chain antibody, or a single-domain antibody, such as heavy-chain only antibody. In some embodiments, the second binding moiety is an antibody fragment, such as a Fab, Fv, scFv, or $V_H H$. In some embodiments, the second binding moiety is an antibody fragment that specifically binds to an antigen selected from the group consisting of NKG2D ligands, CLL1, WT1, CS1, CD123, Folate Receptor β, FLT3R, B7H6, TIM3, MUC1, c-kit, CD44v6, Lewis-Y (CD174), CD99, CD27 and CD70.

In some embodiments, the second binding moiety is a CLL1-binding domain. In some embodiments, the CLL1-binding domain is an antibody fragment (e.g., an scFv or a $V_H H$) of an anti-CLL1 antibody. In some embodiments, the CLL1-binding domain is an scFv derived from CLT030. In some embodiments, the CLL1-binding domain is an anti-CLL1 sdAb.

C-type lectin-like molecule-1 (CLL1), also known as CLEC12A, C-type lectin domain family 12 member A, DCAL-2, MICL, and CD371, is a type II transmembrane glycoprotein that functions as an inhibitory receptor. The expression of CLL1 is restricted in myeloid lineage cells, as well as in the majority of AML blasts. In particular, CLL1 is selectively present on leukemic stem cells in acute myeloid leukemia (AML), but absent in normal hematopoietic stem cells. CD33 can be a suitable tumor antigen target for immunotherapeutic agents against AML. See, e.g., Wang J. et al. (2018) *J. Hematol. Oncol.*, 11:7; Zhao X. et al., (2010), *Haematologica*, 95(1): 71-78; and Lu H. et al. (2014) *Angew Chem. Int. Ed. Engl.* 53(37): 9841-9845.

In some embodiments, the second binding moiety is a CD123-binding domain. In some embodiments, the CD123-binding domain is an antibody fragment (e.g., an scFv or a $V_H H$) of an anti-CD123 antibody. In some embodiments, the CD123-binding domain is a ligand of CD123, or an IL-3 domain. In some embodiments, the IL-3 domain is derived from human IL-3, such as full-length or a functional fragment of human IL-3.

IL-3 (interleukin-3) gene is mapped on chromosome 5, encoding a protein 152 amino acids long. IL-3 is a cytokine, capable of supporting a broad range of cellular activities such as cell growth, differentiation and apoptosis. IL-13 acts by binding to the interleukin-3 receptor (IL-3R), also known as CD123 antigen. IL-3R is a heterodimeric receptor, comprising a ligand specific alpha subunit and a signal transducing beta subunit, shared by the receptors for IL-3, colony stimulating factor 2 (CSF2/GM-CSF), and interleukin 5 (IL5). Activation of the IL-3R results in the phosphorylation of the βc chain, recruitment of SH2-containing adaptor molecules such as Vav1, and downstream signal transduction via Jak2/STAT5 and the Ras/MAPK pathway.

IL-3R is a 75 kD glycoprotein and becomes 43 kD when hydrolyzed by N-glycosidase. IL-3R has three extracellular domains which are responsible for specific binding to IL-3, a transmembrane domain, and a short intercellular domain which is indispensable for intracellular signaling (Sato et al. 1993). IL-3R is a heterodimeric receptor with low affinity and high specificity for IL-3. Upon binding to IL-3, the IL-3R is activated and promotes cell proliferation and survival (Liu et al. 2015).

CD123 is overexpressed on AML blasts (i.e., myeloblasts). AML blasts and leukemia stem cells (LSCs) in 75 to 89% of AML patients express CD123. In sharp contrast, there is low or undetectable expression of CD123 on normal hematopoietic stem cells (HSCs) (Frankel et al. 2014; Jordan et al. 2000). Apart from AML, CD123 is also overexpressed in a variety of hematologic malignancies, including B cell lineage acute lymphoblastic leukemia, chronic myeloid leukemia, plasmacytoid dendritic cell neoplasm, and hairy cell leukemia (Munoz et al. 2001). This expression profile makes CD123 a valuable biomarker in clinical diagnosis, prognosis and intervention of the diseases. Currently, early phase clinical trials have demonstrated that CD123-targeting therapies are safe and without major adverse effects on hematopoiesis. The anti-leukemic activities of CD123-targeting therapies in humans are still being investigated.

In some embodiments, the second binding moiety is a ligand, or a ligand binding domain of a receptor, such as an extracellular domain of a receptor. In some embodiments, the second binding moiety is a ligand or ligand binding domain derived from a molecule selected from the group consisting of NKG2A, NKG2C, NKG2F, IL-3, IL-13, LLT1, AICL, DNAM-1, and NKp80. In some embodiments, the second binding moiety is an extracellular domain of NKG2D. In some embodiments, the second binding moiety comprises the amino acid sequence of SEQ ID NO: 154.

```
NKG2D-L binding domain
                                    SEQ ID NO: 154
FNQEVQIPLTESYCGPCPKNWICYKNNCYQFFDESKNWYESQASCMSQN

ASLLKVYSKEDQDLLKLVKSYHWMGLVHIPTNGSWQWEDGSILSPNLLT

IIEMQKGDCALYASSFKGYIENCSTPNTYICMQRTV
```

NKG2D is a unique member of the NKG2 family, which are C-type lectin receptors that stimulate or inhibit cytotoxic activity of NK cells. NKG2D is a type II transmembrane-anchored glycoprotein, expressed primarily on the surface of NK cells and CD8⁺ T cells (e.g., αβ T cells and γδ T cells). It is highly conserved across multiple species, with 70% sequence identity shared between the human and murine receptors. Unlike the other NKG2 receptors that heterodimerize with CD94 and bind to nonclassical MHC glycoproteins class I, NKG2D forms homodimers and bind to cellular stress-inducible molecules. Accumulating evidence indicates that NKG2D plays a crucial role in immunosurveillance against stressed or abnormal cells, such as autologous tumor cells and virus-infected cells.

A variety of NKG2D ligands have been identified in humans, including MIC molecules (MHC class I chain-related proteins A and B, or MICA and MICB) encoded by genes in the MHC family, and ULBP molecules (UL16-binding proteins, also known as RAET1 proteins) which are clustered on human chromosome 6 (Bahram et al. 2005). All NKG2D ligands are homologous to MHC class I molecules and exhibit considerable allelic variation. Although NKG2D ligand RNAs are broadly expressed on all tissues and organs of the body, NKG2D ligands are generally absent from the surface of normal adult cells (Le Bert and Gasser 2014). However, the expression of NKG2D ligands is induced or upregulated primarily in tissues of epithelial origin in response to cellular stress, including heat shock, DNA damage, and stalled DNA replication. Presence of NKG2D ligands on a cell flags the cell for NK cell targeting and potential elimination (Le Bert and Gasser 2014). Interestingly, high activity of DNA repair pathways in transformed cells across a variety of hematologic and solid tumors lead to expression of NKG2D ligands, which renders these cells susceptible to NK-mediated lysis (Sentman et al. 2006).

NKG2D is encoded by KLRK1 gene. NKG2D is a transmembrane receptor protein comprising three domains: cytoplasmic domain (residues 1-51 of human NKG2D), transmembrane domain (residues 52-72 of human NKG2D), and extracellular domain (residues 73-216 of human NKG2D). The extracellular domain of NKG2D contains a C-type lectin domain (residues 98-213 of human NKG2D).

Transmembrane Domain

The chimeric receptors of the present application comprise a transmembrane domain that can be directly or indirectly fused to the extracellular domain. The transmembrane domain may be derived either from a natural or from a synthetic source. As used herein, a "transmembrane domain" refers to any protein structure that is thermodynamically stable in a cell membrane, preferably a eukaryotic cell membrane. Transmembrane domains compatible for use in the chimeric receptors described herein may be obtained from a naturally occurring protein. Alternatively, it can be a synthetic, non-naturally occurring protein segment, e.g., a hydrophobic protein segment that is thermodynamically stable in a cell membrane.

Transmembrane domains are classified based on the three dimensional structure of the transmembrane domain. For example, transmembrane domains may form an alpha helix, a complex of more than one alpha helix, a beta-barrel, or any other stable structure capable of spanning the phospholipid bilayer of a cell. Furthermore, transmembrane domains may also or alternatively be classified based on the transmembrane domain topology, including the number of passes that the transmembrane domain makes across the membrane and the orientation of the protein. For example, single-pass membrane proteins cross the cell membrane once, and multi-pass membrane proteins cross the cell membrane at least twice (e.g., 2, 3, 4, 5, 6, 7 or more times). Membrane proteins may be defined as Type I, Type II or Type III depending upon the topology of their termini and membrane-passing segment(s) relative to the inside and outside of the cell. Type I membrane proteins have a single membrane-spanning region and are oriented such that the N-terminus of the protein is present on the extracellular side of the lipid bilayer of the cell and the C-terminus of the protein is present on the cytoplasmic side. Type II membrane proteins also have a single membrane-spanning region but are oriented such that the C-terminus of the protein is present on the extracellular side of the lipid bilayer of the cell and the N-terminus of the protein is present on the cytoplasmic side. Type III membrane proteins have multiple membrane-spanning segments and may be further sub-classified based on the number of transmembrane segments and the location of N- and C-termini.

In some embodiments, the transmembrane domain of the CAR described herein is derived from a Type I single-pass membrane protein. In some embodiments, transmembrane domains from multi-pass membrane proteins may also be compatible for use in the CARs described herein. Multi-pass membrane proteins may comprise a complex (at least 2, 3, 4, 5, 6, 7 or more) alpha helices or a beta sheet structure. Preferably, the N-terminus and the C-terminus of a multi-pass membrane protein are present on opposing sides of the lipid bilayer, e.g., the N-terminus of the protein is present on the cytoplasmic side of the lipid bilayer and the C-terminus of the protein is present on the extracellular side.

In some embodiments, the transmembrane domain of the chimeric receptor comprises a transmembrane domain chosen from the transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, 4-1BB, CD154, KIRDS2, OX40, CD2, CD27, LFA-1 (CD11a, CD18), ICOS (CD278), 4-1BB (4-1BB), GITR, CD40, BAFFR, HVEM (LIGHTR), SLAMF7, NKp80 (KLRF1), CD160, CD19, IL-2R beta, IL-2R gamma, IL-7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CDIOO (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C. In some embodiments, the transmembrane domain is derived from a molecule selected from the group consisting of CD8α, CD4, CD28, 4-1BB, CD80, CD86, CD152 and PD1.

In some embodiments, the transmembrane domain is derived from CD8. In some embodiments, the transmembrane domain is a transmembrane domain of CD8α comprising the amino acid sequence of IYIWAPLAGTCGVLLLSLVITLYC (SEQ ID NO: 138). In some embodiments, the transmembrane domain is derived from CD28. In some embodiments, the transmembrane domain is a transmembrane domain of CD28 comprising the amino acid sequence of FWVLVVVGGVLACYSLLVTVAFIIFWV (SEQ ID NO: 139).

Transmembrane domains for use in the chimeric receptors described herein can also comprise at least a portion of a synthetic, non-naturally occurring protein segment. In some embodiments, the transmembrane domain is a synthetic, non-naturally occurring alpha helix or beta sheet. In some embodiments, the protein segment is at least approximately 20 amino acids, e.g., at least 18, 19, 20, 21, 22, 23, 24, 25, 26, 27, 28, 29, 30, or more amino acids. Examples of synthetic transmembrane domains are known in the art, for example in U.S. Pat. No. 7,052,906 B1 and PCT Publication No. WO 2000/032776 A2, the relevant disclosures of which are incorporated by reference herein.

The transmembrane domain may comprise a transmembrane region and a cytoplasmic region located at the C-terminal side of the transmembrane domain. The cytoplasmic region of the transmembrane domain may comprise three or more amino acids and, in some embodiments, helps to orient the transmembrane domain in the lipid bilayer. In some embodiments, one or more cysteine residues are present in the transmembrane region of the transmembrane domain. In some embodiments, one or more cysteine residues are present in the cytoplasmic region of the transmembrane domain. In some embodiments, the cytoplasmic region of the transmembrane domain comprises positively charged amino acids. In some embodiments, the cytoplasmic region of the transmembrane domain comprises the amino acids arginine, serine, and lysine.

In some embodiments, the transmembrane region of the transmembrane domain comprises hydrophobic amino acid residues. In some embodiments, the transmembrane domain of the chimeric receptor comprises an artificial hydrophobic sequence. For example, a triplet of phenylalanine, tryptophan and valine may be present at the C terminus of the transmembrane domain. In some embodiments, the transmembrane region comprises mostly hydrophobic amino acid residues, such as alanine, leucine, isoleucine, methionine, phenylalanine, tryptophan, or valine. In some embodiments, the transmembrane region is hydrophobic. In some embodiments, the transmembrane region comprises a poly-leucine-alanine sequence. The hydropathy, or hydrophobic or hydrophilic characteristics of a protein or protein segment, can be assessed by any method known in the art, for example the Kyte and Doolittle hydropathy analysis.

Intracellular Signaling Domain

The chimeric receptors of the present application comprise an intracellular signaling domain. The intracellular signaling domain of a single chimeric receptor or the intracellular signaling domains of two chimeric receptors in a chimeric receptor system is responsible for activation of at least one of the normal effector functions of the immune effector cell expressing the chimeric receptor(s). The term "effector function" refers to a specialized function of a cell. Effector function of a T cell, for example, may be cytolytic activity or helper activity including the secretion of cytokines. Thus the term "cytoplasmic signaling domain" refers to the portion of a protein which transduces the effector function signal and directs the cell to perform a specialized function. While usually the entire cytoplasmic signaling domain can be employed, in many cases it is not necessary to use the entire chain. To the extent that a truncated portion of the cytoplasmic signaling domain is used, such truncated portion may be used in place of the intact chain as long as it transduces the effector function signal. The term cytoplasmic signaling domain is thus meant to include any truncated portion of the cytoplasmic signaling domain sufficient to transduce the effector function signal.

In some embodiments, the intracellular signaling domain comprises a primary intracellular signaling sequence of an immune effector cell. In some embodiments, the chimeric receptor comprises an intracellular signaling domain consisting essentially of a primary intracellular signaling sequence of an immune effector cell. "Primary intracellular signaling sequence" refers to cytoplasmic signaling sequence that acts in a stimulatory manner to induce immune effector functions. In some embodiments, the primary intracellular signaling sequence contains a signaling motif known as immunoreceptor tyrosine-based activation motif, or ITAM. An "ITAM," as used herein, is a conserved protein motif that is generally present in the tail portion of signaling molecules expressed in many immune cells. The motif may comprises two repeats of the amino acid sequence YxxL/I separated by 6-8 amino acids, wherein each x is independently any amino acid, producing the conserved motif YxxL/Ix(6-8)YxxL/I. ITAMs within signaling molecules are important for signal transduction within the cell, which is mediated at least in part by phosphorylation of tyrosine residues in the ITAM following activation of the signaling molecule. ITAMs may also function as docking sites for other proteins involved in signaling pathways. Exemplary ITAM-containing primary cytoplasmic signaling sequences include those derived from CD3ζ, FcR gamma (FCER1G), FcR beta (Fc Epsilon Rib), CD3 gamma, CD3 delta, CD3 epsilon, CD5, CD22, CD79a, CD79b, and CD66d.

In some embodiments, the primary intracellular signaling sequence is derived from CD3ζ, i.e., the primary intracellular signaling sequence is a CD3ζ intracellular signaling sequence. In some embodiments, the intracellular signaling domain consists of the cytoplasmic signaling domain of CD3ζ. In some embodiments, the primary intracellular signaling sequence is a cytoplasmic signaling domain of wildtype CD3ζ. In some embodiments, the primary intracellular signaling sequence is a functional mutant of the cytoplasmic signaling domain of CD3ζ containing one or more mutations, such as Q65K. In some embodiments, the CD3ζ intracellular signaling sequence comprises the amino acid sequence of SEQ ID NO: 140.

```
CD3ζ intracellular signaling sequence
                                       SEQ ID NO: 140
RVKFSRSADAPAYKQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR
```

In some embodiments, the intracellular signaling domain comprises an intracellular co-stimulatory sequence. In some embodiments, the intracellular signaling domain consists of an intracellular co-stimulatory sequence. In some embodiments, the intracellular signaling domain does not comprise a primary intracellular signaling sequence of an immune effector cell (e.g., T cell). In some embodiments, the intracellular signaling domain comprises both a primary intracellular signaling sequence of an immune effector cell (e.g., T cell) and an intracellular co-stimulatory sequence. In some embodiments, the intracellular signaling domain does not comprise an intracellular co-stimulatory sequence. In some embodiments, the first chimeric receptor comprises an intracellular signaling domain comprising a primary intracellular signaling sequence of an immune effector cell (e.g., T cell), and the second chimeric receptor comprises an intracellular signaling domain comprising an intracellular co-stimulatory sequence. In some embodiments, the first chimeric receptor comprises an intracellular signaling domain comprising an intracellular co-stimulatory sequence, and the second chimeric receptor comprises an intracellular signaling domain comprising a primary intracellular signaling sequence of an immune effector cell (e.g., T cell).

Many immune effector cells require co-stimulation, in addition to stimulation of an antigen-specific signal, to promote cell proliferation, differentiation and survival, as well as to activate effector functions of the cell. In some embodiments, the chimeric receptor comprises at least one intracellular co-stimulatory sequence. The term "intracellular co-stimulatory sequence," as used herein, refers to at least a portion of a protein that mediates signal transduction within a cell to induce an immune response such as an effector function. The intracellular co-stimulatory sequence of the chimeric receptor described herein can be a cytoplasmic signaling domain from a co-stimulatory protein, which transduces a signal and modulates responses mediated by immune cells, such as T cells, NK cells, macrophages, neutrophils, or eosinophils. "Intracellular co-stimulatory sequence" can be the cytoplasmic portion of a co-stimulatory molecule. The term "co-stimulatory molecule" refers to a cognate binding partner on an immune cell (such as T cell) that specifically binds with a co-stimulatory ligand, thereby mediating a co-stimulatory response by the immune cell, such as, but not limited to, proliferation and survival.

In some embodiments, the intracellular signaling domain comprises a single intracellular co-stimulatory sequence. In some embodiments, the intracellular signaling domain comprises two or more (such as about any of 2, 3, 4, or more) intracellular co-stimulatory sequences. In some embodiments, the intracellular signaling domain comprises two or more of the same intracellular co-stimulatory sequences, for example, two copies of the intracellular co-stimulatory sequence of CD28. In some embodiments, the intracellular signaling domain comprises two or more intracellular co-stimulatory sequences from different co-stimulatory proteins, such as any two or more co-stimulatory proteins described herein. In some embodiments, the intracellular signaling domain comprises a primary intracellular signaling sequence (such as cytoplasmic signaling domain of CD3ζ) and one or more intracellular co-stimulatory sequences. In some embodiments, the one or more intracellular co-stimulatory sequences and the primary intracellular signaling sequence (such as cytoplasmic signaling domain of CD3ζ) are fused to each other via optional peptide linkers. The primary intracellular signaling sequence, and the one or more intracellular co-stimulatory sequences may be arranged in any suitable order. In some embodiments, the one or more intracellular co-stimulatory sequences are located between the transmembrane domain and the primary intracellular signaling sequence (such as cytoplasmic signaling domain of CD3ζ). Multiple intracellular co-stimulatory sequences may provide additive or synergistic stimulatory effects.

Activation of an intracellular co-stimulatory sequence in a host cell (e.g., an immune cell) may induce the cell to increase or decrease the production and secretion of cytokines, phagocytic properties, proliferation, differentiation, survival, and/or cytotoxicity. The intracellular co-stimulatory sequence of any co-stimulatory molecule may be compatible for use in the chimeric receptors described herein. The type(s) of intracellular co-stimulatory sequence is selected based on factors such as the type of the immune effector cells in which the effector molecules would be expressed (e.g., T cells, NK cells, macrophages, neutrophils, or eosinophils) and the desired immune effector function (e.g., ADCC effect). Examples of intracellular co-stimulatory sequences for use in the chimeric receptors can be the cytoplasmic signaling domain of co-stimulatory proteins, including, without limitation, members of the B7/CD28 family (e.g., B7-1/CD80, B7-2/CD86, B7-H1/PD-L1, B7-H2, B7-H3, B7-H4, B7-H6, B7-H7, BTLA/CD272, CD28, CTLA-4, Gi24/VISTA/B7-H5, ICOS/CD278, PD-1, PD-L2/B7-DC, and PDCD6); members of the TNF superfamily (e.g., 4-1BB/TNFSF9/4-1BB, 4-1BB Ligand/TNFSF9, BAFF/BLyS/TNFSF13B, BAFF R/TNFRSF13C, CD27/TNFRSF7, CD27 Ligand/TNFSF7, CD30/TNFRSF8, CD30 Ligand/TNFSF8, CD40/TNFRSF5, CD40 TNFSF5, CD40 Ligand/TNFSF5, DR3/TNFRSF25, GITR/TNFRSF18, GITR Ligand/TNFSF18, HVEM/TNFRSF14, LIGHT/TNFSF14, Lymphotoxin-alpha/TNF-beta, OX40/TNFRSF4, OX40 Ligand/TNFSF4, RELT/TNFRSF19L, TACI/TNFRSF13B, TL1A/TNFSF15, TNF-alpha, and TNF RII/TNFRSF1B); members of the SLAM family (e.g., 2B4/CD244/SLAMF4, BLAME/SLAMF8, CD2, CD2F-10/SLAMF9, CD48/SLAMF2, CD58/LFA-3, CD84/SLAMF5, CD229/SLAMF3, CRACC/SLAMF7, NTB-A/SLAMF6, and SLAM/CD150); and any other co-stimulatory molecules, such as CD2, CD7, CD53, CD82/Kai-1, CD90/Thy1, CD96, CD160, CD200, CD300a/LMIR1, HLA Class I, HLA-DR, Ikaros, Integrin alpha 4/CD49d, Integrin alpha 4 beta 1, Integrin alpha 4 beta 7/LPAM-1, LAG-3, TCL1A, TCL1B, CRTAM, DAP12, Dectin-1/CLEC7A, DPPIV/CD26, EphB6, TIM-1/KIM-1/HAVCR, TIM-4, TSLP, TSLP R, lymphocyte function associated antigen-1 (LFA-1), and NKG2C.

In some embodiments, the one or more intracellular co-stimulatory sequences are selected from the group consisting of CD27, CD28, 4-1BB, OX40, CD30, CD40, CD3, lymphocyte function-associated antigen-1(LFA-1), CD2, CD7, LIGHT, NKG2C, B7-H3 and ligands that specially bind to CD83.

In some embodiments, the intracellular signaling domain in the chimeric receptor of the present application comprises an intracellular co-stimulatory sequence derived from CD28. In some embodiments, the intracellular signaling domain comprises a cytoplasmic signaling domain of CD3ζ and an intracellular co-stimulatory sequence of CD28. In some embodiments, the intracellular signaling domain comprises an intracellular co-stimulatory sequence of CD28 comprising the amino acid sequence of RSKRSRLLHSDYMNMTPRRPGPTRKHYQPYAP PRDFAAYRS (SEQ ID NO: 141).

In some embodiments, the intracellular signaling domain in the CAR of the present application comprises an intracellular co-stimulatory sequence derived from 4-1BB (i.e., CD137). In some embodiments, the intracellular signaling domain comprises a cytoplasmic signaling domain of CD3ζ and an intracellular co-stimulatory sequence of 4-1BB. In some embodiments, the intracellular signaling domain comprises an intracellular co-stimulatory sequence of 4-1BB comprising the amino acid sequence of KRGRKKLLYIFKQPFMRPVQTTQEEDGCSCRFPEE EEGGCEL (SEQ ID NO: 142).

In some embodiments, the intracellular signaling domain in the CAR of the present application comprises an intracellular co-stimulatory sequence derived from ICOS. In some embodiments, the intracellular signaling domain comprises a cytoplasmic signaling domain of CD3ζ and an intracellular co-stimulatory sequence of ICOS. In some embodiments, the intracellular signaling domain comprises an intracellular co-stimulatory sequence of ICOS comprising the amino acid sequence of CWLTKKKYSSSVHDPNGEYMFMRAVN-TAKKSR LTDVTL (SEQ ID NO: 143).

In some embodiments, the intracellular signaling domain in the CAR of the present application comprises an intracellular co-stimulatory sequence of CD28 and an intracellular co-stimulatory sequence of 4-1BB. In some embodiments, the intracellular signaling domain comprises a cytoplasmic signaling domain of CD3ζ, an intracellular co-stimulatory sequence of CD28, and an intracellular co-stimulatory sequence of 4-1BB.

In some embodiments, the intracellular signaling domain comprises a polypeptide comprising a cytoplasmic signaling domain of CD3ζ. In some embodiments, the intracellular signaling domain comprises a polypeptide comprising an intracellular co-stimulatory sequence of CD28. In some embodiments, the intracellular signaling domain comprises a polypeptide comprising an intracellular co-stimulatory sequence of 4-1BB. In some embodiments, the intracellular signaling domain comprises a polypeptide comprising from the N-terminus to the C-terminus: an intracellular co-stimulatory sequence of 4-1BB, and a cytoplasmic signaling domain of CD3ζ. In some embodiments, the intracellular signaling domain comprises a polypeptide comprising from the N-terminus to the C-terminus: an intracellular co-stimulatory sequence of CD28, an intracellular co-stimulatory sequence of 4-1BB, and a cytoplasmic signaling domain of CD3ζ.

Also within the scope of the present disclosure are variants of any of the intracellular co-stimulatory sequences described herein, such that the intracellular co-stimulatory sequence is capable of modulating the immune response of the immune cell. In some embodiments, the intracellular co-stimulatory sequences comprises up to 10 amino acid residue variations (e.g., 1, 2, 3, 4, 5, or 8) as compared to a wild-type counterpart. Such intracellular co-stimulatory sequences comprising one or more amino acid variations may be referred to as variants. Mutation of amino acid residues of the intracellular co-stimulatory sequence may result in an increase in signaling transduction and enhanced stimulation of immune responses relative to intracellular co-stimulatory sequences that do not comprise the mutation. Mutation of amino acid residues of the intracellular co-stimulatory sequence may result in a decrease in signaling transduction and reduced stimulation of immune responses relative to intracellular co-stimulatory sequences that do not comprise the mutation.

Hinge Region

The chimeric receptors of the present application may comprise a hinge domain that is located between the extracellular domain and the transmembrane domain. A hinge domain is an amino acid segment that is generally found between two domains of a protein and may allow for flexibility of the protein and movement of one or both of the domains relative to one another. Any amino acid sequence that provides such flexibility and movement of the extracellular domain relative to the transmembrane domain of the effector molecule can be used.

The hinge domain may contain about 10-100 amino acids, e.g., about any one of 15-75 amino acids, 20-50 amino acids, or 30-60 amino acids. In some embodiments, the hinge domain may be at least about any one of 10, 11, 12, 13, 14, 15, 16, 17, 18, 19, 20, 21, 22, 23, 24, 25, 26, 27, 28, 29, 30, 35, 40, 45, 50, 55, 60, 65, 70, or 75 amino acids in length.

In some embodiments, the hinge domain is a hinge domain of a naturally occurring protein. Hinge domains of any protein known in the art to comprise a hinge domain are compatible for use in the chimeric receptors described herein. In some embodiments, the hinge domain is at least a portion of a hinge domain of a naturally occurring protein and confers flexibility to the chimeric receptor. In some embodiments, the hinge domain is derived from CD8, such as CD8α. In some embodiments, the hinge domain is a portion of the hinge domain of CD8α, e.g., a fragment containing at least 15 (e.g., 20, 25, 30, 35, or 40) consecutive amino acids of the hinge domain of CD8α. In some embodiments, the hinge domain of CD8α comprises the amino acid sequence of TTTPAPRPPTPAPTIASQPLSLRPEACR-PAAGGAVHTRGLDFACD (SEQ ID NO: 144). In some embodiments, the hinge domain is derived from CD28. In some embodiments, the hinge domain of CD28 comprises the amino acid sequence of IEVMYPPPYLD-NEKSNGTIIHVKGKHLCPSPLFPGPSKP (SEQ ID NO: 145).

Hinge domains of antibodies, such as an IgG, IgA, IgM, IgE, or IgD antibodies, are also compatible for use in the chimeric receptor systems described herein. In some embodiments, the hinge domain is the hinge domain that joins the constant domains CH1 and CH2 of an antibody. In some embodiments, the hinge domain is of an antibody and comprises the hinge domain of the antibody and one or more constant regions of the antibody. In some embodiments, the hinge domain comprises the hinge domain of an antibody and the CH3 constant region of the antibody. In some embodiments, the hinge domain comprises the hinge domain of an antibody and the CH2 and CH3 constant regions of the antibody. In some embodiments, the antibody is an IgG, IgA, IgM, IgE, or IgD antibody. In some embodiments, the antibody is an IgG antibody. In some embodiments, the antibody is an IgG1, IgG2, IgG3, or IgG4 antibody. In some embodiments, the hinge region comprises the hinge region and the CH2 and CH3 constant regions of an IgG1 antibody. In some embodiments, the hinge region comprises the hinge region and the CH3 constant region of an IgG1 antibody.

Non-naturally occurring peptides may also be used as hinge domains for the chimeric receptors described herein. In some embodiments, the hinge domain between the C-terminus of the extracellular ligand-binding domain of an Fc receptor and the N-terminus of the transmembrane domain is a peptide linker, such as a (GxS)n linker, wherein x and n, independently can be an integer between 3 and 12, including 3, 4, 5, 6, 7, 8, 9, 10, 11, 12, or more. In some embodiments, the peptide linker comprises the amino acid sequence of GGGGSGGGGSGGGGS (SEQ ID NO: 146).

Signal Peptide

The chimeric receptors of the present application may comprise a signal peptide (also known as a signal sequence) at the N-terminus of the polypeptide. In general, signal peptides are peptide sequences that target a polypeptide to the desired site in a cell. In some embodiments, the signal peptide targets the effector molecule to the secretory pathway of the cell and will allow for integration and anchoring of the effector molecule into the lipid bilayer. Signal peptides including signal sequences of naturally occurring proteins or synthetic, non-naturally occurring signal sequences may be compatible for use in the chimeric receptors described herein. In some embodiments, the signal peptide is derived from a molecule selected from the group consisting of CD8, GM-CSF receptor α, and IgG1 heavy chain. In some embodiments, the signal peptide is derived from CD8, such as CD8α. In some embodiments, the signal peptide of CD8α comprises the amino acid sequence of MALPVTALLLPLALLLHAARP (SEQ ID NO: 147).

C. Immune Effector Cell Engagers

One aspect of the present application provides an immune effector cell engager comprising: (a) a target cell binding domain comprising an anti-CD33 sdAb (such as any one of the anti-CD33 sdAbs described herein), and (b) an immune effector cell binding domain comprising an antigen-binding fragment that specifically binds to an antigen on an immune effector cell. In some embodiments, the anti-CD33 sdAb comprises any one of the following: (1) a CDR1 comprising the amino acid sequence of SEQ ID NO: 4, a CDR2 comprising the amino acid sequence of SEQ ID NO: 6, and a CDR3 comprising the amino acid sequence of SEQ ID NO: 8, or a variant thereof comprising up to about 5 amino acid substitutions in the CDRs; (2) a CDR1 comprising the amino acid sequence of SEQ ID NO: 11, a CDR2 comprising the amino acid sequence of SEQ ID NO: 13, and a CDR3 comprising the amino acid sequence of SEQ ID NO: 15, or a variant thereof comprising up to about 5 amino acid substitutions in the CDRs; (3) a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22, or a variant thereof comprising up to about 5 amino acid substitutions in the CDRs; (4) a CDR1 comprising the amino acid sequence of SEQ ID NO: 25, a CDR2 comprising the amino acid sequence of SEQ ID NO: 27, and a CDR3 comprising the amino acid sequence of SEQ ID NO: 29, or a variant thereof comprising up to about 5 amino acid substitutions in the CDRs; (5) a CDR1 comprising the amino acid sequence of SEQ ID NO: 32, a CDR2 comprising the amino acid sequence of SEQ ID NO: 34, and a CDR3 comprising the amino acid sequence of SEQ ID NO: 36, or a variant thereof comprising up to about 5 amino acid substitutions in the CDRs; (6) a CDR1 comprising the amino acid sequence of SEQ ID NO: 39, a CDR2 comprising the amino acid sequence of SEQ ID NO: 41, and a CDR3 comprising the amino acid sequence of SEQ ID NO: 43, or a variant thereof comprising up to about 5 amino acid substitutions in the CDRs; (7) a CDR1 comprising the amino acid sequence of SEQ ID NO: 46, a CDR2 comprising the amino acid sequence of SEQ ID NO: 48, and a CDR3 comprising the amino acid sequence of SEQ ID NO: 50, or a variant thereof comprising up to about 5 amino acid substitutions in the CDRs; (8) a CDR1 comprising the amino acid sequence of SEQ ID NO: 53, a CDR2 comprising the amino acid sequence of SEQ ID NO: 55, and a CDR3 comprising the amino acid sequence of SEQ ID NO: 57, or a variant thereof comprising up to about 5 amino acid substitutions in the CDRs; (9) a CDR1 comprising the amino acid sequence of SEQ ID NO: 60, a CDR2 comprising the amino acid sequence of SEQ ID NO: 62, and a CDR3 comprising the amino acid sequence of SEQ ID NO: 64, or a variant thereof comprising up to about 5 amino acid substitutions in the CDRs; (10) a CDR1 comprising the amino acid sequence of SEQ ID NO: 67, a CDR2 comprising the amino acid sequence of SEQ ID NO: 69, and a CDR3 comprising the amino acid sequence of SEQ ID NO: 71, or a variant thereof comprising up to about 5 amino acid substitutions in the CDRs; (11) a CDR1 comprising the amino acid sequence of SEQ ID NO: 74, a CDR2 comprising the amino acid sequence of SEQ ID NO: 76, and a CDR3 comprising the amino acid sequence of SEQ ID NO: 78, or a variant thereof comprising up to about 5 amino acid substitutions in the CDRs; (12) a CDR1 comprising the amino acid sequence of SEQ ID NO: 81, a CDR2 comprising the amino acid sequence of SEQ ID NO: 83, and a CDR3 comprising the amino acid sequence of SEQ ID NO: 85, or a variant thereof comprising up to about 5 amino acid substitutions in the CDRs; (13) a CDR1 comprising the amino acid sequence of SEQ ID NO: 88, a CDR2 comprising the amino acid sequence of SEQ ID NO: 90, and a CDR3 comprising the amino acid sequence of SEQ ID NO: 92, or a variant thereof comprising up to about 5 amino acid substitutions in the CDRs; (14) a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99, or a variant thereof comprising up to about 5 amino acid substitutions in the CDRs; or (15) a CDR1 comprising the amino acid sequence of SEQ ID NO: 102, a CDR2 comprising the amino acid sequence of SEQ ID NO: 104, and a CDR3 comprising the amino acid sequence of SEQ ID NO: 106, or a variant thereof comprising up to about 5 amino acid substitutions in the CDRs. In some embodiments, the anti-CD33 sdAb comprises a $V_H H$ domain comprising the amino acid sequence of any one of SEQ ID NOs: 108-122, or a variant thereof comprising an amino acid sequence having at least about 95% sequence identity to the amino acid sequence of any one of SEQ ID NOs: 108-122. In some embodiments, the antigen-binding fragment in the immune effector cell binding domain is a Fab, scFv, or sdAb. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker. In some embodiments, the immune effector cell binding domain specifically binds to an antigen selected from the group consisting of CD3γ, CD3δ, CD3ε, CD3ζ, CD28, OX40, GITR, CD137, CD27, CD40L, and HVEM.

In some embodiments, there is provided a T cell engager comprising: (a) a target cell binding domain comprising an anti-CD33 sdAb (such as any one of the anti-CD33 sdAbs described herein), and (b) a T cell binding domain comprising an antigen-binding fragment that specifically binds to an antigen on a T cell. In some embodiments, the anti-CD33 sdAb comprises any one of the following: (1) a CDR1 comprising the amino acid sequence of SEQ ID NO: 4, a CDR2 comprising the amino acid sequence of SEQ ID NO: 6, and a CDR3 comprising the amino acid sequence of SEQ ID NO: 8, or a variant thereof comprising up to about 5 amino acid substitutions in the CDRs; (2) a CDR1 comprising the amino acid sequence of SEQ ID NO: 11, a CDR2 comprising the amino acid sequence of SEQ ID NO: 13, and a CDR3 comprising the amino acid sequence of SEQ ID NO: 15, or a variant thereof comprising up to about 5 amino acid substitutions in the CDRs; (3) a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22, or a variant thereof comprising up to about 5 amino acid substitutions in the CDRs; (4) a CDR1 comprising the amino acid sequence of SEQ ID NO: 25, a CDR2 comprising the amino acid sequence of SEQ ID NO: 27, and a CDR3 comprising the amino acid sequence of SEQ ID NO: 29, or a variant thereof comprising up to about 5 amino acid substitutions in the CDRs; (5) a CDR1 comprising the amino acid sequence of SEQ ID NO: 32, a CDR2 comprising the amino acid sequence of SEQ ID NO: 34, and a CDR3 comprising the amino acid sequence of SEQ ID NO: 36, or a variant thereof comprising up to about 5 amino acid substitutions in the CDRs; (6) a CDR1 comprising the amino acid sequence of SEQ ID NO: 39, a CDR2 comprising the amino acid sequence of SEQ ID NO: 41, and a CDR3 comprising the amino acid sequence of SEQ ID NO: 43, or a variant thereof comprising up to about 5 amino acid substitutions in the CDRs; (7) a CDR1 comprising the amino acid sequence of SEQ ID NO: 46, a CDR2 comprising the amino acid sequence of SEQ ID NO: 48, and a CDR3 comprising the amino acid sequence of SEQ ID NO: 50, or a variant thereof comprising up to about 5 amino acid substitutions in the CDRs; (8) a CDR1 comprising the amino acid sequence of SEQ ID NO: 53, a CDR2 comprising the amino acid sequence of SEQ ID NO: 55, and a CDR3 comprising the amino acid sequence of SEQ ID NO: 57, or a variant thereof comprising up to about 5 amino acid substitutions in the CDRs; (9) a CDR1 comprising the amino acid sequence of SEQ ID NO: 60, a CDR2 comprising the amino acid sequence of SEQ ID NO: 62, and a CDR3 comprising the amino acid sequence of SEQ ID NO: 64, or a variant thereof comprising up to about 5 amino acid substitutions in the CDRs; (10) a CDR1 comprising the amino acid sequence of SEQ ID NO: 67, a CDR2 comprising the amino acid sequence of SEQ ID NO: 69, and a CDR3 comprising the amino acid sequence of SEQ ID NO: 71, or a variant thereof comprising up to about 5 amino acid substitutions in the CDRs; (11) a CDR1 comprising the amino acid sequence of SEQ ID NO: 74, a CDR2 comprising the amino acid sequence of SEQ ID NO: 76, and a CDR3 comprising the amino acid sequence of SEQ ID NO: 78, or a variant thereof comprising up to about 5 amino acid substitutions in the CDRs; (12) a CDR1 comprising the amino acid sequence of SEQ ID NO: 81, a CDR2 comprising the amino acid sequence of SEQ ID NO: 83, and a CDR3 comprising the amino acid sequence of SEQ ID NO: 85, or a variant thereof comprising up to about 5 amino acid substitutions in the CDRs; (13) a CDR1 comprising the amino acid sequence of SEQ ID NO: 88, a CDR2 comprising the amino acid sequence of SEQ ID NO: 90, and a CDR3 comprising the amino acid sequence of SEQ ID NO: 92, or a variant thereof comprising up to about 5 amino acid substitutions in the CDRs; (14) a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99, or a variant thereof comprising up to about 5 amino acid substitutions in the CDRs; or (15) a CDR1 comprising the amino acid sequence of SEQ ID NO: 102, a CDR2 comprising the amino acid sequence of SEQ ID NO: 104, and a CDR3 comprising the amino acid sequence of SEQ ID NO: 106, or a variant thereof comprising up to about 5 amino acid substitutions in the CDRs. In some embodiments, the anti-CD33 sdAb comprises a $V_HH$ domain comprising the amino acid sequence of any one of SEQ ID NOs: 108-122, or a variant thereof comprising an amino acid sequence having at least about 95% sequence identity to the amino acid sequence of any one of SEQ ID NOs: 108-122. In some embodiments, the antigen-binding fragment in the T cell binding domain is a Fab, scFv, or sdAb. In some embodiments, the target cell binding domain is fused to the N-terminus of the T cell binding domain. In some embodiments, the target cell binding domain is fused to the C-terminus of T cell binding domain. In some embodiments, the target cell binding domain is fused to the T cell binding domain via a peptide linker. In some embodiments, the immune effector cell binding domain specifically binds to an antigen selected from the group consisting of CD3γ, CD3δ, CD3ε, CD3ζ, CD28, OX40, GITR, CD137, CD27, CD40L, and HVEM. In some embodiments, the immune effector cell binding domain comprises an antigen-binding fragment that specifically binds to CD3, such as CD3ε.

Target Cell Binding Domain

The immune effector cell engagers described herein comprise a target cell binding domain comprising an anti-CD33 sdAb. In some embodiments, the target cell binding domain consists of an anti-CD33 sdAb. In some embodiments, the target cell binding domain comprises an anti-CD33 sdAb and one or more antigen-binding fragments derived from single-domain antibodies or four-chain antibodies that specifically bind to an antigen on a target cell. In some embodiments, the target cell is a tumor cell or a myeloid cell.

In some embodiments, the target cell binding domain has two or more (such as about any one of 2, 3, 4, 5, 6, or more) antigen binding fragments such as single-domain antibodies. In some embodiments, the multivalent target cell binding domain targets CD33 only, and comprises two or more antigen binding fragments for CD33. In some embodiments, the multivalent target cell binding domain targets more than one antigen, and the multivalent target cell binding domain comprises two or more antigen binding fragments for at least one antigen. The antigen binding fragments specific for the same antigen may bind to the same epitope of the antigen or bind to different epitopes of the antigen. The antigen binding fragments specific for the same antigen may comprise the same or different single-domain antibodies.

In some embodiments, the target cell binding domain comprises a plurality of anti-CD33 sdAbs. In some embodiments, the plurality of the anti-CD33 sdAb is fused to each other via peptide bonds or peptide linkers. In some embodiments, each peptide linker is no more than about 50 (such as no more than about any one of 35, 25, 20, 15, 10, or 5) amino acids long.

In some embodiments, the target cell binding domain can specifically bind to two or more (such as about any one of 2, 3, 4, 5, 6, or more) different antigens. In some embodiments, the multispecific target cell binding domain has one antigen binding fragments for each antigen. In some embodiments, the multispecific target cell binding domain has more than two antigen binding fragments for at least one antigen. Each antigen binding fragment may comprise a single-domain antibody.

Depending on the desired antigens to be targeted, the target cell binding domain can be engineered to include the appropriate single-domain antibodies that are specific to the desired antigens. In some embodiments, the target cell binding domain comprises an anti-CD33 sdAb and an anti-CLL1 sdAb. The antigen binding fragments (such as sdAbs) can be arranged in any suitable order. For example, a first sdAb is fused to the N-terminus or the C-terminus of a second sdAb. A suitable peptide linker may be placed between different sdAbs to avoid steric hindrance between the sdAbs.

Immune Effector Cell Binding Domain

The immune effector cell engagers described herein comprise an immune effector cell binding domain. The immune effector cell binding domain comprises an antigen-binding fragment that specifically binds to an antigen on an immune effector cell. Immune effector cells include, but are not limited to, T cells and NK cells.

In some embodiments, the immune effector cell binding domain specifically binds to CD3, such as human CD3ζ. "CD3" is known in the art as a multi-protein complex of six chains (see, Abbas and Lichtman, 2003; Janeway et al., p172 and 178, 1999). In mammals, the complex comprises a CD3 gamma chain, a CD3 delta chain, two CD3 epsilon chains, and a homodimer of CD3 zeta chains. CD3 as used herein may be from various animal species, including human, primate, mouse, rat, or other mammals. In some embodiments, the immune effector cell binding domain comprises an antigen-binding fragment that specifically binds to an individual CD3 chain, such as CD3 gamma chain, CD3 delta chain, or CD3 epsilon chain. In some embodiments, the antigen-binding fragment specifically binds to a complex formed from two or more individual CD3 chains (e.g., a complex of more than one CD3 epsilon chains, a complex of a CD3 gamma and CD3 epsilon chain, a complex of a CD3 delta and CD3 epsilon chain). In some embodiments, the antigen-binding fragment specifically binds to a CD3 epsilon chain.

The antigen-binding fragment targeting CD3 can be of any suitable antigen-binding fragments, including but not limited to Fab, scFv, and sdAb (e.g., $V_HH$). In some embodiments, the antigen-binding fragment is murine, camelid, chimeric, human or humanized. The antigen-binding fragment can be designed based on any known CD3 antibodies in the art, including, but not limited to, SP34 mouse monoclonal antibody, (see, for example, Pressano, S. The EMBO J. 4:337-344, 1985; Alarcon, B. EMBO J. 10:903-912, 1991; Salmeron A. et al., J. Immunol. 147:3047-52, 1991; Yoshino N. et al., Exp. Anim 49:97-110, 2000; Conrad M L. et al., Cytometry 71A:925-33, 2007; and Yang et al., J. Immunol. 137:1097-1100: 1986), Cris-7 monoclonal antibody (Reinherz, E. L. et al. (eds.), Leukocyte typing II, Springer Verlag, New York, (1986)), BC3 monoclonal antibody (Anasetti et al. (1990) J. Exp. Med. 172:1691), OKT3 (Ortho multicenter Transplant Study Group (1985) N. Engl. J. Med. 313:337) and derivatives thereof such as OKT3 ala-ala (Herold et al. (2003) J. Clin. Invest. 11:409), visilizumab (Carpenter et al. (2002) Blood 99:2712), 145-2C11 monoclonal antibody (Hirsch et al. (1988) J. Immunol. 140: 3766), UCHT-1 (Beverley, P C and Callard, R. E. (1981) Eur. J. Immunol. 11: 329-334), anti-CD3 sdAbs (such as 60E11 and 117G03) described in WO2016180982, and CD3 binding molecules described in WO2004/106380; WO2004/106381; WO2010/

037838; WO2008/119567; WO2007/042261; WO2010/0150918; the contents of each of the references are incorporated herein by reference in their entireties. In some embodiments, the anti-CD3 antigen-binding fragment is derived from OKT3, L2K, UCHT1, 60E11 or 117G03. In some embodiments, the anti-CD3 antigen-binding fragment is an scFv derived from OKT3, L2K or UCHT. In some embodiments, the anti-CD3 antigen-binding fragment is a $V_H H$ derived from 60E11 or 117G03. In some embodiments, the anti-CD3 antigen-binding fragment is derived from an antibody that binds to the same epitope as OKT3, L2K, UCHT1, 60E11 or 117G03. In some embodiments, the anti-CD3 antigen-binding fragment is derived from an antibody that specifically binds to CD3 competitively with OKT3, L2K, UCHT1, 60E11 or 117G03.

Signal Peptide

The immune effector cell engagers of the present application may comprise a signal peptide (also known as a signal sequence) at the N-terminus of the polypeptide. In general, signal peptides are peptide sequences that target a polypeptide to the desired site in a cell. In some embodiments, the signal peptide targets the immune effector cell engager to the secretory pathway of the cell and will allow secretion of the immune effector cell engager into the cell culture media. Signal peptides including signal sequences of naturally occurring proteins or synthetic, non-naturally occurring signal sequences. In some embodiments, the signal peptide is derived from a human albumin signal peptide. In some embodiments, the signal peptide is derived from a human azurocidin secretion signal.

Peptide Linkers

The target cell binding domain and the immune effector cell binding domain may be fused to each other via a peptide linker. In some embodiments, the target cell binding domain and the immune effector cell binding domain are directly fused to each other without any peptide linker.

In some embodiments, the various antigen-binding fragments (such as sdAbs) in the multispecific or multivalent target cell binding domain are fused to each other via peptide linker(s). In some embodiments, the antigen-binding fragments (such as sdAbs) are directly fused to each other without any peptide linkers. The peptide linkers connecting different antigen-binding fragments (such as sdAbs) may be the same or different.

Each peptide linker in an immune effector cell engager may have the same or different length and/or sequence depending on the structural and/or functional features of the antigen-binding fragments (such as sdAbs) and/or the various domains. Each peptide linker may be selected and optimized independently. The length, the degree of flexibility and/or other properties of the peptide linker(s) used in the immune effector cell engagers may have some influence on properties, including but not limited to the affinity, specificity or avidity for one or more particular antigens or epitopes. For example, longer peptide linkers may be selected to ensure that two adjacent domains do not sterically interfere with one another. For example, in a multivalent or multispecific target cell binding domain that comprises sdAbs directed against a multimeric antigen, the length and flexibility of the peptide linkers are preferably such that it allows each antigen-binding fragment (such as sdAb) to bind to the antigenic determinant on each of the subunits of the multimer.

In some embodiment, a peptide linker comprises flexible residues (such as glycine and serine) so that the adjacent domains are free to move relative to each other. For example, a $(GGGGS)_3$ linker (SEQ ID NO: 146) can be a suitable peptide linker between the target cell binding domain and the immune effector cell binding domain. In some embodiments, the peptide linker is no more than about 50 (such as no more than about any one of 35, 25, 20, 15, 10, or 5) amino acids long.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acids to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a flexible linker. Exemplary flexible linkers include glycine polymers $(G)_n$, glycine-serine polymers (including, for example, $(GS)_n$, $(GSGGS)_n$, $(GGGS)_n$, and $(GGGGS)_n$, where n is an integer of at least one), glycine-alanine polymers, alanine-serine polymers, and other flexible linkers known in the art. In some embodiments, the peptide linker comprises the amino acid sequence GGGGS (SEQ ID NO: 148), $(GGGGS)_2$ (SEQ ID NO: 149), $(GGGGS)_3$ (SEQ ID NO: 146), $(GGGGS)_5$ (SEQ ID NO: 216), $(GGGS)_2$ (SEQ ID NO: 150), $(GGGS)_4$ (SEQ ID NO: 151), or GSTSGSGKPGSGEGSTKG (SEQ ID NO: 152).

D. Immunoconjugates

In one aspect, the present application provides immunoconjugates comprising an anti-CD33 sdAb (such as any one of the anti-CD33 sdAbs described herein) and an effector molecule. Exemplary effector molecules include, but are not limited to, a drug, a toxin, a radioisotope, a protein, a peptide, a nucleic acid, and a label.

In some embodiments, there is provided an immunoconjugate comprising an anti-CD33 sdAb (such as any one of the anti-CD33 sdAbs described herein) conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some embodiments, an immunoconjugate is an antibody-drug conjugate (ADC) in which an anti-CD33 sdAb is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl.*

Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In some embodiments, an immunoconjugate comprises an anti-CD33 sdAb as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, an immunoconjugate comprises an anti-CD33 sdAb as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, "MRI"), such as iodine-123, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A.).

In some embodiments, any of the anti-CD33 sdAbs provided herein is useful for detecting the presence of CD33 in a biological sample. The term "detecting" as used herein encompasses quantitative or qualitative detection. In certain embodiments, a biological sample is blood, serum or other liquid samples of biological origin. In some embodiments, a biological sample comprises a cell or tissue.

In some embodiments, the present application provides an immunoconjugate comprising an anti-CD33 sdAb (such as any one of the anti-CD33 sdAbs described herein) and a label. In some embodiments, the label is conjugated to the anti-CD33 sdAb. In some embodiments, there is provided a method of detecting CD33 in a cell, comprising contacting the cell with the immunoconjugate. In some embodiments, a method of detecting the presence of CD33 in a biological sample is provided. In some embodiments, the method comprises detecting the presence of CD33 protein in a biological sample. In some embodiments, the CD33 is human CD33. In some embodiments, the method comprises contacting the biological sample with the immunoconjugate under conditions permissive for binding of the anti-CD33 sdAb to CD33, and detecting signal from the label. Such method may be an in vitro or in vivo method. In some embodiments, there is provided a method of diagnosing a disease associated with CD33 expression (e.g., acute myeloid leukemia) in an individual, comprising administering to the individual the immunoconjugate, and detecting the label in the individual. In some embodiments, the immunoconjugate is used to select subjects eligible for therapy with any of the anti-CD33 therapeutic agents described herein (e.g., anti-CD33 sdAb, chimeric receptor, immune effector cell engager, and engineered immune cell), wherein CD33 is a biomarker for selection of patients.

In some embodiments, labeled anti-CD33 sdAbs are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

E. Features of Antibody Moieties

In some embodiments, any antibody moiety in the anti-CD33 constructs described herein may incorporate any of the features, singly or in combination, as described in sections 1-7 below.

1. Antibody Affinity

In some embodiments, an antibody moiety provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In some embodiments, Kd is measured by a radiolabeled antigen binding assay (RIA) performed with the Fab version or $V_HH$ fragment of an antibody of interest and its antigen as described by the following assay. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)).

In some embodiments, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab or V$_H$H of the antibody of interest (0.78 nM to 500 nM) are injected in PBS with 0.05% polysorbate 20 (TWEEN-20') surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody moiety in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In some embodiments, an antibody moiety provided herein is an antibody fragment. Antibody fragments include, but are not limited to, Fab, Fab', Fab'-SH, F(ab')$_2$, Fv, and scFv fragments, V$_H$H, and other fragments described below. For a review of certain antibody fragments, see Hudson et al. *Nat. Med.* 9:129-134 (2003). For a review of scFv fragments, see, e.g., Pluckthiin, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In some embodiments, an antibody moiety provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a camelid species, such as llama) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In some embodiments, the sdAbs are modified, such as humanized, without diminishing the native affinity of the domain for antigen and while reducing its immunogenicity with respect to a heterologous species. For example, the amino acid residues of the antibody variable domain (V$_H$H) of an llama antibody can be determined, and one or more of the Camelid amino acids, for example, in the framework regions, are replaced by their human counterpart as found in the human consensus sequence, without that polypeptide losing its typical character, i.e. the humanization does not significantly affect the antigen binding capacity of the resulting polypeptide. Humanization of Camelid sdAbs requires the introduction and mutagenesis of a limited amount of amino acids in a single polypeptide chain. This is in contrast to humanization of scFv, Fab', (Fab')$_2$ and IgG, which requires the introduction of amino acid changes in two chains, the light and the heavy chain and the preservation of the assembly of both chains.

Single-domain antibodies comprising a V$_H$H-1 domain can be humanized to have human-like sequences. In some embodiments, the FR regions of the V$_H$H-1 domain used herein comprise at least about any one of 50%, 60%, 70%, 80%, 90%, 95% or more of amino acid sequence homology to human V$_H$ framework regions. One exemplary class of humanized V$_H$H domains is characterized in that the V$_H$Hs carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 and a tryptophan at position 103, according to the Kabat numbering. As such, polypeptides belonging to this class show a high amino acid sequence homology to human V$_H$ framework regions and said polypeptides might be administered to a human directly without expectation of an unwanted immune response therefrom, and without the burden of further humanization.

Another exemplary class of humanized Camelid sdAbs has been described in WO 03/035694 and contains hydrophobic FR2 residues typically found in conventional antibodies of human origin or from other species, but compensating this loss in hydrophilicity by the charged arginine residue on position 103 that substitutes the conserved tryptophan residue present in V$_H$ from double-chain antibodies. As such, peptides belonging to these two classes show a high amino acid sequence homology to human V$_H$ framework regions and said peptides might be administered to a human directly without expectation of an unwanted immune response therefrom, and without the burden of further humanization.

4. Human Antibodies

In some embodiments, an antibody moiety provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008). Transgenic mice or rats capable of producing fully human sdAbs are known in the art. See, e.g., US20090307787A1, U.S. Pat. No. 8,754,287, US20150289489A1, US20100122358A1, and WO2004049794.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VELCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

One technique for obtaining V$_H$H sequences directed against a particular antigen or target involves suitably immunizing a transgenic mammal that is capable of expressing heavy chain antibodies (i.e. so as to raise an immune response and/or heavy chain antibodies directed against said antigen or target), obtaining a suitable biological sample from said transgenic mammal that contains (nucleic acid sequences encoding) said V$_H$H sequences (such as a blood sample, serum sample or sample of B-cells), and then generating V$_H$H sequences directed against said antigen or target, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssens et al., Proc. Natl. Acad., Sci. USA. 2006 Oct. 10; 103(41):15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

5. Library-Derived Antibodies

Antibody moieties of the present application may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093

(2004); Fellouse, *Proc. Natl. Acad. Sci. USA* 101(34): 12467-12472 (2004); and Lee et al., *J. Immunol. Methods* 284(1-2): 119-132(2004). Methods for constructing sdAb libraries have been described, for example, see U.S. Pat. No. 7,371,849.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In some embodiments, an antibody moiety provided herein is a multispecific antibody, e.g. a bispecific antibody. Bispecific antibodies can be prepared as full length antibodies or antibody fragments. Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J*. 10: 3655 (1991)), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bispecific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g., Gruber et al., *J. Immunol.*, 152:5368 (1994)); and preparing trispecific antibodies as described, e.g., in Tutt et al. *J. Immunol*. 147: 60 (1991); and creating polypeptides comprising tandem single-domain antibodies (see, e.g., U.S. Patent Application No. 20110028695; and Conrath et al. *J. Biol. Chem.*, 2001; 276(10):7346-50). Engineered antibodies with three or more functional antigen binding sites, including "Octopus antibodies," are also included herein (see, e.g., US 2006/0025576A1).

7. Antibody Variants

In some embodiments, amino acid sequence variants of the antibody moieties provided herein are contemplated. For example, it may be desirable to improve the binding affinity and/or other biological properties of the antibody moiety. Amino acid sequence variants of an antibody moiety may be prepared by introducing appropriate modifications into the nucleic acid sequence encoding the antibody moiety, or by peptide synthesis. Such modifications include, for example, deletions from, and/or insertions into and/or substitutions of residues within the amino acid sequences of the antibody moiety. Any combination of deletion, insertion, and substitution can be made to arrive at the final construct, provided that the final construct possesses the desired characteristics, e.g., antigen-binding.

a) Substitution, Insertion, and Deletion Variants

In some embodiments, antibody variants having one or more amino acid substitutions are provided. Sites of interest for substitutional mutagenesis include the HVRs and FRs. Conservative substitutions are shown in Table 7 under the heading of "Preferred substitutions." More substantial changes are provided in Table 7 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 7

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |

TABLE 7-continued

Amino Acid Substitutions

| Original Residue | Exemplary Substitutions | Preferred Substitutions |
|---|---|---|
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody moiety to bind antigen. For example, conservative alterations (e.g., conservative substitutions as provided herein) that do not substantially reduce binding affinity may be made in HVRs. Such alterations may be outside of HVR "hotspots" or CDRs. In some embodiments of the variant $V_H H$ sequences provided above, each HVR either is unaltered, or contains no more than one, two or three amino acid substitutions.

A useful method for identification of residues or regions of an antibody moiety that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody moiety with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In some embodiments, an antibody moiety provided herein is altered to increase or decrease the extent to which the antibody moiety is glycosylated. Addition or deletion of glycosylation sites to an antibody moiety may be conveniently accomplished by altering the amino acid sequence such that one or more glycosylation sites is created or removed.

Where the antibody moiety comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the present application may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4): 680-688 (2006); and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In some embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CYTOTOX 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In some embodiments, it may be desirable to create cysteine engineered antibodies, e.g., "thioMAbs," in which one or more residues of an antibody moiety are substituted with cysteine residues. In particular embodiments, the substituted residues occur at accessible sites of the antibody moiety. By substituting those residues with cysteine, reactive thiol groups are thereby positioned at accessible sites of the antibody moiety and may be used to conjugate the antibody to other moieties, such as drug moieties or linker-drug moieties, to create an immunoconjugate, as described further herein. In some embodiments, any one or more of the following residues may be substituted with cysteine: A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In some embodiments, an antibody moiety provided herein may be further modified to contain additional non-proteinaceous moieties that are known in the art and readily available. The moieties suitable for derivatization of the antibody moiety include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody moiety may vary, and if more than one polymer are attached, they can be the same or different molecules. In general, the number and/or type of polymers used for derivatization can be determined based on considerations including, but not limited to, the particular properties or functions of the antibody moiety to be improved, whether the antibody moiety derivative will be used in a therapy under defined conditions, etc.

III. Methods of Preparing Anti-CD33 Constructs

The anti-CD33 constructs, including anti-CD33 sdAbs, immune effector cell engagers, and antibody moieties of the immunoconjugates as described herein may be prepared using any methods known in the art or as described herein. Compositions and methods of preparing anti-CD33 chimeric receptors and chimeric receptor systems are described in Section IV.

Methods of preparing sdAbs have been described. See, for example, Els Pardon et al, *Nature Protocol,* 2014; 9(3): 674. Single-domain antibodies (such as $V_H$Hs) may be obtained using methods known in the art such as by immunizing a *Camelid* species (such as camel or llama) and obtaining hybridomas therefrom, or by cloning a library of sdAbs using molecular biology techniques known in the art and subsequent selection by ELISA with individual clones of unselected libraries or by using phage display.

For recombinant production of the sdAbs, the nucleic acids encoding the sdAbs are isolated and inserted into a replicable vector for further cloning (amplification of the DNA) or for expression. DNA encoding the sdAb is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

Nucleic Acids and Vectors

Nucleic acid molecules comprising polynucleotides that encode one or more chains of any one of the anti-CD33 constructs described herein are provided.

In some embodiments, there is provided an isolated nucleic acid encoding any one of the anti-CD33 sdAbs described herein. In some embodiments, an isolated nucleic acid encoding an anti-CD33 sdAb is provided wherein the nucleic acid comprises a sequence having at least about any one of 85%, 86%, 87%, 88%, 89%, 90%, 91%, 92%, 93%, 94%, 95%, 96%, 97%, 98%, 99%, or 100% sequence identity to the nucleic acid sequence of any one of SEQ ID NOs: 123-137. In some embodiments, there is provided an isolated nucleic acid comprising a nucleic acid sequence selected from the group consisting of SEQ ID NOs: 123-137.

Nucleic acid molecules may be constructed using recombinant DNA techniques conventional in the art. In some embodiments, a nucleic acid molecule is an expression vector that is suitable for expression in a selected host cell.

Vectors comprising polynucleotides that encode any one of the anti-CD33 constructs described herein are provided. Such vectors include, but are not limited to, DNA vectors, phage vectors, viral vectors, retroviral vectors, etc. In some embodiments, the vector is an expression vector.

Host Cells

In some embodiments, the anti-CD33 construct may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO—S, DG44. Lec13 CHO cells, and FUT8 CHO cells; PER.C6® cells (Crucell); and NS0 cells. In some embodiments, the anti-CD33 construct may be expressed in yeast. See, e.g., U.S. Publication No. US 2006/0270045 A1. In some embodiments, a particular eukaryotic host cell is selected based on its ability to make desired post-translational modifications to the anti-CD33 construct. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., Molecular Cloning, A Laboratory Manual, 3$^{rd}$ ed. Cold Spring Harbor Laboratory Press (2001). Nucleic acids may be transiently or stably transfected in the desired host cells, according to any suitable method.

The invention also provides host cells comprising any of the polynucleotides or vectors described herein. In some embodiments, the invention provides a host cell comprising an anti-CD33 construct. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactic*).

EXPRESSION AND PURIFICATION

In some embodiments, a method of making an anti-CD33 construct is provided, wherein the method comprises culturing a host cell comprising a nucleic acid encoding the anti-CD33 construct under conditions suitable for expression of the anti-CD33 construct, and optionally recovering the anti-CD33 construct from the host cell (or host cell culture medium).

The anti-CD33 construct may be purified by any suitable method. Such methods include, but are not limited to, the use of affinity matrices or hydrophobic interaction chromatography. Suitable affinity ligands include the ROR1 ECD and ligands that bind antibody constant regions. For example, a Protein A, Protein G, Protein A/G, or an antibody affinity column may be used to bind the constant region and to purify an anti-CD33 construct comprising a constant region. Hydrophobic interactive chromatography, for example, a butyl or phenyl column, may also suitable for purifying some polypeptides such as antibodies. Ion exchange chromatography (e.g. anion exchange chromatography and/or cation exchange chromatography) may also suitable for purifying some polypeptides such as antibodies. Mixed-mode chromatography (e.g. reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

In some embodiments, an anti-CD33 construct is produced in a cell-free system. Nonlimiting exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

Also provided are anti-CD33 constructs prepared by any one of the methods described herein. In some embodiments, the anti-CD33 construct is prepared in a host cell. In some embodiments, the anti-CD33 construct is prepared in a cell-free system. In some embodiments, the anti-CD33 construct is purified. In some embodiments, the present application provides a cell culture media comprising an anti-CD33 construct. In some embodiments, the present application provides a host cell culture fluid comprising an anti-CD33 construct.

IV. Engineered Immune Cells

One aspect of the present application provides host cells (such as immune cells) comprising any one of the anti-CD33 chimeric receptors or chimeric receptor systems as described herein.

Thus, in some embodiments, there is provided an engineered immune cell (such as T cell) comprising an anti-CD33 chimeric receptor comprising: (a) an extracellular domain comprising an anti-CD33 sdAb (such as any one of the anti-CD33 sdAbs described herein); (b) a transmembrane domain; and (c) an intracellular signaling domain. In some embodiments, the intracellular signaling domain comprises a primary intracellular signaling sequence of an immune effector cell (such as T cell). In some embodiments, the primary intracellular signaling sequence is derived from CD3ζ, FcRγ, FcRβ, CD3γ, CD3δ, CD3ε, CD5, CD22, CD79a, CD79b, or CD66d. In some embodiments, the primary intracellular signaling sequence is derived from CD3ζ. In some embodiments, the intracellular signaling domain comprises an intracellular co-stimulatory sequence. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the engineered immune cell expresses a safety-switch antigen or epitope, such as CD52, EGFR, or CD20.

In some embodiments, there is provided an engineered immune cell (such as T cell) comprising an anti-CD33 chimeric receptor comprising: (a) an extracellular domain comprising an anti-CD33 sdAb (such as any one of the anti-CD33 sdAbs described herein); (b) a transmembrane domain; and (c) an intracellular signaling domain comprising a CD3ζ intracellular signaling sequence and an intracellular co-stimulatory sequence derived from CD28 or 4-1BB. In some embodiments, the engineered immune cell expresses a safety-switch antigen or epitope, such as CD52, EGFR, or CD20.

In some embodiments, there is provided an engineered immune cell (such as T cell) comprising: (a) a first chimeric receptor comprising an extracellular domain comprising an anti-CD33 sdAb (such as any one of the anti-CD33 sdAbs described herein), a transmembrane domain, and an intracellular signaling domain comprising a primary intracellular signaling sequence of an immune effector cell (e.g., T cell) and an intracellular co-stimulatory sequence; (b) a second chimeric receptor comprising an extracellular domain comprising a second binding moiety (e.g., sdAb, scFv, or an extracellular domain of a receptor) that specifically binds to a second antigen or epitope, a transmembrane domain, and an intracellular signaling domain comprising a primary intracellular signaling sequence of an immune effector cell (e.g., T cell) and an intracellular co-stimulatory sequence. In some embodiments, the intracellular signaling domain of each of the first chimeric receptor and the second chimeric receptor comprises a CD3ζ intracellular signaling sequence and an intracellular co-stimulatory sequence derived from CD28 or 4-1BB. In some embodiments, the second binding moiety is an anti-CLL1 or anti-CD123 sdAb or scFv. In some embodiments, the second binding moiety is an extracellular domain of NKG2D. In some embodiments, the engineered immune cell expresses a safety-switch antigen or epitope, such as CD52, EGFR, or CD20.

In some embodiments, there is provided an engineered immune cell (such as T cell) comprising: (a) a first chimeric receptor comprising an extracellular domain comprising an anti-CD33 sdAb (such as any one of the anti-CD33 sdAbs described herein), a transmembrane domain, and an intracellular signaling domain comprising a primary intracellular signaling sequence of an immune effector cell (e.g., T cell); (b) a second chimeric receptor comprising an extracellular domain comprising a second binding moiety (e.g., sdAb, scFv, or an extracellular domain of a receptor) that specifically binds to a second antigen or epitope, a transmembrane domain, and an intracellular signaling domain comprising an intracellular co-stimulatory sequence. In some embodiments, the intracellular signaling domain of the first chimeric receptor comprises a CD3ζ intracellular signaling sequence. In some embodiments, the intracellular signaling domain of the second chimeric receptor comprises an intracellular co-stimulatory sequence derived from CD28 or 4-1BB. In some embodiments, the second binding moiety is an anti-CLL1 or anti-CD123 sdAb or scFv. In some embodiments, the second binding moiety is an extracellular domain of NKG2D. In some embodiments, the engineered immune cell expresses a safety-switch antigen or epitope, such as CD52, EGFR, or CD20.

In some embodiments, there is provided an engineered immune cell (such as T cell) comprising: (a) a first chimeric receptor comprising an extracellular domain comprising an anti-CD33 sdAb (such as any one of the anti-CD33 sdAbs described herein), a transmembrane domain, and an intracellular domain comprising an intracellular signaling domain comprising an intracellular co-stimulatory sequence; (b) a second chimeric receptor comprising an extracellular domain comprising a second binding moiety (e.g., sdAb, scFv, or an extracellular domain of a receptor) that specifically binds to a second antigen or epitope, a transmembrane domain, and an intracellular signaling domain comprising a primary intracellular signaling sequence of an immune effector cell (e.g., T cell). In some embodiments, the intracellular signaling domain of the first chimeric receptor comprises an intracellular co-stimulatory sequence derived from CD28 or 4-1BB. In some embodiments, the intracellular signaling domain of the second chimeric receptor comprises a CD3ζ intracellular signaling sequence. In some embodiments, the second binding moiety is an anti-CLL1 or anti-CD123 sdAb or scFv. In some embodiments, the second binding moiety is an extracellular domain of NKG2D. In some embodiments, the engineered immune cell expresses a safety-switch antigen or epitope, such as CD52, EGFR, or CD20.

In some embodiments according to any one of the engineered immune cells described above, the anti-CD33 sdAb comprises any one of the following: (1) a CDR1 comprising the amino acid sequence of SEQ ID NO: 4, a CDR2 comprising the amino acid sequence of SEQ ID NO: 6, and a CDR3 comprising the amino acid sequence of SEQ ID NO: 8, or a variant thereof comprising up to about 5 amino acid substitutions in the CDRs; (2) a CDR1 comprising the amino acid sequence of SEQ ID NO: 11, a CDR2 comprising the amino acid sequence of SEQ ID NO: 13, and a CDR3 comprising the amino acid sequence of SEQ ID NO: 15, or a variant thereof comprising up to about 5 amino acid substitutions in the CDRs; (3) a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22, or a variant thereof comprising up to about 5 amino acid substitutions in the CDRs; (4) a CDR1 comprising the amino acid sequence of SEQ ID NO: 25, a CDR2 comprising the amino acid sequence of SEQ ID NO: 27, and a CDR3 comprising the amino acid sequence of SEQ ID NO: 29, or a variant thereof comprising up to about 5 amino acid substitutions in the CDRs; (5) a CDR1 comprising the amino acid sequence of SEQ ID NO: 32, a CDR2 comprising the amino acid sequence of SEQ ID NO: 34, and a CDR3 comprising the amino acid sequence of SEQ ID NO: 36, or a variant thereof comprising up to about 5 amino acid substitutions in the CDRs; (6) a CDR1 comprising the amino acid sequence of SEQ ID NO: 39, a CDR2 comprising the amino acid sequence of SEQ ID NO: 41, and a CDR3 comprising the amino acid sequence of SEQ ID NO: 43, or a variant thereof comprising up to about 5 amino acid substitutions in the CDRs; (7) a CDR1 comprising the amino acid sequence of SEQ ID NO: 46, a CDR2 comprising the amino acid sequence of SEQ ID NO: 48, and a CDR3 comprising the amino acid sequence of SEQ ID NO: 50, or a variant thereof comprising up to about 5 amino acid substitutions in the CDRs; (8) a CDR1 comprising the amino acid sequence of SEQ ID NO: 53, a CDR2 comprising the amino acid sequence of SEQ ID NO: 55, and a CDR3 comprising the amino acid sequence of SEQ ID NO: 57, or a variant thereof comprising up to about 5 amino acid substitutions in the CDRs; (9) a CDR1 comprising the amino acid sequence of SEQ ID NO: 60, a CDR2 comprising the amino acid sequence of SEQ ID NO: 62, and a CDR3 comprising the amino acid sequence of SEQ ID NO: 64, or a variant thereof comprising up to about 5 amino acid substitutions in the CDRs; (10) a CDR1 comprising the amino acid sequence of SEQ ID NO: 67, a CDR2 comprising the amino acid sequence of SEQ ID NO: 69, and a CDR3 comprising the amino acid sequence of SEQ ID NO: 71, or a variant thereof comprising up to about 5 amino acid substitutions in the CDRs; (11) a CDR1 comprising the amino acid sequence of SEQ ID NO: 74, a CDR2 comprising the amino acid sequence of SEQ ID NO: 76, and a CDR3 comprising the amino acid sequence of SEQ ID NO: 78, or a variant thereof comprising up to about 5 amino acid substitutions in the CDRs; (12) a CDR1 comprising the amino acid sequence of SEQ ID NO: 81, a CDR2 comprising the amino acid sequence of SEQ ID NO: 83, and a CDR3 comprising the amino acid sequence of SEQ ID NO: 85, or a variant thereof comprising up to about 5 amino acid substitutions in the CDRs; (13) a CDR1 comprising the amino acid sequence of SEQ ID NO: 88, a CDR2 comprising the amino acid sequence of SEQ ID NO: 90, and a CDR3 comprising the amino acid sequence of SEQ ID NO: 92, or a variant thereof comprising up to about 5 amino acid substitutions in the CDRs; (14) a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99, or a variant thereof comprising up to about 5 amino acid substitutions in the CDRs; or (15) a CDR1 comprising the amino acid sequence of SEQ ID NO: 102, a CDR2 comprising the amino acid sequence of SEQ ID NO: 104, and a CDR3 comprising the amino acid sequence of SEQ ID NO: 106, or a variant thereof comprising up to about 5 amino acid substitutions in the CDRs. In some embodiments, the anti-CD33 sdAb comprises a $V_HH$ domain comprising the amino acid sequence of any one of SEQ ID NOs: 108-122, or a variant thereof comprising an amino acid sequence having at least about 95% sequence identity to the amino acid sequence of any one of SEQ ID NOs: 108-122. In some embodiments, the chimeric receptor further comprises a hinge domain (e.g., a CD8 hinge domain) located between the C-terminus of the extracellular domain and the N-terminus of the transmembrane domain. In some embodiments, the chimeric receptor further comprises a signal peptide (such as a CD8 signal peptide).

The engineered immune cell may further express one or more therapeutic proteins and/or immunomodulators, such as immune checkpoint inhibitors. See, for example, International Patent Application NOs. PCT/CN2016/073489 and PCT/CN2016/087855, which are incorporated herein by reference in their entirety.

Nucleic Acids and Vectors

In some embodiments, there is provided an isolated nucleic acid encoding any of the anti-CD33 chimeric receptors or chimeric receptor systems provided herein. In some embodiments, there is provided a nucleic acid comprising a first polynucleotide encoding a first chimeric receptor comprising: an extracellular domain comprising an anti-CD33 sdAb, a transmembrane domain, and an intracellular signaling domain; and a second polynucleotide encoding a second chimeric receptor comprising: an extracellular domain comprising a second binding moiety that specifically binds to a second antigen or epitope, a transmembrane domain, and an intracellular signaling domain. In some embodiments, the first polynucleotide is operably linked to a first promoter, and the second polynucleotide is operably linked to a second promoter. In some embodiments, the first polynucleotide and the second polynucleotide are linked to the same promoter. In some embodiments, the first polynucleotide and the second polynucleotide are operably linked to each other via a third polynucleotide encoding a self-cleaving peptide, such as T2A, P2A, or F2A. In some embodiments, the self-cleaving peptide is P2A. In some embodiments, the self-cleaving peptide comprises the amino acid sequence of GSGATNFSLLKQAGDVEENPGP (SEQ ID NO: 153). In some embodiments, the isolated nucleic acid is a DNA. In some embodiments, the isolated nucleic acid is an RNA.

In some embodiments, the present application provides vectors for cloning and expressing any one of the anti-CD33 chimeric receptors or chimeric receptor systems described herein. In some embodiments, the vector is suitable for replication and integration in eukaryotic cells, such as mammalian cells. In some embodiments, the vector is a viral vector. Examples of viral vectors include, but are not limited to, adenoviral vectors, adeno-associated virus vectors, lentiviral vector, retroviral vectors, vaccinia vector, herpes simplex viral vector, and derivatives thereof. Viral vector technology is well known in the art and is described, for example, in Sambrook et al. (2001, Molecular Cloning: A Laboratory Manual, Cold Spring Harbor Laboratory, New York), and in other virology and molecular biology manuals.

A number of viral based systems have been developed for gene transfer into mammalian cells. For example, retroviruses provide a convenient platform for gene delivery systems. The heterologous nucleic acid can be inserted into a vector and packaged in retroviral particles using techniques known in the art. The recombinant virus can then be isolated and delivered to the engineered mammalian cell in vitro or ex vivo. A number of retroviral systems are known in the art. In some embodiments, adenovirus vectors are used. A number of adenovirus vectors are known in the art. In some embodiments, lentivirus vectors are used. In some embodiments, self-inactivating lentiviral vectors are used. For example, self-inactivating lentiviral vectors carrying chimeric receptors can be packaged with protocols known in the art. The resulting lentiviral vectors can be used to transduce a mammalian cell (such as primary human T cells) using methods known in the art. Vectors derived from retroviruses such as lentivirus are suitable tools to achieve long-term gene transfer, because they allow long-term, stable integration of a transgene and its propagation in progeny cells. Lentiviral vectors also have low immunogenicity, and can transduce non-proliferating cells.

In some embodiments, the vector is a non-viral vector. In some embodiments, the vector is a transposon, such as a Sleeping Beauty (SB) transposon system, or a PiggyBac transposon system. In some embodiments, the vector is a polymer-based non-viral vector, including for example, poly (lactic-co-glycolic acid) (PLGA) and poly lactic acid (PLA), poly(ethylene imine) (PEI), and dendrimers. In some embodiments, the vector is a cationic-lipid based non-viral vector, such as cationic liposome, lipid nanoemulsion, and solid lipid nanoparticle (SLN). In some embodiments, the vector is a peptide-based gene non-viral vector, such as poly-L-lysine. Any of the known non-viral vectors suitable for genome editing can be used for introducing the chimeric receptor-encoding nucleic acids to the engineered immune cells. See, for example, Yin H. et al. *Nature Rev. Genetics* (2014) 15:521-555; Aronovich E L et al. "The Sleeping Beauty transposon system: a non-viral vector for gene therapy." *Hum. Mol. Genet.* (2011) R1: R14-20; and Zhao S. et al. "PiggyBac transposon vectors: the tools of the human gene editing." *Transl. Lung Cancer Res.* (2016) 5(1): 120-125, which are incorporated herein by reference. In some embodiments, any one or more of the nucleic acids encoding a chimeric receptor or chimeric receptor system is introduced to the engineered immune cells by a physical method, including, but not limited to electroporation, sonoporation, photoporation, magnetofection, hydroporation.

In some embodiments, the vector comprises any one of the nucleic acids encoding an anti-CD33 constructs as described herein. The nucleic acid can be cloned into the vector using any known molecular cloning methods in the art, including, for example, using restriction endonuclease sites and one or more selectable markers. In some embodiments, the nucleic acid is operably linked to a promoter. Varieties of promoters have been explored for gene expression in mammalian cells, and any of the promoters known in the art may be used in the present invention. Promoters may be roughly categorized as constitutive promoters or regulated promoters, such as inducible promoters.

In some embodiments, the nucleic acid encoding the chimeric receptor is operably linked to a constitutive promoter. Constitutive promoters allow heterologous genes (also referred to as transgenes) to be expressed constitutively in the host cells. Exemplary constitutive promoters contemplated herein include, but are not limited to, Cytomegalovirus (CMV) promoters, human elongation factors-1alpha (hEF1α), ubiquitin C promoter (UbiC), phosphoglycerokinase promoter (PGK), simian virus 40 early promoter (SV40), and chicken β-Actin promoter coupled with CMV early enhancer (CAGG). The efficiencies of such constitutive promoters on driving transgene expression have been widely compared in a huge number of studies. For example, Michael C. Milone et al compared the efficiencies of CMV, hEF1α, UbiC and PGK to drive chimeric receptor expression in primary human T cells, and concluded that hEF1α promoter not only induced the highest level of transgene expression, but was also optimally maintained in the CD4 and CD8 human T cells (Molecular Therapy, 17(8): 1453-1464 (2009)). In some embodiments, the nucleic acid encoding the chimeric receptor is operably linked to a hEF1α promoter.

In some embodiments, the nucleic acid encoding the chimeric receptor is operably linked to an inducible promoter. Inducible promoters belong to the category of regulated promoters. The inducible promoter can be induced by one or more conditions, such as a physical condition, microenvironment of the engineered immune cell, or the physiological state of the engineered immune cell, an inducer (i.e., an inducing agent), or a combination thereof. In some embodiments, the inducing condition does not induce the expression of endogenous genes in the engineered mammalian cell, and/or in the subject that receives the pharmaceutical composition. In some embodiments, the inducing condition is selected from the group consisting of: inducer, irradiation (such as ionizing radiation, light), temperature (such as heat), redox state, tumor environment, and the activation state of the engineered mammalian cell.

In some embodiments, the vector also contains a selectable marker gene or a reporter gene to select cells expressing the chimeric receptor from the population of host cells transfected through lentiviral vectors. Both selectable markers and reporter genes may be flanked by appropriate regulatory sequences to enable expression in the host cells. For example, the vector may contain transcription and translation terminators, initiation sequences, and promoters useful for regulation of the expression of the nucleic acid sequences.

In some embodiments, the vector comprises one or more nucleic acids encoding chimeric receptors. In some embodiments, the vector comprises a nucleic acid comprising a first nucleic acid sequence encoding a first chimeric receptor and a second nucleic acid sequence encoding a second chimeric receptor, wherein the first nucleic acid is operably linked to the second nucleic acid via a third nucleic acid sequence encoding a self-cleaving peptide. In some embodiments, the self-cleaving peptide is selected from the group consisting of T2A, P2A and F2A. In some embodiments, the self-cleaving peptide is P2A. In some embodiments, the self-cleaving peptide comprises the amino acid sequence of SEQ ID NO: 153. In some embodiments, the vector further comprises a nucleic acid encoding a safety-switch antigen or epitope. In some embodiments, the safety-switch antigen or epitope is derived from CD52, EGFR or CD20.

Immune Cells

In some embodiments, the engineered immune cells are immune effector cells. "Immune effector cells" are immune cells that can perform immune effector functions. In some embodiments, the immune effector cells express at least FcγRIII and perform ADCC effector function. Examples of immune effector cells which mediate ADCC include peripheral blood mononuclear cells (PBMC), natural killer (NK) cells, monocytes, cytotoxic T cells, neutrophils, and eosinophils.

In some embodiments, the immune cells are T cells, such as cytotoxic T cell and/or helper T cell. In some embodiments, the T cells are CD4$^+$/CD8$^-$, CD4$^-$/CD8$^+$, CD4$^+$/CD8$^+$, CD4$^-$/CD8$^-$, or combinations thereof. In some embodiments, the T cells produce IL-2, TFN, and/or TNF upon expressing the CAR and binding to the target cells, such as CD33$^+$ tumor cells. In some embodiments, the CD8$^+$ T cells lyse antigen-specific target cells upon expressing the CAR and binding to the target cells. In some embodiments, the immune cells are γδ T cells.

In some embodiments, the immune cells are NK cells. In other embodiments, the immune cells can be derived from established cell lines, for example, NK-92 cells.

In some embodiments, the immune cells are natural killer T cells.

In some embodiments, the immune cells are differentiated from a stem cell, such as a hematopoietic stem cell, a pluripotent stem cell, an iPS, or an embryonic stem cell.

The engineered immune cells are prepared by introducing the CARs into the immune cells, such as T cells. In some embodiments, the CAR is introduced to the immune cells by transfecting any one of the isolated nucleic acids or any one of the vectors described in Section III. In some embodiments, the CAR is introduced to the immune cells by inserting proteins into the cell membrane while passing cells through a microfluidic system, such as CELL SQUEEZE® (see, for example, U.S. Patent Application Publication No. 20140287509).

Methods of introducing vectors or isolated nucleic acids into a mammalian cell are known in the art. The vectors described can be transferred into an immune cell by physical, chemical, or biological methods.

Physical methods for introducing the vector into an immune cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001) Molecular Cloning: A Laboratory Manual, Cold Spring Harbor Laboratory, New York. In some embodiments, the vector is introduced into the cell by electroporation.

Biological methods for introducing the vector into an immune cell include the use of DNA and RNA vectors. Viral vectors have become the most widely used method for inserting genes into mammalian, e.g., human cells.

Chemical means for introducing the vector into an immune cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro is a liposome (e.g., an artificial membrane vesicle).

In some embodiments, RNA molecules encoding any one of the chimeric receptors or chimeric receptor systems described herein may be prepared by a conventional method (e.g., in vitro transcription) and then introduced into the immune cells via known methods such as mRNA electroporation. See, e.g., Rabinovich et al., Human Gene Therapy 17:1027-1035.

In some embodiments, the transduced or transfected immune cell is propagated ex vivo after introduction of the vector or isolated nucleic acid. In some embodiments, the transduced or transfected immune cell is cultured to propagate for at least about any of 1 day, 2 days, 3 days, 4 days, 5 days, 6 days, 7 days, 10 days, 12 days, or 14 days. In some embodiments, the transduced or transfected immune cell is further evaluated or screened to select the engineered mammalian cell.

Reporter genes may be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al. FEBS Letters 479: 79-82 (2000)). Suitable expression systems are well known and may be prepared using known techniques or obtained commercially.

Other methods to confirm the presence of the nucleic acid encoding the chimeric receptors or chimeric receptor systems in the engineered immune cell, include, for example, molecular biological assays well known to those of skill in the art, such as Southern and Northern blotting, RT-PCR and PCR; biochemical assays, such as detecting the presence or absence of a particular peptide, e.g., by immunological methods (such as ELISAs and Western blots).

1. Sources of Immune Cells

Prior to expansion and genetic modification of the immune cells, a source of immune cells (e.g., T cells) is obtained from an individual. Immune cells (e.g., T cells) can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, any number of immune cell (e.g., T cell) lines available in the art, may be used. In some embodiments, immune cells (e.g., T cells) can be obtained from a unit of blood collected from a subject using any number of techniques known to the skilled artisan, such as FICOLL™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in some embodiments, T cells are isolated by incubation with anti-CD3/anti-CD28-conjugated beads, such as DYNABEADS® M-450 CD3/CD28 T, for a time period sufficient for positive selection of the desired T cells. In some embodiments, the time period is about 30 minutes. In a further embodiment, the time period ranges from 30 minutes to 36 hours or longer and all integer values there between. In a further embodiment, the time period is at least 1, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of $CD8^+$ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used. In some embodiments, it may be desirable to perform the selection procedure and use the "unselected" cells in the activation and expansion process. "Unselected" cells can also be subjected to further rounds of selection.

Enrichment of an immune cell (e.g., T cell) population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, CD62Lhi, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as $CD28^-$ negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In some embodiments, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In some embodiments, the concentration of cells used is $5 \times 10^6$/ml. In some embodiments, the concentration used can be from about $1 \times 10^5$/ml to $1 \times 10^6$/ml, and any integer value in between.

In some embodiments, the cells may be incubated on a rotator for varying lengths of time at varying speeds at either 2-10° C., or at room temperature.

Immune cells (e.g., T cells) for stimulation can also be frozen after a washing step. Without being bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In some embodiments, cryopreserved cells are thawed and washed as described herein and allowed to rest for one hour at room temperature prior to activation.

Also contemplated in the present application is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in immunotherapy for any number of diseases or conditions that would benefit from immunotherapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the immune cells (e.g., T cells) may be expanded, frozen, and used at a later time. In certain embodiments, samples are collected from a patient shortly after diagnosis of a particular disease as described herein but prior to any treatments. In some embodiments, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In some embodiments, immune cells (e.g., T cells) are obtained from a patient directly following treatment. In this regard, it has been observed that following certain cancer treatments, in particular treatments with drugs that damage the immune system, shortly after treatment during the period when patients would normally be recovering from the treatment, the quality of immune cells (e.g., T cells) obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

2. Activation and Expansion of Immune Cells

Whether prior to or after genetic modification of the immune cells (e.g., T cells) with the chimeric receptors or chimeric receptor systems described herein, the immune cells (e.g., T cells) can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, T cells can be expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9): 13191328, 1999; Garland et al., J. Immunol Meth. 227(1-2):53-63, 1999).

In some embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In some embodiments, the T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In some embodiments, the mixture may be cultured for several hours (about 3 hours) to about 14 days or any hourly integer value in between. In another embodiment, the mixture may be cultured for 21 days. In one embodiment of the invention the beads and the immune cells (e.g., T cells) are cultured together for about eight days. In another embodiment, the beads and immune cells (e.g., T cells) are cultured together for 2-3 days. Several cycles of stimulation may also be desired such that culture time of immune cells (e.g., T cells) can be 60 days or more. Conditions appropriate for immune cell (e.g., T cell) culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of immune cells (e.g., T cells). Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). Immune cells (e.g., T cells) that have been exposed to varied stimulation times may exhibit different characteristics. For example, typical blood or apheresed peripheral blood mononuclear cell products have a helper T cell population (TH, CD4$^+$) that is greater than the cytotoxic or suppressor T cell population (TC, CD8). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

V. Pharmaceutical Compositions

Further provided by the present application are pharmaceutical compositions comprising any one of the anti-CD33 constructs (including anti-CD33 sdAbs, chimeric receptors, immune effector cell engagers, and immunoconjugates), or any one of the engineered immune cells comprising any one of the anti-CD33 chimeric receptors or chimeric receptor systems as described herein, and a pharmaceutically acceptable carrier. Pharmaceutical compositions can be prepared by mixing an anti-CD33 construct, or a plurality of engineered immune cells having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or nonionic surfactants.

In order for the pharmaceutical compositions to be used for in vivo administration, they must be sterile. The pharmaceutical composition may be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The pharmaceutical compositions described herein may also contain more than one active compound or agent as necessary for the particular indication being treated, preferably those with complementary activities that do not adversely affect each other. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules)

or in macroemulsions. Such techniques are disclosed in *Remington's Pharmaceutical Sciences* 18th edition.

VI. Methods of Treatment

One aspect of the present application provides methods of treating a disease (such as cancer) in an individual, comprising administering to the individual an effective amount of any one of the anti-CD33 constructs described herein. In some embodiments, the present application provides methods and compositions for use in cell immunotherapy. In some embodiments, the cell immunotherapy is for treating cancer, including but not limited to hematological malignancies and solid tumors. Any of the anti-CD33 sdAbs, immune effector cell engagers, chimeric receptors, immunoconjugates, and engineered immune cells (such as CAR-T cells) described herein may be used in the method of treating cancer. Exemplary cancer types include, but are not limited to, acute myeloid leukemia (AML), chronic myelogenous leukemia (CML), and myelodysplastic syndrome (MDS). In some embodiments, the methods and compositions described herein may be used for treating other diseases that are associated with CD33.

In some embodiments, there is provided a method of treating a disease (such as cancer, e.g., AML, CML or MDS) in an individual (such as a human individual), comprising administering to the individual an effective amount of a pharmaceutical composition comprising an anti-CD33 construct comprising an sdAb moiety that specifically binds to CD33, wherein the sdAb moiety (e.g., $V_HH$) comprises: (1) a CDR1 comprising the amino acid sequence of SEQ ID NO: 4, a CDR2 comprising the amino acid sequence of SEQ ID NO: 6, and a CDR3 comprising the amino acid sequence of SEQ ID NO: 8, or a variant thereof comprising up to about 5 amino acid substitutions in the CDRs; (2) a CDR1 comprising the amino acid sequence of SEQ ID NO: 11, a CDR2 comprising the amino acid sequence of SEQ ID NO: 13, and a CDR3 comprising the amino acid sequence of SEQ ID NO: 15, or a variant thereof comprising up to about 5 amino acid substitutions in the CDRs; (3) a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22, or a variant thereof comprising up to about 5 amino acid substitutions in the CDRs; (4) a CDR1 comprising the amino acid sequence of SEQ ID NO: 25, a CDR2 comprising the amino acid sequence of SEQ ID NO: 27, and a CDR3 comprising the amino acid sequence of SEQ ID NO: 29, or a variant thereof comprising up to about 5 amino acid substitutions in the CDRs; (5) a CDR1 comprising the amino acid sequence of SEQ ID NO: 32, a CDR2 comprising the amino acid sequence of SEQ ID NO: 34, and a CDR3 comprising the amino acid sequence of SEQ ID NO: 36, or a variant thereof comprising up to about 5 amino acid substitutions in the CDRs; (6) a CDR1 comprising the amino acid sequence of SEQ ID NO: 39, a CDR2 comprising the amino acid sequence of SEQ ID NO: 41, and a CDR3 comprising the amino acid sequence of SEQ ID NO: 43, or a variant thereof comprising up to about 5 amino acid substitutions in the CDRs; (7) a CDR1 comprising the amino acid sequence of SEQ ID NO: 46, a CDR2 comprising the amino acid sequence of SEQ ID NO: 48, and a CDR3 comprising the amino acid sequence of SEQ ID NO: 50, or a variant thereof comprising up to about 5 amino acid substitutions in the CDRs; (8) a CDR1 comprising the amino acid sequence of SEQ ID NO: 53, a CDR2 comprising the amino acid sequence of SEQ ID NO: 55, and a CDR3 comprising the amino acid sequence of SEQ ID NO: 57, or a variant thereof comprising up to about 5 amino acid substitutions in the CDRs; (9) a CDR1 comprising the amino acid sequence of SEQ ID NO: 60, a CDR2 comprising the amino acid sequence of SEQ ID NO: 62, and a CDR3 comprising the amino acid sequence of SEQ ID NO: 64, or a variant thereof comprising up to about 5 amino acid substitutions in the CDRs; (10) a CDR1 comprising the amino acid sequence of SEQ ID NO: 67, a CDR2 comprising the amino acid sequence of SEQ ID NO: 69, and a CDR3 comprising the amino acid sequence of SEQ ID NO: 71, or a variant thereof comprising up to about 5 amino acid substitutions in the CDRs; (11) a CDR1 comprising the amino acid sequence of SEQ ID NO: 74, a CDR2 comprising the amino acid sequence of SEQ ID NO: 76, and a CDR3 comprising the amino acid sequence of SEQ ID NO: 78, or a variant thereof comprising up to about 5 amino acid substitutions in the CDRs; (12) a CDR1 comprising the amino acid sequence of SEQ ID NO: 81, a CDR2 comprising the amino acid sequence of SEQ ID NO: 83, and a CDR3 comprising the amino acid sequence of SEQ ID NO: 85, or a variant thereof comprising up to about 5 amino acid substitutions in the CDRs; (13) a CDR1 comprising the amino acid sequence of SEQ ID NO: 88, a CDR2 comprising the amino acid sequence of SEQ ID NO: 90, and a CDR3 comprising the amino acid sequence of SEQ ID NO: 92, or a variant thereof comprising up to about 5 amino acid substitutions in the CDRs; (14) a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99, or a variant thereof comprising up to about 5 amino acid substitutions in the CDRs; or (15) a CDR1 comprising the amino acid sequence of SEQ ID NO: 102, a CDR2 comprising the amino acid sequence of SEQ ID NO: 104, and a CDR3 comprising the amino acid sequence of SEQ ID NO: 106, or a variant thereof comprising up to about 5 amino acid substitutions in the CDRs. In some embodiments, the anti-CD33 sdAb comprises a $V_HH$ domain comprising the amino acid sequence of any one of SEQ ID NOs: 108-122, or a variant thereof comprising an amino acid sequence having at least about 95% sequence identity to the amino acid sequence of any one of SEQ ID NOs: 108-122. In some embodiments, the anti-CD33 construct is a heavy-chain only antibody. In some embodiments, the anti-CD33 construct is a multispecific antibody, such as a bispecific antibody. In some embodiments, the anti-CD33 construct is an immunoconjugate.

In some embodiments, there is provided a method of treating a disease (such as cancer, e.g., AML, CML or MDS) in an individual (such as a human individual), comprising administering to the individual an effective amount of a pharmaceutical composition comprising an immune effector cell engager comprising: (a) a target cell binding domain comprising an anti-CD33 sdAb (such as any one of the anti-CD33 sdAbs described herein), and (b) an immune effector cell binding domain comprising an antigen-binding fragment that specifically binds to an antigen on an immune effector cell. In some embodiments, the anti-CD33 sdAb comprises any one of the following: (1) a CDR1 comprising the amino acid sequence of SEQ ID NO: 4, a CDR2 comprising the amino acid sequence of SEQ ID NO: 6, and a CDR3 comprising the amino acid sequence of SEQ ID NO: 8, or a variant thereof comprising up to about 5 amino acid substitutions in the CDRs; (2) a CDR1 comprising the amino acid sequence of SEQ ID NO: 11, a CDR2 comprising the amino acid sequence of SEQ ID NO: 13, and a CDR3 comprising the amino acid sequence of SEQ ID NO: 15, or a variant thereof comprising up to about 5 amino acid substitutions in the CDRs; (3) a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22, or a variant thereof comprising up to about 5 amino acid substitutions in the CDRs; (4) a CDR1 comprising the amino acid sequence of SEQ ID NO: 25, a CDR2 comprising the amino acid sequence of SEQ ID NO: 27, and a CDR3 comprising the amino acid sequence of SEQ ID NO: 29, or a variant thereof comprising up to about 5 amino acid substitutions in the CDRs; (5) a CDR1 comprising the amino acid sequence of SEQ ID NO: 32, a CDR2 comprising the amino acid sequence of SEQ ID NO: 34, and a CDR3 comprising the amino acid sequence of SEQ ID NO: 36, or a variant thereof comprising up to about 5 amino acid substitutions in the CDRs; (6) a CDR1 comprising the amino acid sequence of SEQ ID NO: 39, a CDR2 comprising the amino acid sequence of SEQ ID NO: 41, and a CDR3 comprising the amino acid sequence of SEQ ID NO: 43, or a variant thereof comprising up to about 5 amino acid substitutions in the CDRs; (7) a CDR1 comprising the amino acid sequence of SEQ ID NO: 46, a CDR2 comprising the amino acid sequence of SEQ ID NO: 48, and a CDR3 comprising the amino acid sequence of SEQ ID NO: 50, or a variant thereof comprising up to about 5 amino acid substitutions in the CDRs; (8) a CDR1 comprising the amino acid sequence of SEQ ID NO: 53, a CDR2 comprising the amino acid sequence of SEQ ID NO: 55, and a CDR3 comprising the amino acid sequence of SEQ ID NO: 57, or a variant thereof comprising up to about 5 amino acid substitutions in the CDRs; (9) a CDR1 comprising the amino acid sequence of SEQ ID NO: 60, a CDR2 comprising the amino acid sequence of SEQ ID NO: 62, and a CDR3 comprising the amino acid sequence of SEQ ID NO: 64, or a variant thereof comprising up to about 5 amino acid substitutions in the CDRs; (10) a CDR1 comprising the amino acid sequence of SEQ ID NO: 67, a CDR2 comprising the amino acid sequence of SEQ ID NO: 69, and a CDR3 comprising the amino acid sequence of SEQ ID NO: 71, or a variant thereof comprising up to about 5 amino acid substitutions in the CDRs; (11) a CDR1 comprising the amino acid sequence of SEQ ID NO: 74, a CDR2 comprising the amino acid sequence of SEQ ID NO: 76, and a CDR3 comprising the amino acid sequence of SEQ ID NO: 78, or a variant thereof comprising up to about 5 amino acid substitutions in the CDRs; (12) a CDR1 comprising the amino acid sequence of SEQ ID NO: 81, a CDR2 comprising the amino acid sequence of SEQ ID NO: 83, and a CDR3 comprising the amino acid sequence of SEQ ID NO: 85, or a variant thereof comprising up to about 5 amino acid substitutions in the CDRs; (13) a CDR1 comprising the amino acid sequence of SEQ ID NO: 88, a CDR2 comprising the amino acid sequence of SEQ ID NO: 90, and a CDR3 comprising the amino acid sequence of SEQ ID NO: 92, or a variant thereof comprising up to about 5 amino acid substitutions in the CDRs; (14) a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99, or a variant thereof comprising up to about 5 amino acid substitutions in the CDRs; or (15) a CDR1 comprising the amino acid sequence of SEQ ID NO: 102, a CDR2 comprising the amino acid sequence of SEQ ID NO: 104, and a CDR3 comprising the amino acid sequence of SEQ ID NO: 106, or a variant thereof comprising up to about 5 amino acid substitutions in the CDRs. In some embodiments, the anti-CD33 sdAb comprises a $V_HH$ domain comprising the amino acid sequence of any one of SEQ ID NOs: 108-122, or a variant thereof comprising an amino acid sequence having at least about 95% sequence identity to the amino acid sequence of any one of SEQ ID NOs: 108-122. In some embodiments, the antigen-binding fragment in the immune effector cell binding domain is a Fab, scFv, or sdAb. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker. In some embodiments, the immune effector cell is T cell. In some embodiments, the immune effector cell binding domain specifically binds to an antigen selected from the group consisting of CD3γ, CD3δ, CD3ε, CD3ζ, CD28, OX40, GITR, CD137, CD27, CD40L, and HVEM.

In some embodiments, there is provided a method of treating a disease (such as cancer, e.g., AML, CML, or MDS) in an individual (such as a human individual), comprising administering to the individual an effective amount of a pharmaceutical composition comprising an engineered immune cell (e.g., T cell) comprising: an anti-CD33 chimeric receptor comprising: (a) an extracellular domain comprising an anti-CD33 sdAb (such as any one of the anti-CD33 sdAbs described herein); (b) a transmembrane domain; and (c) an intracellular signaling domain. In some embodiments, the intracellular signaling domain comprises a primary intracellular signaling sequence of an immune effector cell (such as T cell). In some embodiments, the primary intracellular signaling sequence is derived from CD3ζ, FcRγ, FcRβ, CD3γ, CD3δ, CD3ε, CD5, CD22, CD79a, CD79b, or CD66d. In some embodiments, the primary intracellular signaling sequence is derived from CD3ζ. In some embodiments, the intracellular signaling domain comprises an intracellular co-stimulatory sequence. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB. In some embodiments, the anti-CD33 chimeric receptor comprises: (a) an extracellular domain comprising an anti-CD33 sdAb (such as any one of the anti-CD33 sdAbs described herein); (b) a transmembrane domain; and (c) an intracellular signaling domain comprising a CD3ζ intracellular signaling sequence and an intracellular co-stimulatory sequence derived from CD28 or 4-1BB. In some embodiments, the anti-CD33 sdAb comprises any one of the following: (1) a CDR1 comprising the amino acid sequence of SEQ ID NO: 4, a CDR2 comprising the amino acid sequence of SEQ ID NO: 6, and a CDR3 comprising the amino acid sequence of SEQ ID NO: 8, or a variant thereof comprising up to about 5 amino acid substitutions in the CDRs; (2) a CDR1 comprising the amino acid sequence of SEQ ID NO: 11, a CDR2 comprising the amino acid sequence of SEQ ID NO: 13, and a CDR3 comprising the amino acid sequence of SEQ ID NO: 15, or a variant thereof comprising up to about 5 amino acid substitutions in the CDRs; (3) a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22, or a variant thereof comprising up to about 5 amino acid substitutions in the CDRs; (4) a CDR1 comprising the amino acid sequence of SEQ ID NO: 25, a CDR2 comprising the amino acid sequence of SEQ ID NO: 27, and a CDR3 comprising the amino acid sequence of SEQ ID NO: 29, or a variant thereof comprising up to about 5 amino acid substitutions in the CDRs; (5) a CDR1 comprising the amino acid sequence of SEQ ID NO: 32, a CDR2 comprising the amino acid sequence of SEQ ID NO: 34, and a CDR3 comprising the amino acid sequence of SEQ ID NO: 36, or a variant thereof comprising up to about 5 amino acid substitutions in the CDRs; (6) a CDR1 comprising the amino acid sequence of SEQ ID NO: 39, a CDR2 comprising the amino acid sequence of SEQ ID NO: 41, and a CDR3 comprising the amino acid sequence of SEQ ID NO: 43, or a variant thereof comprising up to about 5 amino acid substitutions in the CDRs; (7) a CDR1 comprising the amino acid sequence of SEQ ID NO: 46, a CDR2 comprising the amino acid sequence of SEQ ID NO: 48, and a CDR3 comprising the amino acid sequence of SEQ ID NO: 50, or a variant thereof comprising up to about 5 amino acid substitutions in the CDRs; (8) a CDR1 comprising the amino acid sequence of SEQ ID NO: 53, a CDR2 comprising the amino acid sequence of SEQ ID NO: 55, and a CDR3 comprising the amino acid sequence of SEQ ID NO: 57, or a variant thereof comprising up to about 5 amino acid substitutions in the CDRs; (9) a CDR1 comprising the amino acid sequence of SEQ ID NO: 60, a CDR2 comprising the amino acid sequence of SEQ ID NO: 62, and a CDR3 comprising the amino acid sequence of SEQ ID NO: 64, or a variant thereof comprising up to about 5 amino acid substitutions in the CDRs; (10) a CDR1 comprising the amino acid sequence of SEQ ID NO: 67, a CDR2 comprising the amino acid sequence of SEQ ID NO: 69, and a CDR3 comprising the amino acid sequence of SEQ ID NO: 71, or a variant thereof comprising up to about 5 amino acid substitutions in the CDRs; (11) a CDR1 comprising the amino acid sequence of SEQ ID NO: 74, a CDR2 comprising the amino acid sequence of SEQ ID NO: 76, and a CDR3 comprising the amino acid sequence of SEQ ID NO: 78, or a variant thereof comprising up to about 5 amino acid substitutions in the CDRs; (12) a CDR1 comprising the amino acid sequence of SEQ ID NO: 81, a CDR2 comprising the amino acid sequence of SEQ ID NO: 83, and a CDR3 comprising the amino acid sequence of SEQ ID NO: 85, or a variant thereof comprising up to about 5 amino acid substitutions in the CDRs; (13) a CDR1 comprising the amino acid sequence of SEQ ID NO: 88, a CDR2 comprising the amino acid sequence of SEQ ID NO: 90, and a CDR3 comprising the amino acid sequence of SEQ ID NO: 92, or a variant thereof comprising up to about 5 amino acid substitutions in the CDRs; (14) a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99, or a variant thereof comprising up to about 5 amino acid substitutions in the CDRs; or (15) a CDR1 comprising the amino acid sequence of SEQ ID NO: 102, a CDR2 comprising the amino acid sequence of SEQ ID NO: 104, and a CDR3 comprising the amino acid sequence of SEQ ID NO: 106, or a variant thereof comprising up to about 5 amino acid substitutions in the CDRs. In some embodiments, the anti-CD33 sdAb comprises a VHH domain comprising the amino acid sequence of any one of SEQ ID NOs: 108-122, or a variant thereof comprising an amino acid sequence having at least about 95% sequence identity to the amino acid sequence of any one of SEQ ID NOs: 108-122. In some embodiments, the anti-CD33 chimeric receptor comprises the amino acid sequence of any one of SEQ ID NOs: 155-169, or a variant thereof comprising an amino acid sequence having at least about 95% sequence identity to the amino acid sequence of any one of SEQ ID NOs: 155-169. In some embodiments, the anti-CD33 chimeric receptor comprises the amino acid sequence of SEQ ID NO: 157. In some embodiments, the engineered immune cell expresses a safety-switch antigen or epitope, such as CD52, EGFR, or CD20. In some embodiments, the method further comprises subsequently administering an effective amount of a therapeutic antibody specifically binding to the safety-switch antigen or epitope.

In some embodiments, there is provided a method of treating a disease (such as cancer, e.g., AML, CML or MDS) in an individual (such as a human individual), comprising administering to the individual an effective amount of a pharmaceutical composition comprising an engineered immune cell (e.g., T cell) comprising a multispecific (e.g., bispecific) chimeric receptor comprising: (a) an extracellular domain comprising an anti-CD33 sdAb (such as any one of the anti-CD33 sdAbs described herein) and a second sdAb that specifically binds to a second antigen or epitope (e.g., sdAb, scFv, or an extracellular domain of a receptor); (b) a transmembrane domain; and (c) an intracellular signaling domain. In some embodiments, the intracellular signaling domain comprises a CD3ζ intracellular signaling sequence and an intracellular co-stimulatory sequence derived from CD28 or 4-1BB. In some embodiments, the second binding moiety is an anti-CLL1 or anti-CD123 sdAb or scFv. In some embodiments, the second binding moiety is an extracellular domain of NKG2D. In some embodiments, the anti-CD33 sdAb comprises any one of the following: (1) a CDR1 comprising the amino acid sequence of SEQ ID NO: 4, a CDR2 comprising the amino acid sequence of SEQ ID NO: 6, and a CDR3 comprising the amino acid sequence of SEQ ID NO: 8, or a variant thereof comprising up to about 5 amino acid substitutions in the CDRs; (2) a CDR1 comprising the amino acid sequence of SEQ ID NO: 11, a CDR2 comprising the amino acid sequence of SEQ ID NO: 13, and a CDR3 comprising the amino acid sequence of SEQ ID NO: 15, or a variant thereof comprising up to about 5 amino acid substitutions in the CDRs; (3) a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22, or a variant thereof comprising up to about 5 amino acid substitutions in the CDRs; (4) a CDR1 comprising the amino acid sequence of SEQ ID NO: 25, a CDR2 comprising the amino acid sequence of SEQ ID NO: 27, and a CDR3 comprising the amino acid sequence of SEQ ID NO: 29, or a variant thereof comprising up to about 5 amino acid substitutions in the CDRs; (5) a CDR1 comprising the amino acid sequence of SEQ ID NO: 32, a CDR2 comprising the amino acid sequence of SEQ ID NO: 34, and a CDR3 comprising the amino acid sequence of SEQ ID NO: 36, or a variant thereof comprising up to about 5 amino acid substitutions in the CDRs; (6) a CDR1 comprising the amino acid sequence of SEQ ID NO: 39, a CDR2 comprising the amino acid sequence of SEQ ID NO: 41, and a CDR3 comprising the amino acid sequence of SEQ ID NO: 43, or a variant thereof comprising up to about 5 amino acid substitutions in the CDRs; (7) a CDR1 comprising the amino acid sequence of SEQ ID NO: 46, a CDR2 comprising the amino acid sequence of SEQ ID NO: 48, and a CDR3 comprising the amino acid sequence of SEQ ID NO: 50, or a variant thereof comprising up to about 5 amino acid substitutions in the CDRs; (8) a CDR1 comprising the amino acid sequence of SEQ ID NO: 53, a CDR2 comprising the amino acid sequence of SEQ ID NO: 55, and a CDR3 comprising the amino acid sequence of SEQ ID NO: 57, or a variant thereof comprising up to about 5 amino acid substitutions in the CDRs; (9) a CDR1 comprising the amino acid sequence of SEQ ID NO: 60, a CDR2 comprising the amino acid sequence of SEQ ID NO: 62, and a CDR3 comprising the amino acid sequence of SEQ ID NO: 64, or a variant thereof comprising up to about 5 amino acid substitutions in the CDRs; (10) a CDR1 comprising the amino acid sequence of SEQ ID NO: 67, a CDR2 comprising the amino acid sequence of SEQ ID NO: 69, and a CDR3 comprising the amino acid sequence of SEQ ID NO: 71, or a variant thereof comprising up to about 5 amino acid substitutions in the CDRs; (11) a CDR1 comprising the amino acid sequence of SEQ ID NO: 74, a CDR2 comprising the amino acid sequence of SEQ ID NO: 76, and a CDR3 comprising the amino acid sequence of SEQ ID NO: 78, or a variant thereof comprising up to about 5 amino acid substitutions in the CDRs; (12) a CDR1 comprising the amino acid sequence of SEQ ID NO: 81, a CDR2 comprising the amino acid sequence of SEQ ID NO: 83, and a CDR3 comprising the amino acid sequence of SEQ ID NO: 85, or a variant thereof comprising up to about 5 amino acid substitutions in the CDRs; (13) a CDR1 comprising the amino acid sequence of SEQ ID NO: 88, a CDR2 comprising the amino acid sequence of SEQ ID NO: 90, and a CDR3 comprising the amino acid sequence of SEQ ID NO: 92, or a variant thereof comprising up to about 5 amino acid substitutions in the CDRs; (14) a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99, or a variant thereof comprising up to about 5 amino acid substitutions in the CDRs; or (15) a CDR1 comprising the amino acid sequence of SEQ ID NO: 102, a CDR2 comprising the amino acid sequence of SEQ ID NO: 104, and a CDR3 comprising the amino acid sequence of SEQ ID NO: 106, or a variant thereof comprising up to about 5 amino acid substitutions in the CDRs. In some embodiments, the anti-CD33 sdAb comprises a $V_HH$ domain comprising the amino acid sequence of any one of SEQ ID NOs: 108-122, or a variant thereof comprising an amino acid sequence having at least about 95% sequence identity to the amino acid sequence of any one of SEQ ID NOs: 108-122. In some embodiments, the multispecific chimeric receptor comprising a polypeptide comprising the amino acid sequence of any one of SEQ ID NOs: 170-181, or a variant thereof comprising an amino acid sequence having at least about 95% sequence identity to the amino acid sequence of any one of SEQ ID NOs: 170-181. In some embodiments, the multispecific chimeric receptor comprises the amino acid sequence of SEQ ID NO: 170, 171 or 174. In some embodiments, the engineered immune cell expresses a safety-switch antigen or epitope, such as CD52, EGFR, or CD20. In some embodiments, the method further comprises subsequently administering an effective amount of a therapeutic antibody specifically binding to the safety-switch antigen or epitope.

In some embodiments, there is provided a method of treating a disease (such as cancer, e.g., AML, CML, or MDS) in an individual (such as a human individual), comprising administering to the individual an effective amount of a pharmaceutical composition comprising an engineered immune cell (e.g., T cell) comprising: (a) a first chimeric receptor comprising an extracellular domain comprising an anti-CD33 sdAb (such as any one of the anti-CD33 sdAbs described herein), a transmembrane domain, and an intracellular signaling domain comprising a primary intracellular signaling sequence of an immune effector cell (e.g., a CD3ζ intracellular signaling sequence); (b) a second chimeric receptor comprising an extracellular domain comprising a second binding moiety (e.g., sdAb, scFv, or an extracellular domain of a receptor) that specifically binds to a second antigen or epitope, a transmembrane domain, and an intracellular signaling domain comprising an intracellular co-stimulatory sequence (e.g., an intracellular co-stimulatory sequence derived from CD28 or 4-1BB). In some embodiments, there is provided a method of treating a disease (such as cancer, e.g., AML, CML, or MDS) in an individual (such as a human individual), comprising administering to the individual an effective amount of a pharmaceutical composition comprising an engineered immune cell (e.g., T cell) comprising: (a) a first chimeric receptor comprising an extracellular domain comprising an anti-CD33 sdAb (such as any one of the anti-CD33 sdAbs described herein), a transmembrane domain, and an intracellular domain comprising an intracellular signaling domain comprising an intracellular co-stimulatory sequence (e.g., an intracellular co-stimulatory sequence derived from CD28 or 4-1BB); (b) a second chimeric receptor comprising an extracellular domain comprising a second binding moiety (e.g., sdAb, scFv, or an extracellular domain of a receptor) that specifically binds to a second antigen or epitope, a transmembrane domain, and an intracellular signaling domain comprising a primary intracellular signaling sequence of an immune effector cell (e.g., a CD3ζ intracellular signaling sequence). In some embodiments, the second binding moiety is an anti-CLL1 or anti-CD123 sdAb or scFv. In some embodiments, the second binding moiety is an extracellular domain of NKG2D. In some embodiments, the anti-CD33 sdAb comprises any one of the following: (1) a CDR1 comprising the amino acid sequence of SEQ ID NO: 4, a CDR2 comprising the amino acid sequence of SEQ ID NO: 6, and a CDR3 comprising the amino acid sequence of SEQ ID NO: 8, or a variant thereof comprising up to about 5 amino acid substitutions in the CDRs; (2) a CDR1 comprising the amino acid sequence of SEQ ID NO: 11, a CDR2 comprising the amino acid sequence of SEQ ID NO: 13, and a CDR3 comprising the amino acid sequence of SEQ ID NO: 15, or a variant thereof comprising up to about 5 amino acid substitutions in the CDRs; (3) a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22, or a variant thereof comprising up to about 5 amino acid substitutions in the CDRs; (4) a CDR1 comprising the amino acid sequence of SEQ ID NO: 25, a CDR2 comprising the amino acid sequence of SEQ ID NO: 27, and a CDR3 comprising the amino acid sequence of SEQ ID NO: 29, or a variant thereof comprising up to about 5 amino acid substitutions in the CDRs; (5) a CDR1 comprising the amino acid sequence of SEQ ID NO: 32, a CDR2 comprising the amino acid sequence of SEQ ID NO: 34, and a CDR3 comprising the amino acid sequence of SEQ ID NO: 36, or a variant thereof comprising up to about 5 amino acid substitutions in the CDRs; (6) a CDR1 comprising the amino acid sequence of SEQ ID NO: 39, a CDR2 comprising the amino acid sequence of SEQ ID NO: 41, and a CDR3 comprising the amino acid sequence of SEQ ID NO: 43, or a variant thereof comprising up to about 5 amino acid substitutions in the CDRs; (7) a CDR1 comprising the amino acid sequence of SEQ ID NO: 46, a CDR2 comprising the amino acid sequence of SEQ ID NO: 48, and a CDR3 comprising the amino acid sequence of SEQ ID NO: 50, or a variant thereof comprising up to about 5 amino acid substitutions in the CDRs; (8) a CDR1 comprising the amino acid sequence of SEQ ID NO: 53, a CDR2 comprising the amino acid sequence of SEQ ID NO: 55, and a CDR3 comprising the amino acid sequence of SEQ ID NO: 57, or a variant thereof comprising up to about 5 amino acid substitutions in the CDRs; (9) a CDR1 comprising the amino acid sequence of SEQ ID NO: 60, a CDR2 comprising the amino acid sequence of SEQ ID NO: 62, and a CDR3 comprising the amino acid sequence of SEQ ID NO: 64, or a variant thereof comprising up to about 5 amino acid substitutions in the CDRs; (10) a CDR1 comprising the amino acid sequence of SEQ ID NO: 67, a CDR2 comprising the amino acid sequence of SEQ ID NO: 69, and a CDR3 comprising the amino acid sequence of SEQ ID NO: 71, or a variant thereof comprising up to about 5 amino acid substitutions in the CDRs; (11) a CDR1 comprising the amino acid sequence of SEQ ID NO: 74, a CDR2 comprising the amino acid sequence of SEQ ID NO: 76, and a CDR3 comprising the amino acid sequence of SEQ ID NO: 78, or a variant thereof comprising up to about 5 amino acid substitutions in the CDRs; (12) a CDR1 comprising the amino acid sequence of SEQ ID NO: 81, a CDR2 comprising the amino acid sequence of SEQ ID NO: 83, and a CDR3 comprising the amino acid sequence of SEQ ID NO: 85, or a variant thereof comprising up to about 5 amino acid substitutions in the CDRs; (13) a CDR1 comprising the amino acid sequence of SEQ ID NO: 88, a CDR2 comprising the amino acid sequence of SEQ ID NO: 90, and a CDR3 comprising the amino acid sequence of SEQ ID NO: 92, or a variant thereof comprising up to about 5 amino acid substitutions in the CDRs; (14) a CDR1 comprising the amino acid sequence of SEQ ID NO: 95, a CDR2 comprising the amino acid sequence of SEQ ID NO: 97, and a CDR3 comprising the amino acid sequence of SEQ ID NO: 99, or a variant thereof comprising up to about 5 amino acid substitutions in the CDRs; or (15) a CDR1 comprising the amino acid sequence of SEQ ID NO: 102, a CDR2 comprising the amino acid sequence of SEQ ID NO: 104, and a CDR3 comprising the amino acid sequence of SEQ ID NO: 106, or a variant thereof comprising up to about 5 amino acid substitutions in the CDRs. In some embodiments, the anti-CD33 sdAb comprises a $V_HH$ domain comprising the amino acid sequence of any one of SEQ ID NOs: 108-122, or a variant thereof comprising an amino acid sequence having at least about 95% sequence identity to the amino acid sequence of any one of SEQ ID NOs: 108-122. In some embodiments, the engineered immune cell comprises a dual chimeric receptor construct comprising the first chimeric receptor fused to the second chimeric receptor via a self-cleaving peptide (e.g., P2A peptide). In some embodiments, the dual chimeric receptor construct comprises the amino acid sequence of any one of SEQ ID NOs: 183-185, or a variant thereof comprising an amino acid sequence having at least about 95% sequence identity to the amino acid sequence of any one of SEQ ID NOs: 183-185. In some embodiments, the engineered immune cell expresses a safety-switch antigen or epitope, such as CD52, EGFR, or CD20. In some embodiments, the method further comprises subsequently administering an effective amount of a therapeutic antibody specifically binding to the safety-switch antigen or epitope.

The methods described herein are suitable for treating various cancers, including both solid cancer and liquid cancer. The methods are applicable to cancers of all stages, including early stage, advanced stage and metastatic cancer. The methods described herein may be used as a first therapy, second therapy, third therapy, or combination therapy with other types of cancer therapies known in the art, such as chemotherapy, surgery, radiation, gene therapy, immunotherapy, bone marrow transplantation, stem cell transplantation, targeted therapy, cryotherapy, ultrasound therapy, photodynamic therapy, radio-frequency ablation or the like, in an adjuvant setting or a neoadjuvant setting. In some embodiments, the cancer is acute myeloid leukemia (AML), chronic myelogenous leukemia(CML) or myelodysplastic syndromes (MDS).

Administration of the anti-CD33 constructs or pharmaceutical compositions thereof may be carried out in any convenient manner, including by injection, ingestion, transfusion, implantation or transplantation. The pharmaceutical compositions may be administered to a patient transarterially, subcutaneously, intradermally, intratumorally, intranodally, intramedullary, intramuscularly, intravenously, or intraperitoneally. In some embodiments, the pharmaceutical composition is administered systemically. In some embodiments, the pharmaceutical composition is administered to an individual by infusion, such as intravenous infusion. Infusion techniques for immunotherapy are known in the art (see, e.g., Rosenberg et al., New Eng. J. of Med. 319: 1676 (1988)). In some embodiments, the pharmaceutical composition is administered to an individual by intradermal or subcutaneous injection. In some embodiments, the compositions are administered by intravenous injection. In some embodiments, the compositions are injected directly into a tumor, or a lymph node. In some embodiments, the pharmaceutical composition is administered locally to a site of tumor, such as directly into tumor cells, or to a tissue having tumor cells.

Dosages and desired drug concentration of pharmaceutical compositions of the present application may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46. It is within the scope of the present application that different formulations will be effective for different treatments and different disorders, and that administration intended to treat a specific organ or tissue may necessitate delivery in a manner different from that to another organ or tissue.

In some embodiments, wherein the pharmaceutical composition comprises any one of the anti-CD33 constructs described herein, the pharmaceutical composition is administered at a dosage of about 10 ng/kg up to about 100 mg/kg of body weight of the individual or more per day, for example, at about 1 mg/kg/day to 10 mg/kg/day, depending upon the route of administration.

In some embodiments, wherein the pharmaceutical composition comprises any one of the engineered immune cells described herein, the pharmaceutical composition is administered at a dosage of at least about any of $10^4$, $10^5$, $10^6$, $10^7$, $10^8$, or $10^9$ cells/kg of body weight of the individual. In some embodiments, the pharmaceutical composition is administered at a dosage of any of about $10^4$ to about $10^5$, about $10^5$ to about $10^6$, about $10^6$ to about $10^7$, about $10^7$ to about $10^8$, about $10^8$ to about $10^9$, about $10^4$ to about $10^9$, about $10^4$ to about $10^6$, about $10^6$ to about $10^8$, or about $10^5$ to about $10^7$ cells/kg of body weight of the individual. In some embodiments, the pharmaceutical composition is administered at a dose of at least about any $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$ cells/kg or more.

In some embodiments, the pharmaceutical composition is administered for a single time. In some embodiments, the pharmaceutical composition is administered for multiple times (such as any of 2, 3, 4, 5, 6, or more times). In some embodiments, the pharmaceutical composition is administered once per week to once per year. In some embodiments, the interval between administrations is about 1 week to a year. The optimal dosage and treatment regime for a particular patient can readily be determined by one skilled in the art of medicine by monitoring the patient for signs of disease and adjusting the treatment accordingly.

Moreover, dosages may be administered by one or more separate administrations, or by continuous infusion. In some embodiments, the pharmaceutical composition is administered in split doses, such as about any one of 2, 3, 4, 5, or more doses. In some embodiments, the split doses are administered over about a week. In some embodiments, the dose is equally split. In some embodiments, the split doses are about 20%, about 30% and about 50% of the total dose. In some embodiments, the interval between consecutive split doses is about 1 day, 2 days, 3 days or longer. For repeated administrations over several days or longer, depending on the condition, the treatment is sustained until a desired suppression of disease symptoms occurs. However, other dosage regimens may be useful. The progress of this therapy is easily monitored by conventional techniques and assays.

In some embodiments, the amount of the pharmaceutical composition is effective to cause an objective clinical response in the individual. In some embodiments, the amount of the pharmaceutical composition is effective to cause disease remission (partial or complete) in the individual. In some embodiments, the amount of the pharmaceutical composition is effective to prevent relapse or disease progression of the cancer in the individual. In some embodiments, the amount of the pharmaceutical composition is effective to prolong survival (such as disease free survival) in the individual. In some embodiments, the pharmaceutical composition is effective to improve quality of life in the individual.

In some embodiments, the amount of the pharmaceutical composition is effective to inhibit growth or reducing the size of a solid or lymphatic tumor. In some embodiments, the size of the solid or lymphatic tumor is reduced for at least about 10% (including for example at least about any of 20%, 30%, 40%, 60%, 70%, 80%, 90%, or 100%). In some embodiments, a method of inhibiting growth or reducing the size of a solid or lymphatic tumor in an individual is provided.

In some embodiments, the amount of the pharmaceutical composition is effective to inhibit tumor metastasis in the individual. In some embodiments, at least about 10% (including for example at least about any of 20%, 30%, 40%, 60%, 70%, 80%, 90%, or 100%) metastasis is inhibited. In some embodiments, a method of inhibiting metastasis to lymph node is provided. In some embodiments, a method of inhibiting metastasis to the lung is provided. In some embodiments, a method of inhibiting metastasis to the liver is provided. Metastasis can be assessed by any known methods in the art, such as by blood tests, bone scans, x-ray scans, CT scans, PET scans, and biopsy.

VII. Kits and Articles of Manufacture

Further provided are kits, unit dosages, and articles of manufacture comprising any one of the anti-CD33 sdAbs, anti-CD33 constructs (such as chimeric receptors, immune effector cell engagers, and immunoconjugates), or engineered immune cells described herein. In some embodiments, a kit is provided which contains any one of the pharmaceutical compositions described herein. In some embodiments, the kit further comprises instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The articles of manufacture may comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder (such as cancer) described herein, and may have a sterile access port (for example the container may be an intravenous solution bag or a vial having a stopper pierceable by a hypodermic injection needle). The label or package insert indicates that the composition is used for treating a particular disease or condition in an individual. The label or package insert will further comprise instructions for administering the composition to the individual. The label may indicate directions for reconstitution and/or use. The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or articles of manufacture may include multiple unit doses of the pharmaceutical composition and instructions for use, packaged in quantities sufficient for storage and use in pharmacies, for example, hospital pharmacies and compounding pharmacies.

EXAMPLES

The examples below are intended to be purely exemplary of the invention and should therefore not be considered to limit the invention in any way. The following examples and detailed description are offered by way of illustration and not by way of limitation.

Example 1: Generation of Anti-CD33 sdAbs

Recombinant human CD33 protein and recombinant Cynomolgus CD33 protein having the respective amino acid sequences in Table 8 were obtained commercially.

TABLE 8

Extracellular domains of CD33 proteins

| Protein | Description | Sequence |
|---|---|---|
| huCD33 | human CD33 | (SEQ ID NO: 1)<br>DPNFWLQVQESVTVQEGLCVLVPCTFFHPIPYYDKNSPVHGYWFREGAIISR<br>DSPVATNKLDQEVQEETQGRFRLLGDPSRNNCSLSIVDARRRDNGSYFFRME<br>RGSTKYSYKSPQLSVHVTDLTHRPKILIPGTLEPGHSKNLTCSVSWACEQGTP<br>PIFSWLSAAPTSLGPRTTHSSVLIITPRPQDHGTNLTCQVKFAGAGVTTERTIQ<br>LNVTYVPQNPTTGIFPGDGSGKQETRAGVVHGAIGGAGVTALLALCLCLIFFI<br>VKTHRRKAARTAVGRNDTHPTTGSASPKHQKKSKLHGPTETSSCSGAAPTV<br>EMDEELHYASLNFHGMNPSKDTSTEYSEVRTQ |
| cynoCD33 | cynomolgus monkey CD33 | (SEQ ID NO: 2)<br>MDPRVRLEVQESVTVQEGLCVLVPCTFFHPVPYHTRNSPVHGYWFREGAIV<br>SLDSPVATNKLDQEVQEETQGRFRLLGDPSRNNCSLSIVDARRRDNGSYFFR<br>MEKGSTKYSYKSTQLSVHVTDLTHRPQILIPGALDPDHSKNLTCSVPWACEQ<br>GTPPIFSWMSAAPTSLGLRTTHSSV<br>LIITPRPQDHGTNLTCQVKFPGAGVTTERTIQLNVSYASQNPRTDIFLGDGSG<br>KQGVVQGAIGGAGVTVLLALCLCLIFFTVKTHRRKAARTAVGRIDTHPATGP<br>TSSKHQKKSKLHGATETSGCSGTTLTVEMDEELHYASLNFHGMNPSEDTSTE<br>YSEVRTO |

Animal Immunization

One camel was immunized with recombinant human CD33 protein under all current animal welfare regulations. For immunization, the antigen was formulated as an emulsion with CFA (primary immunization) or IFA (boost immunization). The antigen was administered by double-spot injections intramuscularly at the neck. The animal received two injections of the emulsion, containing 100 μg of CD33 protein and 4 subsequent injections containing 50 μg of CD33 protein at weekly intervals. At different time points during immunization, 10 ml blood samples were collected from the animal and sera were prepared. Conventional IgG (IgG1) and heavy chain antibodies (HCAbs, IgG2 and IgG3) were fractioned from the pre-immune and immunized sera. The induction of an antigen specific humoral immune response was verified using the fractioned IgG1, IgG2 and IgG3 in an enzyme-linked immune sorbent assay (ELISA)-based experiment with immobilized human and Cynomolgus CD33.

Figure 1B:
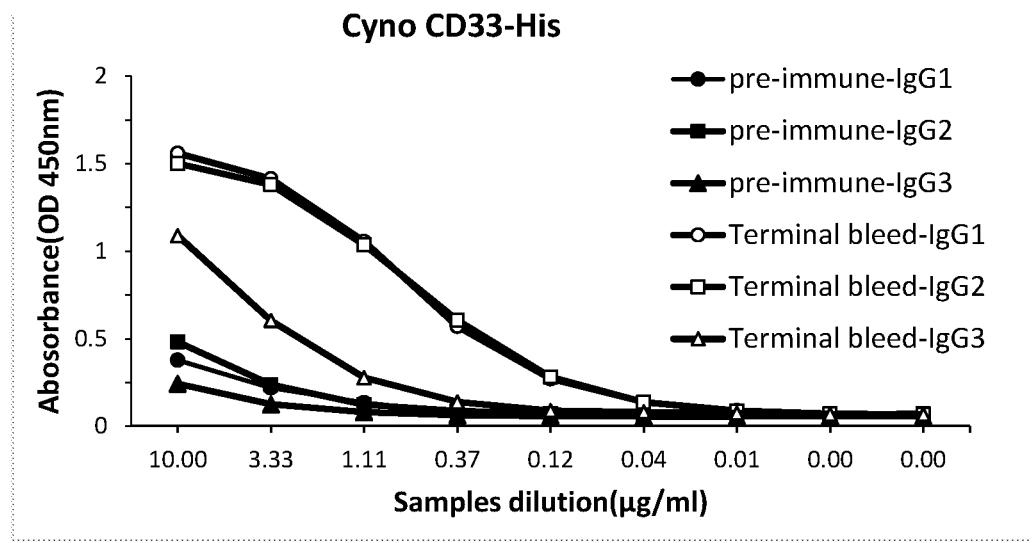
FIG. 1B shows immune response of immunized camel against recombinant cynomolgus CD33 proteins.

As shown in FIGS. 1A-1B, immunized camel showed good immune response towards human and cynomolgus CD33 and the immunized library showed superior quality. The immune response peaks at the sixth immunizations. Five days after the sixth immunization, 150 ml blood sample was collected from a camel. About 1×10$^9$ peripheral blood lymphocytes (PBLs), as the genetic source of the conventional and camel heavy chain immunoglobulins, were isolated from the blood. The maximal diversity of antibodies is expected to be equal to the number of B-lymphocytes, which is about 10% of the number of PBLs (1×10$^8$). The fraction of HCAb-producing B-lymphocytes in a camel is about 20% of total B-lymphocytes. Therefore, the maximal diversity of HCAbs in the blood sample is estimated to be approximately 2×10$^7$.

Phage Display Library Construction

Total RNA was extracted from lymphocytes of the immunized camel using TRIZOL® Reagent. cDNA was synthesized based on RNA template with an oligo(dT)$_{20}$ primer using PRIMESCRIPT™ 1st Strand cDNA Synthesis Kit. V$_H$H were amplified from camel cDNA, purified and ligated in an in-house produced phagemid vector. The ligation product was used to transform SS320 electrocompetent cells. The resulting library was supplemented with 20% glycerol and stored at −80° C.

A camel sdAb library was constructed. The size of the library is estimated to be larger than 10$^9$. More than 100 randomly picked clones were sequenced. The insert rate, i.e. the percentage of clones with sdAb inserts, was 98.7%. The in-frame rate, i.e. the percentage of clones with sdAb DNA inserted that could be corrected translated into an sdAb amino acid sequence, was 96.6%.

Binder Isolation and High-Throughput Screening

The immunized sdAb phage library was rescued according to a standard protocol and stored after filter sterilization at 4° C. for further use. Binders were isolated with the above libraries using solid-phase panning as well as cell-based panning. At least one round of panning was carried for both approaches using both libraries until CD33-specific antibodies were significantly enriched. Output phage of each round were analyzed for the number of total output clones, percentage of CD33 positive clones by ELISA and sequence diversity of CD33-specific binders. Based on these results the best panning output was selected for high-throughput screening.

After one round of panning of the immunized camelid library, CD33-specific binders were significantly enriched. Thousands of clones were screened. Seventy-eight camelid sdAb binders that bound both human and cynomolgus CD33 proteins and cell lines were obtained. All these binders have unique sequences.

The selected output phage was used to infect exponentially growing E. coli cells. The double-strand DNA of the output was extracted, the sdAb insert cut from the phagemid vector and inserted into an antibody fragment expression vector for high-throughput screening. The resulting plasmid was used to transform exponentially growing E. coli cells, which were plated and grown overnight. Colonies were picked and grown in 96 deep well plates containing 1 ml 2YT medium. The expression of antibody fragment was induced by adding 1 mM IPTG.

The sdAb proteins in the supernatant were analyzed for their ability to bind to CD33 ECD proteins by ELISA and CD33-overexpressing MV4-11 cell lines by FACS. All binders were sequenced and some were subjected to for further characterization including affinity ranking by surface plasmon resonance (SPR) on a BIACORE® T200 instrument. The experiments were carried out as follows: the crude sdAb proteins were captured through an affinity tag onto the sensorchip. High-concentration (100 nM) of human CD33 flowed over the sensorchip surface, and was allowed to bind the antibody fragments. On-rate ($k_{on}$) and off-rate ($k_{off}$) were roughly calculated based on the association and dissociation of one antigen concentration, and were used to estimate the equilibrium dissociation constant ($K_D$). The binding affinities and cell binding properties of 15 anti-CD33 sdAbs are shown in FIG. 2.

Humanization of Camel sdAbs

Selected camel sdAbs were humanized using CDR grafting technology (see, e.g., U.S. Pat. No. 5,225,539). Briefly, the camel sdAb sequence was compared to those available in the Research Collaboratory for Structural Bioinformatics (RCSB) protein databank. A homology model of the camel sdAb was generated based on the nearest VH structures. From the model structure, residues that are in the proximity of CDRs or buried inside the molecule (i.e. with sidechain solvent accessible surface area less than 15%) were identified.

The camel sdAb sequence was BLASTed against NCBI human germline V gene database so the human VH germline sequence with highest identity to the sdAb (i.e. human acceptor) was identified (Foote and Winter, *J. Mol. Biol.* 224:487-499 (1992); Morea V. et al., *Methods* 20:267-279 (2000); Chothia C. et al., *J. Mol. Biol.* 186:651-663 (1985).) In the CDR grafting approach, CDRs of the human acceptor were replaced by those of the camel sdAb, which makes the straight-graft sequence. Straight-graft antibody usually loses binding activity, which need to be restored by replacing the framework residues that are critical for the activity of the antibody with non-human residues. Amino acid residues that are in the proximity of CDRs or buried inside the molecule are usually important for the activity and structure of the antibody, therefore should be potential back-mutation sites. A series of humanized variants were designed using this method.

The camelid and humanized sdAb sequences were fused with human IgG1 hinge and Fc, providing the chimeric and humanized HCAb sequences. The DNA encoding these HCAbs were synthesized and inserted into pTT5 vector. HCAb expression plasmids were used to transfect HEK293 cells. Crude HCAb proteins secreted to the medium were subjected to SPR affinity measurement as follows: Briefly, capturing antibody anti-human Fc pAb (GE healthcare) was immobilized on a BIACORE® CM5 chip to approximately 6,000 RU using EDC-activated amine coupling chemistry. HCAb of interest was captured for 300 seconds onto the sensorchip surface. Human CD33 protein was flowed over the sensorchip surface at a series of increasing concentrations. Association and dissociation phases were monitored. Captured antibody and antigen were removed between cycles using 10 mM Glycine-HCl, pH 2.0 buffer in order to ensure a fresh binding surface for the antigen. The resulting sensorgrams were fit globally using a 1:1 binding model in order to calculate on- and off-rates ($k_a$ and $k_d$, respectively), as well as affinities ($K_D$).

Example 2: Generation and Screening of Anti-CD33 CAR-T

Cloning of Anti-CD33 CAR Constructs

Exemplary anti-CD33 CAR constructs were designed in the format as shown in Table 3. The sequences of these CARs followed this pattern from the N-terminus to the C-terminus: leader sequence, target binding moiety (TBM, i.e. anti-CD33 sdAb), CD8α hinge, CD8α transmembrane (TM) region, the cytoplasmic portion of the 4-1BB (CD137) molecule, and the cytoplasmic portion of the CD3ζ molecule.

DNA encoding each CAR construct was codon optimized and synthesized. The CAR sequences were ligated into a lentiviral vector plasmid with human EF1 alpha promoter for expression.

A construct encoding anti-CD33 benchmark CAR ("BM CAR") was also prepared for comparative analysis using the sequence shown below.

```
SEQ ID NO: 212 (BM CAR):
MALPVTALLLPLALLLHAARPQVQLVQSGAEVKKPGESVKVSCKASGYT

FTNYGMNWVKQAPGQGLEWMGWINTYTGEPTYADKFQGRVTMTTDTSTS

TAYMEIRNLGGDDTAVYYCARWSWSDGYYVYFDYWGQGTSVTVSSGGGG

SGGGGSGGGGSDIVMTQSPDSLTVSLGERTTINCKSSQSVLDSSTNKNS

LAWYQQKPGQPPKLLLSWASTRESGIPDRFSGSGSGTDFTLTIDSPQPE

DSATYYCQQSAHFPITFGQGTRLEIKTTTPAPRPPTPAPTIASQPLSLR

PEACRPAAGGAVHTRGLDFACDIYIWAPLAGTCGVLLLSLVITLYCKRG

RKKLLYIFKQPFMRPVQTTQEEDGCSCRFPEEEEGGCELRVKFSRSADA

PAYKQGQNQLYNELNLGRREEYDVLDKRRGRDPEMGGKPRRKNPQEGLY

NELQKDKMAEAYSEIGMKGERRRGKGHDGLYQGLSTATKDTYDALHMQA

LPPR
```

Generation of Anti-CD33 CAR-T
1. Preparation of Lentivirus

The lentivirus packaging plasmid mixture including pCMV-ΔR-8.47 and pMD2.G (Addgene, Cat #12259) was mixed with the appropriate CAR-encoding plasmid at a pre-optimized ratio with polyethylenimine. HEK293 cells were transfected with the mixture and were cultured overnight. The culture supernatant was collected and centrifuged to remove cell debris. The supernatant was filtered through a 0.45 μm PES filter. The virus particles were pelleted, and rinsed with pre-chilled DPBS. The virus was aliquoted and stored at −80° C. immediately. The virus titer was determined by measuring supT1 cell line transduction efficiency by flow cytometric assay.

2. T Cell Transduction

Leukocytes were collected from healthy donors by apheresis. Peripheral blood mononuclear cells (PBMCs) were isolated using FICOLL-PAQUE™ PLUS Media. Human T cells were purified from PMBCs using Pan T cell isolation kit (Miltenyi, Cat #130-096-535. The purified T cells were subsequently pre-activated for 48 hours with human T cell activation/expansion kit (Miltenyi, Cat #130-091-441). Anti-CD3/CD28 MACSiBead particles were added at a bead-to-cell ratio of 1:2. The pre-activated T cells were transduced with lentivirus stock in the presence of 8 μs/ml polybrene. The cells were cultured in 6-well tissue culture plates (Corning, Corning, N.Y.) with 4×10⁶ T cells/ well. The cells were cultured for approximately 48 hours at 37° C. The transduced cells were centrifuged, decanted and resuspended at $0.5 \times 10^6$ cells/ml in fresh media supplemented with 300 IU/ml IL-2 for culture. The cell concentration was adjusted to $0.5 \times 10^6$ cells/ml every 2 to 3 days.

For CAR expression detection on T cells, protein L and rabbit-anti-sdAb (GenScript, Piscataway, N.J.) were added to detect the cell surface scFvs and sdAbs, respectively.

Evaluation of In Vitro Activity of Anti-CD33 CAR-T Cells

1. In Vitro Cytotoxicity Assay

For quick evaluation of anti-tumor activities of CAR-T cells in vitro, LDH (lactate dehydrogenase) assay for cytotoxicity was performed. On day 5 or day 9 post transduction, transduced T cells were harvested and co-incubated with target cell lines, CD33-expressing AML tumor cell lines MV4-11 or THP-1, at E/T ratio (Effector:CAR-T/Target) ratio of 1:1 or 3:1 for 20 hours, respectively. Un-transduced T cells (unT) from the same batch were used as negative control. CD33 benchmark CAR-T cells ("BM CAR") was used as positive control. The assay was performed following the manufacturer's manual (Roche, 11644793001). The cytotoxicity was calculated by the equation below ($[LDH]_{E+T}$: the LDH released from E/T co-incubation, $[LDH]_E$: the LDH released from Effector only, $[LDH]_{max}$: the LDH released from target cells treated with Triton X-100, $[LDH]_{min}$: the LDH released from untreated target cells):

$$\text{Cytotoxicity \%} = \frac{[LDH]_{E+T} - [LDH]_E - [LDH]_{min}}{[LDH]_{max} - [LDH]_{min}} \times 100$$

Figure 4A:
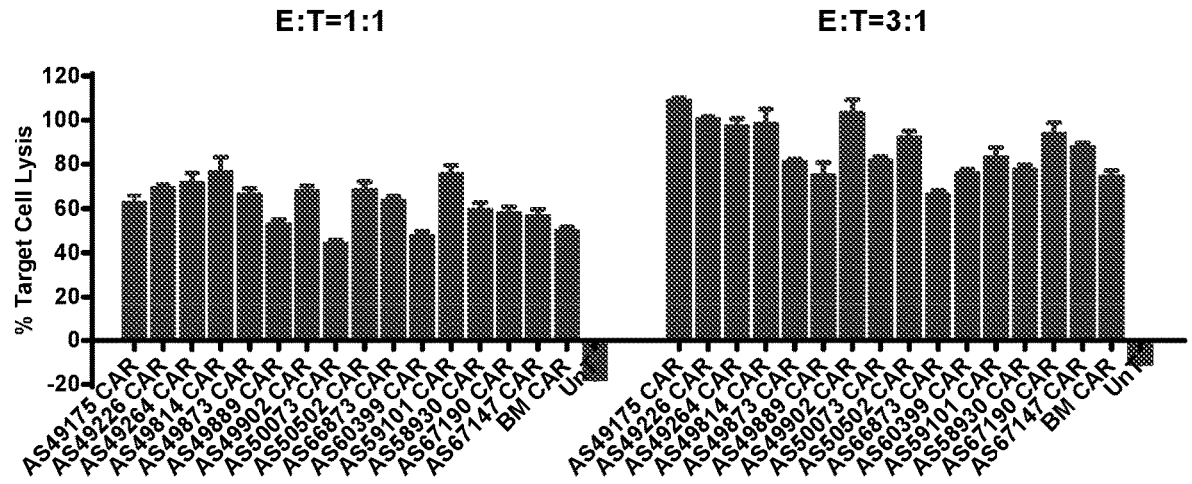
FIGS. 4A-4B shows in vitro cytotoxicity of T cells transduced with exemplary chimeric receptor constructs against MV4-11 cells at effector cell:target cell (E:T) ratio of 1:1 or 3:1 as assayed by LDH method. UnT cells were used as negative control, and BM CAR-T cells were used as positive control.
Figure 4B:
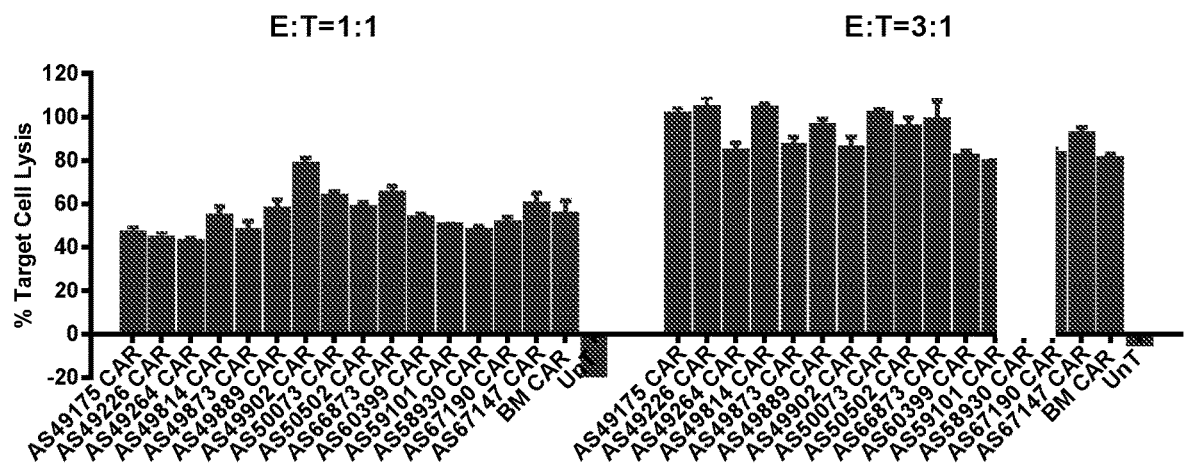

All CAR constructs effectively transduced human T cells with CAR expression rates between 35.5% and 72.3%. Cell growth and viability of transduced cells were not affected relative to nontransduced T cells in the same batch of experiments. As shown in FIGS. 3-4B, all anti-CD33 CAR-T cells tested showed strong in vitro cytotoxicity against MV4-11 and THP-1 cells. Also, the anti-CD33 CAR-T cells displayed dose-dependent targeting of both AML cells. At E:T=3:1, the percentages of target cell lysis for all CAR-T cells are between 75% and 100%. Cytotoxicity of all anti-CD33 CAR-T cells was comparable to that of the BM CAR-T cells. These results indicate that most of the anti-CD33 CAR constructs described herein have potent in vitro cytotoxicity against the two AML cell lines.

2. CytokineSecretion by HTRF

Another measure of effector T-cell activation and proliferation is the production of effector cytokines such as IFN-γ and TNF-α. Supernatants from the in vitro cytotoxicity assay were collected to assess CAR-induced cytokine release. HTRF assays for IFN-γ (Cisbio, Cat #62HIFNG-PEH) were performed according to the manufacturer's manual.

Figure 5A:
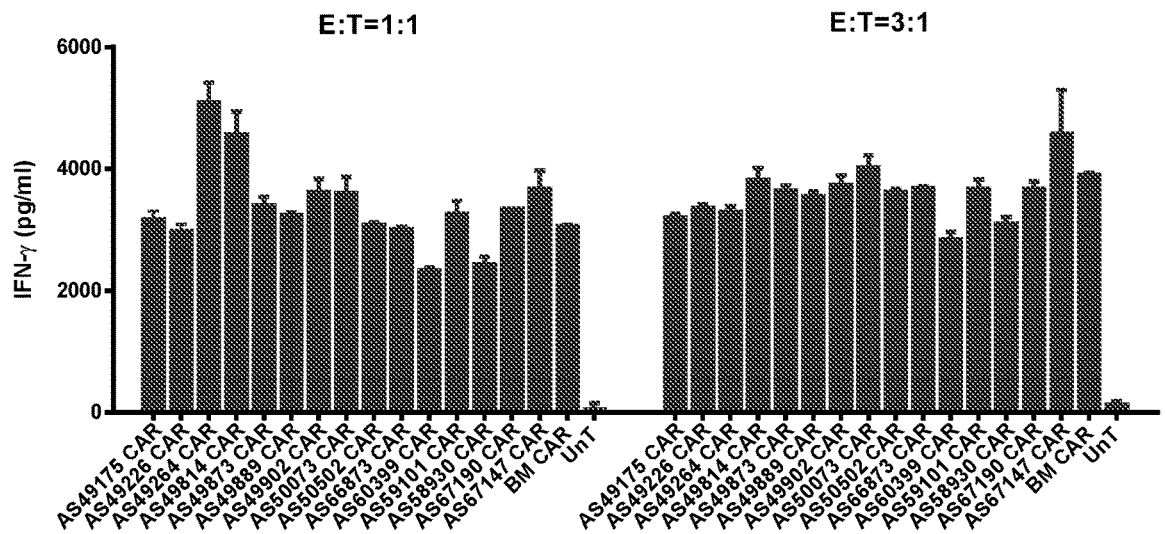
FIG. 5A shows in vitro cytokine release of T cells transduced with exemplary chimeric receptor constructs against MV4-11 cells at effector cell:target cell (E:T) ratio of 1:1 or 3:1. UnT cells were used as negative control, and BM CAR-T cells were used as positive control.
Figure 5B:
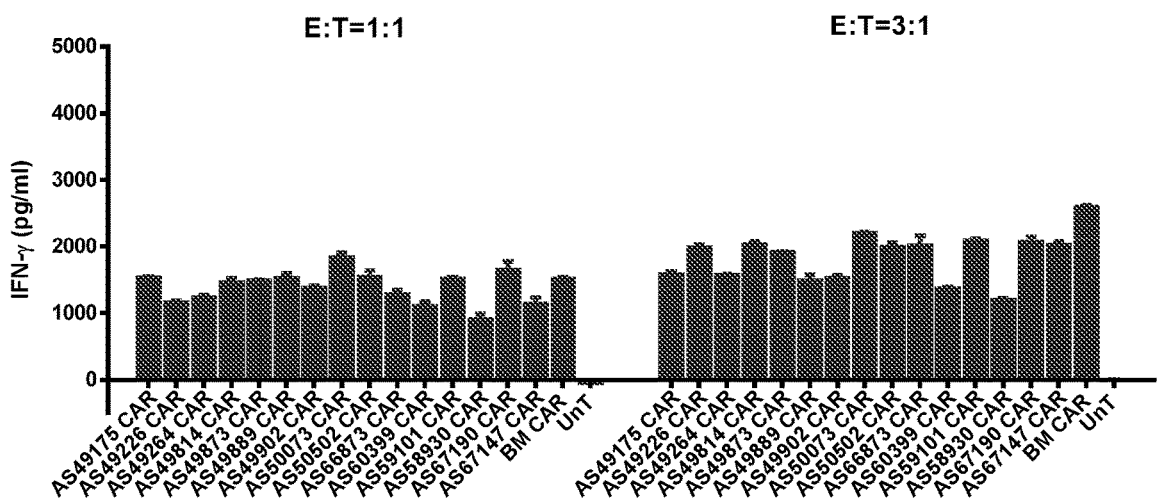
FIG. 5B shows in vitro cytokine release of T cells transduced with exemplary chimeric receptor constructs against THP-1 cells at effector cell:target cell (E:T) ratio of 1:1 or 3:1. UnT cells were used as negative control, and BM CAR-T cells were used as positive control.

Anti-CD33 CAR-T cells were co-cultured with MV4-11 and THP-1 target cells. The culture supernatants were collected after 20 h to assess IFNγ release as a measure of T cell activation. As shown in FIGS. 5A-5B, anti-CD33 CAR-T cells co-cultured with MV4-11 and THP-1 target cells secreted significant amounts of IFNγ, and the level of which was comparable to that by BM CAR-T cells.

Evaluation of Toxicity of Anti-CD33 CAR-T Cells Using CFU Assay

In order to evaluate the possible side toxicity of anti-CD33 CAR-T cells, we assessed the killing effect of anti-CD33 CAR-T cells against autologous normal hematopoietic cells by a colony forming assay using CD34-enriched normal cord blood (CB) samples. $CD34^+$ cord blood (CB) cells (HemaCare, Catlog: CB34C-2) were CD34 immunomagnetically selected and co-cultured with CD33 CAR-T cells or media alone (untreated) for 6 hours at an E:T (CAR-T:CB cells) of 10:1. The mixed cells were then plated in METHOCULT™ H4034 Optimum medium with a total cell number of 5000 (n=3), cultured for 5-7 days and scored for the presence of total colony forming unit. BM CAR-T cells were used as positive control. Untransduced T cells were used as negative controls. Data represent mean values ±SEM of colony in triplicated petri dishes for each sample.

Figure 6A:
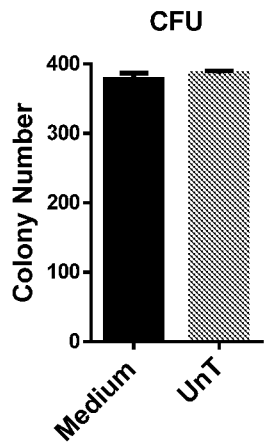
FIGS. 6A-6B show in vitro toxicity of T cells transduced with exemplary chimeric receptor constructs against hematopoietic stem cells (HSC) as determined by CFU assay. UnT cells were used as negative control, and BM CAR-T cells were used as positive control.
Figure 6B:
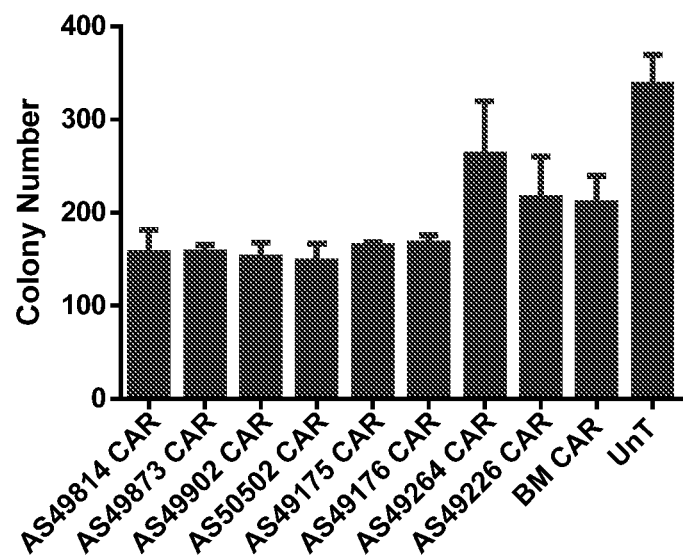

As shown in FIG. 6A, HSCs pre-incubated with UnT cells did not exhibit abnormal development compared to the vehicle control, as the colony numbers of the UnT group is the same as that of the medium group. Compared to UnT, the development of HSCs pre-incubated with anti-CD33 CAR-T cells or BM CAR-T cells was both inhibited as fewer colonies formed in these groups than in the UnT group (FIG. 6). There was no significant difference between AS49226 CAR and BM CAR groups. However, more colonies formed when the HSCs were co-incubated with AS49264 CAR-T cells than with BM CAR-T cells. These findings suggest that the engineered AS49264 CAR-T cells may be safely used as a therapy for AML without the potential toxicity associated with HSC targeting.

Evaluation of Anti-CD33 CAR-T In Vivo Mouse Model

Figure 7A:
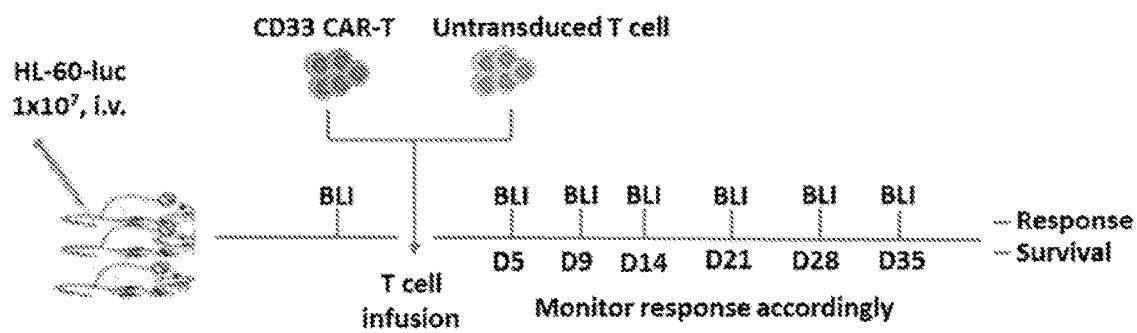
FIG. 7A shows a schematic of in vivo efficacy study of exemplary anti-CD33 CAR-T treatment in an HL-60-Luc xenograft mouse model.
Figure 7B:
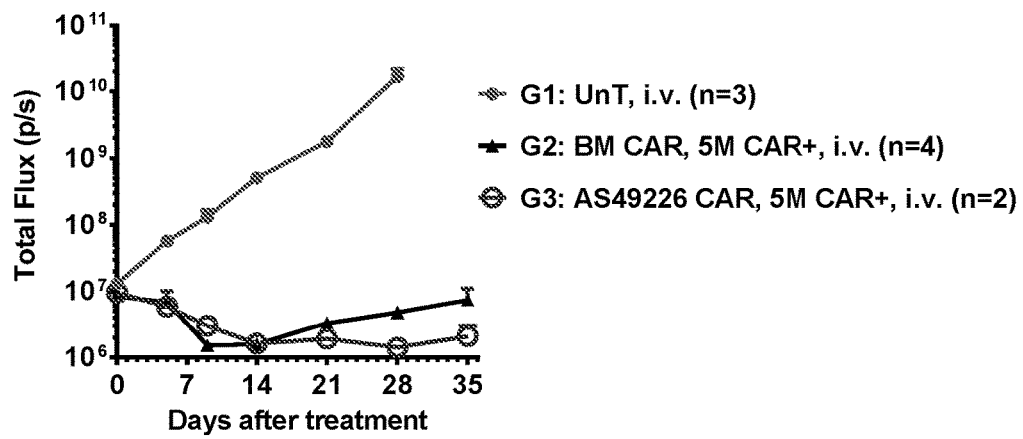
FIG. 7B shows tumor reduction in the HL-60-Luc xenograft mouse model in response to anti-CD33 CAR-T treatment. UnT cells were used as negative control, and BM CAR-T cells were used as positive control.

Anti-tumor activity of an exemplary anti-CD33 CAR-T (AS49226 CAR-T) was assessed in vivo in a HL-60-Luc xenograft mouse model according to the schedule shown in FIG. 7A. $1 \times 10^7$ HL-60-Luc cells with the firefly luciferase reporter gene expression were implanted subcutaneously on day 0 in NOD/SCID IL-2RγCnull (NSG) mice. Bioluminescent imaging (BLI) is conducted weekly or biweekly post tumor inoculation to monitor model development. The animals were randomized based on the BLI photon numbers and animal body weights. After randomization, a single dose ($6 \times 10^6$ cells) of CAR-T cells or UnT cells were infused intravenously. Weekly BLI imaging was performed to record tumor growth. Control mice treated with UnT cells showed a rapid progression of leukemia, most of which died around day 28. In contrast, mice treated with AS49226 CAR-T cells displayed a significant decrease in systemic leukemic burden as evidenced by BLI, and exhibited much slower tumor growth than mice treated with BM CAR-T cells (FIG. 7B).

Figure 8A:
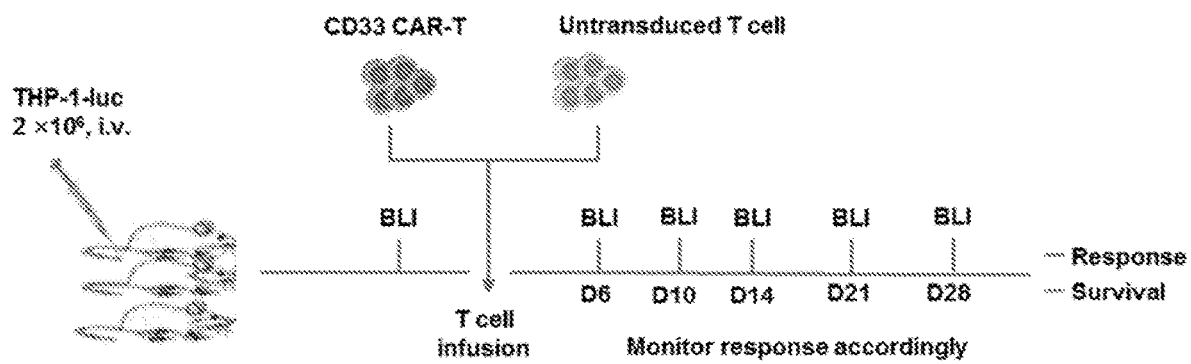
FIG. 8A shows a schematic of an in vivo efficacy study of exemplary anti-CD33 CAR-T treatment in a THP-1-Luc xenograft mouse model.
Figure 8B:
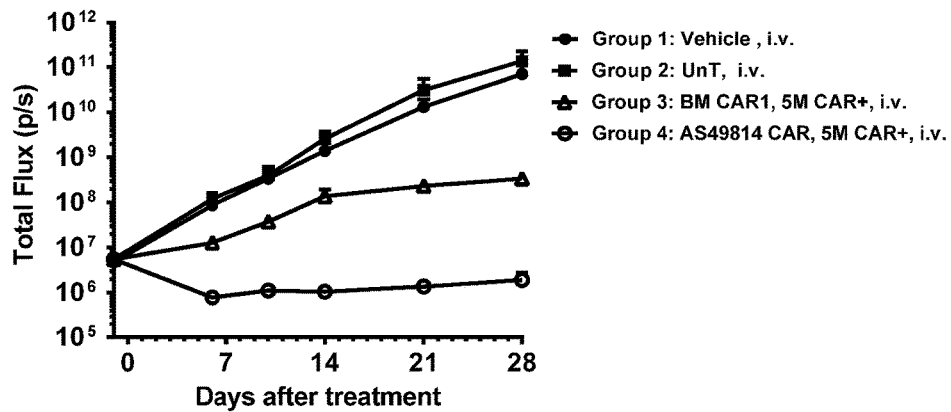
FIG. 8B shows tumor reduction in THP-1-Luc xenograft mice in response to anti-CD33 CAR-T treatment. UnT cells were used as negative control, and BM CAR1-T cells were used as positive control.

Additionally, anti-tumor activity of an exemplary anti-CD33 CAR-T (AS49814 CAR-T) was assessed in vivo in a THP-1-Luc xenograft mouse model according to the study design shown in FIG. 8A. $2 \times 10^6$ THP-1-Luc cells with the firefly luciferase reporter gene expression were implanted subcutaneously on day 0 in NOD/SCID IL-2RγCnull (NSG) mice. Bioluminescent imaging (BLI) was conducted weekly or biweekly post tumor inoculation to monitor model development. The animals were randomized based on the BLI photon numbers and animal body weights. After randomization, a single dose of CAR-T cells or unT cells were infused intravenously. Weekly BLI imaging was performed to record tumor growth. Control mice treated with UnT cells showed a rapid progression of leukemia, most of which died around day 28. In contrast, mice treated with AS49814 CAR-T cells were tumor free after 7 days post injection (BLI around $10^6$), while mice treated with BM CAR1 (an anti-CD33 CAR; sequence shown below) T cells suffered from significant tumor growth (FIG. 8B).

SEQ ID NO: 213 (BM CAR1):

SEQ ID NO: 213 (BM CAR1):
MALPVTALLLPLALLLHAARPDIQMTQSPSSLSASVGDRVTITCRASQS

VSTSSYNYMHWYQQKPGKPPKLLIKYASNLESGVPSRFSGSGSGTDFTL

TISSLQPEDFATYYCQHSWEIPLTFGQGTKVEIKGGGGSGGGGSGGGGS

EVQLVQSGAEVKKPGASVKVSCKASGYSFTDYYMHWVRQAPGQGLEWIG

RINPYNGAAFYSQNFKDRVTLTVDTSTSTAYLELSSLRSEDTAVYYCAI

ERGADLEGYAMDYWGQGTLVTVSSTTTPAPRPPTPAPTIASQPLSLRPE

ACRPAAGGAVHTRGLDFACDIYIWAPLAGTCGVLLLSLVITLYCRSKRS

RLLHSDYMNMTPRRPGPTRKHYQPYAPPRDFAAYRSRVKFSRSADAPAY

QQGQNQLYNELNLGRREEYDVLDKRRGRDPEMGGKPQRRKNPQEGLYNE

LQKDKMAEAYSEIGMKGERRRGKGHDGLYQGLSTATKDTYDALHMQALP

PRGSGATNFSLLKQAGDVEENPGPMALPVTALLLPLALLLHAARPMADY

KDIVMTQSHKFLLVSVGDRVSITCKASQDVSTAVAWYQQKPGQSPKLLI

YSASYRYTGVPDRFIGSGSGTDFTLTISSVQAEDLADYFCQQHYSTPLT

FGAGTKLEIKRGGGGSGGGGSGGGGSSGGGSEVQLKESGPGLVAPSQSL

SITCTVSGFPLTSYGVSWVRQPPGKGLEWLGVIWGDGSTNYHSALISRL

SISKDNSKSQVFLKLNNLQTDDTATYYCARDTYYPYYAMDYWGQGTSVT

VSSTTTPAPRPPTPAPTIASQPLSLRPEACRPAAGGAVHTRGLDFACDI

YIWAPLAGTCGVLLLSLVITLYCKRGRKKLLYIFKQPFMRPVQTTQEED

GCSCRFPEEEEGGCELRVKFSRSADAPAYQQGQNQLYNELNLGRREEYD

VLDKRRGRDPEMGGKPQRRKNPQEGLYNELQKDKMAEAYSEIGMKGERR

RGKGHDGLYQGLSTATKDTYDALHMQALPPR

Figure 9A:
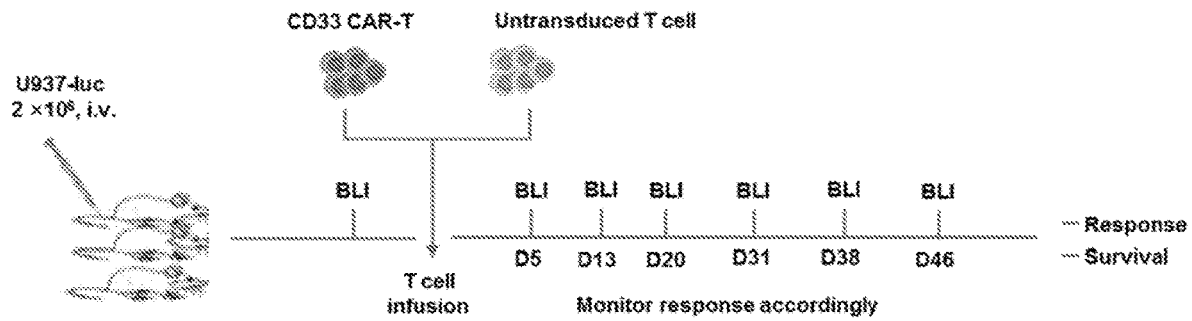
FIG. 9A shows a schematic of an in vivo efficacy study of exemplary anti-CD33 CAR-T treatment in a U937-Luc xenograft mouse model.
Figure 9B:
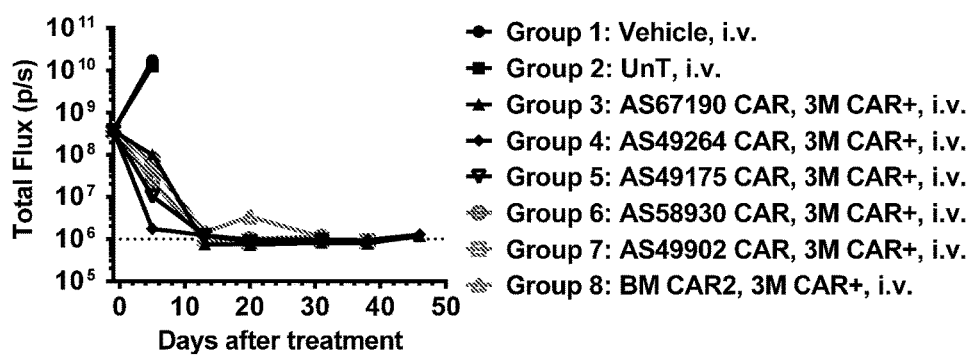
FIG. 9B shows tumor reduction in U937-Luc xenograft mice in response to anti-CD33 CAR-T treatment. UnT cells were used as negative control, and BM CAR2-T cells were used as positive control.

Anti-tumor activities of exemplary anti-CD33 CAR-T cells (AS67190, AS49264, AS49175, AS58930 and AS49902 CAR-T cells) were assessed in vivo in a U937-Luc xenograft mouse model according to the schedule shown in FIG. 9A. $2\times10^6$ U937-Luc cells with the firefly luciferase reporter gene expression were implanted subcutaneously on day 0 in NOD/SCID IL-2RγCnull (NSG) mice. Bioluminescent imaging (BLI) was conducted weekly or biweekly post tumor inoculation to monitor model development. The animals were randomized based on the BLI photon numbers and animal body weights. After randomization, a single dose of CAR-T cells or unT cells were infused intravenously. Weekly BLI imaging was performed to record tumor growth. Control mice treated with UnT cells showed a rapid progression of leukemia, most of which died around day 5. In contrast, mice treated with anti-CD33 CAR-T cells were tumor free (BLI around $10^6$) after 2 weeks injection, and the anti-tumor activities of the anti-CD33 CAR-T cells tested were stronger than that of the BM CAR2 (an anti-CD33 CAR; sequence shown below) T cells (FIG. 9B).

SEQ ID NO: 214 (BM CAR2):
MALPVTALLLPLALLLHAARPMADYKDIVMTQSHKFLLVSVGDRVSITC

KASQDVSTAVAWYQQKPGQSPKLLIYSASYRYTGVPDRFIGSGSGTDFT

LTISSVQAEDLADYFCQQHYSTPLTFGAGTKLEIKRGGGGSGGGGSGGG

GSSGGGSEVQLKESGPGLVAPSQSLSITCTVSGFPLTSYGVSWVRQPPG

KGLEWLGVIWGDGSTNYHSALISRLSISKDNSKSQVFLKLNNLQTDDTA

TYYCARDTYYPYYAMDYWGQGTSVTVSSTTTPAPRPPTPAPTIASQPLS

LRPEACRPAAGGAVHTRGLDFACDIYIWAPLAGTCGVLLLSLVITLYCK

RGRKKLLYIFKQPFMRPVQTTQEEDGCSCRFPEEEEGGCELRVKFSRSA

DAPAYQQGQNQLYNELNLGRREEYDVLDKRRGRDPEMGGKPQRRKNPQE

GLYNELQKDKMAEAYSEIGMKGERRRGKGHDGLYQGLSTATKDTYDALH

MQALPPR

According to above results, our anti-CD33 CAR-T cells were more potent in tumor elimination than BM CAR-T cells in vivo.

In Vivo Antibody Mediated CAR-T Elimination

To assess completeness and to identify optimal timing of antibody-mediated CAR T-cell elimination, mice engrafted with HL60 (n=5 to 8 mice per cohort; week 0 time point) are administered 1 dose of $1.0\times10^6$ CAR-T intravenously (IV) (week 3 time point). Animals are then treated with 1 dose, 1 or 5 mg/kg intraperitoneally (IP), of the humanized anti-CD52 antibody alemtuzumab (Genzyme) at 1, 2, or 3 weeks post-CAR-T (week 2, 3, or 4 time points). In subsequent experiments, mice engrafted with luciferase-expressing AML cell lines are treated IV with saline, untransduced T cells (UTD), or CAR-T ($1.0\times10^6$ cells per mouse). T cells are then depleted with 1 mg/kg alemtuzumab IP at 4 weeks after CAR-T (week 5 time point) Animals are assessed weekly by BLI and FC quantification of human AML and CAR T cells, as described above. Murine bone marrow and spleens are harvested for human AML and T-cell quantification by FC. Histopathologic and immunohistochemical analyses of murine tissues are performed in some studies to assess completeness of T-cell ablation with alemtuzumab.

Additional cohorts of HL60 (n=5 per treatment) are treated with saline, UTD, or CAR-T-CD20 ($1.0\times10^6$ cells per mouse) as described above Animals are subsequently treated with the anti-CD20 antibody rituximab (Roche) at a dose of 1 mg/kg IP at 4 weeks following CAR-T-CD20 to eliminate T cells. Animals are assessed by BLI and FC to quantify leukemia burden and CAR T cells.

For cetuximab mediated T cell depletion, additional cohorts of HL60 (n=5 per treatment) are treated with saline, UTD, or CAR-T-EGFR ($1.0\times10^6$ cells per mouse) as described above Animals are subsequently treated with the anti-EGFR antibody cetuximab (Bristol-Myers Squibb) at a dose of 1 mg/kg IP at 4 weeks following CAR-T-CD20 to eliminate T cells Animals are assessed by BLI and FC to quantify leukemia burden and CAR T cells.

Evaluating CAR-T Toxicity in Humanized Mouse Model

For reconstruction of human immune system (HIS) in mouse, NSG mice are infused by cord blood derived CD34+ cells. Reconstruction is confirmed by peripheral blood flow cytometry. For CAR-T preparation, autologous T cells derived from HIS mice are expanded and transduced with the candidate CAR expressing lentivirus. For toxicity study, HIS mice are infused with $2\times10^6$ autologous CAR-T. After then, animal health status and body weight are assessed twice per week and human blood cell population in mouse peripheral blood are monitored by flow cytometry weekly. 4 weeks after T cell infusion, animals are euthanized and organs are harvested and analyzed.

Evaluating CAR-T Toxicity in Non-Human Primate (NHP) Model

For CAR-T preparation, autologous T cells derived from Cynomolgus macaques and are expanded and transduced with the candidate CAR expressing lentivirus. For short-term toxicity study, animals are pre-treated with cyclophosphamide before an infusion of CAR-T cells. After CAR-T infusion, recipient animals are monitored daily for clinical signs and symptoms of CRS and neurotoxicity. The CAR-T cell persistence and cell population change are assessed by peripheral blood flow cytometry. CRS related cytokine levels are assessed by ELISA. 5 weeks after T cell infusion, animals are euthanized and organs are harvested and analyzed.

Example 3: Generation and Evaluation of Additional CAR Constructs

Generation of CAR Constructs

Leading anti-CD33 sdAbs from Example 2 are used as CD33-binding domain to construct additional CARs and CAR systems as shown in FIGS. 10A-10E.

Figure 10A:
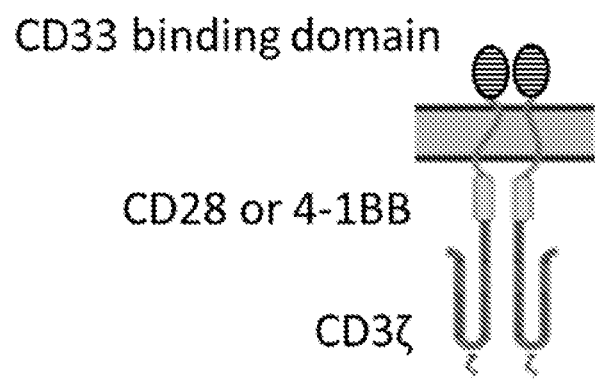
FIGS. 10A-10E depict schematic diagrams of CAR constructs, including regular CAR (FIG. 10A), Tandem CAR (FIG. 10B), Dual CARs (FIG. 10C), and Split CARs (FIGS. 10D-10E).
Figure 10B:
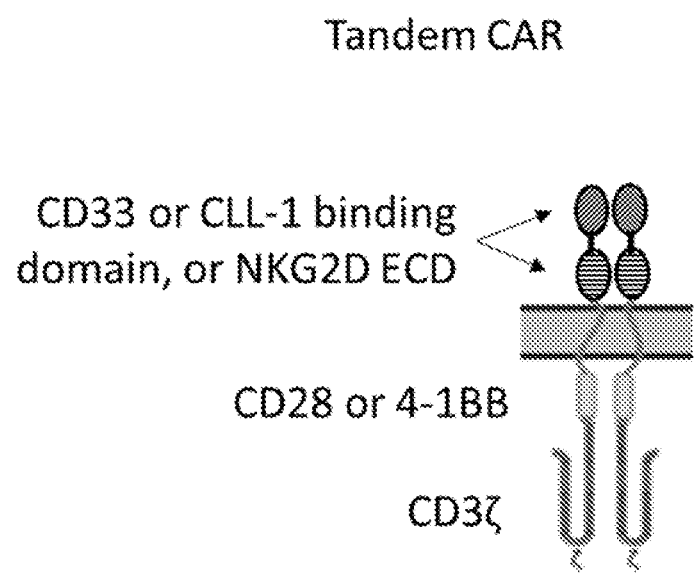
Figure 10C:
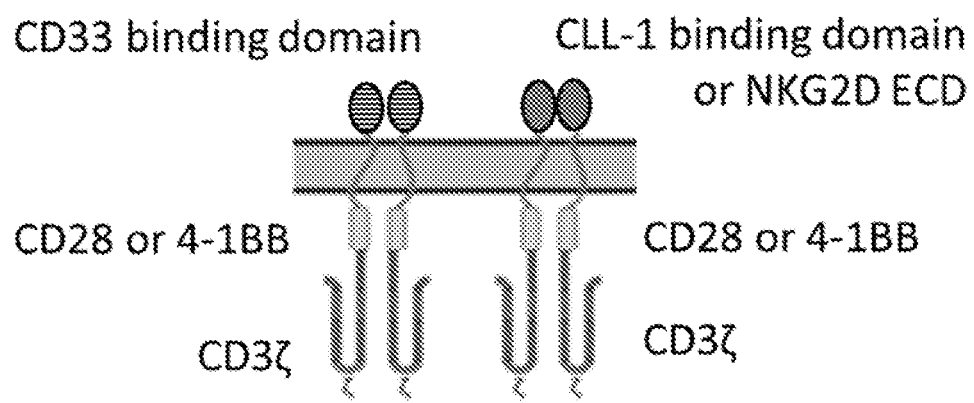
Figure 10D:
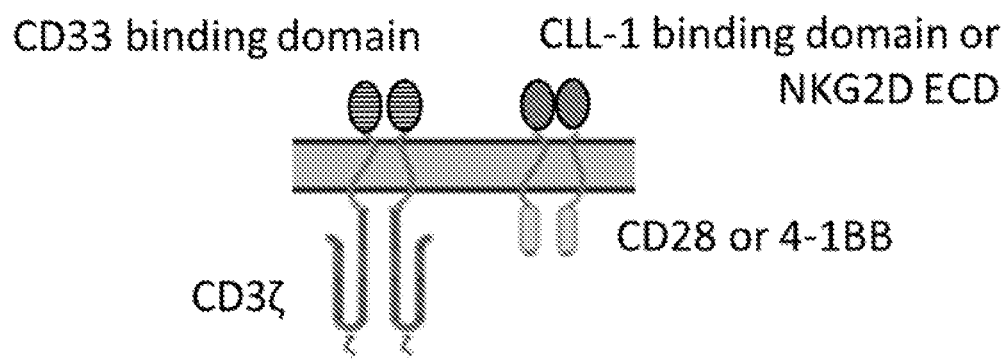
Figure 10E:
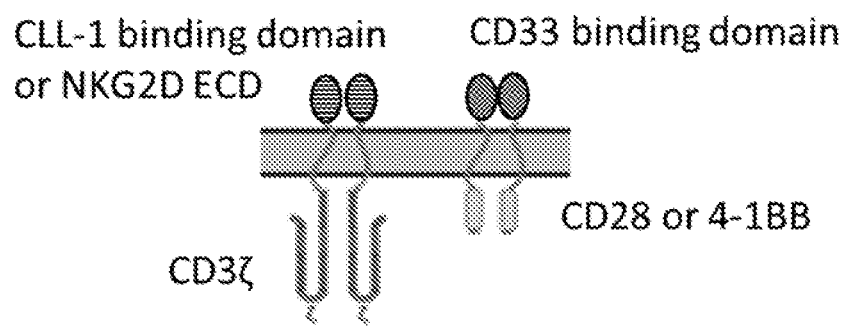

For example, "regular CARs" as shown in FIG. 10A having a monospecific extracellular domain, and an intracellular signaling domain comprising both an intracellular co-stimulatory sequence and a CD3ζ intracellular signaling sequence can respond and kill CD33 expressing cells. "Tandem CARs" as shown in FIG. 10B are constructed by fusing two binding domains specifically recognizing different targets via a peptide linker to form the extracellular domain in a single CAR molecule. Tandem CARs can respond to cells expressing either one of the two target molecules, such as CD33, CLL1 and NKG2D ligands. Tandem CARs are expected to bind to target cells expressing both target molecules simultaneously with higher affinity and specificity, resulting in improved response at a low dosage. "Dual CARs" as shown in FIG. 10C are constructed by expressing two fully functional CARs against distinct targets. Dual CARs can respond to cells expressing either CD33 or any one of CLL1, CD123 or NKG2D ligands. "Split CARs" as shown in FIGS. 10D-10E have complete response to cells expressing both CD33 and either one of CLL1 or NKG2D ligands, but have only marginal response to cells expressing only one of CD33, CLL1 or NKG2D ligands, which may result in a better safety profile.

Evaluation of CAR Constructs

The CAR constructs, with or without safety switch, are tested for their in vitro cytotoxicity against AML cell lines, in vivo efficacy in xenograft AML animal models, in vitro hematopoietic toxicity with a CFU assay, in vivo elimination by corresponding antibodies and in vivo toxicity with HIS mice and NHP studies.

Example 4: Generation and Evaluation of Anti-CD33/CLL1 Tandem CAR Constructs Cloning of Anti-CD33/CLL1 Tandem CAR Constructs Exemplary tandem CARs as shown in FIG. 10B were constructed by fusing two binding domains specifically recognizing different targets (CLL1 and CD33) via a peptide linker to form the extracellular domain in a single CAR molecule. Anti-CLL1/CD33 tandem CARs were cloned into a lentiviral expression vector with the intracellular co-stimulatory sequence of CD28 and intracellular domain of CD3ζ as shown in FIG. 10B and Table 4. The CAR constructs were cloned into an expression vector with an EF1α promoter for expression. Sequences of exemplary tandem CARs are shown below.

```
SEQ ID NO: 170 (Tan1):
MALPVTALLLPLALLLHAARPQVQLVESGGGSVQAGGALSLSCAASGYTVRIDYMGWYRQTPG
KGREPVATIASNGGTAYADSVEGRFTISQDNAKNSVYLQMNTLKPGDTAMYYCAAGTWPTLTY
FGQGTQVTVSSGGGGSEVQLVESGGGSVQAGGSLRLSCAASGYTYSINCMGWFRQAPGKEREG
VAVISTGGGRTDYRDSVKGRFTISQDNAKNTVYLQMNSLKPEDTAMYYCAGKTTYPGYGCGLG
RSAYNYWGQGTQVTVSSIEVMYPPPYLDNEKSNGTIIHVKGKHLCPSPLFPGPSKPFWVLVVVG
GVLACYSLLVTVAFIIFWVRSKRSLLHSDYMNMTPRRPGPTRKHYQPYAPPRDFAAYRSRVKF
SRSADAPAYKQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPR

SEQ ID NO: 171 (Tan2):
MALPVTALLLPLALLLHAARPQVQLVESGGGSVQAGGALSLSCAASGYTVRIDYMGWYRQTPG
KGREPVATIASNGGTAYADSVEGRFTISQDNAKNSVYLQMNTLKPGDTAMYYCAAGTWPTLTY
FGQGTQVTVSSGGGGSGGGGSEVQLVESGGGSVQAGGSLRLSCAASGYTYSINCMGWFRQAPG
KEREGVAVISTGGGRTDYRDSVKGRFTISQDNAKNTVYLQMNSLKPEDTAMYYCAGKTTYPGY
GCGLGRSAYNYWGQGTQVTVSSIEVMYPPPYLDNEKSNGTIIHVKGKHLCPSPLFPGPSKPFWVL
VVVGGVLACYSLLVTVAFIIFWVRSKRSLLHSDYMNMTPRRPGPTRKHYQPYAPPRDFAAYRS
RVKFSRSADAPAYKQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR

SEQ ID NO: 172 (Tan3):
MALPVTALLLPLALLLHAARPQVQLVESGGGSVQAGGALSLSCAASGYTVRIDYMGWYRQTPG
KGREPVATIASNGGTAYADSVEGRFTISQDNAKNSVYLQMNTLKPGDTAMYYCAAGTWPTLTY
FGQGTQVTVSSGGGGSGGGGSGGGGSEVQLVESGGGSVQAGGSLRLSCAASGYTYSINCMGWF
RQAPGKEREGVAVISTGGGRTDYRDSVKGRFTISQDNAKNTVYLQMNSLKPEDTAMYYCAGKT
TYPGYGCGLGRSAYNYWGQGTQVTVSSIEVMYPPPYLDNEKSNGTIIHVKGKHLCPSPLFPGPSK
PFWVLVVVGGVLACYSLLVTVAFIIFWVRSKRSLLHSDYMNMTPRRPGPTRKHYQPYAPPRDF
AAYRSRVKFSRSADAPAYKQGQNQLYNELNLGRREEYDVLDKRRGRDPEMGGKPRRKNPQEG
LYNELQKDKMAEAYSEIGMKGERRRGKGHDGLYQGLSTATKDTYDALHMQALPPR

SEQ ID NO: 173 (Tan4):
MALPVTALLLPLALLLHAARPQVQLVESGGGSVQAGGALSLSCAASGYTVRIDYMGWYRQTPG
KGREPVATIASNGGTAYADSVEGRFTISQDNAKNSVYLQMNTLKPGDTAMYYCAAGTWPTLTY
FGQGTQVTVSSGGGGSGGGGSGGGGSGGGGSEVQLVESGGGSVQAGGSLRLSCAASGYTYSIN
CMGWFRQAPGKEREGVAVISTGGGRTDYRDSVKGRFTISQDNAKNTVYLQMNSLKPEDTAMY
```

-continued

YCAGKTTYPGYGCGLGRSAYNYWGQGTQVTVSSIEVMYPPPYLDNEKSNGTIIHVKGKHLCPSP
LFPGPSKPFWVLVVVGGVLACYSLLVTVAFIIFWVRSKRSRLLHSDYMNMTPRRPGPTRKHYQP
YAPPRDFAAYRSRVKFSRSADAPAYKQGQNQLYNELNLGRREEYDVLDKRRGRDPEMGGKPRR
KNPQEGLYNELQKDKMAEAYSEIGMKGERRRGKGHDGLYQGLSTATKDTYDALHMQALPPR

SEQ ID NO: 174 (Tan5):
MALPVTALLLPLALLLHAARPQVQLVESGGGSVQAGGALSLSCAASGYTVRIDYMGWYRQTPG
KGREPVATIASNGGTAYADSVEGRFTISQDNAKNSVYLQMNTLKPGDTAMYYCAAGTWPTLTY
FGQGTQVTVSSGGGGSGGGGSGGGGSGGGGSGGGGSEVQLVESGGGSVQAGGSLRLSCAASGY
TYSINCMGWFRQAPGKEREGVAVISTGGGRTDYRDSVKGRFTISQDNAKNTVYLQMNSLKPED
TAMYYCAGKTTYPGYGCGLGRSAYNYWGQGTQVTVSSIEVMYPPPYLDNEKSNGTIIHVKGKH
LCPSPLFPGPSKPFWVLVVVGGVLACYSLLVTVAFIIFWVRSKRSRLLHSDYMNMTPRRPGPTRK
HYQPYAPPRDFAAYRSRVKFSRSADAPAYKQGQNQLYNELNLGRREEYDVLDKRRGRDPEMG
GKPRRKNPQEGLYNELQKDKMAEAYSEIGMKGERRRGKGHDGLYQGLSTATKDTYDALHMQA
LPPR

SEQ ID NO: 175 (Tan6):
MALPVTALLLPLALLLHAARPQVQLVESGGGSVQAGGALSLSCAASGYTVRIDYMGWYRQTPG
KGREPVATIASNGGTAYADSVEGRFTISQDNAKNSVYLQMNTLKPGDTAMYYCAAGTWPTLTY
FGQGTQVTVSSGSTSGSGKPGSGEGSTKGEVQLVESGGGSVQAGGSLRLSCAASGYTYSINCMG
WFRQAPGKEREGVAVISTGGGRTDYRDSVKGRFTISQDNAKNTVYLQMNSLKPEDTAMYYCAG
KTTYPGYGCGLGRSAYNYWGQGTQVTVSSIEVMYPPPYLDNEKSNGTIIHVKGKHLCPSPLFPGP
SKPFWVLVVVGGVLACYSLLVTVAFIIFWVRSKRSRLLHSDYMNMTPRRPGPTRKHYQPYAPPR
DFAAYRSRVKFSRSADAPAYKQGQNQLYNELNLGRREEYDVLDKRRGRDPEMGGKPRRKNPQ
EGLYNELQKDKMAEAYSEIGMKGERRRGKGHDGLYQGLSTATKDTYDALHMQALPPR

SEQ ID NO: 176 (Tan7):
MALPVTALLLPLALLLHAARPEVQLVESGGGSVQAGGSLRLSCAASGYTYSINCMGWFRQAPG
KEREGVAVISTGGGRTDYRDSVKGRFTISQDNAKNTVYLQMNSLKPEDTAMYYCAGKTTYPGY
GCGLGRSAYNYWGQGTQVTVSSGGGGSQVQLVESGGGSVQAGGALSLSCAASGYTVRIDYMG
WYRQTPGKGREPVATIASNGGTAYADSVEGRFTISQDNAKNSVYLQMNTLKPGDTAMYYCAA
GTWPTLTYFGQGTQVTVSSIEVMYPPPYLDNEKSNGTIIHVKGKHLCPSPLFPGPSKPFWVLVVV
GGVLACYSLLVTVAFIIFWVRSKRSRLLHSDYMNMTPRRPGPTRKHYQPYAPPRDFAAYRSRVK
FSRSADAPAYKQGQNQLYNELNLGRREEYDVLDKRRGRDPEMGGKPRRKNPQEGLYNELQKD
KMAEAYSEIGMKGERRRGKGHDGLYQGLSTATKDTYDALHMQALPPR

SEQ ID NO: 177 (Tan8):
MALPVTALLLPLALLLHAARPEVQLVESGGGSVQAGGSLRLSCAASGYTYSINCMGWFRQAPG
KEREGVAVISTGGGRTDYRDSVKGRFTISQDNAKNTVYLQMNSLKPEDTAMYYCAGKTTYPGY
GCGLGRSAYNYWGQGTQVTVSSGGGGSGGGGSQVQLVESGGGSVQAGGALSLSCAASGYTVR
IDYMGWYRQTPGKGREPVATIASNGGTAYADSVEGRFTISQDNAKNSVYLQMNTLKPGDTAMY
YCAAGTWPTLTYFGQGTQVTVSSIEVMYPPPYLDNEKSNGTIIHVKGKHLCPSPLFPGPSKPFWV
LVVVGGVLACYSLLVTVAFIIFWVRSKRSRLLHSDYMNMTPRRPGPTRKHYQPYAPPRDFAAYR
SRVKFSRSADAPAYKQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR

SEQ ID NO: 178 (Tan9):
MALPVTALLLPLALLLHAARPEVQLVESGGGSVQAGGSLRLSCAASGYTYSINCMGWFRQAPG
KEREGVAVISTGGGRTDYRDSVKGRFTISQDNAKNTVYLQMNSLKPEDTAMYYCAGKTTYPGY
GCGLGRSAYNYWGQGTQVTVSSGGGGSGGGGSGGGGSQVQLVESGGGSVQAGGALSLSCAAS
GYTVRIDYMGWYRQTPGKGREPVATIASNGGTAYADSVEGRFTISQDNAKNSVYLQMNTLKPG
DTAMYYCAAGTWPTLTYFGQGTQVTVSSIEVMYPPPYLDNEKSNGTIIHVKGKHLCPSPLFPGPS
KPFWVLVVVGGVLACYSLLVTVAFIIFWVRSKRSRLLHSDYMNMTPRRPGPTRKHYQPYAPPRD
FAAYRSRVKFSRSADAPAYKQGQNQLYNELNLGRREEYDVLDKRRGRDPEMGGKPRRKNPQE
GLYNELQKDKMAEAYSEIGMKGERRRGKGHDGLYQGLSTATKDTYDALHMQALPPR

SEQ ID NO: 179 (Tan10):
MALPVTALLLPLALLLHAARPEVQLVESGGGSVQAGGSLRLSCAASGYTYSINCMGWFRQAPG
KEREGVAVISTGGGRTDYRDSVKGRFTISQDNAKNTVYLQMNSLKPEDTAMYYCAGKTTYPGY
GCGLGRSAYNYWGQGTQVTVSSGGGGSGGGGSGGGGSGGGGSQVQLVESGGGSVQAGGALSL
SCAASGYTVRIDYMGWYRQTPGKGREPVATIASNGGTAYADSVEGRFTISQDNAKNSVYLQMN
TLKPGDTAMYYCAAGTWPTLTYFGQGTQVTVSSIEVMYPPPYLDNEKSNGTIIHVKGKHLCPSP
LFPGPSKPFWVLVVVGGVLACYSLLVTVAFIIFWVRSKRSRLLHSDYMNMTPRRPGPTRKHYQP
YAPPRDFAAYRSRVKFSRSADAPAYKQGQNQLYNELNLGRREEYDVLDKRRGRDPEMGGKPRR
KNPQEGLYNELQKDKMAEAYSEIGMKGERRRGKGHDGLYQGLSTATKDTYDALHMQALPPR

SEQ ID NO: 180 (Tan11):
MALPVTALLLPLALLLHAARPEVQLVESGGGSVQAGGSLRLSCAASGYTYSINCMGWFRQAPG
KEREGVAVISTGGGRTDYRDSVKGRFTISQDNAKNTVYLQMNSLKPEDTAMYYCAGKTTYPGY
GCGLGRSAYNYWGQGTQVTVSSGGGGSGGGGSGGGGSGGGGSGGGGSQVQLVESGGGSVQA
GGALSLSCAASGYTVRIDYMGWYRQTPGKGREPVATIASNGGTAYADSVEGRFTISQDNAKNSV
YLQMNTLKPGDTAMYYCAAGTWPTLTYFGQGTQVTVSSIEVMYPPPYLDNEKSNGTIIHVKGK
HLCPSPLFPGPSKPFWVLVVVGGVLACYSLLVTVAFIIFWVRSKRSRLLHSDYMNMTPRRPGPTR
KHYQPYAPPRDFAAYRSRVKFSRSADAPAYKQGQNQLYNELNLGRREEYDVLDKRRGRDPEM
GGKPRRKNPQEGLYNELQKDKMAEAYSEIGMKGERRRGKGHDGLYQGLSTATKDTYDALHMQ
ALPPR

SEQ ID NO: 181 (Tan12):
MALPVTALLLPLALLLHAARPEVQLVESGGGSVQAGGSLRLSCAASGYTYSINCMGWFRQAPG
KEREGVAVISTGGGRTDYRDSVKGRFTISQDNAKNTVYLQMNSLKPEDTAMYYCAGKTTYPGY
GCGLGRSAYNYWGQGTQVTVSSGSTSGSGKPGSGEGSTKGQVQLVESGGGSVQAGGALSLSCA

-continued

```
ASGYTVRIDYMGWYRQTPGKGREPVATIASNGGTAYADSVEGRFTISQDNAKNSVYLQMNTLK
PGDTAMYYCAAGTWPTLTYFGQGTQVTVSSIEVMYPPPYLDNEKSNGTIIHVKGKHLCPSPLFPG
PSKPFWVLVVVGGVLACYSLLVTVAFIIFWVRSKRSRLLHSDYMNMTPRRPGPTRKHYQPYAPP
RDFAAYRSRVKFSRSADAPAYKQGQNQLYNELNLGRREEYDVLDKRRGRDPEMGGKPRRKNP
QEGLYNELQKDKMAEAYSEIGMKGERRRGKGHDGLYQGLSTATKDTYDALHMQALPPR
```

Generation of Anti-CD33/CLL1 Tandem CAR-T Cells

Lentiviruses encoding the tandem CARs (Tan 1-Tan 12), AS49264 CAR, and AS82658-28z CAR were prepared as described in Example 2. T lymphocytes were collected and transduced with the lentiviruses according to the protocol in Example 2.

Evaluation of In Vitro Activity of Anti-CD33/CLL1 tandm CAR-T Cells

1. In Vitro Cytotoxicity Assay

The anti-tumor activities of tandem CAR-T cells were assessed using the in vitro LDH assay as described in Example 2.

Figure 11:
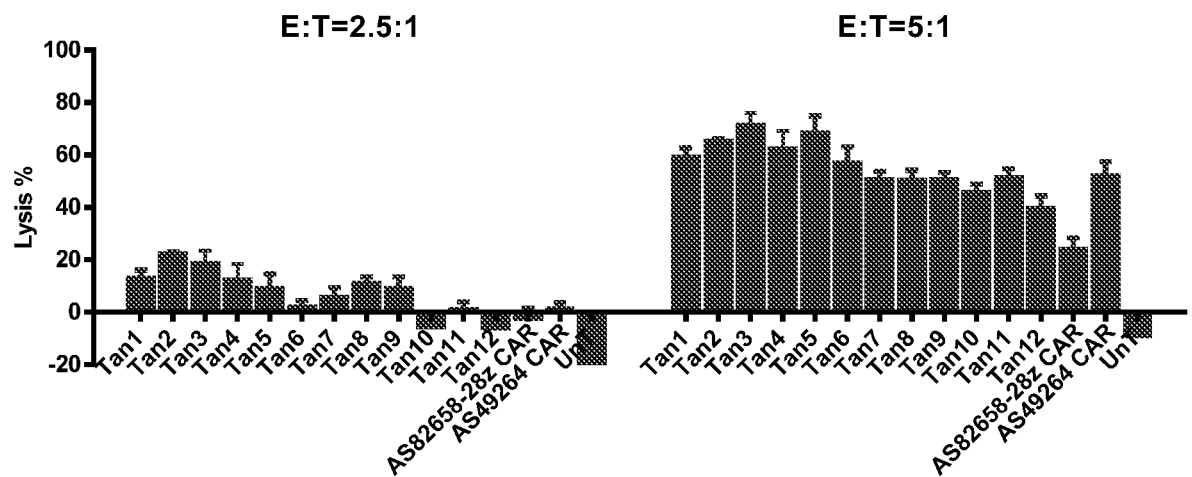
FIG. 11 shows the in vitro cytotoxicity of CLL1/CD33 tandem CAR-T cells against acute myeloid leukemia cell line THP-1.

As shown in FIG. 11, in vitro cytotoxicity of Tandem CARs against THP-1 was higher than any single CAR-T cells (AS82658-28z or AS49264 CAR-T), which indicated that tamdem CARs against two targets would be more efficient for tumor elimination.

```
SEQ ID NO: 215 (AS82658-28z):
MALPVTALLLPLALLLHAARPQVQLVESGGGSVQAGGALSLSCAASGYT

VRIDYMGWYRQTPGKGREPVATIASNGGTAYADSVEGRFTISQDNAKNS

VYLQMNTLKPGDTAMYYCAAGTWPTLTYFGQGTQVTVSSIEVMYPPPYL

DNEKSNGTIIHVKGKHLCPSPLFPGPSKPFWVLVVVGGVLACYSLLVTV

AFIIFWVRSKRSRLLHSDYMNMTPRRPGPTRKHYQPYAPPRDFAAYRSR

VKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKD

TYDALHMQALPPR
```

2. Long-Term Co-Culture Assay

To evaluate the long-term killing efficacy of CAR-T cells, we performed long-term co-culture assays, which mimic the dynamic killing process in vivo. AML tumor cell lines (e.g., U937) were labeled with CFSE (SIGMA-ALDRICH, Cat #21888-25MG-F). Transduced or non-transduced T cells ($1\times10^5$/well) were co-cultured with tumor cells (e.g., CFSE-U937 cells, $4\times10^5$ well) at an E:T ratio of 1:4 in 24-well plates, in the absence of exogenous cytokines (IL-2). Part of the cells were harvested and stained for CD3 after 2 or 3 days' co-culture. Tumor cells were identified by $CFSE^+$ signal. For serial co-culture assays, the remaining T cells were then re-challenged with fresh CFSE-U937 cells at the same E:T ratio. Co-cultures were carried on until tumor cells outgrew. The T cell proliferation rate at each time point is calculated by dividing the number of T cells at the time point by the number of T cells at a previous time point.

Figure 12A:
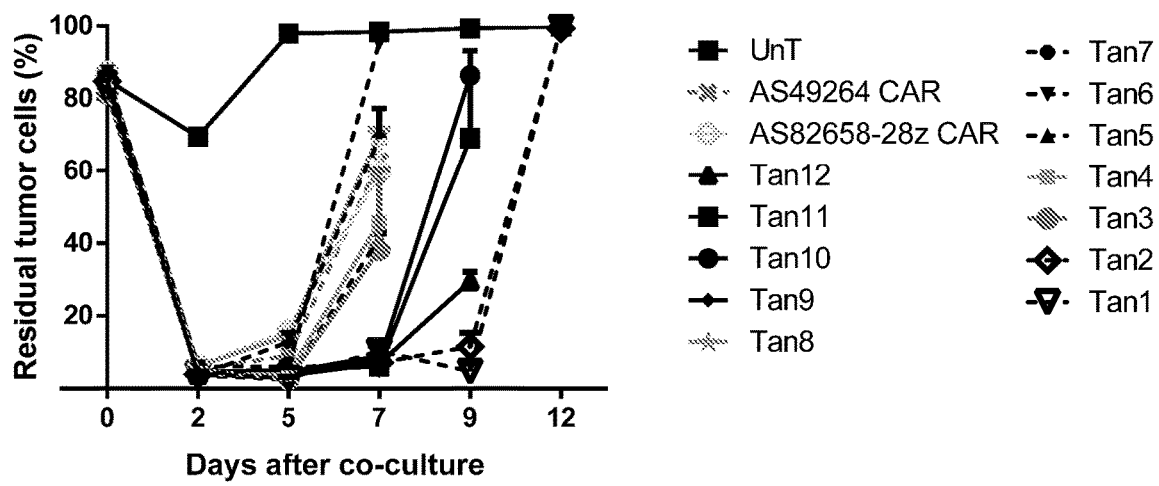
FIGS. 12A-12B show the potency of CLL1/CD33 tandem CAR-T cells in inhibiting tumor cell growth in long-term co-cultures with U937 cells.
Figure 12B:
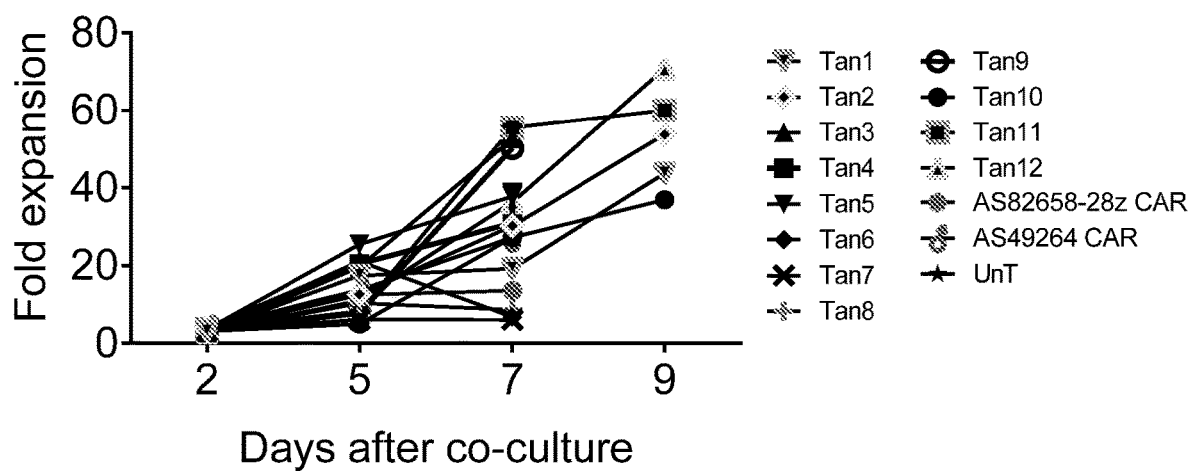

The killing efficacy of various tandem CAR-T cells in the repeated tumor stimulation assay is shown in FIG. 12A. The single-target anti-CLL1 CAR-T cells (AS82658-28z) and anti-CD33 CAR-T cells (AS49264 CAR-T) were exhausted after 3 rounds of tumor stimulation, while most tandem CAR-T cells persisted until 4 or 5 rounds of tumor stimulation. Also, tandem CAR-T cells proliferated faster than AS82658-28z or AS49264 CAR-T cells in vitro (FIG. 12B). These results demonstrate that CLL1/CD33 tandem CAR-T cells have more potent anti-tumor activity than single-target CAR-T cells in vitro.

3. IFN-γ and GM-CSF Secretion Detected by HTRF

Another measure of effector T-cell activation and proliferation is the production of effector cytokines such as IFN-γ and GM-CSF. Supernatants from the long-term co-culture assay were collected to assess CAR-induced cytokine release. HTRF assays for IFN-γ (Cisbio, Cat #62HIFNG-PEH) and GM-CSF (Cisbio, Cat #62HGMCSFPEG) were performed according to the manufacturer's manual.

Figure 13A:
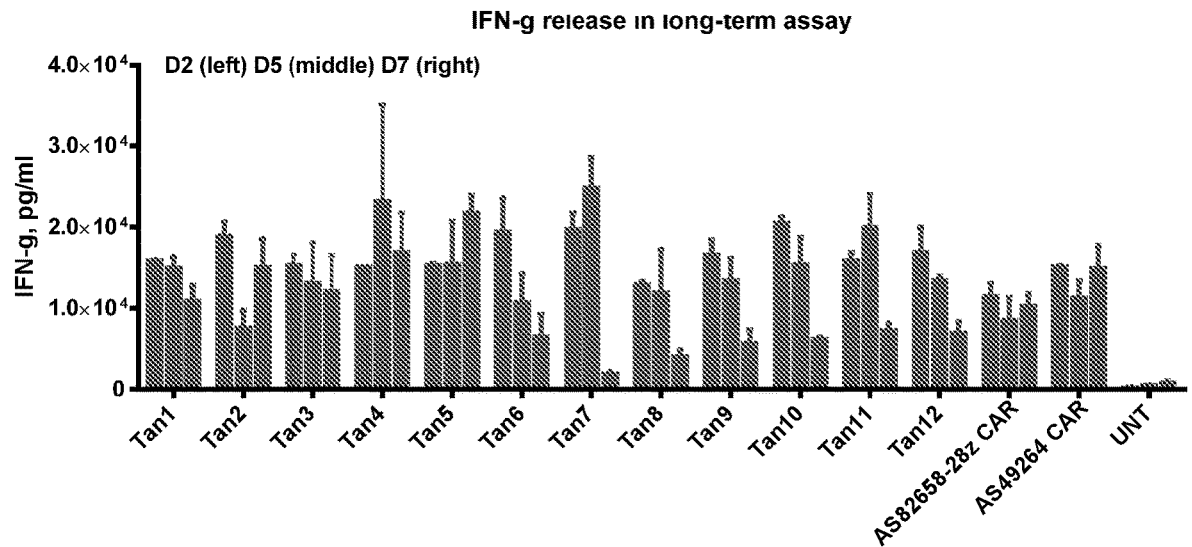
FIGS. 13A-13B show cytokine release in long-term co-culture assays.
Figure 13B:
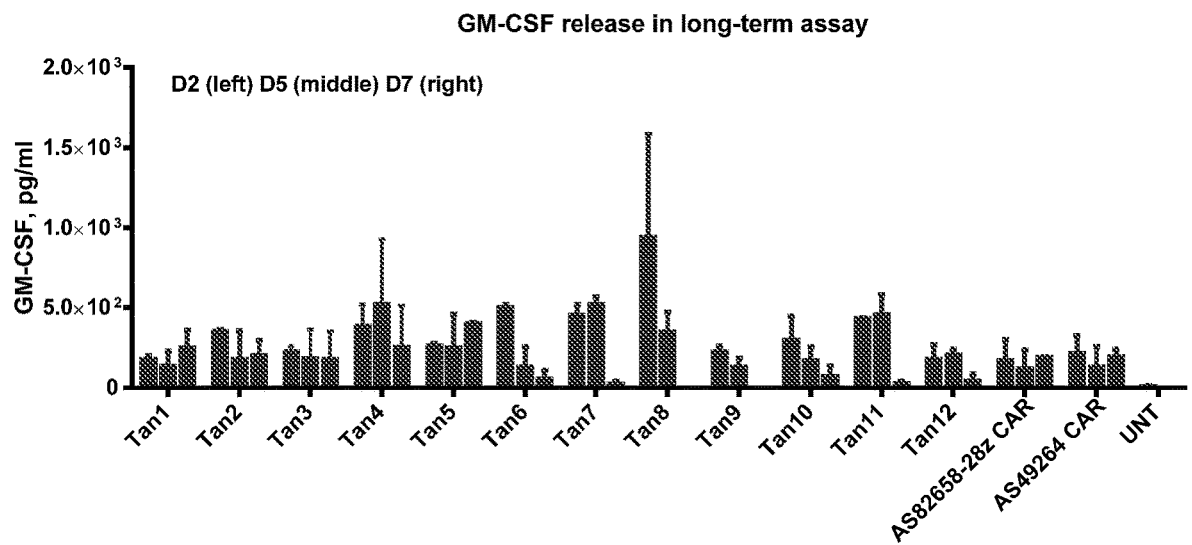

Results of a representative cytokines release assay are shown in FIGS. 13A-13B. Tandem CAR-T cells released comparable levels of cytokines as the single-target CAR-T cells (AS82658-28z and AS49264 CAR-T), when co-cultured with U937 cells in vitro.

Example 5: Generation and Evaluation of Anti-CD33/CLL1 Dual CAR Constructs

Cloning of Anti-CD33/CLL1 Dual CAR Constructs

Exemplary dual CARs as shown in FIG. 10C were constructed by expressing two fully functional CARs against CLL1 and CD33 respectively. The CAR constructs as shown in Table 6 were cloned into an expression vector with an EF1α promoter for expression. The sequences of exemplary dual CARs are shown below.

```
SEQ ID NO: 183 (Dual1):
MALPVTALLLPLALLLHAARPQVQLVESGGDLVRPGGSLRLSCAASGFTFSIYDMNWVRQAPGK
GLEWVAGISGNGYSTSYAESVKGRFTISRDNAKNTVYLQLSSLKFEDTAMYYCVRDAERWDEN
DLRRKGQGTQVTVSSIEVMYPPPYLDNEKSNGTIIHVKGKHLCPSPLFPGPSKPFWVLVVVGGVL
ACYSLLVTVAFIIFWVRSKRSRLLHSDYMNMTPRRPGPTRKHYQPYAPPRDFAAYRSRVKFSRSA
DAPAYKQGQNQLYNELNLGRREEYDVLDKRRGRDPEMGGKPRRKNPQEGLYNELQKDKMAE
AYSEIGMKGERRRGKGHDGLYQGLSTATKDTYDALHMQALPPRGSGATNFSLLKQAGDVEENP
GPMALPVTALLLPLALLLHAARPQIQLVESGGGSVQAGGSLRLSCVASGYIGGHYYMGWFRQAP
GKEREGVAAIDIDSDGRTRYAGSVQGRFTISQDNAKNTLHLQMSSLKPEDTGMYYCAVGVGWV
PARLTPQAVSYWGKGTLVTVSSTTTPAPRPPTPAPTIASQPLSLRPEACRPAAGGAVHTRGLDFA
CDIYIWAPLAGTCGVLLLSLVITLYCKRGRKKLLYIFKQPFMRPVQTTQEEDGCSCRFPEEEEGGC
ELRVKFSRSADAPAYKQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR SEQ ID NO: 184 (Dual2):
MALPVTALLLPLALLLHAARPQVQLVESGGDLVRPGGSLRLSCAASGFTFSIYDMNWVRQAPGK
GLEWVAGISGNGYSTSYAESVKGRFTISRDNAKNTVYLQLSSLKFEDTAMYYCVRDAERWDEN
DLRRKGQGTQVTVSSIEVMYPPPYLDNEKSNGTIIHVKGKHLCPSPLFPGPSKPFWVLVVVGGVL
ACYSLLVTVAFIIFWVRSKRSRLLHSDYMNMTPRRPGPTRKHYQPYAPPRDFAAYRSRVKFSRSA
```

-continued
DAPAYKQGQNQLYNELNLGRREEYDVLDKRRGRDPEMGGKPRRKNPQEGLYNELQKDKMAE
AYSEIGMKGERRRGKGHDGLYQGLSTATKDTYDALHMQALPPRGSGATNFSLLKQAGDVEENP
GPMALPVTALLLPLALLLHAARPQVQLVESGGGLVQAGGSLRLSCTASGFTFDNYVMGWFRQA
PGKEREGVSCIGWSGGSTYYADSVKGRFTISRDNAKNTLYLQMNSLKPEDTAMYYCAADQGKC
SLGSAGADDMDYWGRGTLVTVSSTTTPAPRPPTPAPTIASQPLSLRPEACRPAAGGAVHTRGLDF
ACDIYIWAPLAGTCGVLLLSLVITLYCKRGRKKLLYIFKQPFMRPVQTTQEEDGCSCRFPEEEEGG
CELRVKFSRSADAPAYKQGQNQLYNELNLGRREEYDVLDKRRGRDPEMGGKPRRKNPQEGLY
NELQKDKMAEAYSEIGMKGERRRGKGHDGLYQGLSTATKDTYDALHMQALPPR SEQ ID NO: 185 (Dual3):
MALPVTALLLPLALLLHAARPQVQLVESGGGLVQPGGSLRLSCAASGFTFSVYDMNWFRQAPG
KGLEWVSGITGNGYTTSYADSVKGRFTISRDNAKNTLYLQLNSLKSEDTAMYYCAKETNRGQG
TQVTVSSIEVMYPPPYLDNEKSNGTIIHVKGKHLCPSPLFPGPSKPFWVLVVVGGVLACYSLLVT
VAFIIFWVRSKRSRLLHSDYMNMTPRRPGPTRKHYQPYAPPRDFAAYRSRVKFSRSADAPAYKQ
GQNQLYNELNLGRREEYDVLDKRRGRDPEMGGKPRRKNPQEGLYNELQKDKMAEAYSEIGMK
GERRRGKGHDGLYQGLSTATKDTYDALHMQALPPRGSGATNFSLLKQAGDVEENPGPMALPVT
ALLLPLALLLHAARPQVQLVESGGGLVQAGGSLRLSCAASGNVFRFNIMGWYRQAPGNQRELV
ASIDDGGDRSYADSVEGRFTISRENGKKIMYLQMNSLKPEDTAVYYCAAGLGTYLNGRVSMAT
NYWGQGTQVTVSSTTTPAPRPPTPAPTIASQPLSLRPEACRPAAGGAVHTRGLDFACDIYIWAPL
AGTCGVLLLSLVITLYCKRGRKKLLYIFKQPFMRPVQTTQEEDGCSCRFPEEEEGGCELRVKFSRS
ADAPAYKQGQNQLYNELNLGRREEYDVLDKRRGRDPEMGGKPRRKNPQEGLYNELQKDKMA
EAYSEIGMKGERRRGKGHDGLYQGLSTATKDTYDALHMQALPPR SEQ ID NO: 186 (AS82472-28z CAR):
MALPVTALLLPLALLLHAARPQVQLVESGGDLVRPGGSLRLSCAASGFTFSIYDMNWVRQAPGK
GLEWVAGISGNGYSTSYAESVKGRFTISRDNAKNTVYLQLSSLKFEDTAMYYCVRDAERWDEN
DLRRKGQGTQVTVSSIEVMYPPPYLDNEKSNGTIIHVKGKHLCPSPLFPGPSKPFWVLVVVGGVL
ACYSLLVTVAFIIFWVRSKRSRLLHSDYMNMTPRRPGPTRKHYQPYAPPRDFAAYRSRVKFSRSA
DAPAYKQGQNQLYNELNLGRREEYDVLDKRRGRDPEMGGKPRRKNPQEGLYNELQKDKMAE
AYSEIGMKGERRRGKGHDGLYQGLSTATKDTYDALHMQALPPR SEQ ID NO: 187 (AS82494-28z CAR):
MALPVTALLLPLALLLHAARPQVQLVESGGGLVQPGGSLRLSCAASGFTFSVYDMNWFRQAPG
KGLEWVSGITGNGYTTSYADSVKGRFTISRDNAKNTLYLQLNSLKSEDTAMYYCAKETNRGQG
TQVTVSSIEVMYPPPYLDNEKSNGTIIHVKGKHLCPSPLFPGPSKPFWVLVVVGGVLACYSLLVT
VAFIIFWVRSKRSRLLHSDYMNMTPRRPGPTRKHYQPYAPPRDFAAYRSRVKFSRSADAPAYKQ
GQNQLYNELNLGRREEYDVLDKRRGRDPEMGGKPRRKNPQEGLYNELQKDKMAEAYSEIGMK
GERRRGKGHDGLYQGLSTATKDTYDALHMQALPPR Generation of Anti-CD33/CLL1 Dual CAR-T Cells Lentiviruses encoding the dual CAR constructs (dual 1-dual 3) as well as the individual CARs contained therein were prepared as described in Example 2. T lymphocytes were collected and transduced with the lentiviruses according to the protocol in Example 2.

Evaluation of In Vitro Activity of Anti-CD33/CLL1 Dual CAR-T Cells

In Vitro Cytotoxicity Assay

The anti-tumor activities of dual CAR-T cells were assessed using the in vitro LDH (lactate dehydrogenase) assay as described in Example 2.

Figure 14A:
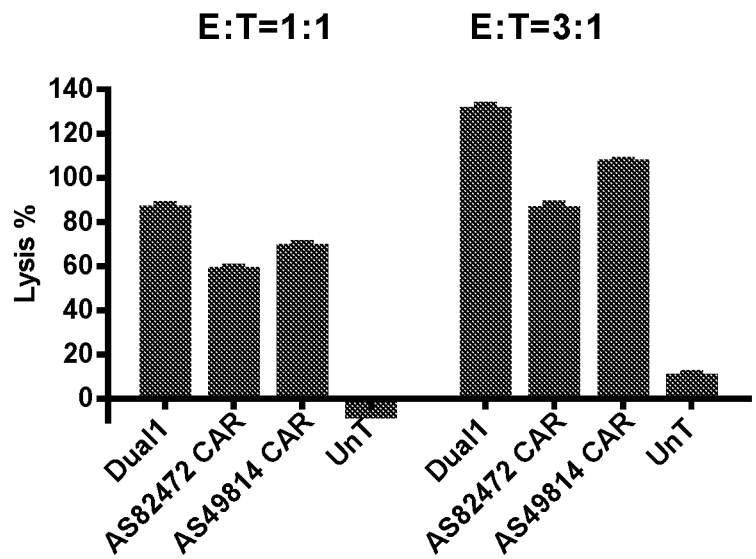
FIGS. 14A-14C show in vitro cytotoxicity of CLL1/CD33 dual CAR-T cells against acute myeloid leukemia cell line THP-1.
Figure 14B:
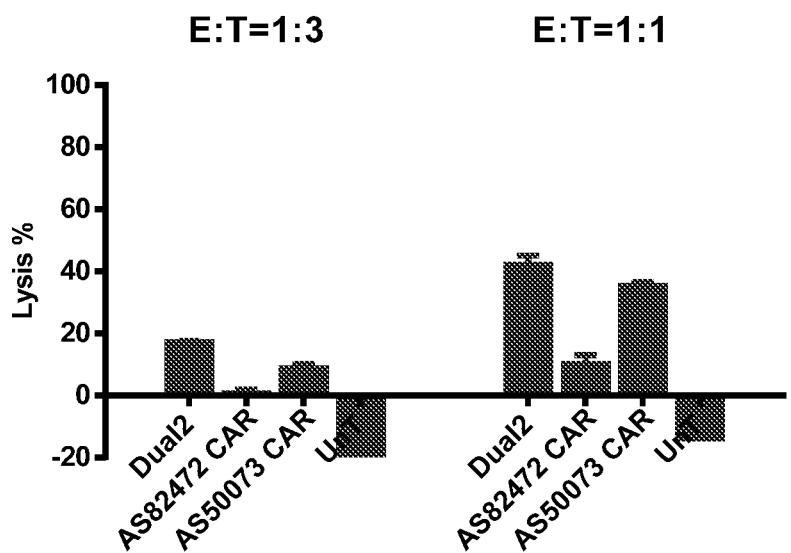
Figure 14C:
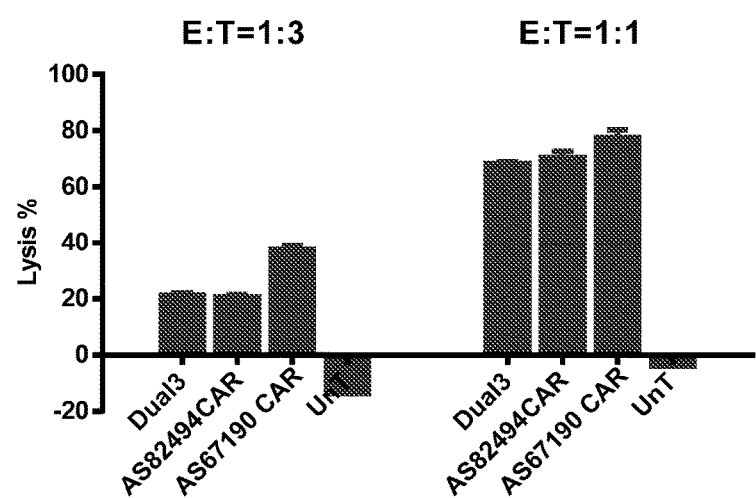

As shown in FIGS. 14A-14C, in vitro cytotoxicity of dual CARs against THP-1 was stronger than anti-CLL1 CAR-T cells, and was comparable to that of anti-CD33 CAR-T cells. These data indicates that dual CAR-T cells against two distinct targets (e.g., CLL1 and CD33) are more efficacious than single-target CAR-T cells for tumor elimination.

Evaluation of Anti-CD33/CLL1 Dual CAR-T In Vivo Mouse Model

The in vivo efficacy of dual CAR-T cells was evaluated in a U937-Luc xenograft mouse model as described in Example 2.

Figure 15A:
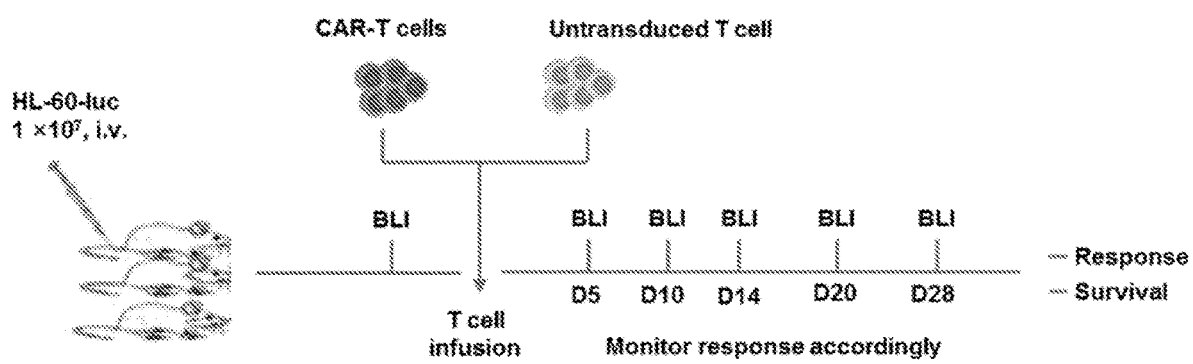
FIGS. 15A-15D show the in vivo efficacy of CLL1/CD33 dual CAR-T cells and single-target CAR-T cells in a HL-60-
Figure 15B:
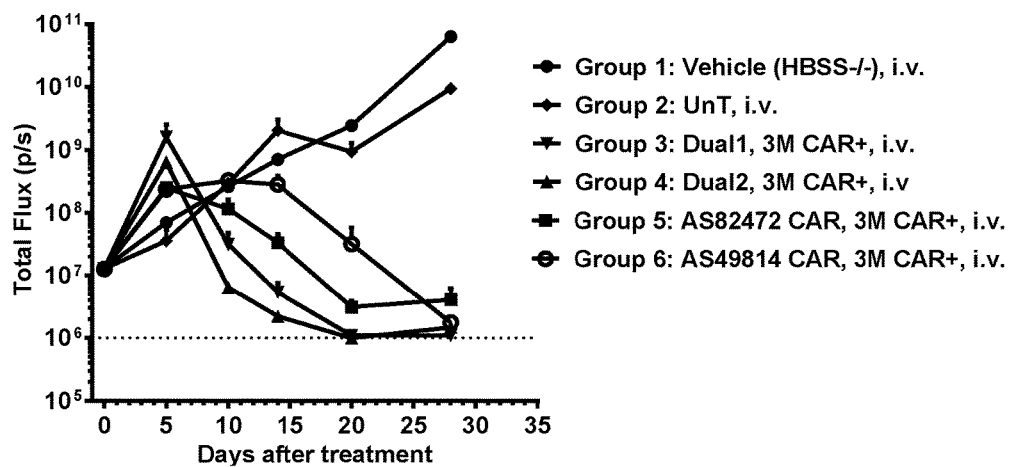
Figure 15C:
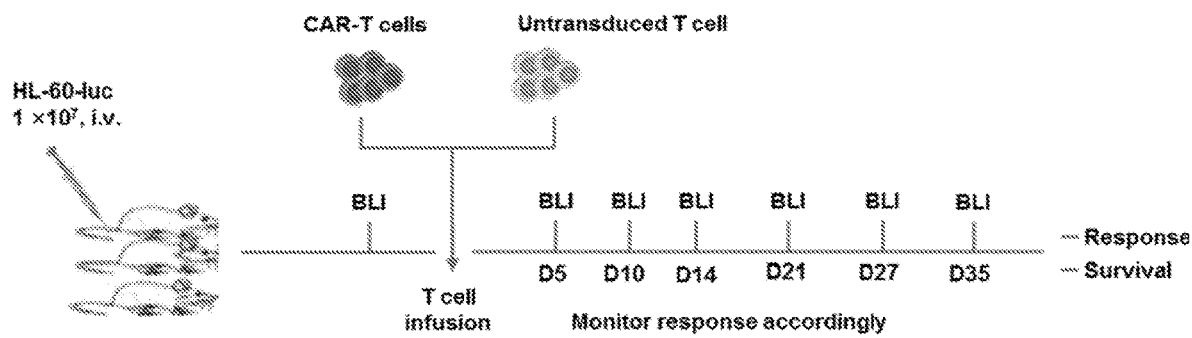
Figure 15D:
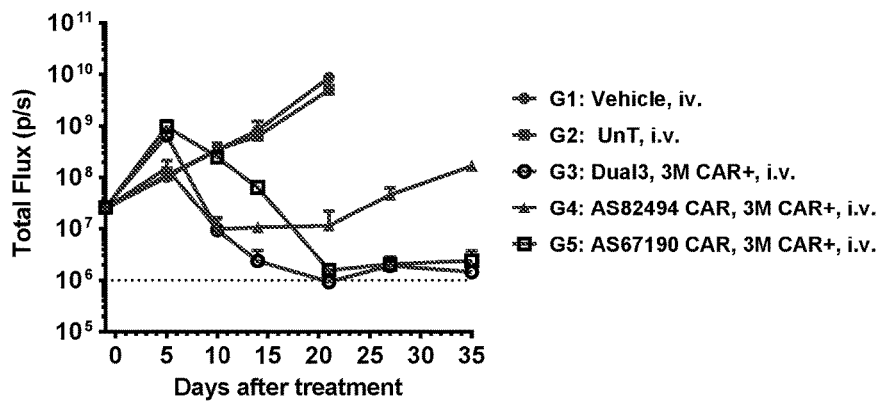

As shown in FIGS. 15B and 15D, mice treated with dual CAR-T cells (Dual1, Dual2 and Dual3) or single-target CAR-T cells were tumor free (BLI around $10^6$) after 3-4 weeks post injection, while mice with UnT cells or vehicle exhibited rapid tumor progression and had to be euthanized before the end of the experiment. Tumor growth in mice treated with dual CAR-T cells was significant slower than that in mice treated with single-target CAR T-cells (AS82472 CAR, AS49814 CAR and AS67190 CAR). Combined with the results from Example 4, these data demonstrates that dual target CAR-T cells (tandem CARs or dual CARs) are more efficacious as tumor therapy than single-target CAR-T cells.

What is claimed is:

1. An anti-CD33 construct comprising a single domain antibody ("sdAb") moiety that specifically binds to CD33, wherein the sdAb moiety comprises:
a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22.

2. The anti-CD33 construct of claim 1, wherein the sdAb moiety comprises an amino acid sequence having at least 95% sequence identity to the amino acid sequence set forth in SEQ ID NO: 110.

3. The anti-CD33 construct of claim 1, wherein the anti-CD33 construct comprises an extracellular domain comprising the sdAb moiety, a transmembrane domain, and an intracellular signaling domain comprising a primary intracellular signaling sequence.

4. The anti-CD33 construct of claim 3, wherein the intracellular signaling domain further comprises an intracellular co-stimulatory sequence.

5. The anti-CD33 construct of claim 1, wherein the anti-CD33 construct comprises an extracellular domain comprising the sdAb moiety, a transmembrane domain, and an intracellular signaling domain comprising an intracellular co-stimulatory sequence.

6. The anti-CD33 construct of claim 3, wherein the extracellular domain of the anti-CD33 construct further comprises a second binding moiety that specifically binds to a second antigen or epitope.

7. The anti-CD33 construct of claim 6, wherein the second binding moiety is an sdAb or scFv that specifically binds to CLL1 or CD123.

8. The anti-CD33 construct of claim 6, wherein the second binding moiety is an extracellular domain of NKG2D.

9. The anti-CD33 construct of claim 6, wherein the extracellular domain comprises: the anti-CD33 sdAb moiety and an anti-CLL1 sdAb moiety, wherein the anti-CD33 sdAb moiety comprises: a CDR1 comprising the amino acid sequence of SEQ ID NO: 18, a CDR2 comprising the amino acid sequence of SEQ ID NO: 20, and a CDR3 comprising the amino acid sequence of SEQ ID NO: 22.

10. The anti-CD33 construct of claim 3, wherein the anti-CD33 construct comprises the amino acid sequence of any one of SEQ ID NOs: 157 and 170-181.

11. A nucleic acid encoding the anti-CD33 construct of claim 1.

12. An engineered immune cell comprising the anti-CD33 construct of claim 1.

13. The engineered immune cell of claim 12, wherein the immune cell is a T cell.

14. The anti-CD33 construct of claim 1, wherein the anti-CD33 construct is a multispecific molecule.

15. The anti-CD33 construct of claim 14, wherein the anti-CD33 construct comprises the sdAb moiety linked to a second binding moiety that specifically binds to a second antigen or epitope.

16. The anti-CD33 construct of claim 1, wherein the anti-CD33 construct is an immunoconjugate comprising the sdAb moiety and an effector molecule.

17. A pharmaceutical composition comprising the anti-CD33 construct of claim 1.

18. A method of treating an individual having a cancer, comprising administering to the individual an effective amount of the anti-CD33 construct of claim 1.

\* \* \* \* \*

SEQUENCE LISTING

```
<160> NUMBER OF SEQ ID NOS: 216

<210> SEQ ID NO 1
<211> LENGTH: 347
<212> TYPE: PRT
<213> ORGANISM: Homo sapiens

<400> SEQUENCE: 1

Asp Pro Asn Phe Trp Leu Gln Val Gln Glu Ser Val Thr Val Gln Glu
1               5                   10                  15

Gly Leu Cys Val Leu Val Pro Cys Thr Phe Phe His Pro Ile Pro Tyr
```

```
            20                  25                  30
Tyr Asp Lys Asn Ser Pro Val His Gly Tyr Trp Phe Arg Glu Gly Ala
            35                  40                  45

Ile Ile Ser Arg Asp Ser Pro Val Ala Thr Asn Lys Leu Asp Gln Glu
    50                  55                  60

Val Gln Glu Glu Thr Gln Gly Arg Phe Arg Leu Leu Gly Asp Pro Ser
65                  70                  75                  80

Arg Asn Asn Cys Ser Leu Ser Ile Val Asp Ala Arg Arg Arg Asp Asn
                85                  90                  95

Gly Ser Tyr Phe Phe Arg Met Glu Arg Gly Ser Thr Lys Tyr Ser Tyr
            100                 105                 110

Lys Ser Pro Gln Leu Ser Val His Val Thr Asp Leu Thr His Arg Pro
        115                 120                 125

Lys Ile Leu Ile Pro Gly Thr Leu Glu Pro Gly His Ser Lys Asn Leu
    130                 135                 140

Thr Cys Ser Val Ser Trp Ala Cys Glu Gln Gly Thr Pro Pro Ile Phe
145                 150                 155                 160

Ser Trp Leu Ser Ala Ala Pro Thr Ser Leu Gly Pro Arg Thr Thr His
                165                 170                 175

Ser Ser Val Leu Ile Ile Thr Pro Arg Pro Gln Asp His Gly Thr Asn
            180                 185                 190

Leu Thr Cys Gln Val Lys Phe Ala Gly Ala Gly Val Thr Thr Glu Arg
        195                 200                 205

Thr Ile Gln Leu Asn Val Thr Tyr Val Pro Gln Asn Pro Thr Thr Gly
    210                 215                 220

Ile Phe Pro Gly Asp Gly Ser Gly Lys Gln Glu Thr Arg Ala Gly Val
225                 230                 235                 240

Val His Gly Ala Ile Gly Gly Ala Gly Val Thr Ala Leu Leu Ala Leu
                245                 250                 255

Cys Leu Cys Leu Ile Phe Phe Ile Val Lys Thr His Arg Arg Lys Ala
            260                 265                 270

Ala Arg Thr Ala Val Gly Arg Asn Asp Thr His Pro Thr Thr Gly Ser
        275                 280                 285

Ala Ser Pro Lys His Gln Lys Lys Ser Lys Leu His Gly Pro Thr Glu
    290                 295                 300

Thr Ser Ser Cys Ser Gly Ala Ala Pro Thr Val Glu Met Asp Glu Glu
305                 310                 315                 320

Leu His Tyr Ala Ser Leu Asn Phe His Gly Met Asn Pro Ser Lys Asp
                325                 330                 335

Thr Ser Thr Glu Tyr Ser Glu Val Arg Thr Gln
            340                 345

<210> SEQ ID NO 2
<211> LENGTH: 344
<212> TYPE: PRT
<213> ORGANISM: Macaca fascicularis

<400> SEQUENCE: 2

Met Asp Pro Arg Val Arg Leu Glu Val Gln Glu Ser Val Thr Val Gln
1               5                   10                  15

Glu Gly Leu Cys Val Leu Val Pro Cys Thr Phe Phe His Pro Val Pro
                20                  25                  30

Tyr His Thr Arg Asn Ser Pro Val His Gly Tyr Trp Phe Arg Glu Gly
            35                  40                  45
```

```
Ala Ile Val Ser Leu Asp Ser Pro Val Ala Thr Asn Lys Leu Asp Gln
 50                  55                  60

Glu Val Gln Glu Thr Gln Gly Arg Phe Arg Leu Leu Gly Asp Pro
 65                  70                  75                  80

Ser Arg Asn Asn Cys Ser Leu Ser Ile Val Asp Ala Arg Arg Asp
                 85                  90                  95

Asn Gly Ser Tyr Phe Phe Arg Met Glu Lys Gly Ser Thr Lys Tyr Ser
                100                 105                 110

Tyr Lys Ser Thr Gln Leu Ser Val His Val Thr Asp Leu Thr His Arg
            115                 120                 125

Pro Gln Ile Leu Ile Pro Gly Ala Leu Asp Pro Asp His Ser Lys Asn
130                 135                 140

Leu Thr Cys Ser Val Pro Trp Ala Cys Glu Gln Gly Thr Pro Pro Ile
145                 150                 155                 160

Phe Ser Trp Met Ser Ala Ala Pro Thr Ser Leu Gly Leu Arg Thr Thr
                165                 170                 175

His Ser Ser Val Leu Ile Ile Thr Pro Arg Pro Gln Asp His Gly Thr
                180                 185                 190

Asn Leu Thr Cys Gln Val Lys Phe Pro Gly Ala Gly Val Thr Thr Glu
            195                 200                 205

Arg Thr Ile Gln Leu Asn Val Ser Tyr Ala Ser Gln Asn Pro Arg Thr
210                 215                 220

Asp Ile Phe Leu Gly Asp Gly Ser Gly Lys Gln Gly Val Val Gln Gly
225                 230                 235                 240

Ala Ile Gly Gly Ala Gly Val Thr Val Leu Leu Ala Leu Cys Leu Cys
                245                 250                 255

Leu Ile Phe Phe Thr Val Lys Thr His Arg Arg Lys Ala Ala Arg Thr
                260                 265                 270

Ala Val Gly Arg Ile Asp Thr His Pro Ala Thr Gly Pro Thr Ser Ser
            275                 280                 285

Lys His Gln Lys Lys Ser Lys Leu His Gly Ala Thr Glu Thr Ser Gly
290                 295                 300

Cys Ser Gly Thr Thr Leu Thr Val Glu Met Asp Glu Glu Leu His Tyr
305                 310                 315                 320

Ala Ser Leu Asn Phe His Gly Met Asn Pro Ser Glu Asp Thr Ser Thr
                325                 330                 335

Glu Tyr Ser Glu Val Arg Thr Gln
            340

<210> SEQ ID NO 3
<211> LENGTH: 25
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Ala Glu Ser Gly Gly Gly Leu Val Gln Ala Gly Gly
1               5                   10                  15

Ser Leu Arg Leu Ser Cys Thr Ala Ser
            20                  25

<210> SEQ ID NO 4
<211> LENGTH: 10
<212> TYPE: PRT
<213> ORGANISM: Artificial Sequence
<220> FEATURE:
```

```
<223> OTHER INFORMATION: Synthetic Construct

<400> SEQUENCE: 4

Gly Phe Thr Phe Asp Asp Tyr Val Met Gly
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic Construct

<400> SEQUENCE: 5

Trp Phe Arg Gln Ala Pro Gly Lys Glu Arg Glu Gly Val Ser
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Synthetic Construct

<400> SEQUENCE: 6

Cys Ile Ser Trp Ser Gly Asp Thr Thr Tyr Tyr Ala Asp Ser Val Lys
1               5                   10                  15

Gly

<210> SEQ ID NO 7
<211> LENGTH: 32
<212> TYPE: PRT
<213> ORGANISM: Artificial Sequence
<220> FEATURE:
<223> OTHER INFORMATION: Synthetic Construct

<400> SEQUENCE: 7

Arg Phe Thr Ala Ser Arg Asp Asn Ala Lys Asn Thr Leu Tyr Leu Gln
1               5                   10                  15

Met Asn Ser Leu Lys Pro Glu Asp Thr Ala Met Tyr Tyr Cys Ala Ala
            20                  25                  30

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8

Asp Gln Gly Lys Cys Ser Leu Ala Ser Ala Glu Pro Asp Asp Met Asp
1               5                   10                  15

Tyr

<210> SEQ ID NO 9
<211> LENGTH: 11
<212> TYPE: PRT
<213> ORGANISM: Artificial Sequence
<220> FEATURE:
<223> OTHER INFORMATION: Synthetic Construct

<400> SEQUENCE: 9

Trp Gly Arg Gly Thr Leu Val Thr Val Ser Ser
1               5                   10
```

```
<210> SEQ ID NO 10
<211> LENGTH: 25
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Ala Glu Ser Gly Gly Gly Ser Val Gln Ala Gly Gly
1               5                   10                  15

Ser Leu Arg Leu Ser Cys Ala Ala Ser
            20                  25

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Gly Val Thr Phe Ser Ser Thr Ser Val Ala
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic Construct

<400> SEQUENCE: 12

Trp Phe Arg Gln Ala Pro Gly Lys Glu Arg Glu Gly Val Ala
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Synthetic Construct

<400> SEQUENCE: 13

Tyr Ile Tyr Thr Gly Asp Ser Ser Thr Tyr Tyr Ala Asp Ser Val Lys
1               5                   10                  15

Gly

<210> SEQ ID NO 14
<211> LENGTH: 32
<212> TYPE: PRT
<213> ORGANISM: Artificial Sequence
<220> FEATURE:
<223> OTHER INFORMATION: Synthetic Construct

<400> SEQUENCE: 14

Arg Phe Thr Ile Ala Gln Asp Asn Ala Lys Asn Ala Val Tyr Leu Gln
1               5                   10                  15

Met Asn Ser Leu Lys Pro Glu Asp Thr Ala Met Tyr Tyr Cys Ala Ala
            20                  25                  30

<210> SEQ ID NO 15
<211> LENGTH: 12
<212> TYPE: PRT
<213> ORGANISM: Artificial Sequence
<220> FEATURE:
```

```
<223> OTHER INFORMATION: Synthetic Construct

<400> SEQUENCE: 15

Asp Gly Phe Leu Leu Asn His Arg Ser Tyr Gln Tyr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic Construct

<400> SEQUENCE: 16

Trp Gly Gln Gly Thr Gln Val Thr Val Ser Ser
1               5                   10

<210> SEQ ID NO 17
<211> LENGTH: 25
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Gly Ser Val Gln Ala Gly Gly
1               5                   10                  15

Ser Leu Arg Leu Ser Cys Ala Ala Ser
            20                  25

<210> SEQ ID NO 18
<211> LENGTH: 10
<212> TYPE: PRT
<213> ORGANISM: Artificial Sequence
<220> FEATURE:
<223> OTHER INFORMATION: Synthetic Construct

<400> SEQUENCE: 18

Gly Tyr Thr Tyr Ser Ile Asn Cys Met Gly
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetic Construct

<400> SEQUENCE: 19

Trp Phe Arg Gln Ala Pro Gly Lys Glu Arg Glu Gly Val Ala
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20

Val Ile Ser Thr Gly Gly Gly Arg Thr Asp Tyr Arg Asp Ser Val Lys
1               5                   10                  15

Gly

<210> SEQ ID NO 21
```

```
<211> LENGTH: 32
<212> TYPE: PRT
<213> ORGANISM: Artificial Sequence
<220> FEATURE:
<223> OTHER INFORMATION: Synthetic Construct

<400> SEQUENCE: 21

Arg Phe Thr Ile Ser Gln Asp Asn Ala Lys Asn Thr Val Tyr Leu Gln
1               5                   10                  15

Met Asn Ser Leu Lys Pro Glu Asp Thr Ala Met Tyr Tyr Cys Ala Gly
            20                  25                  30

<210> SEQ ID NO 22
<211> LENGTH: 18
<212> TYPE: PRT
<213> ORGANISM: Artificial Sequence
<220> FEATURE:
<223> OTHER INFORMATION: Synthetic Construct

<400> SEQUENCE: 22

Lys Thr Thr Tyr Pro Gly Tyr Gly Cys Gly Leu Gly Arg Ser Ala Tyr
1               5                   10                  15

Asn Tyr

<210> SEQ ID NO 23
<211> LENGTH: 11
<212> TYPE: PRT
<213> ORGANISM: Artificial Sequence
<220> FEATURE:
<223> OTHER INFORMATION: Synthetic Construct

<400> SEQUENCE: 23

Trp Gly Gln Gly Thr Gln Val Thr Val Ser Ser
1               5                   10

<210> SEQ ID NO 24
<211> LENGTH: 25
<212> TYPE: PRT
<213> ORGANISM: Artificial Sequence
<220> FEATURE:
<223> OTHER INFORMATION: Synthetic Construct

<400> SEQUENCE: 24

Gln Ile Gln Leu Val Glu Ser Gly Gly Gly Ser Val Gln Ala Gly Gly
1               5                   10                  15

Ser Leu Arg Leu Ser Cys Val Ala Ser
            20                  25

<210> SEQ ID NO 25
<211> LENGTH: 10
<212> TYPE: PRT
<213> ORGANISM: Artificial Sequence
<220> FEATURE:
<223> OTHER INFORMATION: Synthetic Construct

<400> SEQUENCE: 25

Gly Tyr Ile Gly Gly His Tyr Tyr Met Gly
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic Construct
```

```
<400> SEQUENCE: 26

Trp Phe Arg Gln Ala Pro Gly Lys Glu Arg Glu Gly Val Ala
1               5                   10

<210> SEQ ID NO 27
<211> LENGTH: 18
<212> TYPE: PRT
<213> ORGANISM: Artificial Sequence
<220> FEATURE:
<223> OTHER INFORMATION: Synthetic Construct

<400> SEQUENCE: 27

Ala Ile Asp Ile Asp Ser Asp Gly Arg Thr Arg Tyr Ala Gly Ser Val
1               5                   10                  15

Gln Gly

<210> SEQ ID NO 28
<211> LENGTH: 32
<212> TYPE: PRT
<213> ORGANISM: Artificial Sequence
<220> FEATURE:
<223> OTHER INFORMATION: Synthetic Construct

<400> SEQUENCE: 28

Arg Phe Thr Ile Ser Gln Asp Asn Ala Lys Asn Thr Leu His Leu Gln
1               5                   10                  15

Met Ser Ser Leu Lys Pro Glu Asp Thr Gly Met Tyr Tyr Cys Ala Val
                20                  25                  30

<210> SEQ ID NO 29
<211> LENGTH: 16
<212> TYPE: PRT
<213> ORGANISM: Artificial Sequence
<220> FEATURE:
<223> OTHER INFORMATION: Synthetic Construct

<400> SEQUENCE: 29

Gly Val Gly Trp Val Pro Ala Arg Leu Thr Pro Gln Ala Val Ser Tyr
1               5                   10                  15

<210> SEQ ID NO 30
<211> LENGTH: 11
<212> TYPE: PRT
<213> ORGANISM: Artificial Sequence
<220> FEATURE:
<223> OTHER INFORMATION: Synthetic Construct

<400> SEQUENCE: 30

Trp Gly Lys Gly Thr Leu Val Thr Val Ser Ser
1               5                   10

<210> SEQ ID NO 31
<211> LENGTH: 25
<212> TYPE: PRT
<213> ORGANISM: Artificial Sequence
<220> FEATURE:
<223> OTHER INFORMATION: Synthetic Construct

<400> SEQUENCE: 31

Glu Val Gln Leu Val Glu Ser Gly Gly Gly Ser Val Gln Ala Gly Gly
1               5                   10                  15

Ser Leu Arg Leu Ser Cys Val Ala Ser
                20                  25
```

```
<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Gly Tyr Thr Tyr Gly Ile Asn Cys Met Gly
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic Construct

<400> SEQUENCE: 33

Trp Phe Arg Gln Ala Pro Gly Lys Glu Arg Glu Gly Ile Ala
1               5                   10

<210> SEQ ID NO 34
<211> LENGTH: 17
<212> TYPE: PRT
<213> ORGANISM: Artificial Sequence
<220> FEATURE:
<223> OTHER INFORMATION: Synthetic Construct

<400> SEQUENCE: 34

Ala Ile Ser Thr Gly Gly Gly Thr Thr Gly Val Ala Asp Ser Val Lys
1               5                   10                  15

Gly

<210> SEQ ID NO 35
<211> LENGTH: 32
<212> TYPE: PRT
<213> ORGANISM: Artificial Sequence
<220> FEATURE:
<223> OTHER INFORMATION: Synthetic Construct

<400> SEQUENCE: 35

Arg Phe Thr Ile Ser Gln Asp Asn Ala Lys Asn Thr Val Tyr Leu Gln
1               5                   10                  15

Met Asn Ser Leu Lys Pro Glu Asp Thr Ala Met Tyr Tyr Cys Ala Ala
                20                  25                  30

<210> SEQ ID NO 36
<211> LENGTH: 19
<212> TYPE: PRT
<213> ORGANISM: Artificial Sequence
<220> FEATURE:
<223> OTHER INFORMATION: Synthetic Construct

<400> SEQUENCE: 36

Arg Ser Thr Tyr Ser Gly Tyr Ala Cys Val Tyr Ser Glu Val Asn Gly
1               5                   10                  15

Tyr Asn Tyr

<210> SEQ ID NO 37
<211> LENGTH: 11
<212> TYPE: PRT
<213> ORGANISM: Artificial Sequence
<220> FEATURE:
<223> OTHER INFORMATION: Synthetic Construct
```

```
<400> SEQUENCE: 37

Arg Gly Gln Gly Thr Gln Val Thr Val Ser Ser
1               5                  10

<210> SEQ ID NO 38
<211> LENGTH: 25
<212> TYPE: PRT
<213> ORGANISM: Artificial Sequence
<220> FEATURE:
<223> OTHER INFORMATION: Synthetic Construct

<400> SEQUENCE: 38

Glu Val Gln Leu Val Glu Ser Gly Gly Gly Ser Val Gln Ala Gly Gly
1               5                  10                  15

Ser Leu Arg Leu Ser Cys Val Ala Ser
            20                  25

<210> SEQ ID NO 39
<211> LENGTH: 10
<212> TYPE: PRT
<213> ORGANISM: Artificial Sequence
<220> FEATURE:
<223> OTHER INFORMATION: Synthetic Construct

<400> SEQUENCE: 39

Gly Tyr Thr Trp Cys Arg Tyr Asp Met Ser
1               5                  10

<210> SEQ ID NO 40
<211> LENGTH: 14
<212> TYPE: PRT
<213> ORGANISM: Artificial Sequence
<220> FEATURE:
<223> OTHER INFORMATION: Synthetic Construct

<400> SEQUENCE: 40

Trp Tyr Arg Gln Ala Pro Gly Lys Glu Arg Glu Phe Val Ser
1               5                  10

<210> SEQ ID NO 41
<211> LENGTH: 16
<212> TYPE: PRT
<213> ORGANISM: Artificial Sequence
<220> FEATURE:
<223> OTHER INFORMATION: Synthetic Construct

<400> SEQUENCE: 41

Gly Phe Asp Asn Asp Gly Thr Thr Ser Tyr Ala Asp Ser Val Lys Gly
1               5                  10                  15

<210> SEQ ID NO 42
<211> LENGTH: 32
<212> TYPE: PRT
<213> ORGANISM: Artificial Sequence
<220> FEATURE:
<223> OTHER INFORMATION: Synthetic Construct

<400> SEQUENCE: 42

Arg Phe Thr Ile Ser Gln Asp Asn Asp Lys Asn Thr Val Tyr Leu Gln
1               5                  10                  15

Met Asn Ser Leu Lys Pro Glu Asp Thr Ala Met Tyr Tyr Cys Lys Glu
            20                  25                  30

<210> SEQ ID NO 43
<211> LENGTH: 18
```

```
-continued

<212> TYPE: PRT
<213> ORGANISM: Artificial Sequence
<220> FEATURE:
<223> OTHER INFORMATION: Synthetic Construct

<400> SEQUENCE: 43

Asp Arg Ser Arg Gly Ser Leu Asp Gly Arg Val Cys Pro Leu Ser Tyr
1               5                   10                  15

Asp Asn

<210> SEQ ID NO 44
<211> LENGTH: 11
<212> TYPE: PRT
<213> ORGANISM: Artificial Sequence
<220> FEATURE:
<223> OTHER INFORMATION: Synthetic Construct

<400> SEQUENCE: 44

Trp Gly Gln Gly Thr Gln Val Thr Val Ser Ser
1               5                   10

<210> SEQ ID NO 45
<211> LENGTH: 25
<212> TYPE: PRT
<213> ORGANISM: Artificial Sequence
<220> FEATURE:
<223> OTHER INFORMATION: Synthetic Construct

<400> SEQUENCE: 45

Glu Val Gln Leu Val Glu Ser Gly Gly Gly Leu Val Gln Ala Gly Gly
1               5                   10                  15

Ser Leu Arg Leu Ser Cys Thr Ala Ser
            20                  25

<210> SEQ ID NO 46
<211> LENGTH: 10
<212> TYPE: PRT
<213> ORGANISM: Artificial Sequence
<220> FEATURE:
<223> OTHER INFORMATION: Synthetic Construct

<400> SEQUENCE: 46

Gly Phe Thr Phe Asp Asp Tyr Val Met Gly
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Synthetic Construct

<400> SEQUENCE: 47

Trp Phe Arg Gln Ala Pro Gly Lys Glu Arg Glu Gly Val Ser
1               5                   10

<210> SEQ ID NO 48
<211> LENGTH: 17
<212> TYPE: PRT
<213> ORGANISM: Artificial Sequence
<220> FEATURE:
<223> OTHER INFORMATION: Synthetic Construct

<400> SEQUENCE: 48

Cys Ile Ser Trp Ser Gly Asp Thr Thr Tyr Tyr Ala Asp Ser Val Lys
1               5                   10                  15
```

Gly

<210> SEQ ID NO 49
<211> LENGTH: 32
<212> TYPE: PRT
<213> ORGANISM: Artificial Sequence
<220> FEATURE:
<223> OTHER INFORMATION: Synthetic Construct

<400> SEQUENCE: 49

```
Arg Phe Thr Val Ser Arg Asp Asn Ala Lys Asn Thr Leu Tyr Leu Gln
1               5                   10                  15

Met Asn Ser Leu Lys Pro Glu Asp Thr Ala Met Tyr Tyr Cys Ala Ala
            20                  25                  30
```

<210> SEQ ID NO 50
<211> LENGTH: 15
<212> TYPE: PRT
<213> ORGANISM: Artificial Sequence
<220> FEATURE:
<223> OTHER INFORMATION: Synthetic Construct

<400> SEQUENCE: 50

```
Asp Gln Ser Leu Cys Ser Leu Ala Pro Pro Tyr Asn Tyr Ala Tyr
1               5                   10                  15
```

<210> SEQ ID NO 51
<211> LENGTH: 11
<212> TYPE: PRT
<213> ORGANISM: Artificial Sequence
<220> FEATURE:
<223> OTHER INFORMATION: Synthetic Construct

<400> SEQUENCE: 51

```
Trp Gly Gln Gly Thr Gln Val Thr Val Ser Ser
1               5                   10
```

<210> SEQ ID NO 52
<211> LENGTH: 25
<212> TYPE: PRT
<213> ORGANISM: Artificial Sequence
<220> FEATURE:
<223> OTHER INFORMATION: Synthetic Construct

<400> SEQUENCE: 52

```
Gln Val Gln Leu Val Glu Ser Gly Gly Gly Leu Val Gln Ala Gly Gly
1               5                   10                  15

Ser Leu Arg Leu Ser Cys Thr Ala Ser
            20                  25
```

<210> SEQ ID NO 53
<211> LENGTH: 10
<212> TYPE: PRT
<213> ORGANISM: Artificial Sequence
<220> FEATURE:
<223> OTHER INFORMATION: Synthetic Construct

<400> SEQUENCE: 53

```
Gly Phe Thr Phe Asp Asn Tyr Val Met Gly
1               5                   10
```

<210> SEQ ID NO 54
<211> LENGTH: 14
<212> TYPE: PRT
<213> ORGANISM: Artificial Sequence

```
<220> FEATURE:
<223> OTHER INFORMATION: Synthetic Construct

<400> SEQUENCE: 54

Trp Phe Arg Gln Ala Pro Gly Lys Glu Arg Glu Gly Val Ser
1               5                   10

<210> SEQ ID NO 55
<211> LENGTH: 17
<212> TYPE: PRT
<213> ORGANISM: Artificial Sequence
<220> FEATURE:
<223> OTHER INFORMATION: Synthetic Construct

<400> SEQUENCE: 55

Cys Ile Gly Trp Ser Gly Gly Ser Thr Tyr Tyr Ala Asp Ser Val Lys
1               5                   10                  15

Gly

<210> SEQ ID NO 56
<211> LENGTH: 32
<212> TYPE: PRT
<213> ORGANISM: Artificial Sequence
<220> FEATURE:
<223> OTHER INFORMATION: Synthetic Construct

<400> SEQUENCE: 56

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Met Tyr Tyr Cys Ala Ala
            20                  25                  30

<210> SEQ ID NO 57
<211> LENGTH: 17
<212> TYPE: PRT
<213> ORGANISM: Artificial Sequence
<220> FEATURE:
<223> OTHER INFORMATION: Synthetic Construct

<400> SEQUENCE: 57

Asp Gln Gly Lys Cys Ser Leu Gly Ser Ala Gly Ala Asp Asp Met Asp
1               5                   10                  15

Tyr

<210> SEQ ID NO 58
<211> LENGTH: 11
<212> TYPE: PRT
<213> ORGANISM: Artificial Sequence
<220> FEATURE:
<223> OTHER INFORMATION: Synthetic Construct

<400> SEQUENCE: 58

Trp Gly Arg Gly Thr Leu Val Thr Val Ser Ser
1               5                   10

<210> SEQ ID NO 59
<211> LENGTH: 25
<212> TYPE: PRT
<213> ORGANISM: Artificial Sequence
<220> FEATURE:
<223> OTHER INFORMATION: Synthetic Construct

<400> SEQUENCE: 59

Glu Val Gln Leu Val Glu Ser Gly Gly Gly Ser Val Gln Ala Gly Gly
1               5                   10                  15
```

```
Ser Leu Arg Leu Ser Cys Ala Ala Pro
            20                  25

<210> SEQ ID NO 60
<211> LENGTH: 10
<212> TYPE: PRT
<213> ORGANISM: Artificial Sequence
<220> FEATURE:
<223> OTHER INFORMATION: Synthetic Construct

<400> SEQUENCE: 60

Gly Tyr Thr Tyr Cys Thr Tyr Asp Met Met
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Synthetic Construct

<400> SEQUENCE: 61

Trp Tyr Arg Gln Ala Leu Gly Lys Glu Arg Glu Phe Val Ser
1               5                   10

<210> SEQ ID NO 62
<211> LENGTH: 16
<212> TYPE: PRT
<213> ORGANISM: Artificial Sequence
<220> FEATURE:
<223> OTHER INFORMATION: Synthetic Construct

<400> SEQUENCE: 62

Ala Val Tyr Thr Asp Gly Ser Thr Leu Tyr Ala Asp Ser Val Lys Gly
1               5                   10                  15

<210> SEQ ID NO 63
<211> LENGTH: 32
<212> TYPE: PRT
<213> ORGANISM: Artificial Sequence
<220> FEATURE:
<223> OTHER INFORMATION: Synthetic Construct

<400> SEQUENCE: 63

Arg Phe Thr Ile Ser Gln Asp Asn Ala Lys Asn Thr Leu Tyr Leu Gln
1               5                   10                  15

Met Asn Ser Leu Lys Pro Glu Asp Thr Ala Met Tyr Tyr Cys Lys Thr
            20                  25                  30

<210> SEQ ID NO 64
<211> LENGTH: 12
<212> TYPE: PRT
<213> ORGANISM: Artificial Sequence
<220> FEATURE:
<223> OTHER INFORMATION: Synthetic Construct

<400> SEQUENCE: 64

Glu Thr Ala Val Thr Tyr Asp Lys Pro Cys Asp Phe
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic Construct
```

<400> SEQUENCE: 65

Trp Gly Gln Gly Thr Gln Val Thr Val Ser Ser
1               5                   10

<210> SEQ ID NO 66
<211> LENGTH: 25
<212> TYPE: PRT
<213> ORGANISM: Artificial Sequence
<220> FEATURE:
<223> OTHER INFORMATION: Synthetic Construct

<400> SEQUENCE: 66

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 67
<211> LENGTH: 10
<212> TYPE: PRT
<213> ORGANISM: Artificial Sequence
<220> FEATURE:
<223> OTHER INFORMATION: Synthetic Construct

<400> SEQUENCE: 67

Gly Ser Ile Phe Ser Ile Thr Ala Met Gly
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Synthetic Construct

<400> SEQUENCE: 68

Trp Tyr Arg Gln Ala Pro Gly Lys Gln Arg Glu Leu Val Ala
1               5                   10

<210> SEQ ID NO 69
<211> LENGTH: 16
<212> TYPE: PRT
<213> ORGANISM: Artificial Sequence
<220> FEATURE:
<223> OTHER INFORMATION: Synthetic Construct

<400> SEQUENCE: 69

Thr Val Thr Ser Gly Gly Ser Thr Lys Tyr Val Glu Ser Val Lys Gly
1               5                   10                  15

<210> SEQ ID NO 70
<211> LENGTH: 32
<212> TYPE: PRT
<213> ORGANISM: Artificial Sequence
<220> FEATURE:
<223> OTHER INFORMATION: Synthetic Construct

<400> SEQUENCE: 70

Arg Phe Thr Ile Ser Asn Asp Asn Ala Lys Asn Thr Val Tyr Leu Gln
1               5                   10                  15

Met Asn Ser Leu Lys Pro Glu Asp Thr Ala Val Tyr Tyr Cys Trp Ala
            20                  25                  30

<210> SEQ ID NO 71

```
<211> LENGTH: 16
<212> TYPE: PRT
<213> ORGANISM: Artificial Sequence
<220> FEATURE:
<223> OTHER INFORMATION: Synthetic Construct

<400> SEQUENCE: 71

Asp Ile Val Ala Arg Trp Asn Ser Asp Tyr Asn Val Tyr Asp Asp Tyr
1               5                   10                  15

<210> SEQ ID NO 72
<211> LENGTH: 11
<212> TYPE: PRT
<213> ORGANISM: Artificial Sequence
<220> FEATURE:
<223> OTHER INFORMATION: Synthetic Construct

<400> SEQUENCE: 72

Trp Gly Gln Gly Thr Gln Val Thr Val Ser Ser
1               5                   10

<210> SEQ ID NO 73
<211> LENGTH: 25
<212> TYPE: PRT
<213> ORGANISM: Artificial Sequence
<220> FEATURE:
<223> OTHER INFORMATION: Synthetic Construct

<400> SEQUENCE: 73

Gln Val Lys Leu Glu Glu Ser Gly Gly Gly Leu Val Gln Glu Gly Gly
1               5                   10                  15

Ser Leu Arg Leu Ser Cys Ala Ala Ser
            20                  25

<210> SEQ ID NO 74
<211> LENGTH: 10
<212> TYPE: PRT
<213> ORGANISM: Artificial Sequence
<220> FEATURE:
<223> OTHER INFORMATION: Synthetic Construct

<400> SEQUENCE: 74

Gly Thr Ile Tyr Thr Asp Ser Thr Ile Tyr
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Synthetic Construct

<400> SEQUENCE: 75

Trp Tyr Arg Gln Ala Pro Gly Lys Gln Arg Glu Leu Val Ala
1               5                   10

<210> SEQ ID NO 76
<211> LENGTH: 16
<212> TYPE: PRT
<213> ORGANISM: Artificial Sequence
<220> FEATURE:
<223> OTHER INFORMATION: Synthetic Construct

<400> SEQUENCE: 76

Ser Ile Thr Arg Gly Gly Asp Thr Lys Tyr Val Asp Ser Val Lys Gly
1               5                   10                  15
```

<210> SEQ ID NO 77
<211> LENGTH: 32
<212> TYPE: PRT
<213> ORGANISM: Artificial Sequence
<220> FEATURE:
<223> OTHER INFORMATION: Synthetic Construct

<400> SEQUENCE: 77

Arg Phe Ala Ile Ser Ser Asp Asn Ala Lys Asn Thr Val Tyr Leu Gln
1               5                   10                  15

Met Asn Ser Leu Lys Pro Glu Asp Thr Ala Val Tyr Tyr Cys Asn Leu
            20                  25                  30

<210> SEQ ID NO 78
<211> LENGTH: 13
<212> TYPE: PRT
<213> ORGANISM: Artificial Sequence
<220> FEATURE:
<223> OTHER INFORMATION: Synthetic Construct

<400> SEQUENCE: 78

Tyr Tyr Arg Thr Gly Pro Ser Ser Tyr Tyr Arg Asn Asp
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic Construct

<400> SEQUENCE: 79

Trp Gly Gln Gly Thr Gln Val Thr Val Ser Ser
1               5                   10

<210> SEQ ID NO 80
<211> LENGTH: 25
<212> TYPE: PRT
<213> ORGANISM: Artificial Sequence
<220> FEATURE:
<223> OTHER INFORMATION: Synthetic Construct

<400> SEQUENCE: 80

Ala Val Gln Leu Val Glu Ser Gly Gly Gly Leu Val Gln Pro Gly Gly
1               5                   10                  15

Ser Leu Arg Leu Ser Cys Ala Val Ser
            20                  25

<210> SEQ ID NO 81
<211> LENGTH: 10
<212> TYPE: PRT
<213> ORGANISM: Artificial Sequence
<220> FEATURE:
<223> OTHER INFORMATION: Synthetic Construct

<400> SEQUENCE: 81

Gly Ile Tyr Tyr Ser Ile Asn Leu Met Gly
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Synthetic Construct

```
<400> SEQUENCE: 82

Trp Tyr Arg Gln Ala Pro Gly Lys Pro Arg Glu Leu Ala Ala
1               5                   10

<210> SEQ ID NO 83
<211> LENGTH: 16
<212> TYPE: PRT
<213> ORGANISM: Artificial Sequence
<220> FEATURE:
<223> OTHER INFORMATION: Synthetic Construct

<400> SEQUENCE: 83

Ser Ile Thr Asp Ser Gly Ile Thr Asn Tyr Ala Asp Ser Val Lys Gly
1               5                   10                  15

<210> SEQ ID NO 84
<211> LENGTH: 32
<212> TYPE: PRT
<213> ORGANISM: Artificial Sequence
<220> FEATURE:
<223> OTHER INFORMATION: Synthetic Construct

<400> SEQUENCE: 84

Arg Phe Thr Ile Ser Arg Asp Asn Ala Lys Asn Thr Val His Leu Gln
1               5                   10                  15

Met Asn Asn Leu Lys Pro Glu Asp Thr Ala Val Tyr Tyr Cys Lys Pro
            20                  25                  30

<210> SEQ ID NO 85
<211> LENGTH: 4
<212> TYPE: PRT
<213> ORGANISM: Artificial Sequence
<220> FEATURE:
<223> OTHER INFORMATION: Synthetic Construct

<400> SEQUENCE: 85

Met Gly Val Asn
1

<210> SEQ ID NO 86
<211> LENGTH: 11
<212> TYPE: PRT
<213> ORGANISM: Artificial Sequence
<220> FEATURE:
<223> OTHER INFORMATION: Synthetic Construct

<400> SEQUENCE: 86

Trp Gly Gln Gly Ile Gln Val Thr Val Ser Ser
1               5                   10

<210> SEQ ID NO 87
<211> LENGTH: 25
<212> TYPE: PRT
<213> ORGANISM: Artificial Sequence
<220> FEATURE:
<223> OTHER INFORMATION: Synthetic Construct

<400> SEQUENCE: 87

Ala Val Gln Leu Val Glu Ser Gly Gly Gly Leu Val Gln Ala Gly Gly
1               5                   10                  15

Ser Leu Arg Leu Ser Cys Thr Ala Ser
            20                  25

<210> SEQ ID NO 88
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 88

Gly Ser Ile Leu Arg Thr Tyr Glu Met Gly
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Synthetic Construct

<400> SEQUENCE: 89

Trp Tyr Arg Gln Ala Pro Gly Ser Gln Arg Glu Leu Val Ala
1               5                   10

<210> SEQ ID NO 90
<211> LENGTH: 16
<212> TYPE: PRT
<213> ORGANISM: Artificial Sequence
<220> FEATURE:
<223> OTHER INFORMATION: Synthetic Construct

<400> SEQUENCE: 90

Ser Ile Thr Ser Asp Gly Asp Thr Asn Tyr Val Asp Ser Val Lys Gly
1               5                   10                  15

<210> SEQ ID NO 91
<211> LENGTH: 32
<212> TYPE: PRT
<213> ORGANISM: Artificial Sequence
<220> FEATURE:
<223> OTHER INFORMATION: Synthetic Construct

<400> SEQUENCE: 91

Arg Phe Thr Ile Ser Arg Asp Asn Gly Lys Asn Met Val Tyr Leu Gln
1               5                   10                  15

Met Asn Ser Leu Lys Pro Asp Asp Thr Ala Val Tyr Tyr Cys Asn Ala
            20                  25                  30

<210> SEQ ID NO 92
<211> LENGTH: 13
<212> TYPE: PRT
<213> ORGANISM: Artificial Sequence
<220> FEATURE:
<223> OTHER INFORMATION: Synthetic Construct

<400> SEQUENCE: 92

Val Ile Leu Ser Pro Ser Tyr Ser Met Arg Thr Ser His
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Synthetic Construct

<400> SEQUENCE: 93

Trp Gly Gln Gly Thr Gln Val Thr Val Ser Ser
1               5                   10
```

```
<210> SEQ ID NO 94
<211> LENGTH: 25
<212> TYPE: PRT
<213> ORGANISM: Artificial Sequence
<220> FEATURE:
<223> OTHER INFORMATION: Synthetic Construct

<400> SEQUENCE: 94

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 95
<211> LENGTH: 10
<212> TYPE: PRT
<213> ORGANISM: Artificial Sequence
<220> FEATURE:
<223> OTHER INFORMATION: Synthetic Construct

<400> SEQUENCE: 95

Gly Asn Val Phe Arg Phe Asn Ile Met Gly
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Synthetic Construct

<400> SEQUENCE: 96

Trp Tyr Arg Gln Ala Pro Gly Asn Gln Arg Glu Leu Val Ala
1               5                   10

<210> SEQ ID NO 97
<211> LENGTH: 16
<212> TYPE: PRT
<213> ORGANISM: Artificial Sequence
<220> FEATURE:
<223> OTHER INFORMATION: Synthetic Construct

<400> SEQUENCE: 97

Ser Ile Asp Asp Gly Gly Asp Arg Ser Tyr Ala Asp Ser Val Glu Gly
1               5                   10                  15

<210> SEQ ID NO 98
<211> LENGTH: 32
<212> TYPE: PRT
<213> ORGANISM: Artificial Sequence
<220> FEATURE:
<223> OTHER INFORMATION: Synthetic Construct

<400> SEQUENCE: 98

Arg Phe Thr Ile Ser Arg Glu Asn Gly Lys Lys Ile Met Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 99
<211> LENGTH: 16
<212> TYPE: PRT
<213> ORGANISM: Artificial Sequence
<220> FEATURE:
<223> OTHER INFORMATION: Synthetic Construct

<400> SEQUENCE: 99
```

Gly Leu Gly Thr Tyr Leu Asn Gly Arg Val Ser Met Ala Thr Asn Tyr
1               5                   10                  15

<210> SEQ ID NO 100
<211> LENGTH: 11
<212> TYPE: PRT
<213> ORGANISM: Artificial Sequence
<220> FEATURE:
<223> OTHER INFORMATION: Synthetic Construct

<400> SEQUENCE: 100

Trp Gly Gln Gly Thr Gln Val Thr Val Ser Ser
1               5                   10

<210> SEQ ID NO 101
<211> LENGTH: 25
<212> TYPE: PRT
<213> ORGANISM: Artificial Sequence
<220> FEATURE:
<223> OTHER INFORMATION: Synthetic Construct

<400> SEQUENCE: 101

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 102
<211> LENGTH: 10
<212> TYPE: PRT
<213> ORGANISM: Artificial Sequence
<220> FEATURE:
<223> OTHER INFORMATION: Synthetic Construct

<400> SEQUENCE: 102

Gly Asp Thr Phe Ser Phe Ala Ala Met Gly
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetic Construct

<400> SEQUENCE: 103

Trp Tyr Arg Gln Ala Pro Gly Lys Gln Arg Glu Leu Val Ala
1               5                   10

<210> SEQ ID NO 104
<211> LENGTH: 16
<212> TYPE: PRT
<213> ORGANISM: Artificial Sequence
<220> FEATURE:
<223> OTHER INFORMATION: Synthetic Construct

<400> SEQUENCE: 104

Ser Ile Ser Phe Ser Gly Gly Glu Ser Thr Val Tyr Ala Asn Ser Val
1               5                   10                  15

<210> SEQ ID NO 105
<211> LENGTH: 34
<212> TYPE: PRT
<213> ORGANISM: Artificial Sequence
<220> FEATURE:
<223> OTHER INFORMATION: Synthetic Construct

<400> SEQUENCE: 105

Arg Gly Arg Phe Thr Ile Ser Gly Asp Asn Ala Lys Asn Arg Val Ser
1               5                   10                  15

Leu Glu Met Asn Asn Leu Lys Pro Glu Asp Thr Ala Val Tyr Tyr Cys
            20                  25                  30

Thr Ala

<210> SEQ ID NO 106
<211> LENGTH: 11
<212> TYPE: PRT
<213> ORGANISM: Artificial Sequence
<220> FEATURE:
<223> OTHER INFORMATION: Synthetic Construct

<400> SEQUENCE: 106

Lys Arg Gly Pro Tyr Leu Pro Gly Pro Glu Tyr
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Synthetic Construct

<400> SEQUENCE: 107

Trp Gly Gln Gly Thr Gln Val Thr Val Ser Ser
1               5                   10

<210> SEQ ID NO 108
<211> LENGTH: 126
<212> TYPE: PRT
<213> ORGANISM: Artificial Sequence
<220> FEATURE:
<223> OTHER INFORMATION: Synthetic Construct

<400> SEQUENCE: 108

Glu Val Gln Leu Ala Glu Ser Gly Gly Gly Leu Val Gln Ala Gly Gly
1               5                   10                  15

Ser Leu Arg Leu Ser Cys Thr Ala Ser Gly Phe Thr Phe Asp Asp Tyr
            20                  25                  30

Val Met Gly Trp Phe Arg Gln Ala Pro Gly Lys Glu Arg Glu Gly Val
        35                  40                  45

Ser Cys Ile Ser Trp Ser Gly Asp Thr Thr Tyr Tyr Ala Asp Ser Val
    50                  55                  60

Lys Gly Arg Phe Thr Ala Ser Arg Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Asp Gln Gly Lys Cys Ser Leu Ala Ser Ala Glu Pro Asp Asp
            100                 105                 110

Met Asp Tyr Trp Gly Arg Gly Thr Leu Val Thr Val Ser Ser
        115                 120                 125

<210> SEQ ID NO 109
<211> LENGTH: 121
<212> TYPE: PRT
<213> ORGANISM: Artificial Sequence
<220> FEATURE:
<223> OTHER INFORMATION: Synthetic Construct

<400> SEQUENCE: 109

Glu Val Gln Leu Ala Glu Ser Gly Gly Gly Ser Val Gln Ala Gly Gly
1               5                   10                  15

Ser Leu Arg Leu Ser Cys Ala Ala Ser Gly Val Thr Phe Ser Ser Thr
            20                  25                  30

Ser Val Ala Trp Phe Arg Gln Ala Pro Gly Lys Glu Arg Glu Gly Val
        35                  40                  45

Ala Tyr Ile Tyr Thr Gly Asp Ser Ser Thr Tyr Ala Asp Ser Val
    50                  55                  60

Lys Gly Arg Phe Thr Ile Ala Gln Asp Asn Ala Lys Asn Ala Val Tyr
65                  70                  75                  80

Leu Gln Met Asn Ser Leu Lys Pro Glu Asp Thr Ala Met Tyr Tyr Cys
                85                  90                  95

Ala Ala Asp Gly Phe Leu Leu Asn His Arg Ser Tyr Gln Tyr Trp Gly
            100                 105                 110

Gln Gly Thr Gln Val Thr Val Ser Ser
            115                 120

<210> SEQ ID NO 110
<211> LENGTH: 127
<212> TYPE: PRT
<213> ORGANISM: Artificial Sequence
<220> FEATURE:
<223> OTHER INFORMATION: Synthetic Construct

<400> SEQUENCE: 110

Glu Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Tyr Ser Ile Asn
            20                  25                  30

Cys Met Gly Trp Phe Arg Gln Ala Pro Gly Lys Glu Arg Glu Gly Val
        35                  40                  45

Ala Val Ile Ser Thr Gly Gly Arg Thr Asp Tyr Arg Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Gly Lys Thr Thr Tyr Pro Gly Tyr Gly Cys Gly Leu Gly Arg Ser
            100                 105                 110

Ala Tyr Asn Tyr Trp Gly Gln Gly Thr Gln Val Thr Val Ser Ser
        115                 120                 125

<210> SEQ ID NO 111
<211> LENGTH: 126
<212> TYPE: PRT
<213> ORGANISM: Artificial Sequence
<220> FEATURE:
<223> OTHER INFORMATION: Synthetic Construct

<400> SEQUENCE: 111

Gln Ile Gln Leu Val Glu Ser Gly Gly Gly Ser Val Gln Ala Gly Gly
1               5                   10                  15

Ser Leu Arg Leu Ser Cys Val Ala Ser Gly Tyr Ile Gly Gly His Tyr
            20                  25                  30

Tyr Met Gly Trp Phe Arg Gln Ala Pro Gly Lys Glu Arg Glu Gly Val
        35                  40                  45

```
Ala Ala Ile Asp Ile Asp Ser Asp Gly Arg Thr Arg Tyr Ala Gly Ser
    50                  55                  60

Val Gln Gly Arg Phe Thr Ile Ser Gln Asp Asn Ala Lys Asn Thr Leu
 65                  70                  75                  80

His Leu Gln Met Ser Ser Leu Lys Pro Glu Asp Thr Gly Met Tyr Tyr
                 85                  90                  95

Cys Ala Val Gly Val Gly Trp Val Pro Ala Arg Leu Thr Pro Gln Ala
                100                 105                 110

Val Ser Tyr Trp Gly Lys Gly Thr Leu Val Thr Val Ser Ser
                115                 120                 125

<210> SEQ ID NO 112
<211> LENGTH: 128
<212> TYPE: PRT
<213> ORGANISM: Artificial Sequence
<220> FEATURE:
<223> OTHER INFORMATION: Synthetic Construct

<400> SEQUENCE: 112

Glu Val Gln Leu Val Glu Ser Gly Gly Gly Ser Val Gln Ala Gly Gly
 1               5                  10                  15

Ser Leu Arg Leu Ser Cys Val Ala Ser Gly Tyr Thr Tyr Gly Ile Asn
                 20                  25                  30

Cys Met Gly Trp Phe Arg Gln Ala Pro Gly Lys Glu Arg Glu Gly Ile
                 35                  40                  45

Ala Ala Ile Ser Thr Gly Gly Thr Thr Gly Val Ala Asp Ser Val
    50                  55                  60

Lys Gly Arg Phe Thr Ile Ser Gln Asp Asn Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Arg Ser Thr Tyr Ser Gly Tyr Ala Cys Val Tyr Ser Glu Val
                100                 105                 110

Asn Gly Tyr Asn Tyr Arg Gly Gln Gly Thr Gln Val Thr Val Ser Ser
                115                 120                 125

<210> SEQ ID NO 113
<211> LENGTH: 126
<212> TYPE: PRT
<213> ORGANISM: Artificial Sequence
<220> FEATURE:
<223> OTHER INFORMATION: Synthetic Construct

<400> SEQUENCE: 113

Glu Val Gln Leu Val Glu Ser Gly Gly Gly Ser Val Gln Ala Gly Gly
 1               5                  10                  15

Ser Leu Arg Leu Ser Cys Val Ala Ser Gly Tyr Thr Trp Cys Arg Tyr
                 20                  25                  30

Asp Met Ser Trp Tyr Arg Gln Ala Pro Gly Lys Glu Arg Glu Phe Val
                 35                  40                  45

Ser Gly Phe Asp Asn Asp Gly Thr Thr Ser Tyr Ala Asp Ser Val Lys
    50                  55                  60

Gly Arg Phe Thr Ile Ser Gln Asp Asn Asp Lys Asn Thr Val Tyr Leu
 65                  70                  75                  80

Gln Met Asn Ser Leu Lys Pro Glu Asp Thr Ala Met Tyr Tyr Cys Lys
                 85                  90                  95

Glu Asp Arg Ser Arg Gly Ser Leu Asp Gly Arg Val Cys Pro Leu Ser
                100                 105                 110
```

```
Tyr Asp Asn Trp Gly Gln Gly Thr Gln Val Thr Val Ser Ser
        115                 120                 125

<210> SEQ ID NO 114
<211> LENGTH: 124
<212> TYPE: PRT
<213> ORGANISM: Artificial Sequence
<220> FEATURE:
<223> OTHER INFORMATION: Synthetic Construct

<400> SEQUENCE: 114

Glu Val Gln Leu Val Glu Ser Gly Gly Gly Leu Val Gln Ala Gly Gly
1               5                   10                  15

Ser Leu Arg Leu Ser Cys Thr Ala Ser Gly Phe Thr Phe Asp Asp Tyr
            20                  25                  30

Val Met Gly Trp Phe Arg Gln Ala Pro Gly Lys Glu Arg Glu Gly Val
        35                  40                  45

Ser Cys Ile Ser Trp Ser Gly Asp Thr Thr Tyr Tyr Ala Asp Ser Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Asp Gln Ser Leu Cys Ser Leu Ala Pro Pro Tyr Asn Tyr Ala
            100                 105                 110

Tyr Trp Gly Gln Gly Thr Gln Val Thr Val Ser Ser
        115                 120

<210> SEQ ID NO 115
<211> LENGTH: 126
<212> TYPE: PRT
<213> ORGANISM: Artificial Sequence
<220> FEATURE:
<223> OTHER INFORMATION: Synthetic Construct

<400> SEQUENCE: 115

Gln Val Gln Leu Val Glu Ser Gly Gly Gly Leu Val Gln Ala Gly Gly
1               5                   10                  15

Ser Leu Arg Leu Ser Cys Thr Ala Ser Gly Phe Thr Phe Asp Asn Tyr
            20                  25                  30

Val Met Gly Trp Phe Arg Gln Ala Pro Gly Lys Glu Arg Glu Gly Val
        35                  40                  45

Ser Cys Ile Gly Trp Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Asp Gln Gly Lys Cys Ser Leu Gly Ser Ala Gly Ala Asp Asp
            100                 105                 110

Met Asp Tyr Trp Gly Arg Gly Thr Leu Val Thr Val Ser Ser
        115                 120                 125

<210> SEQ ID NO 116
<211> LENGTH: 120
<212> TYPE: PRT
<213> ORGANISM: Artificial Sequence
<220> FEATURE:
<223> OTHER INFORMATION: Synthetic Construct
```

<400> SEQUENCE: 116

Glu Val Gln Leu Val Glu Ser Gly Gly Gly Ser Val Gln Ala Gly Gly
1               5                   10                  15

Ser Leu Arg Leu Ser Cys Ala Ala Pro Gly Tyr Thr Tyr Cys Thr Tyr
            20                  25                  30

Asp Met Met Trp Tyr Arg Gln Ala Leu Gly Lys Glu Arg Glu Phe Val
        35                  40                  45

Ser Ala Val Tyr Thr Asp Gly Ser Thr Leu Tyr Ala Asp Ser Val Lys
    50                  55                  60

Gly Arg Phe Thr Ile Ser Gln Asp Asn Ala Lys Asn Thr Leu Tyr Leu
65                  70                  75                  80

Gln Met Asn Ser Leu Lys Pro Glu Asp Thr Ala Met Tyr Tyr Cys Lys
                85                  90                  95

Thr Glu Thr Ala Val Thr Tyr Asp Lys Pro Cys Asp Phe Trp Gly Gln
                100                 105                 110

Gly Thr Gln Val Thr Val Ser Ser
            115                 120

<210> SEQ ID NO 117
<211> LENGTH: 124
<212> TYPE: PRT
<213> ORGANISM: Artificial Sequence
<220> FEATURE:
<223> OTHER INFORMATION: Synthetic Construct

<400> SEQUENCE: 117

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Thr
            20                  25                  30

Ala Met Gly Trp Tyr Arg Gln Ala Pro Gly Lys Gln Arg Glu Leu Val
        35                  40                  45

Ala Thr Val Thr Ser Gly Gly Ser Thr Lys Tyr Val Glu Ser Val Lys
    50                  55                  60

Gly Arg Phe Thr Ile Ser Asn Asp Asn Ala Lys Asn Thr Val Tyr Leu
65                  70                  75                  80

Gln Met Asn Ser Leu Lys Pro Glu Asp Thr Ala Val Tyr Tyr Cys Trp
                85                  90                  95

Ala Asp Ile Val Ala Arg Trp Asn Ser Asp Tyr Asn Val Tyr Asp Asp
                100                 105                 110

Tyr Trp Gly Gln Gly Thr Gln Val Thr Val Ser Ser
            115                 120

<210> SEQ ID NO 118
<211> LENGTH: 121
<212> TYPE: PRT
<213> ORGANISM: Artificial Sequence
<220> FEATURE:
<223> OTHER INFORMATION: Synthetic Construct

<400> SEQUENCE: 118

Gln Val Lys Leu Glu Glu Ser Gly Gly Gly Leu Val Gln Glu Gly Gly
1               5                   10                  15

Ser Leu Arg Leu Ser Cys Ala Ala Ser Gly Thr Ile Tyr Thr Asp Ser
            20                  25                  30

Thr Ile Tyr Trp Tyr Arg Gln Ala Pro Gly Lys Gln Arg Glu Leu Val
        35                  40                  45

Ala Ser Ile Thr Arg Gly Gly Asp Thr Lys Tyr Val Asp Ser Val Lys
    50                  55                  60

Gly Arg Phe Ala Ile Ser Ser Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Leu Tyr Tyr Arg Thr Gly Pro Ser Ser Tyr Tyr Arg Asn Asp Trp Gly
                100                 105                 110

Gln Gly Thr Gln Val Thr Val Ser Ser
                115                 120

<210> SEQ ID NO 119
<211> LENGTH: 112
<212> TYPE: PRT
<213> ORGANISM: Artificial Sequence
<220> FEATURE:
<223> OTHER INFORMATION: Synthetic Construct

<400> SEQUENCE: 119

Ala Val Gln Leu Val Glu Ser Gly Gly Gly Leu Val Gln Pro Gly Gly
1               5                   10                  15

Ser Leu Arg Leu Ser Cys Ala Val Ser Gly Ile Tyr Tyr Ser Ile Asn
                20                  25                  30

Leu Met Gly Trp Tyr Arg Gln Ala Pro Gly Lys Pro Arg Glu Leu Ala
            35                  40                  45

Ala Ser Ile Thr Asp Ser Gly Ile Thr Asn Tyr Ala Asp Ser Val Lys
    50                  55                  60

Gly Arg Phe Thr Ile Ser Arg Asp Asn Ala Lys Asn Thr Val His Leu
65                  70                  75                  80

Gln Met Asn Asn Leu Lys Pro Glu Asp Thr Ala Val Tyr Tyr Cys Lys
                85                  90                  95

Pro Met Gly Val Asn Trp Gly Gln Gly Ile Gln Val Thr Val Ser Ser
                100                 105                 110

<210> SEQ ID NO 120
<211> LENGTH: 121
<212> TYPE: PRT
<213> ORGANISM: Artificial Sequence
<220> FEATURE:
<223> OTHER INFORMATION: Synthetic Construct

<400> SEQUENCE: 120

Ala Val Gln Leu Val Glu Ser Gly Gly Gly Leu Val Gln Ala Gly Gly
1               5                   10                  15

Ser Leu Arg Leu Ser Cys Thr Ala Ser Gly Ser Ile Leu Arg Thr Tyr
                20                  25                  30

Glu Met Gly Trp Tyr Arg Gln Ala Pro Gly Ser Gln Arg Glu Leu Val
            35                  40                  45

Ala Ser Ile Thr Ser Asp Gly Asp Thr Asn Tyr Val Asp Ser Val Lys
    50                  55                  60

Gly Arg Phe Thr Ile Ser Arg Asp Asn Gly Lys Asn Met Val Tyr Leu
65                  70                  75                  80

Gln Met Asn Ser Leu Lys Pro Asp Asp Thr Ala Val Tyr Tyr Cys Asn
                85                  90                  95

Ala Val Ile Leu Ser Pro Ser Tyr Ser Met Arg Thr Ser His Trp Gly
                100                 105                 110

Gln Gly Thr Gln Val Thr Val Ser Ser

-continued

```
                115                 120

<210> SEQ ID NO 121
<211> LENGTH: 124
<212> TYPE: PRT
<213> ORGANISM: Artificial Sequence
<220> FEATURE:
<223> OTHER INFORMATION: Synthetic Construct

<400> SEQUENCE: 121

Gln Val Gln Leu Val Glu Ser Gly Gly Gly Leu Val Gln Ala Gly Gly
1               5                   10                  15

Ser Leu Arg Leu Ser Cys Ala Ala Ser Gly Asn Val Phe Arg Phe Asn
            20                  25                  30

Ile Met Gly Trp Tyr Arg Gln Ala Pro Gly Asn Gln Arg Glu Leu Val
        35                  40                  45

Ala Ser Ile Asp Asp Gly Gly Asp Arg Ser Tyr Ala Asp Ser Val Glu
    50                  55                  60

Gly Arg Phe Thr Ile Ser Arg Glu Asn Gly Lys Lys Ile Met Tyr Leu
65                  70                  75                  80

Gln Met Asn Ser Leu Lys Pro Glu Asp Thr Ala Val Tyr Tyr Cys Ala
                85                  90                  95

Ala Gly Leu Gly Thr Tyr Leu Asn Gly Arg Val Ser Met Ala Thr Asn
            100                 105                 110

Tyr Trp Gly Gln Gly Thr Gln Val Thr Val Ser Ser
        115                 120

<210> SEQ ID NO 122
<211> LENGTH: 121
<212> TYPE: PRT
<213> ORGANISM: Artificial Sequence
<220> FEATURE:
<223> OTHER INFORMATION: Synthetic Construct

<400> SEQUENCE: 122

Glu Val Gln Leu Val Glu Ser Gly Gly Gly Leu Val Gln Ala Gly Gly
1               5                   10                  15

Ser Leu Arg Leu Ser Cys Ala Ala Ser Gly Asp Thr Phe Ser Phe Ala
            20                  25                  30

Ala Met Gly Trp Tyr Arg Gln Ala Pro Gly Lys Gln Arg Glu Leu Val
        35                  40                  45

Ala Ser Ile Ser Phe Ser Gly Gly Glu Ser Thr Val Tyr Ala Asn Ser
    50                  55                  60

Val Arg Gly Arg Phe Thr Ile Ser Gly Asp Asn Ala Lys Asn Arg Val
65                  70                  75                  80

Ser Leu Glu Met Asn Asn Leu Lys Pro Glu Asp Thr Ala Val Tyr Tyr
                85                  90                  95

Cys Thr Ala Lys Arg Gly Pro Tyr Leu Pro Gly Pro Glu Tyr Trp Gly
            100                 105                 110

Gln Gly Thr Gln Val Thr Val Ser Ser
        115                 120

<210> SEQ ID NO 123
<211> LENGTH: 378
<212> TYPE: DNA
<213> ORGANISM: Artificial Sequence
<220> FEATURE:
<223> OTHER INFORMATION: Synthetic Construct

<400> SEQUENCE: 123
```

```
gaggtgcagc tggcggagtc tggggggaggc ttggtgcagg caggggggtc tctgagactc      60
tcctgtacag cctctggatt cacttttgat gattatgtca tgggctggtt ccgccaggcc     120
ccagggaagg agcgcgaggg ggtctcatgt attagctgga gtggtgacac cacatactat     180
gcagactccg tgaagggccg attcaccgcc tccagagaca cgccaagaa cacgctgtat      240 ctgcaaatga acagcctgaa acctgaggac acggccatgt attattgtgc ggcagatcaa     300
ggtaaatgct cccttgcgag cgcggaaccg gacgacatgg actactgggg cagagggacc     360
ctggtcaccg tctcctca                                                    378
```

```
<210> SEQ ID NO 124
<211> LENGTH: 363
<212> TYPE: DNA
<213> ORGANISM: Artificial Sequence
<220> FEATURE:
<223> OTHER INFORMATION: Synthetic Construct

<400> SEQUENCE: 124
gaggtgcaac tggcggagtc tggggggaggc tcggtgcagg ctggagggtc tctgagactc     60
tcctgtgcag cctctggagt caccttagt agcacgtccg tggcctggtt ccgccaggct     120
ccagggaagg agcgcgaggg ggtcgcatat atttatactg gtgatagtag cacatactat     180
gccgactccg tgaagggccg attcaccatc gcccaagaca cgccaagaa cgcggtgtat      240 ctgcaaatga acagcctgaa acctgaggac actgccatgt actactgtgc ggcagatggg     300 ttttactga atcaccgctc ataccaatac tggggccagg ggacccaggt caccgtctcc      360
tca                                                                    363
```

```
<210> SEQ ID NO 125
<211> LENGTH: 381
<212> TYPE: DNA
<213> ORGANISM: Artificial Sequence
<220> FEATURE:
<223> OTHER INFORMATION: Synthetic Construct

<400> SEQUENCE: 125
gaggtgcaac tggtggagtc tggggggaggc tcggtgcagg ctggagggtc tctgagactc     60
tcctgtgcag cctctggata cacctacagt atcaactgca tgggctggtt ccgccaggct     120
ccagggaagg agcgcgaggg ggtcgcggtt attagtactg gtggtggacg cacagactat     180
cgcgactccg tgaagggccg attcaccatc tcccaagaca cgccaagaa cacggtgtat      240 ctgcaaatga acagcctgaa acctgaggac actgccatgt actactgtgc gggtaaaacg     300
acctatccag ggtatggctg cggacttggg agatcggcct ataactactg ggccagggg     360 acccaggtca ccgtctcctc a                                               381
```

```
<210> SEQ ID NO 126
<211> LENGTH: 378
<212> TYPE: DNA
<213> ORGANISM: Artificial Sequence
<220> FEATURE:
<223> OTHER INFORMATION: Synthetic Construct

<400> SEQUENCE: 126
cagattcagc tggtggagtc tggggggaggc tcggtgcagg ctggagggtc tctgaggctc      60
tcctgtgtag cctctggata catcggcggt cactactaca tggggtggtt ccgccaggct     120
ccagggaagg agcgcgaggg ggtcgcagct atagatattg atagtgatgg taggacaagg     180
```

```
tacgcaggct ccgtgcaggg ccgattcacc atctcccaag acaacgccaa gaacactctg    240
catctgcaaa tgagcagcct gaaacctgag gacactggca tgtactactg tgcggttggt    300
gtgggttggg tccccgcgag acttacaccc caagccgtga gctactgggg caaaggaacc    360
ctggtcaccg tctcctca                                                  378
```

<210> SEQ ID NO 127
<211> LENGTH: 384
<212> TYPE: DNA
<213> ORGANISM: Artificial Sequence
<220> FEATURE:
<223> OTHER INFORMATION: Synthetic Construct

<400> SEQUENCE: 127

```
gaggtgcaac tggtggagtc tgggggaggc tcggtgcagg ctggagggtc tctgagactc     60
tcctgtgtag cctctggata cacctacggt atcaactgca tgggctggtt ccgccaggct    120
ccagggaagg agcgcgaggg gatcgcagct attagcactg gtggtggtac cacaggcgtt    180
gccgactccg tgaagggccg attcaccatc tcccaagaca cgccaagaa cacggtgtat     240 ctgcaaatga acagcctgaa accggaggac actgccatgt actactgtgc ggcgagatcg    300
acttatagcg gctatgcgtg cgtgtactcg gaagtgaatg ggtataacta ccggggccag    360
gggacccagg tcaccgtctc ctca                                           384
```

<210> SEQ ID NO 128
<211> LENGTH: 378
<212> TYPE: DNA
<213> ORGANISM: Artificial Sequence
<220> FEATURE:
<223> OTHER INFORMATION: Synthetic Construct

<400> SEQUENCE: 128

```
gaggtgcaac tggtggagtc tgggggaggc tcggtgcagg ctggaggatc tctgagactc     60
tcctgtgtag cctctggata cacctggtgt aggtacgaca tgagctggta ccggcaggct    120
ccaggaaagg agcgcgagtt cgtctcaggt tttgataatg atggtaccac aagttacgct    180
gactccgtga agggccgatt caccatctcc caagacaacg caagaacac ggtgtatctg    240 caaatgaaca gcctgaaacc tgaggacacg gccatgtatt actgtaaaga agatcgttcc    300
cggggtagct tggacggacg cgtatgtcca ttgtcttatg caactgggg ccaggggacc    360 caggtcaccg tctcctca                                                  378
```

<210> SEQ ID NO 129
<211> LENGTH: 372
<212> TYPE: DNA
<213> ORGANISM: Artificial Sequence
<220> FEATURE:
<223> OTHER INFORMATION: Synthetic Construct

<400> SEQUENCE: 129

```
gaggtgcagc tggtggagtc tgggggaggc ttggtgcagg caggggggtc tctgagactc     60
tcctgtacag cctctggatt cacttttgat gattatgtca tgggctggtt ccgccaggct    120
ccagggaagg agcgcgaggg ggtctcatgt attagctgga gtggtgatac cacatactat    180
gcagactccg tgaagggccg attcaccgtc tccagagaca cgccaagaa cacgctgtat     240 ctgcaaatga acagcctgaa acctgaggac acggccatgt attactgtgc ggcagatcag    300
agtctttgct ctctagcacc cccctacaat tatgcctact ggggccaggg gacccaggtc    360
accgtctcct ca                                                        372
```

<210> SEQ ID NO 130
<211> LENGTH: 378
<212> TYPE: DNA
<213> ORGANISM: Artificial Sequence
<220> FEATURE:
<223> OTHER INFORMATION: Synthetic Construct

<400> SEQUENCE: 130

| | |
|---|---|
| caggtgcagc tggtggagtc tgggggaggc ttggtgcagg cagggggtc tctgagactc | 60 |
| tcctgtacag cctctggatt cactttgat aattatgtca tgggctggtt ccgccaggct | 120 |
| ccagggaagg agcgcgaggg ggtctcatgt attggctgga gtggtggtag cacatactat | 180 |
| gcagactccg tgaagggccg attcaccatc tccagagaca acgccaagaa cacgctgtat | 240 |
| ctgcaaatga acagcctgaa acctgaggac acggccatgt attactgtgc ggcagatcaa | 300 |
| ggtaaatgct cccttgggag cgcgggtgcg gacgacatgg actactgggg cagagggacc | 360 |
| ctggtcaccg tctcctca | 378 |

<210> SEQ ID NO 131
<211> LENGTH: 360
<212> TYPE: DNA
<213> ORGANISM: Artificial Sequence
<220> FEATURE:
<223> OTHER INFORMATION: Synthetic Construct

<400> SEQUENCE: 131

| | |
|---|---|
| gaggtgcagc tggtggagtc tgggggaggc tcggtgcagg ctggcgggtc tctgagactc | 60 |
| tcctgtgctg cccctggata cacctactgt acttacgaca tgatgtggta ccgccaggct | 120 |
| ctagggaaag agcgcgagtt cgtctcagct gtttatactg atggtagcac tctctacgca | 180 |
| gactccgtga agggccgatt caccatctcc caagacaacg ccagaacac gctgtatctg | 240 |
| caaatgaaca gcctgaaacc tgaggacacg gccatgtatt actgtaaaac agaaacggcc | 300 |
| gtgacctatg acaagccttg cgacttttgg ggccagggga cccaggtcac cgtctcctca | 360 |

<210> SEQ ID NO 132
<211> LENGTH: 372
<212> TYPE: DNA
<213> ORGANISM: Artificial Sequence
<220> FEATURE:
<223> OTHER INFORMATION: Synthetic Construct

<400> SEQUENCE: 132

| | |
|---|---|
| caggtgcagc tggtggagtc tgggggaggc ttggtgcagc ctgggggggtc tctgagactc | 60 |
| tcctgtgcag cctctggaag catcttcagt atcactgcca tgggctggta ccgccaggct | 120 |
| ccagggaagc agcgcgagtt ggtcgcaacc gttacgagtg gtggtagtac aaagtatgta | 180 |
| gagtccgtga agggccgatt caccatctcc aacgacaacg ccagaacac ggtgtatctg | 240 |
| caaatgaaca gcctgaaacc tgaggacacg gccgtctatt actgttgggc agatatcgta | 300 |
| gctcggtgga atagcgacta taatgtttac gatgactact ggggccaggg gacccaggtc | 360 |
| accgtctcct ca | 372 |

<210> SEQ ID NO 133
<211> LENGTH: 363
<212> TYPE: DNA
<213> ORGANISM: Artificial Sequence
<220> FEATURE:
<223> OTHER INFORMATION: Synthetic Construct -continued

<400> SEQUENCE: 133

| caggtaaagc tggaggagtc tgggggaggc ttggtgcagg aggggggtc tctgagactc | 60 |
| tcctgtgcgg cctctggaac catctatacg gacagtacca tatactggta ccggcaggct | 120 |
| ccagggaagc agcgcgagtt ggtcgctagt attacgcgtg gtggtgatac aaagtatgta | 180 |
| gactccgtga agggccgatt cgccatctcc agcgacaacg ccaagaacac ggtgtatctt | 240 |
| caaatgaaca gcctgaaacc tgaggacaca gccgtctatt attgtaatct atattatcgc | 300 |
| acaggcccct cttcttacta caggaatgac tggggccagg gacccaggt cactgtctcc | 360 |
| tcg | 363 |

<210> SEQ ID NO 134
<211> LENGTH: 336
<212> TYPE: DNA
<213> ORGANISM: Artificial Sequence
<220> FEATURE:
<223> OTHER INFORMATION: Synthetic Construct

<400> SEQUENCE: 134

| gcggtgcagc tggtggagtc tgggggaggc ttggtgcagc ctgggggtc tctgagactc | 60 |
| tcctgtgcag tctctggaat ctattacagt atcaatctca tgggctggta ccgccaggct | 120 |
| cccgggaagc cgcgcgagtt ggcagcatcg attactgata gtggtatcac aaactatgca | 180 |
| gactccgtga agggccgatt caccatctcc agagacaacg ccaagaacac ggtgcatctg | 240 |
| caaatgaaca acctgaaacc tgaggacacg gccgtctatt actgtaaacc gatgggtgta | 300 |
| aactggggcc aggggatcca ggtcaccgtc tcctca | 336 |

<210> SEQ ID NO 135
<211> LENGTH: 363
<212> TYPE: DNA
<213> ORGANISM: Artificial Sequence
<220> FEATURE:
<223> OTHER INFORMATION: Synthetic Construct

<400> SEQUENCE: 135

| gcggtgcagc tagtggagtc tgggggaggc ttggtgcagg ctgggggtc tctgagactc | 60 |
| tcctgtacag cctctggaag catcctcaga acatatgaga tgggctggta ccgccaggct | 120 |
| ccagggagcc agcgcgagtt ggtcgcaagt attactagtg atggcgatac aaactatgtc | 180 |
| gactccgtga agggccgatt caccatctcc agagacaacg gcaagaatat ggtatatctg | 240 |
| caaatgaaca gcctgaaacc tgacgacaca gccgtctatt actgtaatgc agtcatttta | 300 |
| tctccttcct attctatgag aacttcccac tggggccagg gacccaggt caccgtctcc | 360 |
| tca | 363 |

<210> SEQ ID NO 136
<211> LENGTH: 372
<212> TYPE: DNA
<213> ORGANISM: Artificial Sequence
<220> FEATURE:
<223> OTHER INFORMATION: Synthetic Construct

<400> SEQUENCE: 136

| caggtgcagc tggtggagtc tgggggaggc ttggtgcagg ctgggggctc tctgagactc | 60 |
| tcctgtgcag cctctggaaa cgtctttcgt ttcaatatta tgggtggta ccgccaggct | 120 |
| ccagggaacc agcgcgaatt ggtcgcatca atagacgatg gtggtgaccg aagctatgca | 180 |
| gactccgtgg agggccgatt caccatctcc agagagaacg gcaagaaaat aatgtatctg | 240 |

```
caaatgaata gcctgaaacc cgaggacaca gccgtctatt actgtgcagc gggcctggga    300
acatatctga atggacgtgt tccatggcg actaactact ggggccaggg gacccaggtc     360
accgtctcct ca                                                        372
```

<210> SEQ ID NO 137
<211> LENGTH: 363
<212> TYPE: DNA
<213> ORGANISM: Artificial Sequence
<220> FEATURE:
<223> OTHER INFORMATION: Synthetic Construct
<400> SEQUENCE: 137

```
gaggtgcagc tggtggagtc tgggggaggc ttggtgcagg ctgggggtc tctgagactc      60 tcctgtgcag cctctggaga caccttcagt ttcgctgcca tgggctggta ccgccaggct    120
ccagggaagc agcgcgaatt ggtcgcaagt attagttta gtggtggtga agtacagta     180 tatgcaaact ccgtgagggg ccgtttcacc atctccggag acaacgccaa gaacagagtg    240
tctctcgaaa tgaacaactt gaaacctgag gacacggccg tgtattactg tacggcaaaa    300
aggggaccct atcttcctgg gccggagtac tggggccagg ggacgcaggt caccgtctcc    360
tca                                                                  363
```

<210> SEQ ID NO 138
<211> LENGTH: 24
<212> TYPE: PRT
<213> ORGANISM: Artificial Sequence
<220> FEATURE:
<223> OTHER INFORMATION: Synthetic Construct
<400> SEQUENCE: 138

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 139
<211> LENGTH: 27
<212> TYPE: PRT
<213> ORGANISM: Artificial Sequence
<220> FEATURE:
<223> OTHER INFORMATION: Synthetic Construct
<400> SEQUENCE: 139

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 140
<211> LENGTH: 112
<212> TYPE: PRT
<213> ORGANISM: Artificial Sequence
<220> FEATURE:
<223> OTHER INFORMATION: Synthetic Construct
<400> SEQUENCE: 140

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

-continued

Asp Val Leu Asp Lys Arg Arg Gly Arg Asp Pro Glu Met Gly Gly Lys
             35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
             85                  90                  95

Thr Lys Asp Thr Tyr Asp Ala Leu His Met Gln Ala Leu Pro Pro Arg
            100                 105                 110

<210> SEQ ID NO 141
<211> LENGTH: 41
<212> TYPE: PRT
<213> ORGANISM: Artificial Sequence
<220> FEATURE:
<223> OTHER INFORMATION: Synthetic Construct

<400> SEQUENCE: 141

Arg Ser Lys Arg Ser Arg Leu Leu His Ser Asp Tyr Met Asn Met Thr
 1               5                  10                  15

Pro Arg Arg Pro Gly Pro Thr Arg Lys His Tyr Gln Pro Tyr Ala Pro
             20                  25                  30

Pro Arg Asp Phe Ala Ala Tyr Arg Ser
             35                  40

<210> SEQ ID NO 142
<211> LENGTH: 42
<212> TYPE: PRT
<213> ORGANISM: Artificial Sequence
<220> FEATURE:
<223> OTHER INFORMATION: Synthetic Construct

<400> SEQUENCE: 142

Lys Arg Gly Arg Lys Lys Leu Leu Tyr Ile Phe Lys Gln Pro Phe Met
 1               5                  10                  15

Arg Pro Val Gln Thr Thr Gln Glu Glu Asp Gly Cys Ser Cys Arg Phe
             20                  25                  30

Pro Glu Glu Glu Glu Gly Gly Cys Glu Leu
             35                  40

<210> SEQ ID NO 143
<211> LENGTH: 38
<212> TYPE: PRT
<213> ORGANISM: Artificial Sequence
<220> FEATURE:
<223> OTHER INFORMATION: Synthetic Construct

<400> SEQUENCE: 143

Cys Trp Leu Thr Lys Lys Lys Tyr Ser Ser Ser Val His Asp Pro Asn
 1               5                  10                  15

Gly Glu Tyr Met Phe Met Arg Ala Val Asn Thr Ala Lys Lys Ser Arg
             20                  25                  30

Leu Thr Asp Val Thr Leu
         35

<210> SEQ ID NO 144
<211> LENGTH: 45
<212> TYPE: PRT
<213> ORGANISM: Artificial Sequence
<220> FEATURE:
<223> OTHER INFORMATION: Synthetic Construct

<400> SEQUENCE: 144

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 145
<211> LENGTH: 39
<212> TYPE: PRT
<213> ORGANISM: Artificial Sequence
<220> FEATURE:
<223> OTHER INFORMATION: Synthetic Construct

<400> SEQUENCE: 145

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 146
<211> LENGTH: 15
<212> TYPE: PRT
<213> ORGANISM: Artificial Sequence
<220> FEATURE:
<223> OTHER INFORMATION: Synthetic Construct

<400> SEQUENCE: 146

Gly Gly Gly Gly Ser Gly Gly Gly Ser Gly Gly Gly Gly Ser
1               5                   10                  15

<210> SEQ ID NO 147
<211> LENGTH: 21
<212> TYPE: PRT
<213> ORGANISM: Artificial Sequence
<220> FEATURE:
<223> OTHER INFORMATION: Synthetic Construct

<400> SEQUENCE: 147

Met Ala Leu Pro Val Thr Ala Leu Leu Leu Pro Leu Ala Leu Leu Leu
1               5                   10                  15

His Ala Ala Arg Pro
            20

<210> SEQ ID NO 148
<211> LENGTH: 5
<212> TYPE: PRT
<213> ORGANISM: Artificial Sequence
<220> FEATURE:
<223> OTHER INFORMATION: Synthetic Construct

<400> SEQUENCE: 148

Gly Gly Gly Gly Ser
1               5

<210> SEQ ID NO 149
<211> LENGTH: 10
<212> TYPE: PRT
<213> ORGANISM: Artificial Sequence
<220> FEATURE:

<223> OTHER INFORMATION: Synthetic Construct

<400> SEQUENCE: 149

Gly Gly Gly Gly Ser Gly Gly Gly Gly Ser
1               5                   10

<210> SEQ ID NO 150
<211> LENGTH: 8
<212> TYPE: PRT
<213> ORGANISM: Artificial Sequence
<220> FEATURE:
<223> OTHER INFORMATION: Synthetic Construct

<400> SEQUENCE: 150

Gly Gly Gly Ser Gly Gly Gly Ser
1               5

<210> SEQ ID NO 151
<211> LENGTH: 16
<212> TYPE: PRT
<213> ORGANISM: Artificial Sequence
<220> FEATURE:
<223> OTHER INFORMATION: Synthetic Construct

<400> SEQUENCE: 151

Gly Gly Gly Ser Gly Gly Gly Ser Gly Gly Gly Ser Gly Gly Gly Ser
1               5                   10                  15

<210> SEQ ID NO 152
<211> LENGTH: 18
<212> TYPE: PRT
<213> ORGANISM: Artificial Sequence
<220> FEATURE:
<223> OTHER INFORMATION: Synthetic Construct

<400> SEQUENCE: 152

Gly Ser Thr Ser Gly Ser Gly Lys Pro Gly Ser Gly Glu Gly Ser Thr
1               5                   10                  15

Lys Gly

<210> SEQ ID NO 153
<211> LENGTH: 22
<212> TYPE: PRT
<213> ORGANISM: Artificial Sequence
<220> FEATURE:
<223> OTHER INFORMATION: Synthetic Construct

<400> SEQUENCE: 153

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 154
<211> LENGTH: 134
<212> TYPE: PRT
<213> ORGANISM: Artificial Sequence
<220> FEATURE:
<223> OTHER INFORMATION: Synthetic Construct

<400> SEQUENCE: 154

Phe Asn Gln Glu Val Gln Ile Pro Leu Thr Glu Ser Tyr Cys Gly Pro
1               5                   10                  15

Cys Pro Lys Asn Trp Ile Cys Tyr Lys Asn Asn Cys Tyr Gln Phe Phe
            20                  25                  30

-continued

```
Asp Glu Ser Lys Asn Trp Tyr Glu Ser Gln Ala Ser Cys Met Ser Gln
    35                  40                  45

Asn Ala Ser Leu Leu Lys Val Tyr Ser Lys Glu Asp Gln Asp Leu Leu
 50                  55                  60

Lys Leu Val Lys Ser Tyr His Trp Met Gly Leu Val His Ile Pro Thr
 65                  70                  75                  80

Asn Gly Ser Trp Gln Trp Glu Asp Gly Ser Ile Leu Ser Pro Asn Leu
                 85                  90                  95

Leu Thr Ile Ile Glu Met Gln Lys Gly Asp Cys Ala Leu Tyr Ala Ser
            100                 105                 110

Ser Phe Lys Gly Tyr Ile Glu Asn Cys Ser Thr Pro Asn Thr Tyr Ile
            115                 120                 125

Cys Met Gln Arg Thr Val
            130

<210> SEQ ID NO 155
<211> LENGTH: 370
<212> TYPE: PRT
<213> ORGANISM: Artificial Sequence
<220> FEATURE:
<223> OTHER INFORMATION: Synthetic Construct

<400> SEQUENCE: 155

Met Ala Leu Pro Val Thr Ala Leu Leu Leu Pro Leu Ala Leu Leu Leu
  1               5                  10                  15

His Ala Ala Arg Pro Glu Val Gln Leu Ala Glu Ser Gly Gly Gly Leu
                 20                  25                  30

Val Gln Ala Gly Gly Ser Leu Arg Leu Ser Cys Thr Ala Ser Gly Phe
             35                  40                  45

Thr Phe Asp Asp Tyr Val Met Gly Trp Phe Arg Gln Ala Pro Gly Lys
         50                  55                  60

Glu Arg Glu Gly Val Ser Cys Ile Ser Trp Ser Gly Asp Thr Thr Tyr
 65                  70                  75                  80

Tyr Ala Asp Ser Val Lys Gly Arg Phe Thr Ala Ser Arg Asp Asn Ala
                 85                  90                  95

Lys Asn Thr Leu Tyr Leu Gln Met Asn Ser Leu Lys Pro Glu Asp Thr
            100                 105                 110

Ala Met Tyr Tyr Cys Ala Ala Asp Gln Gly Lys Cys Ser Leu Ala Ser
            115                 120                 125

Ala Glu Pro Asp Asp Met Asp Tyr Trp Gly Arg Gly Thr Leu Val Thr
            130                 135                 140

Val Ser Ser Thr Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175

Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
        195                 200                 205

Ser Leu Val Ile Thr Leu Tyr Cys Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255
```

```
Glu Leu Arg Val Lys Phe Ser Arg Ser Ala Asp Ala Pro Ala Tyr Lys
            260                 265                 270

Gln Gly Gln Asn Gln Leu Tyr Asn Glu Leu Asn Leu Gly Arg Arg Glu
            275                 280                 285

Glu Tyr Asp Val Leu Asp Lys Arg Arg Gly Arg Asp Pro Glu Met Gly
290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
            340                 345                 350

Thr Ala Thr Lys Asp Thr Tyr Asp Ala Leu His Met Gln Ala Leu Pro
            355                 360                 365

Pro Arg
    370

<210> SEQ ID NO 156
<211> LENGTH: 365
<212> TYPE: PRT
<213> ORGANISM: Artificial Sequence
<220> FEATURE:
<223> OTHER INFORMATION: Synthetic Construct

<400> SEQUENCE: 156

Met Ala Leu Pro Val Thr Ala Leu Leu Leu Pro Leu Ala Leu Leu Leu
1               5                   10                  15

His Ala Ala Arg Pro Glu Val Gln Leu Ala Glu Ser Gly Gly Gly Ser
            20                  25                  30

Val Gln Ala Gly Gly Ser Leu Arg Leu Ser Cys Ala Ala Ser Gly Val
        35                  40                  45

Thr Phe Ser Ser Thr Ser Val Ala Trp Phe Arg Gln Ala Pro Gly Lys
    50                  55                  60

Glu Arg Glu Gly Val Ala Tyr Ile Tyr Thr Gly Asp Ser Ser Thr Tyr
65                  70                  75                  80

Tyr Ala Asp Ser Val Lys Gly Arg Phe Thr Ile Ala Gln Asp Asn Ala
                85                  90                  95

Lys Asn Ala Val Tyr Leu Gln Met Asn Ser Leu Lys Pro Glu Asp Thr
            100                 105                 110

Ala Met Tyr Tyr Cys Ala Ala Asp Gly Phe Leu Leu Asn His Arg Ser
        115                 120                 125

Tyr Gln Tyr Trp Gly Gln Gly Thr Gln Val Thr Val Ser Ser Thr Thr
    130                 135                 140

Thr Pro Ala Pro Arg Pro Thr Pro Ala Pro Thr Ile Ala Ser Gln
145                 150                 155                 160

Pro Leu Ser Leu Arg Pro Glu Ala Cys Arg Pro Ala Ala Gly Gly Ala
                165                 170                 175

Val His Thr Arg Gly Leu Asp Phe Ala Cys Asp Ile Tyr Ile Trp Ala
            180                 185                 190

Pro Leu Ala Gly Thr Cys Gly Val Leu Leu Leu Ser Leu Val Ile Thr
        195                 200                 205

Leu Tyr Cys Lys Arg Gly Arg Lys Lys Leu Leu Tyr Ile Phe Lys Gln
    210                 215                 220

Pro Phe Met Arg Pro Val Gln Thr Thr Gln Glu Glu Asp Gly Cys Ser
225                 230                 235                 240
```

```
Cys Arg Phe Pro Glu Glu Glu Gly Gly Cys Glu Leu Arg Val Lys
                245                 250                 255

Phe Ser Arg Ser Ala Asp Ala Pro Ala Tyr Lys Gln Gly Gln Asn Gln
            260                 265                 270

Leu Tyr Asn Glu Leu Asn Leu Gly Arg Arg Glu Glu Tyr Asp Val Leu
            275                 280                 285

Asp Lys Arg Arg Gly Arg Asp Pro Glu Met Gly Gly Lys Pro Arg Arg
290                 295                 300

Lys Asn Pro Gln Glu Gly Leu Tyr Asn Glu Leu Gln Lys Asp Lys Met
305                 310                 315                 320

Ala Glu Ala Tyr Ser Glu Ile Gly Met Lys Gly Glu Arg Arg Arg Gly
                325                 330                 335

Lys Gly His Asp Gly Leu Tyr Gln Gly Leu Ser Thr Ala Thr Lys Asp
                340                 345                 350

Thr Tyr Asp Ala Leu His Met Gln Ala Leu Pro Pro Arg
            355                 360                 365

<210> SEQ ID NO 157
<211> LENGTH: 371
<212> TYPE: PRT
<213> ORGANISM: Artificial Sequence
<220> FEATURE:
<223> OTHER INFORMATION: Synthetic Construct

<400> SEQUENCE: 157

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Ser
                20                  25                  30

Val Gln Ala Gly Gly Ser Leu Arg Leu Ser Cys Ala Ala Ser Gly Tyr
            35                  40                  45

Thr Tyr Ser Ile Asn Cys Met Gly Trp Phe Arg Gln Ala Pro Gly Lys
        50                  55                  60

Glu Arg Glu Gly Val Ala Val Ile Ser Thr Gly Gly Arg Thr Asp
65                  70                  75                  80

Tyr Arg Asp Ser Val Lys Gly Arg Phe Thr Ile Ser Gln Asp Asn Ala
                85                  90                  95

Lys Asn Thr Val Tyr Leu Gln Met Asn Ser Leu Lys Pro Glu Asp Thr
            100                 105                 110

Ala Met Tyr Tyr Cys Ala Gly Lys Thr Thr Tyr Pro Gly Tyr Gly Cys
        115                 120                 125

Gly Leu Gly Arg Ser Ala Tyr Asn Tyr Trp Gly Gln Gly Thr Gln Val
    130                 135                 140

Thr Val Ser Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240
```

```
Glu Glu Asp Gly Cys Ser Cys Arg Phe Pro Glu Glu Glu Gly Gly
                245                 250                 255

Cys Glu Leu Arg Val Lys Phe Ser Arg Ser Ala Asp Ala Pro Ala Tyr
            260                 265                 270

Lys Gln Gly Gln Asn Gln Leu Tyr Asn Glu Leu Asn Leu Gly Arg Arg
        275                 280                 285

Glu Glu Tyr Asp Val Leu Asp Lys Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370

<210> SEQ ID NO 158
<211> LENGTH: 370
<212> TYPE: PRT
<213> ORGANISM: Artificial Sequence
<220> FEATURE:
<223> OTHER INFORMATION: Synthetic Construct

<400> SEQUENCE: 158

Met Ala Leu Pro Val Thr Ala Leu Leu Leu Pro Leu Ala Leu Leu Leu
1               5                   10                  15

His Ala Ala Arg Pro Gln Ile Gln Leu Val Glu Ser Gly Gly Gly Ser
                20                  25                  30

Val Gln Ala Gly Gly Ser Leu Arg Leu Ser Cys Val Ala Ser Gly Tyr
            35                  40                  45

Ile Gly Gly His Tyr Tyr Met Gly Trp Phe Arg Gln Ala Pro Gly Lys
        50                  55                  60

Glu Arg Glu Gly Val Ala Ala Ile Asp Ile Asp Ser Asp Gly Arg Thr
65                  70                  75                  80

Arg Tyr Ala Gly Ser Val Gln Gly Arg Phe Thr Ile Ser Gln Asp Asn
                85                  90                  95

Ala Lys Asn Thr Leu His Leu Gln Met Ser Ser Leu Lys Pro Glu Asp
            100                 105                 110

Thr Gly Met Tyr Tyr Cys Ala Val Gly Val Gly Trp Val Pro Ala Arg
        115                 120                 125

Leu Thr Pro Gln Ala Val Ser Tyr Trp Gly Lys Gly Thr Leu Val Thr
    130                 135                 140

Val Ser Ser Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175

Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
        195                 200                 205

Ser Leu Val Ile Thr Leu Tyr Cys Lys Arg Gly Arg Lys Lys Leu Leu
    210                 215                 220
```

```
Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Gly Gly Cys
            245                 250                 255

Glu Leu Arg Val Lys Phe Ser Arg Ser Ala Asp Ala Pro Ala Tyr Lys
                260                 265                 270

Gln Gly Gln Asn Gln Leu Tyr Asn Glu Leu Asn Leu Gly Arg Arg Glu
                275                 280                 285

Glu Tyr Asp Val Leu Asp Lys Arg Arg Gly Arg Asp Pro Glu Met Gly
            290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
            340                 345                 350

Thr Ala Thr Lys Asp Thr Tyr Asp Ala Leu His Met Gln Ala Leu Pro
                355                 360                 365

Pro Arg
    370

<210> SEQ ID NO 159
<211> LENGTH: 372
<212> TYPE: PRT
<213> ORGANISM: Artificial Sequence
<220> FEATURE:
<223> OTHER INFORMATION: Synthetic Construct

<400> SEQUENCE: 159

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Ser
            20                  25                  30

Val Gln Ala Gly Gly Ser Leu Arg Leu Ser Cys Val Ala Ser Gly Tyr
        35                  40                  45

Thr Tyr Gly Ile Asn Cys Met Gly Trp Phe Arg Gln Ala Pro Gly Lys
    50                  55                  60

Glu Arg Glu Gly Ile Ala Ala Ile Ser Thr Gly Gly Gly Thr Thr Gly
65                  70                  75                  80

Val Ala Asp Ser Val Lys Gly Arg Phe Thr Ile Ser Gln Asp Asn Ala
                85                  90                  95

Lys Asn Thr Val Tyr Leu Gln Met Asn Ser Leu Lys Pro Glu Asp Thr
            100                 105                 110

Ala Met Tyr Tyr Cys Ala Ala Arg Ser Tyr Ser Gly Tyr Ala Cys
        115                 120                 125

Val Tyr Ser Glu Val Asn Gly Tyr Asn Tyr Arg Gly Gln Gly Thr Gln
    130                 135                 140

Val Thr Val Ser Ser Thr Thr Thr Pro Ala Pro Arg Pro Pro Thr Pro
145                 150                 155                 160

Ala Pro Thr Ile Ala Ser Gln Pro Leu Ser Leu Arg Pro Glu Ala Cys
                165                 170                 175

Arg Pro Ala Ala Gly Gly Ala Val His Thr Arg Gly Leu Asp Phe Ala
            180                 185                 190

Cys Asp Ile Tyr Ile Trp Ala Pro Leu Ala Gly Thr Cys Gly Val Leu
        195                 200                 205
```

```
Leu Leu Ser Leu Val Ile Thr Leu Tyr Cys Lys Arg Gly Arg Lys Lys
    210                 215                 220

Leu Leu Tyr Ile Phe Lys Gln Pro Phe Met Arg Pro Val Gln Thr Thr
225                 230                 235                 240

Gln Glu Glu Asp Gly Cys Ser Cys Arg Phe Pro Glu Glu Glu Glu Gly
                245                 250                 255

Gly Cys Glu Leu Arg Val Lys Phe Ser Arg Ser Ala Asp Ala Pro Ala
                260                 265                 270

Tyr Lys Gln Gly Gln Asn Gln Leu Tyr Asn Glu Leu Asn Leu Gly Arg
            275                 280                 285

Arg Glu Glu Tyr Asp Val Leu Asp Lys Arg Arg Gly Arg Asp Pro Glu
        290                 295                 300

Met Gly Gly Lys Pro Arg Arg Lys Asn Pro Gln Glu Gly Leu Tyr Asn
305                 310                 315                 320

Glu Leu Gln Lys Asp Lys Met Ala Glu Ala Tyr Ser Glu Ile Gly Met
                325                 330                 335

Lys Gly Glu Arg Arg Arg Gly Lys Gly His Asp Gly Leu Tyr Gln Gly
                340                 345                 350

Leu Ser Thr Ala Thr Lys Asp Thr Tyr Asp Ala Leu His Met Gln Ala
            355                 360                 365

Leu Pro Pro Arg
    370

<210> SEQ ID NO 160
<211> LENGTH: 370
<212> TYPE: PRT
<213> ORGANISM: Artificial Sequence
<220> FEATURE:
<223> OTHER INFORMATION: Synthetic Construct

<400> SEQUENCE: 160

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Ser
                20                  25                  30

Val Gln Ala Gly Gly Ser Leu Arg Leu Ser Cys Val Ala Ser Gly Tyr
            35                  40                  45

Thr Trp Cys Arg Tyr Asp Met Ser Trp Tyr Arg Gln Ala Pro Gly Lys
        50                  55                  60

Glu Arg Glu Phe Val Ser Gly Phe Asp Asn Asp Gly Thr Thr Ser Tyr
65                  70                  75                  80

Ala Asp Ser Val Lys Gly Arg Phe Thr Ile Ser Gln Asp Asn Asp Lys
                85                  90                  95

Asn Thr Val Tyr Leu Gln Met Asn Ser Leu Lys Pro Glu Asp Thr Ala
            100                 105                 110

Met Tyr Tyr Cys Lys Glu Asp Arg Ser Arg Gly Ser Leu Asp Gly Arg
        115                 120                 125

Val Cys Pro Leu Ser Tyr Asp Asn Trp Gly Gln Gly Thr Gln Val Thr
130                 135                 140

Val Ser Ser Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
            165                 170                 175

Ala Ala Gly Gly Ala Val His Thr Arg Gly Leu Asp Phe Ala Cys Asp
        180                 185                 190
```

Ile Tyr Ile Trp Ala Pro Leu Ala Gly Thr Cys Gly Val Leu Leu Leu
                195                 200                 205

Ser Leu Val Ile Thr Leu Tyr Cys Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Arg Val Lys Phe Ser Arg Ser Ala Asp Ala Pro Ala Tyr Lys
                260                 265                 270

Gln Gly Gln Asn Gln Leu Tyr Asn Glu Leu Asn Leu Gly Arg Arg Glu
            275                 280                 285

Glu Tyr Asp Val Leu Asp Lys Arg Arg Gly Arg Asp Pro Glu Met Gly
            290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
                340                 345                 350

Thr Ala Thr Lys Asp Thr Tyr Asp Ala Leu His Met Gln Ala Leu Pro
            355                 360                 365

Pro Arg
    370

<210> SEQ ID NO 161
<211> LENGTH: 368
<212> TYPE: PRT
<213> ORGANISM: Artificial Sequence
<220> FEATURE:
<223> OTHER INFORMATION: Synthetic Construct

<400> SEQUENCE: 161

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Gln Ala Gly Gly Ser Leu Arg Leu Ser Cys Thr Ala Ser Gly Phe
            35                  40                  45

Thr Phe Asp Asp Tyr Val Met Gly Trp Phe Arg Gln Ala Pro Gly Lys
    50                  55                  60

Glu Arg Glu Gly Val Ser Cys Ile Ser Trp Ser Gly Asp Thr Thr Tyr
65                  70                  75                  80

Tyr Ala Asp Ser Val Lys Gly Arg Phe Thr Val Ser Arg Asp Asn Ala
                85                  90                  95

Lys Asn Thr Leu Tyr Leu Gln Met Asn Ser Leu Lys Pro Glu Asp Thr
            100                 105                 110

Ala Met Tyr Tyr Cys Ala Ala Asp Gln Ser Leu Cys Ser Leu Ala Pro
        115                 120                 125

Pro Tyr Asn Tyr Ala Tyr Trp Gly Gln Gly Thr Gln Val Thr Val Ser
    130                 135                 140

Ser Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

```
Gly Gly Ala Val His Thr Arg Gly Leu Asp Phe Ala Cys Asp Ile Tyr
            180                 185                 190

Ile Trp Ala Pro Leu Ala Gly Thr Cys Gly Val Leu Leu Leu Ser Leu
            195                 200                 205

Val Ile Thr Leu Tyr Cys Lys Arg Gly Lys Lys Leu Leu Tyr Ile
    210                 215                 220

Phe Lys Gln Pro Phe Met Arg Pro Val Gln Thr Thr Gln Glu Glu Asp
225                 230                 235                 240

Gly Cys Ser Cys Arg Phe Pro Glu Glu Glu Gly Cys Glu Leu
                245                 250                 255

Arg Val Lys Phe Ser Arg Ser Ala Asp Ala Pro Ala Tyr Lys Gln Gly
                260                 265                 270

Gln Asn Gln Leu Tyr Asn Glu Leu Asn Leu Gly Arg Arg Glu Glu Tyr
            275                 280                 285

Asp Val Leu Asp Lys Arg Arg Gly Arg Asp Pro Glu Met Gly Gly Lys
    290                 295                 300

Pro Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
                325                 330                 335

Arg Arg Gly Lys Gly His Asp Gly Leu Tyr Gln Gly Leu Ser Thr Ala
                340                 345                 350

Thr Lys Asp Thr Tyr Asp Ala Leu His Met Gln Ala Leu Pro Pro Arg
            355                 360                 365

<210> SEQ ID NO 162
<211> LENGTH: 370
<212> TYPE: PRT
<213> ORGANISM: Artificial Sequence
<220> FEATURE:
<223> OTHER INFORMATION: Synthetic Construct

<400> SEQUENCE: 162

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Thr Ala Ser Gly Phe
        35                  40                  45

Thr Phe Asp Asn Tyr Val Met Gly Trp Phe Arg Gln Ala Pro Gly Lys
    50                  55                  60

Glu Arg Glu Gly Val Ser Cys Ile Gly Trp Ser Gly Gly Ser Thr Tyr
65                  70                  75                  80

Tyr Ala Asp Ser Val Lys Gly Arg Phe Thr Ile Ser Arg Asp Asn Ala
                85                  90                  95

Lys Asn Thr Leu Tyr Leu Gln Met Asn Ser Leu Lys Pro Glu Asp Thr
            100                 105                 110

Ala Met Tyr Tyr Cys Ala Ala Asp Gln Gly Lys Cys Ser Leu Gly Ser
        115                 120                 125

Ala Gly Ala Asp Asp Met Asp Tyr Trp Gly Arg Gly Thr Leu Val Thr
    130                 135                 140

Val Ser Ser Thr Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175
```

```
Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
            195                 200                 205

Ser Leu Val Ile Thr Leu Tyr Cys Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Gly Gly Cys
                245                 250                 255

Glu Leu Arg Val Lys Phe Ser Arg Ser Ala Asp Ala Pro Ala Tyr Lys
                260                 265                 270

Gln Gly Gln Asn Gln Leu Tyr Asn Glu Leu Asn Leu Gly Arg Arg Glu
            275                 280                 285

Glu Tyr Asp Val Leu Asp Lys Arg Arg Gly Arg Asp Pro Glu Met Gly
    290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
                340                 345                 350

Thr Ala Thr Lys Asp Thr Tyr Asp Ala Leu His Met Gln Ala Leu Pro
            355                 360                 365

Pro Arg
    370

<210> SEQ ID NO 163
<211> LENGTH: 364
<212> TYPE: PRT
<213> ORGANISM: Artificial Sequence
<220> FEATURE:
<223> OTHER INFORMATION: Synthetic Construct

<400> SEQUENCE: 163

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Ser
            20                  25                  30

Val Gln Ala Gly Gly Ser Leu Arg Leu Ser Cys Ala Ala Pro Gly Tyr
        35                  40                  45

Thr Tyr Cys Thr Tyr Asp Met Met Trp Tyr Arg Gln Ala Leu Gly Lys
    50                  55                  60

Glu Arg Glu Phe Val Ala Val Tyr Thr Asp Gly Ser Thr Leu Tyr
65                  70                  75                  80

Ala Asp Ser Val Lys Gly Arg Phe Thr Ile Ser Gln Asp Asn Ala Lys
                85                  90                  95

Asn Thr Leu Tyr Leu Gln Met Asn Ser Leu Lys Pro Glu Asp Thr Ala
            100                 105                 110

Met Tyr Tyr Cys Lys Thr Glu Thr Ala Val Thr Tyr Asp Lys Pro Cys
        115                 120                 125

Asp Phe Trp Gly Gln Gly Thr Gln Val Thr Val Ser Ser Thr Thr Thr
    130                 135                 140

Pro Ala Pro Arg Pro Pro Thr Pro Ala Pro Thr Ile Ala Ser Gln Pro
145                 150                 155                 160
```

Leu Ser Leu Arg Pro Glu Ala Cys Arg Pro Ala Ala Gly Gly Ala Val
            165                 170                 175

His Thr Arg Gly Leu Asp Phe Ala Cys Asp Ile Tyr Ile Trp Ala Pro
            180                 185                 190

Leu Ala Gly Thr Cys Gly Val Leu Leu Ser Leu Val Ile Thr Leu
            195                 200                 205

Tyr Cys Lys Arg Gly Arg Lys Lys Leu Leu Tyr Ile Phe Lys Gln Pro
    210                 215                 220

Phe Met Arg Pro Val Gln Thr Thr Gln Glu Glu Asp Gly Cys Ser Cys
225                 230                 235                 240

Arg Phe Pro Glu Glu Glu Gly Gly Cys Glu Leu Arg Val Lys Phe
            245                 250                 255

Ser Arg Ser Ala Asp Ala Pro Ala Tyr Lys Gln Gly Gln Asn Gln Leu
            260                 265                 270

Tyr Asn Glu Leu Asn Leu Gly Arg Arg Glu Glu Tyr Asp Val Leu Asp
    275                 280                 285

Lys Arg Arg Gly Arg Asp Pro Glu Met Gly Gly Lys Pro Arg Arg Lys
290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
            325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg
    355                 360

<210> SEQ ID NO 164
<211> LENGTH: 368
<212> TYPE: PRT
<213> ORGANISM: Artificial Sequence
<220> FEATURE:
<223> OTHER INFORMATION: Synthetic Construct

<400> SEQUENCE: 164

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Ser
            35                  40                  45

Ile Phe Ser Ile Thr Ala Met Gly Trp Tyr Arg Gln Ala Pro Gly Lys
    50                  55                  60

Gln Arg Glu Leu Val Ala Thr Val Thr Ser Gly Ser Thr Lys Tyr
65                  70                  75                  80

Val Glu Ser Val Lys Gly Arg Phe Thr Ile Ser Asn Asp Asn Ala Lys
            85                  90                  95

Asn Thr Val Tyr Leu Gln Met Asn Ser Leu Lys Pro Glu Asp Thr Ala
            100                 105                 110

Val Tyr Tyr Cys Trp Ala Asp Ile Val Ala Arg Trp Asn Ser Asp Tyr
            115                 120                 125

Asn Val Tyr Asp Asp Tyr Trp Gly Gln Gly Thr Gln Val Thr Val Ser
    130                 135                 140

Ser Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
            165                 170                 175

Gly Gly Ala Val His Thr Arg Gly Leu Asp Phe Ala Cys Asp Ile Tyr
            180                 185                 190

Ile Trp Ala Pro Leu Ala Gly Thr Cys Gly Val Leu Leu Leu Ser Leu
            195                 200                 205

Val Ile Thr Leu Tyr Cys Lys Arg Gly Arg Lys Lys Leu Leu Tyr Ile
            210                 215                 220

Phe Lys Gln Pro Phe Met Arg Pro Val Gln Thr Thr Gln Glu Glu Asp
225                 230                 235                 240

Gly Cys Ser Cys Arg Phe Pro Glu Glu Glu Gly Gly Cys Glu Leu
            245                 250                 255

Arg Val Lys Phe Ser Arg Ser Ala Asp Ala Pro Ala Tyr Lys Gln Gly
            260                 265                 270

Gln Asn Gln Leu Tyr Asn Glu Leu Asn Leu Gly Arg Arg Glu Glu Tyr
            275                 280                 285

Asp Val Leu Asp Lys Arg Arg Gly Arg Asp Pro Glu Met Gly Gly Lys
            290                 295                 300

Pro Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
            325                 330                 335

Arg Arg Gly Lys Gly His Asp Gly Leu Tyr Gln Gly Leu Ser Thr Ala
            340                 345                 350

Thr Lys Asp Thr Tyr Asp Ala Leu His Met Gln Ala Leu Pro Pro Arg
            355                 360                 365

<210> SEQ ID NO 165
<211> LENGTH: 365
<212> TYPE: PRT
<213> ORGANISM: Artificial Sequence
<220> FEATURE:
<223> OTHER INFORMATION: Synthetic Construct

<400> SEQUENCE: 165

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Glu Gly Gly Ser Leu Arg Leu Ser Cys Ala Ala Ser Gly Thr
            35                  40                  45

Ile Tyr Thr Asp Ser Thr Ile Tyr Trp Tyr Arg Gln Ala Pro Gly Lys
50                  55                  60

Gln Arg Glu Leu Val Ala Ser Ile Thr Arg Gly Gly Asp Thr Lys Tyr
65                  70                  75                  80

Val Asp Ser Val Lys Gly Arg Phe Ala Ile Ser Ser Asp Asn Ala Lys
            85                  90                  95

Asn Thr Val Tyr Leu Gln Met Asn Ser Leu Lys Pro Glu Asp Thr Ala
            100                 105                 110

Val Tyr Tyr Cys Asn Leu Tyr Tyr Arg Thr Gly Pro Ser Ser Tyr Tyr
            115                 120                 125

Arg Asn Asp Trp Gly Gln Gly Thr Gln Val Thr Val Ser Ser Thr Thr
            130                 135                 140

Thr Pro Ala Pro Arg Pro Pro Thr Pro Ala Pro Thr Ile Ala Ser Gln
145                 150                 155                 160

```
Pro Leu Ser Leu Arg Pro Glu Ala Cys Arg Pro Ala Gly Gly Ala
            165                 170                 175

Val His Thr Arg Gly Leu Asp Phe Ala Cys Asp Ile Tyr Ile Trp Ala
            180                 185                 190

Pro Leu Ala Gly Thr Cys Gly Val Leu Leu Ser Leu Val Ile Thr
            195                 200                 205

Leu Tyr Cys Lys Arg Gly Arg Lys Lys Leu Leu Tyr Ile Phe Lys Gln
210                 215                 220

Pro Phe Met Arg Pro Val Gln Thr Thr Gln Glu Glu Asp Gly Cys Ser
225                 230                 235                 240

Cys Arg Phe Pro Glu Glu Glu Glu Gly Gly Cys Glu Leu Arg Val Lys
                    245                 250                 255

Phe Ser Arg Ser Ala Asp Ala Pro Ala Tyr Lys Gln Gly Gln Asn Gln
                260                 265                 270

Leu Tyr Asn Glu Leu Asn Leu Gly Arg Arg Glu Glu Tyr Asp Val Leu
            275                 280                 285

Asp Lys Arg Arg Gly Arg Asp Pro Glu Met Gly Gly Lys Pro Arg Arg
            290                 295                 300

Lys Asn Pro Gln Glu Gly Leu Tyr Asn Glu Leu Gln Lys Asp Lys Met
305                 310                 315                 320

Ala Glu Ala Tyr Ser Glu Ile Gly Met Lys Gly Glu Arg Arg Arg Gly
                325                 330                 335

Lys Gly His Asp Gly Leu Tyr Gln Gly Leu Ser Thr Ala Thr Lys Asp
                340                 345                 350

Thr Tyr Asp Ala Leu His Met Gln Ala Leu Pro Pro Arg
                355                 360                 365

<210> SEQ ID NO 166
<211> LENGTH: 356
<212> TYPE: PRT
<213> ORGANISM: Artificial Sequence
<220> FEATURE:
<223> OTHER INFORMATION: Synthetic Construct

<400> SEQUENCE: 166

Met Ala Leu Pro Val Thr Ala Leu Leu Leu Pro Leu Ala Leu Leu Leu
1               5                   10                  15

His Ala Ala Arg Pro Ala Val Gln Leu Val Glu Ser Gly Gly Gly Leu
            20                  25                  30

Val Gln Pro Gly Gly Ser Leu Arg Leu Ser Cys Ala Val Ser Gly Ile
        35                  40                  45

Tyr Tyr Ser Ile Asn Leu Met Gly Trp Tyr Arg Gln Ala Pro Gly Lys
    50                  55                  60

Pro Arg Glu Leu Ala Ala Ser Ile Thr Asp Ser Gly Ile Thr Asn Tyr
65                  70                  75                  80

Ala Asp Ser Val Lys Gly Arg Phe Thr Ile Ser Arg Asp Asn Ala Lys
                85                  90                  95

Asn Thr Val His Leu Gln Met Asn Asn Leu Lys Pro Glu Asp Thr Ala
            100                 105                 110

Val Tyr Tyr Cys Lys Pro Met Gly Val Asn Trp Gly Gln Gly Ile Gln
        115                 120                 125

Val Thr Val Ser Ser Thr Thr Thr Pro Ala Pro Arg Pro Pro Thr Pro
    130                 135                 140

Ala Pro Thr Ile Ala Ser Gln Pro Leu Ser Leu Arg Pro Glu Ala Cys
145                 150                 155                 160
```

```
Arg Pro Ala Ala Gly Gly Ala Val His Thr Arg Gly Leu Asp Phe Ala
                165                 170                 175
Cys Asp Ile Tyr Ile Trp Ala Pro Leu Ala Gly Thr Cys Gly Val Leu
            180                 185                 190
Leu Leu Ser Leu Val Ile Thr Leu Tyr Cys Lys Arg Gly Arg Lys Lys
        195                 200                 205
Leu Leu Tyr Ile Phe Lys Gln Pro Phe Met Arg Pro Val Gln Thr Thr
    210                 215                 220
Gln Glu Glu Asp Gly Cys Ser Cys Arg Phe Pro Glu Glu Glu Glu Gly
225                 230                 235                 240
Gly Cys Glu Leu Arg Val Lys Phe Ser Arg Ser Ala Asp Ala Pro Ala
                245                 250                 255
Tyr Lys Gln Gly Gln Asn Gln Leu Tyr Asn Glu Leu Asn Leu Gly Arg
            260                 265                 270
Arg Glu Glu Tyr Asp Val Leu Asp Lys Arg Arg Gly Arg Asp Pro Glu
        275                 280                 285
Met Gly Gly Lys Pro Arg Arg Lys Asn Pro Gln Glu Gly Leu Tyr Asn
    290                 295                 300
Glu Leu Gln Lys Asp Lys Met Ala Glu Ala Tyr Ser Glu Ile Gly Met
305                 310                 315                 320
Lys Gly Glu Arg Arg Arg Gly Lys Gly His Asp Gly Leu Tyr Gln Gly
                325                 330                 335
Leu Ser Thr Ala Thr Lys Asp Thr Tyr Asp Ala Leu His Met Gln Ala
            340                 345                 350
Leu Pro Pro Arg
        355

<210> SEQ ID NO 167
<211> LENGTH: 365
<212> TYPE: PRT
<213> ORGANISM: Artificial Sequence
<220> FEATURE:
<223> OTHER INFORMATION: Synthetic Construct

<400> SEQUENCE: 167

Met Ala Leu Pro Val Thr Ala Leu Leu Leu Pro Leu Ala Leu Leu Leu
1               5                   10                  15
His Ala Ala Arg Pro Ala Val Gln Leu Val Glu Ser Gly Gly Gly Leu
            20                  25                  30
Val Gln Ala Gly Gly Ser Leu Arg Leu Ser Cys Thr Ala Ser Gly Ser
        35                  40                  45
Ile Leu Arg Thr Tyr Glu Met Gly Trp Tyr Arg Gln Ala Pro Gly Ser
    50                  55                  60
Gln Arg Glu Leu Val Ala Ser Ile Thr Ser Asp Gly Asp Thr Asn Tyr
65                  70                  75                  80
Val Asp Ser Val Lys Gly Arg Phe Thr Ile Ser Arg Asp Asn Gly Lys
                85                  90                  95
Asn Met Val Tyr Leu Gln Met Asn Ser Leu Lys Pro Asp Asp Thr Ala
            100                 105                 110
Val Tyr Tyr Cys Asn Ala Val Ile Leu Ser Pro Ser Tyr Ser Met Arg
        115                 120                 125
Thr Ser His Trp Gly Gln Gly Thr Gln Val Thr Val Ser Ser Thr Thr
    130                 135                 140
Thr Pro Ala Pro Arg Pro Pro Thr Pro Ala Pro Thr Ile Ala Ser Gln
145                 150                 155                 160
```

```
Pro Leu Ser Leu Arg Pro Glu Ala Cys Arg Pro Ala Ala Gly Gly Ala
                165                 170                 175

Val His Thr Arg Gly Leu Asp Phe Ala Cys Asp Ile Tyr Ile Trp Ala
            180                 185                 190

Pro Leu Ala Gly Thr Cys Gly Val Leu Leu Ser Leu Val Ile Thr
        195                 200                 205

Leu Tyr Cys Lys Arg Gly Arg Lys Leu Leu Tyr Ile Phe Lys Gln
    210                 215                 220

Pro Phe Met Arg Pro Val Gln Thr Thr Gln Glu Asp Gly Cys Ser
225                 230                 235                 240

Cys Arg Phe Pro Glu Glu Glu Gly Gly Cys Glu Leu Arg Val Lys
                245                 250                 255

Phe Ser Arg Ser Ala Asp Ala Pro Ala Tyr Lys Gln Gly Gln Asn Gln
            260                 265                 270

Leu Tyr Asn Glu Leu Asn Leu Gly Arg Arg Glu Glu Tyr Asp Val Leu
        275                 280                 285

Asp Lys Arg Arg Gly Arg Asp Pro Glu Met Gly Gly Lys Pro Arg Arg
    290                 295                 300

Lys Asn Pro Gln Glu Gly Leu Tyr Asn Glu Leu Gln Lys Asp Lys Met
305                 310                 315                 320

Ala Glu Ala Tyr Ser Glu Ile Gly Met Lys Gly Glu Arg Arg Arg Gly
                325                 330                 335

Lys Gly His Asp Gly Leu Tyr Gln Gly Leu Ser Thr Ala Thr Lys Asp
            340                 345                 350

Thr Tyr Asp Ala Leu His Met Gln Ala Leu Pro Pro Arg
        355                 360                 365

<210> SEQ ID NO 168
<211> LENGTH: 368
<212> TYPE: PRT
<213> ORGANISM: Artificial Sequence
<220> FEATURE:
<223> OTHER INFORMATION: Synthetic Construct

<400> SEQUENCE: 168

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Asn
        35                  40                  45

Val Phe Arg Phe Asn Ile Met Gly Trp Tyr Arg Gln Ala Pro Gly Asn
    50                  55                  60

Gln Arg Glu Leu Val Ala Ser Ile Asp Asp Gly Gly Asp Arg Ser Tyr
65                  70                  75                  80

Ala Asp Ser Val Glu Gly Arg Phe Thr Ile Ser Arg Glu Asn Gly Lys
                85                  90                  95

Lys Ile Met Tyr Leu Gln Met Asn Ser Leu Lys Pro Glu Asp Thr Ala
            100                 105                 110

Val Tyr Tyr Cys Ala Ala Gly Leu Gly Thr Tyr Leu Asn Gly Arg Val
        115                 120                 125

Ser Met Ala Thr Asn Tyr Trp Gly Gln Gly Thr Gln Val Thr Val Ser
    130                 135                 140

Ser Thr Thr Thr Pro Ala Pro Arg Pro Pro Thr Pro Ala Pro Thr Ile
145                 150                 155                 160
```

Ala Ser Gln Pro Leu Ser Leu Arg Pro Glu Ala Cys Arg Pro Ala Ala
            165                 170                 175

Gly Gly Ala Val His Thr Arg Gly Leu Asp Phe Ala Cys Asp Ile Tyr
            180                 185                 190

Ile Trp Ala Pro Leu Ala Gly Thr Cys Gly Val Leu Leu Leu Ser Leu
            195                 200                 205

Val Ile Thr Leu Tyr Cys Lys Arg Gly Arg Lys Lys Leu Leu Tyr Ile
    210                 215                 220

Phe Lys Gln Pro Phe Met Arg Pro Val Gln Thr Thr Gln Glu Glu Asp
225                 230                 235                 240

Gly Cys Ser Cys Arg Phe Pro Glu Glu Glu Gly Gly Cys Glu Leu
            245                 250                 255

Arg Val Lys Phe Ser Arg Ser Ala Asp Ala Pro Ala Tyr Lys Gln Gly
            260                 265                 270

Gln Asn Gln Leu Tyr Asn Glu Leu Asn Leu Gly Arg Arg Glu Glu Tyr
            275                 280                 285

Asp Val Leu Asp Lys Arg Arg Gly Arg Asp Pro Glu Met Gly Gly Lys
    290                 295                 300

Pro Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
            325                 330                 335

Arg Arg Gly Lys Gly His Asp Gly Leu Tyr Gln Gly Leu Ser Thr Ala
            340                 345                 350

Thr Lys Asp Thr Tyr Asp Ala Leu His Met Gln Ala Leu Pro Pro Arg
            355                 360                 365

<210> SEQ ID NO 169
<211> LENGTH: 365
<212> TYPE: PRT
<213> ORGANISM: Artificial Sequence
<220> FEATURE:
<223> OTHER INFORMATION: Synthetic Construct

<400> SEQUENCE: 169

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Asp
        35                  40                  45

Thr Phe Ser Phe Ala Ala Met Gly Trp Tyr Arg Gln Ala Pro Gly Lys
    50                  55                  60

Gln Arg Glu Leu Val Ala Ser Ile Ser Phe Gly Gly Glu Ser Thr
65                  70                  75                  80

Val Tyr Ala Asn Ser Val Arg Gly Arg Phe Thr Ile Ser Gly Asp Asn
            85                  90                  95

Ala Lys Asn Arg Val Ser Leu Glu Met Asn Asn Leu Lys Pro Glu Asp
            100                 105                 110

Thr Ala Val Tyr Tyr Cys Thr Ala Lys Arg Gly Pro Tyr Leu Pro Gly
            115                 120                 125

Pro Glu Tyr Trp Gly Gln Gly Thr Gln Val Thr Val Ser Ser Thr Thr
    130                 135                 140

Thr Pro Ala Pro Arg Pro Pro Thr Pro Ala Pro Thr Ile Ala Ser Gln
145                 150                 155                 160

-continued

```
Pro Leu Ser Leu Arg Pro Glu Ala Cys Arg Pro Ala Gly Gly Ala
                165                 170                 175

Val His Thr Arg Gly Leu Asp Phe Ala Cys Asp Ile Tyr Ile Trp Ala
                180                 185                 190

Pro Leu Ala Gly Thr Cys Gly Val Leu Leu Ser Leu Val Ile Thr
                195                 200                 205

Leu Tyr Cys Lys Arg Gly Arg Lys Leu Leu Tyr Ile Phe Lys Gln
                210                 215                 220

Pro Phe Met Arg Pro Val Gln Thr Thr Gln Glu Glu Asp Gly Cys Ser
225                 230                 235                 240

Cys Arg Phe Pro Glu Glu Glu Glu Gly Gly Cys Glu Leu Arg Val Lys
                245                 250                 255

Phe Ser Arg Ser Ala Asp Ala Pro Ala Tyr Lys Gln Gly Gln Asn Gln
                260                 265                 270

Leu Tyr Asn Glu Leu Asn Leu Gly Arg Arg Glu Glu Tyr Asp Val Leu
                275                 280                 285

Asp Lys Arg Arg Gly Arg Asp Pro Glu Met Gly Gly Lys Pro Arg Arg
                290                 295                 300

Lys Asn Pro Gln Glu Gly Leu Tyr Asn Glu Leu Gln Lys Asp Lys Met
305                 310                 315                 320

Ala Glu Ala Tyr Ser Glu Ile Gly Met Lys Gly Glu Arg Arg Arg Gly
                325                 330                 335

Lys Gly His Asp Gly Leu Tyr Gln Gly Leu Ser Thr Ala Thr Lys Asp
                340                 345                 350

Thr Tyr Asp Ala Leu His Met Gln Ala Leu Pro Pro Arg
                355                 360                 365

<210> SEQ ID NO 170
<211> LENGTH: 488
<212> TYPE: PRT
<213> ORGANISM: Artificial Sequence
<220> FEATURE:
<223> OTHER INFORMATION: Synthetic Construct

<400> SEQUENCE: 170

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Ser
                20                  25                  30

Val Gln Ala Gly Gly Ala Leu Ser Leu Ser Cys Ala Ala Ser Gly Tyr
                35                  40                  45

Thr Val Arg Ile Asp Tyr Met Gly Trp Tyr Arg Gln Thr Pro Gly Lys
            50                  55                  60

Gly Arg Glu Pro Val Ala Thr Ile Ala Ser Asn Gly Thr Ala Tyr
65                  70                  75                  80

Ala Asp Ser Val Glu Gly Arg Phe Thr Ile Ser Gln Asp Asn Ala Lys
                85                  90                  95

Asn Ser Val Tyr Leu Gln Met Asn Thr Leu Lys Pro Gly Asp Thr Ala
                100                 105                 110

Met Tyr Tyr Cys Ala Ala Gly Thr Trp Pro Thr Leu Thr Tyr Phe Gly
                115                 120                 125

Gln Gly Thr Gln Val Thr Val Ser Ser Gly Gly Gly Ser Glu Val
            130                 135                 140

Gln Leu Val Glu Ser Gly Gly Gly Ser Val Gln Ala Gly Gly Ser Leu
145                 150                 155                 160
```

```
Arg Leu Ser Cys Ala Ala Ser Gly Tyr Thr Tyr Ser Ile Asn Cys Met
                165                 170                 175
Gly Trp Phe Arg Gln Ala Pro Gly Lys Glu Arg Glu Gly Val Ala Val
            180                 185                 190
Ile Ser Thr Gly Gly Arg Thr Asp Tyr Arg Asp Ser Val Lys Gly
        195                 200                 205
Arg Phe Thr Ile Ser Gln Asp Asn Ala Lys Asn Thr Val Tyr Leu Gln
    210                 215                 220
Met Asn Ser Leu Lys Pro Glu Asp Thr Ala Met Tyr Tyr Cys Ala Gly
225                 230                 235                 240
Lys Thr Thr Tyr Pro Gly Tyr Gly Cys Gly Leu Gly Arg Ser Ala Tyr
                245                 250                 255
Asn Tyr Trp Gly Gln Gly Thr Gln Val Thr Val Ser Ser Ile Glu Val
            260                 265                 270
Met Tyr Pro Pro Pro Tyr Leu Asp Asn Glu Lys Ser Asn Gly Thr Ile
        275                 280                 285
Ile His Val Lys Gly Lys His Leu Cys Pro Ser Pro Leu Phe Pro Gly
    290                 295                 300
Pro Ser Lys Pro Phe Trp Val Leu Val Val Val Gly Gly Val Leu Ala
305                 310                 315                 320
Cys Tyr Ser Leu Leu Val Thr Val Ala Phe Ile Ile Phe Trp Val Arg
                325                 330                 335
Ser Lys Arg Ser Arg Leu Leu His Ser Asp Tyr Met Asn Met Thr Pro
            340                 345                 350
Arg Arg Pro Gly Pro Thr Arg Lys His Tyr Gln Pro Tyr Ala Pro Pro
        355                 360                 365
Arg Asp Phe Ala Ala Tyr Arg Ser Arg Val Lys Phe Ser Arg Ser Ala
    370                 375                 380
Asp Ala Pro Ala Tyr Lys Gln Gly Gln Asn Gln Leu Tyr Asn Glu Leu
385                 390                 395                 400
Asn Leu Gly Arg Arg Glu Glu Tyr Asp Val Leu Asp Lys Arg Arg Gly
                405                 410                 415
Arg Asp Pro Glu Met Gly Gly Lys Pro Arg Arg Lys Asn Pro Gln Glu
            420                 425                 430
Gly Leu Tyr Asn Glu Leu Gln Lys Asp Lys Met Ala Glu Ala Tyr Ser
        435                 440                 445
Glu Ile Gly Met Lys Gly Glu Arg Arg Arg Gly Lys Gly His Asp Gly
    450                 455                 460
Leu Tyr Gln Gly Leu Ser Thr Ala Thr Lys Asp Thr Tyr Asp Ala Leu
465                 470                 475                 480
His Met Gln Ala Leu Pro Pro Arg
                485

<210> SEQ ID NO 171
<211> LENGTH: 493
<212> TYPE: PRT
<213> ORGANISM: Artificial Sequence
<220> FEATURE:
<223> OTHER INFORMATION: Synthetic Construct

<400> SEQUENCE: 171

Met Ala Leu Pro Val Thr Ala Leu Leu Leu Pro Leu Ala Leu Leu Leu
1               5                   10                  15
His Ala Ala Arg Pro Gln Val Gln Leu Val Glu Ser Gly Gly Gly Ser
            20                  25                  30
```

```
Val Gln Ala Gly Gly Ala Leu Ser Leu Ser Cys Ala Ala Ser Gly Tyr
         35                  40                  45

Thr Val Arg Ile Asp Tyr Met Gly Trp Tyr Arg Gln Thr Pro Gly Lys
 50                  55                  60

Gly Arg Glu Pro Val Ala Thr Ile Ala Ser Asn Gly Gly Thr Ala Tyr
 65                  70                  75                  80

Ala Asp Ser Val Glu Gly Arg Phe Thr Ile Ser Gln Asp Asn Ala Lys
                 85                  90                  95

Asn Ser Val Tyr Leu Gln Met Asn Thr Leu Lys Pro Gly Asp Thr Ala
                100                 105                 110

Met Tyr Tyr Cys Ala Ala Gly Thr Trp Pro Thr Leu Thr Tyr Phe Gly
            115                 120                 125

Gln Gly Thr Gln Val Thr Val Ser Ser Gly Gly Gly Ser Gly Gly
        130                 135                 140

Gly Gly Ser Glu Val Gln Leu Val Glu Ser Gly Gly Gly Ser Val Gln
145                 150                 155                 160

Ala Gly Gly Ser Leu Arg Leu Ser Cys Ala Ala Ser Gly Tyr Thr Tyr
                165                 170                 175

Ser Ile Asn Cys Met Gly Trp Phe Arg Gln Ala Pro Gly Lys Glu Arg
            180                 185                 190

Glu Gly Val Ala Val Ile Ser Thr Gly Gly Gly Arg Thr Asp Tyr Arg
            195                 200                 205

Asp Ser Val Lys Gly Arg Phe Thr Ile Ser Gln Asp Asn Ala Lys Asn
210                 215                 220

Thr Val Tyr Leu Gln Met Asn Ser Leu Lys Pro Glu Asp Thr Ala Met
225                 230                 235                 240

Tyr Tyr Cys Ala Gly Lys Thr Thr Tyr Pro Gly Tyr Gly Cys Gly Leu
            245                 250                 255

Gly Arg Ser Ala Tyr Asn Tyr Trp Gly Gln Gly Thr Gln Val Thr Val
            260                 265                 270

Ser Ser Ile Glu Val Met Tyr Pro Pro Pro Tyr Leu Asp Asn Glu Lys
        275                 280                 285

Ser Asn Gly Thr Ile Ile His Val Lys Gly Lys His Leu Cys Pro Ser
        290                 295                 300

Pro Leu Phe Pro Gly Pro Ser Lys Pro Phe Trp Val Leu Val Val Val
305                 310                 315                 320

Gly Gly Val Leu Ala Cys Tyr Ser Leu Leu Val Thr Val Ala Phe Ile
                325                 330                 335

Ile Phe Trp Val Arg Ser Lys Arg Ser Arg Leu Leu His Ser Asp Tyr
            340                 345                 350

Met Asn Met Thr Pro Arg Arg Pro Gly Pro Thr Arg Lys His Tyr Gln
        355                 360                 365

Pro Tyr Ala Pro Pro Arg Asp Phe Ala Ala Tyr Arg Ser Arg Val Lys
370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445
```

Ala Glu Ala Tyr Ser Glu Ile Gly Met Lys Gly Glu Arg Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 172
<211> LENGTH: 498
<212> TYPE: PRT
<213> ORGANISM: Artificial Sequence
<220> FEATURE:
<223> OTHER INFORMATION: Synthetic Construct

<400> SEQUENCE: 172

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Ser
                20                  25                  30

Val Gln Ala Gly Gly Ala Leu Ser Leu Ser Cys Ala Ala Ser Gly Tyr
            35                  40                  45

Thr Val Arg Ile Asp Tyr Met Gly Trp Tyr Arg Gln Thr Pro Gly Lys
50                  55                  60

Gly Arg Glu Pro Val Ala Thr Ile Ala Ser Asn Gly Thr Ala Tyr
65                  70                  75                  80

Ala Asp Ser Val Glu Gly Arg Phe Thr Ile Ser Gln Asp Asn Ala Lys
                85                  90                  95

Asn Ser Val Tyr Leu Gln Met Asn Thr Leu Lys Pro Gly Asp Thr Ala
            100                 105                 110

Met Tyr Tyr Cys Ala Ala Gly Thr Trp Pro Thr Leu Thr Tyr Phe Gly
        115                 120                 125

Gln Gly Thr Gln Val Thr Val Ser Ser Gly Gly Gly Ser Gly Gly
    130                 135                 140

Gly Gly Ser Gly Gly Gly Ser Glu Val Gln Leu Val Glu Ser Gly
145                 150                 155                 160

Gly Gly Ser Val Gln Ala Gly Gly Ser Leu Arg Leu Ser Cys Ala Ala
                165                 170                 175

Ser Gly Tyr Thr Tyr Ser Ile Asn Cys Met Gly Trp Phe Arg Gln Ala
            180                 185                 190

Pro Gly Lys Glu Arg Glu Gly Val Ala Val Ile Ser Thr Gly Gly Gly
        195                 200                 205

Arg Thr Asp Tyr Arg Asp Ser Val Lys Gly Arg Phe Thr Ile Ser Gln
    210                 215                 220

Asp Asn Ala Lys Asn Thr Val Tyr Leu Gln Met Asn Ser Leu Lys Pro
225                 230                 235                 240

Glu Asp Thr Ala Met Tyr Tyr Cys Ala Gly Lys Thr Thr Tyr Pro Gly
                245                 250                 255

Tyr Gly Cys Gly Leu Gly Arg Ser Ala Tyr Asn Tyr Trp Gly Gln Gly
            260                 265                 270

Thr Gln Val Thr Val Ser Ser Ile Glu Val Met Tyr Pro Pro Pro Tyr
        275                 280                 285

Leu Asp Asn Glu Lys Ser Asn Gly Thr Ile Ile His Val Lys Gly Lys
    290                 295                 300

His Leu Cys Pro Ser Pro Leu Phe Pro Gly Pro Ser Lys Pro Phe Trp
305                 310                 315                 320

```
Val Leu Val Val Val Gly Gly Val Leu Ala Cys Tyr Ser Leu Leu Val
            325                 330                 335

Thr Val Ala Phe Ile Ile Phe Trp Val Arg Ser Lys Arg Ser Arg Leu
        340                 345                 350

Leu His Ser Asp Tyr Met Asn Met Thr Pro Arg Arg Pro Gly Pro Thr
            355                 360                 365

Arg Lys His Tyr Gln Pro Tyr Ala Pro Pro Arg Asp Phe Ala Ala Tyr
        370                 375                 380

Arg Ser Arg Val Lys Phe Ser Arg Ser Ala Asp Ala Pro Ala Tyr Lys
385                 390                 395                 400

Gln Gly Gln Asn Gln Leu Tyr Asn Glu Leu Asn Leu Gly Arg Arg Glu
            405                 410                 415

Glu Tyr Asp Val Leu Asp Lys Arg Arg Gly Arg Asp Pro Glu Met Gly
        420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
        450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
            485                 490                 495

Pro Arg

<210> SEQ ID NO 173
<211> LENGTH: 503
<212> TYPE: PRT
<213> ORGANISM: Artificial Sequence
<220> FEATURE:
<223> OTHER INFORMATION: Synthetic Construct

<400> SEQUENCE: 173

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Ser
            20                  25                  30

Val Gln Ala Gly Gly Ala Leu Ser Leu Ser Cys Ala Ala Ser Gly Tyr
        35                  40                  45

Thr Val Arg Ile Asp Tyr Met Gly Trp Tyr Arg Gln Thr Pro Gly Lys
    50                  55                  60

Gly Arg Glu Pro Val Ala Thr Ile Ala Ser Asn Gly Thr Ala Tyr
65                  70                  75                  80

Ala Asp Ser Val Glu Gly Arg Phe Thr Ile Ser Gln Asp Asn Ala Lys
            85                  90                  95

Asn Ser Val Tyr Leu Gln Met Asn Thr Leu Lys Pro Gly Asp Thr Ala
            100                 105                 110

Met Tyr Tyr Cys Ala Ala Gly Thr Trp Pro Thr Leu Thr Tyr Phe Gly
        115                 120                 125

Gln Gly Thr Gln Val Thr Val Ser Ser Gly Gly Gly Ser Gly Gly
        130                 135                 140

Gly Gly Ser Gly Gly Gly Gly Ser Gly Gly Gly Gly Ser Glu Val Gln
145                 150                 155                 160

Leu Val Glu Ser Gly Gly Gly Ser Val Gln Ala Gly Gly Ser Leu Arg
            165                 170                 175

Leu Ser Cys Ala Ala Ser Gly Tyr Thr Tyr Ser Ile Asn Cys Met Gly
```

```
                180                 185                 190
Trp Phe Arg Gln Ala Pro Gly Lys Glu Arg Glu Gly Val Ala Val Ile
            195                 200                 205
Ser Thr Gly Gly Gly Arg Thr Asp Tyr Arg Asp Ser Val Lys Gly Arg
        210                 215                 220
Phe Thr Ile Ser Gln Asp Asn Ala Lys Asn Thr Val Tyr Leu Gln Met
225                 230                 235                 240
Asn Ser Leu Lys Pro Glu Asp Thr Ala Met Tyr Tyr Cys Ala Gly Lys
                245                 250                 255
Thr Thr Tyr Pro Gly Tyr Gly Cys Gly Leu Gly Arg Ser Ala Tyr Asn
            260                 265                 270
Tyr Trp Gly Gln Gly Thr Gln Val Thr Val Ser Ser Ile Glu Val Met
        275                 280                 285
Tyr Pro Pro Pro Tyr Leu Asp Asn Glu Lys Ser Asn Gly Thr Ile Ile
        290                 295                 300
His Val Lys Gly Lys His Leu Cys Pro Ser Pro Leu Phe Pro Gly Pro
305                 310                 315                 320
Ser Lys Pro Phe Trp Val Leu Val Val Val Gly Gly Val Leu Ala Cys
                325                 330                 335
Tyr Ser Leu Leu Val Thr Val Ala Phe Ile Ile Phe Trp Val Arg Ser
            340                 345                 350
Lys Arg Ser Arg Leu Leu His Ser Asp Tyr Met Asn Met Thr Pro Arg
        355                 360                 365
Arg Pro Gly Pro Thr Arg Lys His Tyr Gln Pro Tyr Ala Pro Pro Arg
        370                 375                 380
Asp Phe Ala Ala Tyr Arg Ser Arg Val Lys Phe Ser Arg Ser Ala Asp
385                 390                 395                 400
Ala Pro Ala Tyr Lys Gln Gly Gln Asn Gln Leu Tyr Asn Glu Leu Asn
                405                 410                 415
Leu Gly Arg Arg Glu Glu Tyr Asp Val Leu Asp Lys Arg Arg Gly Arg
            420                 425                 430
Asp Pro Glu Met Gly Gly Lys Pro Arg Arg Lys Asn Pro Gln Glu Gly
        435                 440                 445
Leu Tyr Asn Glu Leu Gln Lys Asp Lys Met Ala Glu Ala Tyr Ser Glu
        450                 455                 460
Ile Gly Met Lys Gly Glu Arg Arg Arg Gly Lys Gly His Asp Gly Leu
465                 470                 475                 480
Tyr Gln Gly Leu Ser Thr Ala Thr Lys Asp Thr Tyr Asp Ala Leu His
                485                 490                 495
Met Gln Ala Leu Pro Pro Arg
            500

<210> SEQ ID NO 174
<211> LENGTH: 508
<212> TYPE: PRT
<213> ORGANISM: Artificial Sequence
<220> FEATURE:
<223> OTHER INFORMATION: Synthetic Construct

<400> SEQUENCE: 174

Met Ala Leu Pro Val Thr Ala Leu Leu Leu Pro Leu Ala Leu Leu Leu
1               5                   10                  15
His Ala Ala Arg Pro Gln Val Gln Leu Val Glu Ser Gly Gly Gly Ser
            20                  25                  30
Val Gln Ala Gly Gly Ala Leu Ser Leu Ser Cys Ala Ala Ser Gly Tyr
```

-continued

```
             35                  40                  45
Thr Val Arg Ile Asp Tyr Met Gly Trp Tyr Arg Gln Thr Pro Gly Lys
 50                  55                  60
Gly Arg Glu Pro Val Ala Thr Ile Ala Ser Asn Gly Gly Thr Ala Tyr
 65                  70                  75                  80
Ala Asp Ser Val Glu Gly Arg Phe Thr Ile Ser Gln Asp Asn Ala Lys
                 85                  90                  95
Asn Ser Val Tyr Leu Gln Met Asn Thr Leu Lys Pro Gly Asp Thr Ala
            100                 105                 110
Met Tyr Tyr Cys Ala Ala Gly Thr Trp Pro Thr Leu Thr Tyr Phe Gly
            115                 120                 125
Gln Gly Thr Gln Val Thr Val Ser Ser Gly Gly Gly Ser Gly Gly
            130                 135                 140
Gly Gly Ser Gly Gly Gly Ser Gly Gly Gly Ser Gly Gly
145                 150                 155                 160
Gly Ser Glu Val Gln Leu Val Glu Ser Gly Gly Gly Ser Val Gln Ala
                165                 170                 175
Gly Gly Ser Leu Arg Leu Ser Cys Ala Ala Ser Gly Tyr Thr Tyr Ser
            180                 185                 190
Ile Asn Cys Met Gly Trp Phe Arg Gln Ala Pro Gly Lys Glu Arg Glu
            195                 200                 205
Gly Val Ala Val Ile Ser Thr Gly Gly Arg Thr Asp Tyr Arg Asp
            210                 215                 220
Ser Val Lys Gly Arg Phe Thr Ile Ser Gln Asp Asn Ala Lys Asn Thr
225                 230                 235                 240
Val Tyr Leu Gln Met Asn Ser Leu Lys Pro Glu Asp Thr Ala Met Tyr
                245                 250                 255
Tyr Cys Ala Gly Lys Thr Thr Tyr Pro Gly Tyr Gly Cys Gly Leu Gly
            260                 265                 270
Arg Ser Ala Tyr Asn Tyr Trp Gly Gln Gly Thr Gln Val Thr Val Ser
            275                 280                 285
Ser Ile Glu Val Met Tyr Pro Pro Tyr Leu Asp Asn Glu Lys Ser
            290                 295                 300
Asn Gly Thr Ile Ile His Val Lys Gly Lys His Leu Cys Pro Ser Pro
305                 310                 315                 320
Leu Phe Pro Gly Pro Ser Lys Pro Phe Trp Val Leu Val Val Val Gly
                325                 330                 335
Gly Val Leu Ala Cys Tyr Ser Leu Leu Val Thr Val Ala Phe Ile Ile
            340                 345                 350
Phe Trp Val Arg Ser Lys Arg Ser Arg Leu Leu His Ser Asp Tyr Met
            355                 360                 365
Asn Met Thr Pro Arg Arg Pro Gly Pro Thr Arg Lys His Tyr Gln Pro
            370                 375                 380
Tyr Ala Pro Pro Arg Asp Phe Ala Ala Tyr Arg Ser Arg Val Lys Phe
385                 390                 395                 400
Ser Arg Ser Ala Asp Ala Pro Ala Tyr Lys Gln Gly Gln Asn Gln Leu
                405                 410                 415
Tyr Asn Glu Leu Asn Leu Gly Arg Arg Glu Glu Tyr Asp Val Leu Asp
            420                 425                 430
Lys Arg Arg Gly Arg Asp Pro Glu Met Gly Gly Lys Pro Arg Arg Lys
            435                 440                 445
Asn Pro Gln Glu Gly Leu Tyr Asn Glu Leu Gln Lys Asp Lys Met Ala
            450                 455                 460
```

```
Glu Ala Tyr Ser Glu Ile Gly Met Lys Gly Glu Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
                500                 505

<210> SEQ ID NO 175
<211> LENGTH: 501
<212> TYPE: PRT
<213> ORGANISM: Artificial Sequence
<220> FEATURE:
<223> OTHER INFORMATION: Synthetic Construct

<400> SEQUENCE: 175

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Ser
                20                  25                  30

Val Gln Ala Gly Gly Ala Leu Ser Leu Ser Cys Ala Ala Ser Gly Tyr
            35                  40                  45

Thr Val Arg Ile Asp Tyr Met Gly Trp Tyr Arg Gln Thr Pro Gly Lys
        50                  55                  60

Gly Arg Glu Pro Val Ala Thr Ile Ala Ser Asn Gly Thr Ala Tyr
65                  70                  75                  80

Ala Asp Ser Val Glu Gly Arg Phe Thr Ile Ser Gln Asp Asn Ala Lys
                85                  90                  95

Asn Ser Val Tyr Leu Gln Met Asn Thr Leu Lys Pro Gly Asp Thr Ala
                100                 105                 110

Met Tyr Tyr Cys Ala Ala Gly Thr Trp Pro Thr Leu Thr Tyr Phe Gly
            115                 120                 125

Gln Gly Thr Gln Val Thr Val Ser Ser Gly Ser Thr Ser Gly Ser Gly
        130                 135                 140

Lys Pro Gly Ser Gly Glu Gly Ser Thr Lys Gly Glu Val Gln Leu Val
145                 150                 155                 160

Glu Ser Gly Gly Gly Ser Val Gln Ala Gly Gly Ser Leu Arg Leu Ser
                165                 170                 175

Cys Ala Ala Ser Gly Tyr Thr Tyr Ser Ile Asn Cys Met Gly Trp Phe
            180                 185                 190

Arg Gln Ala Pro Gly Lys Glu Arg Glu Gly Val Ala Val Ile Ser Thr
        195                 200                 205

Gly Gly Gly Arg Thr Asp Tyr Arg Asp Ser Val Lys Gly Arg Phe Thr
    210                 215                 220

Ile Ser Gln Asp Asn Ala Lys Asn Thr Val Tyr Leu Gln Met Asn Ser
225                 230                 235                 240

Leu Lys Pro Glu Asp Thr Ala Met Tyr Tyr Cys Ala Gly Lys Thr Thr
                245                 250                 255

Tyr Pro Gly Tyr Gly Cys Gly Leu Gly Arg Ser Ala Tyr Asn Tyr Trp
                260                 265                 270

Gly Gln Gly Thr Gln Val Thr Val Ser Ser Ile Glu Val Met Tyr Pro
            275                 280                 285

Pro Pro Tyr Leu Asp Asn Glu Lys Ser Asn Gly Thr Ile Ile His Val
        290                 295                 300

Lys Gly Lys His Leu Cys Pro Ser Pro Leu Phe Pro Gly Pro Ser Lys
305                 310                 315                 320
```

```
Pro Phe Trp Val Leu Val Val Gly Gly Val Leu Ala Cys Tyr Ser
                325                 330                 335

Leu Leu Val Thr Val Ala Phe Ile Ile Phe Trp Val Arg Ser Lys Arg
                340                 345                 350

Ser Arg Leu Leu His Ser Asp Tyr Met Asn Met Thr Pro Arg Arg Pro
                355                 360                 365

Gly Pro Thr Arg Lys His Tyr Gln Pro Tyr Ala Pro Pro Arg Asp Phe
            370                 375                 380

Ala Ala Tyr Arg Ser Arg Val Lys Phe Ser Arg Ser Ala Asp Ala Pro
385                 390                 395                 400

Ala Tyr Lys Gln Gly Gln Asn Gln Leu Tyr Asn Glu Leu Asn Leu Gly
                405                 410                 415

Arg Arg Glu Glu Tyr Asp Val Leu Asp Lys Arg Arg Gly Arg Asp Pro
                420                 425                 430

Glu Met Gly Gly Lys Pro Arg Arg Lys Asn Pro Gln Glu Gly Leu Tyr
                435                 440                 445

Asn Glu Leu Gln Lys Asp Lys Met Ala Glu Ala Tyr Ser Glu Ile Gly
            450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495

Ala Leu Pro Pro Arg
                500

<210> SEQ ID NO 176
<211> LENGTH: 488
<212> TYPE: PRT
<213> ORGANISM: Artificial Sequence
<220> FEATURE:
<223> OTHER INFORMATION: Synthetic Construct

<400> SEQUENCE: 176

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Ser
                20                  25                  30

Val Gln Ala Gly Gly Ser Leu Arg Leu Ser Cys Ala Ala Ser Gly Tyr
            35                  40                  45

Thr Tyr Ser Ile Asn Cys Met Gly Trp Phe Arg Gln Ala Pro Gly Lys
        50                  55                  60

Glu Arg Glu Gly Val Ala Val Ile Ser Thr Gly Gly Arg Thr Asp
65                  70                  75                  80

Tyr Arg Asp Ser Val Lys Gly Arg Phe Thr Ile Ser Gln Asp Asn Ala
                85                  90                  95

Lys Asn Thr Val Tyr Leu Gln Met Asn Ser Leu Lys Pro Glu Asp Thr
                100                 105                 110

Ala Met Tyr Tyr Cys Ala Gly Lys Thr Thr Tyr Pro Gly Tyr Gly Cys
            115                 120                 125

Gly Leu Gly Arg Ser Ala Tyr Asn Tyr Trp Gly Gln Gly Thr Gln Val
        130                 135                 140

Thr Val Ser Ser Gly Gly Gly Ser Gln Val Gln Leu Val Glu Ser
145                 150                 155                 160

Gly Gly Gly Ser Val Gln Ala Gly Gly Ala Leu Ser Leu Ser Cys Ala
                165                 170                 175
```

```
Ala Ser Gly Tyr Thr Val Arg Ile Asp Tyr Met Gly Trp Tyr Arg Gln
            180                 185                 190

Thr Pro Gly Lys Gly Arg Glu Pro Val Ala Thr Ile Ala Ser Asn Gly
            195                 200                 205

Gly Thr Ala Tyr Ala Asp Ser Val Glu Gly Arg Phe Thr Ile Ser Gln
            210                 215                 220

Asp Asn Ala Lys Asn Ser Val Tyr Leu Gln Met Asn Thr Leu Lys Pro
225                 230                 235                 240

Gly Asp Thr Ala Met Tyr Tyr Cys Ala Ala Gly Thr Trp Pro Thr Leu
            245                 250                 255

Thr Tyr Phe Gly Gln Gly Thr Gln Val Thr Val Ser Ser Ile Glu Val
            260                 265                 270

Met Tyr Pro Pro Pro Tyr Leu Asp Asn Glu Lys Ser Asn Gly Thr Ile
            275                 280                 285

Ile His Val Lys Gly Lys His Leu Cys Pro Ser Pro Leu Phe Pro Gly
            290                 295                 300

Pro Ser Lys Pro Phe Trp Val Leu Val Val Val Gly Gly Val Leu Ala
305                 310                 315                 320

Cys Tyr Ser Leu Leu Val Thr Val Ala Phe Ile Ile Phe Trp Val Arg
            325                 330                 335

Ser Lys Arg Ser Arg Leu Leu His Ser Asp Tyr Met Asn Met Thr Pro
            340                 345                 350

Arg Arg Pro Gly Pro Thr Arg Lys His Tyr Gln Pro Tyr Ala Pro Pro
            355                 360                 365

Arg Asp Phe Ala Ala Tyr Arg Ser Arg Val Lys Phe Ser Arg Ser Ala
            370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
            405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
            450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
            485

<210> SEQ ID NO 177
<211> LENGTH: 493
<212> TYPE: PRT
<213> ORGANISM: Artificial Sequence
<220> FEATURE:
<223> OTHER INFORMATION: Synthetic Construct

<400> SEQUENCE: 177

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Ser
            20                  25                  30

Val Gln Ala Gly Gly Ser Leu Arg Leu Ser Cys Ala Ala Ser Gly Tyr
            35                  40                  45
```

```
Thr Tyr Ser Ile Asn Cys Met Gly Trp Phe Arg Gln Ala Pro Gly Lys
 50                  55                  60

Glu Arg Glu Gly Val Ala Val Ile Ser Thr Gly Gly Arg Thr Asp
 65                  70                  75                  80

Tyr Arg Asp Ser Val Lys Gly Arg Phe Thr Ile Ser Gln Asp Asn Ala
                 85                  90                  95

Lys Asn Thr Val Tyr Leu Gln Met Asn Ser Leu Lys Pro Glu Asp Thr
                100                 105                 110

Ala Met Tyr Tyr Cys Ala Gly Lys Thr Thr Tyr Pro Gly Tyr Gly Cys
             115                 120                 125

Gly Leu Gly Arg Ser Ala Tyr Asn Tyr Trp Gly Gln Gly Thr Gln Val
         130                 135                 140

Thr Val Ser Ser Gly Gly Gly Ser Gly Gly Gly Ser Gln Val
145                 150                 155                 160

Gln Leu Val Glu Ser Gly Gly Ser Val Gln Ala Gly Ala Leu
                165                 170                 175

Ser Leu Ser Cys Ala Ala Ser Gly Tyr Thr Val Arg Ile Asp Tyr Met
             180                 185                 190

Gly Trp Tyr Arg Gln Thr Pro Gly Lys Gly Arg Glu Pro Val Ala Thr
         195                 200                 205

Ile Ala Ser Asn Gly Gly Thr Ala Tyr Ala Asp Ser Val Glu Gly Arg
     210                 215                 220

Phe Thr Ile Ser Gln Asp Asn Ala Lys Asn Ser Val Tyr Leu Gln Met
225                 230                 235                 240

Asn Thr Leu Lys Pro Gly Asp Thr Ala Met Tyr Tyr Cys Ala Ala Gly
                245                 250                 255

Thr Trp Pro Thr Leu Thr Tyr Phe Gly Gln Gly Thr Gln Val Thr Val
             260                 265                 270

Ser Ser Ile Glu Val Met Tyr Pro Pro Tyr Leu Asp Asn Glu Lys
         275                 280                 285

Ser Asn Gly Thr Ile Ile His Val Lys Gly Lys His Leu Cys Pro Ser
     290                 295                 300

Pro Leu Phe Pro Gly Pro Ser Lys Pro Phe Trp Val Leu Val Val Val
305                 310                 315                 320

Gly Gly Val Leu Ala Cys Tyr Ser Leu Leu Val Thr Val Ala Phe Ile
                325                 330                 335

Ile Phe Trp Val Arg Ser Lys Arg Ser Arg Leu Leu His Ser Asp Tyr
             340                 345                 350

Met Asn Met Thr Pro Arg Arg Pro Gly Pro Thr Arg Lys His Tyr Gln
         355                 360                 365

Pro Tyr Ala Pro Pro Arg Asp Phe Ala Ala Tyr Arg Ser Arg Val Lys
     370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
             420                 425                 430

Lys Asn Pro Gln Glu Gly Leu Tyr Asn Glu Leu Gln Lys Asp Lys Met
         435                 440                 445

Ala Glu Ala Tyr Ser Glu Ile Gly Met Lys Gly Glu Arg Arg Arg Gly
     450                 455                 460
```

```
Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
            485                 490

<210> SEQ ID NO 178
<211> LENGTH: 498
<212> TYPE: PRT
<213> ORGANISM: Artificial Sequence
<220> FEATURE:
<223> OTHER INFORMATION: Synthetic Construct

<400> SEQUENCE: 178

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Ser
            20                  25                  30

Val Gln Ala Gly Gly Ser Leu Arg Leu Ser Cys Ala Ala Ser Gly Tyr
        35                  40                  45

Thr Tyr Ser Ile Asn Cys Met Gly Trp Phe Arg Gln Ala Pro Gly Lys
    50                  55                  60

Glu Arg Glu Gly Val Ala Val Ile Ser Thr Gly Gly Arg Thr Asp
65                  70                  75                  80

Tyr Arg Asp Ser Val Lys Gly Arg Phe Thr Ile Ser Gln Asp Asn Ala
                85                  90                  95

Lys Asn Thr Val Tyr Leu Gln Met Asn Ser Leu Lys Pro Glu Asp Thr
            100                 105                 110

Ala Met Tyr Tyr Cys Ala Gly Lys Thr Thr Tyr Pro Gly Tyr Gly Cys
        115                 120                 125

Gly Leu Gly Arg Ser Ala Tyr Asn Tyr Trp Gly Gln Gly Thr Gln Val
    130                 135                 140

Thr Val Ser Ser Gly Gly Gly Ser Gly Gly Gly Gly Ser Gly Gly
145                 150                 155                 160

Gly Gly Ser Gln Val Gln Leu Val Glu Ser Gly Gly Gly Ser Val Gln
                165                 170                 175

Ala Gly Gly Ala Leu Ser Leu Ser Cys Ala Ala Ser Gly Tyr Thr Val
            180                 185                 190

Arg Ile Asp Tyr Met Gly Trp Tyr Arg Gln Thr Pro Gly Lys Gly Arg
        195                 200                 205

Glu Pro Val Ala Thr Ile Ala Ser Asn Gly Gly Thr Ala Tyr Ala Asp
    210                 215                 220

Ser Val Glu Gly Arg Phe Thr Ile Ser Gln Asp Asn Ala Lys Asn Ser
225                 230                 235                 240

Val Tyr Leu Gln Met Asn Thr Leu Lys Pro Gly Asp Thr Ala Met Tyr
                245                 250                 255

Tyr Cys Ala Ala Gly Thr Trp Pro Thr Leu Thr Tyr Phe Gly Gln Gly
            260                 265                 270

Thr Gln Val Thr Val Ser Ser Ile Glu Val Met Tyr Pro Pro Pro Tyr
        275                 280                 285

Leu Asp Asn Glu Lys Ser Asn Gly Thr Ile Ile His Val Lys Gly Lys
    290                 295                 300

His Leu Cys Pro Ser Pro Leu Phe Pro Gly Pro Ser Lys Pro Phe Trp
305                 310                 315                 320

Val Leu Val Val Val Gly Gly Val Leu Ala Cys Tyr Ser Leu Leu Val
                325                 330                 335
```

Thr Val Ala Phe Ile Ile Phe Trp Val Arg Ser Lys Arg Ser Arg Leu
              340                 345                 350

Leu His Ser Asp Tyr Met Asn Met Thr Pro Arg Arg Pro Gly Pro Thr
        355                 360                 365

Arg Lys His Tyr Gln Pro Tyr Ala Pro Pro Arg Asp Phe Ala Ala Tyr
370                 375                 380

Arg Ser Arg Val Lys Phe Ser Arg Ser Ala Asp Ala Pro Ala Tyr Lys
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
        420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
        450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg

<210> SEQ ID NO 179
<211> LENGTH: 503
<212> TYPE: PRT
<213> ORGANISM: Artificial Sequence
<220> FEATURE:
<223> OTHER INFORMATION: Synthetic Construct

<400> SEQUENCE: 179

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Ser
                20                  25                  30

Val Gln Ala Gly Gly Ser Leu Arg Leu Ser Cys Ala Ala Ser Gly Tyr
            35                  40                  45

Thr Tyr Ser Ile Asn Cys Met Gly Trp Phe Arg Gln Ala Pro Gly Lys
        50                  55                  60

Glu Arg Glu Gly Val Ala Val Ile Ser Thr Gly Gly Arg Thr Asp
65                  70                  75                  80

Tyr Arg Asp Ser Val Lys Gly Arg Phe Thr Ile Ser Gln Asp Asn Ala
                85                  90                  95

Lys Asn Thr Val Tyr Leu Gln Met Asn Ser Leu Lys Pro Glu Asp Thr
            100                 105                 110

Ala Met Tyr Tyr Cys Ala Gly Lys Thr Thr Tyr Pro Gly Tyr Gly Cys
        115                 120                 125

Gly Leu Gly Arg Ser Ala Tyr Asn Tyr Trp Gly Gln Gly Thr Gln Val
    130                 135                 140

Thr Val Ser Ser Gly Gly Gly Ser Gly Gly Gly Gly Ser Gly Gly
145                 150                 155                 160

Gly Gly Ser Gly Gly Gly Ser Gln Val Gln Leu Val Glu Ser Gly
                165                 170                 175

Gly Gly Ser Val Gln Ala Gly Gly Ala Leu Ser Leu Ser Cys Ala Ala
            180                 185                 190

Ser Gly Tyr Thr Val Arg Ile Asp Tyr Met Gly Trp Tyr Arg Gln Thr

```
                195                 200                 205
Pro Gly Lys Gly Arg Glu Pro Val Ala Thr Ile Ala Ser Asn Gly Gly
            210                 215                 220

Thr Ala Tyr Ala Asp Ser Val Glu Gly Arg Phe Thr Ile Ser Gln Asp
225                 230                 235                 240

Asn Ala Lys Asn Ser Val Tyr Leu Gln Met Asn Thr Leu Lys Pro Gly
                245                 250                 255

Asp Thr Ala Met Tyr Tyr Cys Ala Ala Gly Thr Trp Pro Thr Leu Thr
            260                 265                 270

Tyr Phe Gly Gln Gly Thr Gln Val Thr Val Ser Ser Ile Glu Val Met
        275                 280                 285

Tyr Pro Pro Pro Tyr Leu Asp Asn Glu Lys Ser Asn Gly Thr Ile Ile
        290                 295                 300

His Val Lys Gly Lys His Leu Cys Pro Ser Pro Leu Phe Pro Gly Pro
305                 310                 315                 320

Ser Lys Pro Phe Trp Val Leu Val Val Val Gly Gly Val Leu Ala Cys
                325                 330                 335

Tyr Ser Leu Leu Val Thr Val Ala Phe Ile Ile Phe Trp Val Arg Ser
            340                 345                 350

Lys Arg Ser Arg Leu Leu His Ser Asp Tyr Met Asn Met Thr Pro Arg
        355                 360                 365

Arg Pro Gly Pro Thr Arg Lys His Tyr Gln Pro Tyr Ala Pro Pro Arg
        370                 375                 380

Asp Phe Ala Ala Tyr Arg Ser Arg Val Lys Phe Ser Arg Ser Ala Asp
385                 390                 395                 400

Ala Pro Ala Tyr Lys Gln Gly Gln Asn Gln Leu Tyr Asn Glu Leu Asn
                405                 410                 415

Leu Gly Arg Arg Glu Glu Tyr Asp Val Leu Asp Lys Arg Arg Gly Arg
            420                 425                 430

Asp Pro Glu Met Gly Gly Lys Pro Arg Arg Lys Asn Pro Gln Glu Gly
        435                 440                 445

Leu Tyr Asn Glu Leu Gln Lys Asp Lys Met Ala Glu Ala Tyr Ser Glu
        450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
                485                 490                 495

Met Gln Ala Leu Pro Pro Arg
            500

<210> SEQ ID NO 180
<211> LENGTH: 508
<212> TYPE: PRT
<213> ORGANISM: Artificial Sequence
<220> FEATURE:
<223> OTHER INFORMATION: Synthetic Construct

<400> SEQUENCE: 180

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Ser
                20                  25                  30

Val Gln Ala Gly Gly Ser Leu Arg Leu Ser Cys Ala Ala Ser Gly Tyr
            35                  40                  45

Thr Tyr Ser Ile Asn Cys Met Gly Trp Phe Arg Gln Ala Pro Gly Lys
```

-continued

```
                50                  55                  60
Glu Arg Glu Gly Val Ala Val Ile Ser Thr Gly Gly Arg Thr Asp
65                  70                  75                  80

Tyr Arg Asp Ser Val Lys Gly Arg Phe Thr Ile Ser Gln Asp Asn Ala
                85                  90                  95

Lys Asn Thr Val Tyr Leu Gln Met Asn Ser Leu Lys Pro Glu Asp Thr
                100                 105                 110

Ala Met Tyr Tyr Cys Ala Gly Lys Thr Thr Tyr Pro Gly Tyr Gly Cys
                115                 120                 125

Gly Leu Gly Arg Ser Ala Tyr Asn Tyr Trp Gly Gln Gly Thr Gln Val
            130                 135                 140

Thr Val Ser Ser Gly Gly Gly Ser Gly Gly Gly Ser Gly Gly
145                 150                 155                 160

Gly Gly Ser Gly Gly Gly Gly Ser Gly Gly Gly Ser Gln Val Gln
                165                 170                 175

Leu Val Glu Ser Gly Gly Gly Ser Val Gln Ala Gly Gly Ala Leu Ser
                180                 185                 190

Leu Ser Cys Ala Ala Ser Gly Tyr Thr Val Arg Ile Asp Tyr Met Gly
            195                 200                 205

Trp Tyr Arg Gln Thr Pro Gly Lys Gly Arg Glu Pro Val Ala Thr Ile
210                 215                 220

Ala Ser Asn Gly Gly Thr Ala Tyr Ala Asp Ser Val Glu Gly Arg Phe
225                 230                 235                 240

Thr Ile Ser Gln Asp Asn Ala Lys Asn Ser Val Tyr Leu Gln Met Asn
                245                 250                 255

Thr Leu Lys Pro Gly Asp Thr Ala Met Tyr Tyr Cys Ala Ala Gly Thr
                260                 265                 270

Trp Pro Thr Leu Thr Tyr Phe Gly Gln Gly Thr Gln Val Thr Val Ser
                275                 280                 285

Ser Ile Glu Val Met Tyr Pro Pro Pro Tyr Leu Asp Asn Glu Lys Ser
            290                 295                 300

Asn Gly Thr Ile Ile His Val Lys Gly Lys His Leu Cys Pro Ser Pro
305                 310                 315                 320

Leu Phe Pro Gly Pro Ser Lys Pro Phe Trp Val Leu Val Val Val Gly
                325                 330                 335

Gly Val Leu Ala Cys Tyr Ser Leu Leu Val Thr Val Ala Phe Ile Ile
                340                 345                 350

Phe Trp Val Arg Ser Lys Arg Ser Arg Leu Leu His Ser Asp Tyr Met
                355                 360                 365

Asn Met Thr Pro Arg Arg Pro Gly Pro Thr Arg Lys His Tyr Gln Pro
370                 375                 380

Tyr Ala Pro Pro Arg Asp Phe Ala Ala Tyr Arg Ser Arg Val Lys Phe
385                 390                 395                 400

Ser Arg Ser Ala Asp Ala Pro Ala Tyr Lys Gln Gly Gln Asn Gln Leu
                405                 410                 415

Tyr Asn Glu Leu Asn Leu Gly Arg Arg Glu Glu Tyr Asp Val Leu Asp
                420                 425                 430

Lys Arg Arg Gly Arg Asp Pro Glu Met Gly Gly Lys Pro Arg Arg Lys
            435                 440                 445

Asn Pro Gln Glu Gly Leu Tyr Asn Glu Leu Gln Lys Asp Lys Met Ala
            450                 455                 460

Glu Ala Tyr Ser Glu Ile Gly Met Lys Gly Glu Arg Arg Arg Gly Lys
465                 470                 475                 480
```

Gly His Asp Gly Leu Tyr Gln Gly Leu Ser Thr Ala Thr Lys Asp Thr
            485                 490                 495

Tyr Asp Ala Leu His Met Gln Ala Leu Pro Pro Arg
            500                 505

<210> SEQ ID NO 181
<211> LENGTH: 501
<212> TYPE: PRT
<213> ORGANISM: Artificial Sequence
<220> FEATURE:
<223> OTHER INFORMATION: Synthetic Construct

<400> SEQUENCE: 181

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Ser
            20                  25                  30

Val Gln Ala Gly Gly Ser Leu Arg Leu Ser Cys Ala Ala Ser Gly Tyr
        35                  40                  45

Thr Tyr Ser Ile Asn Cys Met Gly Trp Phe Arg Gln Ala Pro Gly Lys
    50                  55                  60

Glu Arg Glu Gly Val Ala Val Ile Ser Thr Gly Gly Arg Thr Asp
65                  70                  75                  80

Tyr Arg Asp Ser Val Lys Gly Arg Phe Thr Ile Ser Gln Asp Asn Ala
                85                  90                  95

Lys Asn Thr Val Tyr Leu Gln Met Asn Ser Leu Lys Pro Glu Asp Thr
            100                 105                 110

Ala Met Tyr Tyr Cys Ala Gly Lys Thr Thr Tyr Pro Gly Tyr Gly Cys
        115                 120                 125

Gly Leu Gly Arg Ser Ala Tyr Asn Tyr Trp Gly Gln Gly Thr Gln Val
    130                 135                 140

Thr Val Ser Ser Gly Ser Thr Ser Gly Ser Gly Lys Pro Gly Ser Gly
145                 150                 155                 160

Glu Gly Ser Thr Lys Gly Gln Val Gln Leu Val Glu Ser Gly Gly Gly
                165                 170                 175

Ser Val Gln Ala Gly Gly Ala Leu Ser Leu Ser Cys Ala Ala Ser Gly
            180                 185                 190

Tyr Thr Val Arg Ile Asp Tyr Met Gly Trp Tyr Arg Gln Thr Pro Gly
        195                 200                 205

Lys Gly Arg Glu Pro Val Ala Thr Ile Ala Ser Asn Gly Gly Thr Ala
    210                 215                 220

Tyr Ala Asp Ser Val Glu Gly Arg Phe Thr Ile Ser Gln Asp Asn Ala
225                 230                 235                 240

Lys Asn Ser Val Tyr Leu Gln Met Asn Thr Leu Lys Pro Gly Asp Thr
                245                 250                 255

Ala Met Tyr Tyr Cys Ala Ala Gly Thr Trp Pro Thr Leu Thr Tyr Phe
            260                 265                 270

Gly Gln Gly Thr Gln Val Thr Val Ser Ser Ile Glu Val Met Tyr Pro
        275                 280                 285

Pro Pro Tyr Leu Asp Asn Glu Lys Ser Asn Gly Thr Ile Ile His Val
    290                 295                 300

Lys Gly Lys His Leu Cys Pro Ser Pro Leu Phe Pro Gly Pro Ser Lys
305                 310                 315                 320

Pro Phe Trp Val Leu Val Val Val Gly Gly Val Leu Ala Cys Tyr Ser
                325                 330                 335

```
Leu Leu Val Thr Val Ala Phe Ile Ile Phe Trp Val Arg Ser Lys Arg
            340                 345                 350

Ser Arg Leu Leu His Ser Asp Tyr Met Asn Met Thr Pro Arg Arg Pro
            355                 360                 365

Gly Pro Thr Arg Lys His Tyr Gln Pro Tyr Ala Pro Pro Arg Asp Phe
            370                 375                 380

Ala Ala Tyr Arg Ser Arg Val Lys Phe Ser Arg Ser Ala Asp Ala Pro
385                 390                 395                 400

Ala Tyr Lys Gln Gly Gln Asn Gln Leu Tyr Asn Glu Leu Asn Leu Gly
            405                 410                 415

Arg Arg Glu Glu Tyr Asp Val Leu Asp Lys Arg Arg Gly Arg Asp Pro
            420                 425                 430

Glu Met Gly Gly Lys Pro Arg Arg Lys Asn Pro Gln Glu Gly Leu Tyr
            435                 440                 445

Asn Glu Leu Gln Lys Asp Lys Met Ala Glu Ala Tyr Ser Glu Ile Gly
            450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
            485                 490                 495

Ala Leu Pro Pro Arg
            500

<210> SEQ ID NO 182
<211> LENGTH: 368
<212> TYPE: PRT
<213> ORGANISM: Artificial Sequence
<220> FEATURE:
<223> OTHER INFORMATION: Synthetic Construct

<400> SEQUENCE: 182

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Asn
            35                  40                  45

Val Phe Arg Phe Asn Ile Met Gly Trp Tyr Arg Gln Ala Pro Gly Asn
        50                  55                  60

Gln Arg Glu Leu Val Ala Ser Ile Asp Asp Gly Gly Asp Arg Ser Tyr
65                  70                  75                  80

Ala Asp Ser Val Glu Gly Arg Phe Thr Ile Ser Arg Glu Asn Gly Lys
                85                  90                  95

Lys Ile Met Tyr Leu Gln Met Asn Ser Leu Lys Pro Glu Asp Thr Ala
            100                 105                 110

Val Tyr Tyr Cys Ala Ala Gly Leu Gly Thr Tyr Leu Asn Gly Arg Val
            115                 120                 125

Ser Met Ala Thr Asn Tyr Trp Gly Gln Gly Thr Gln Val Thr Val Ser
        130                 135                 140

Ser Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Ile Tyr
            180                 185                 190
```

```
Ile Trp Ala Pro Leu Ala Gly Thr Cys Gly Val Leu Leu Ser Leu
            195                 200                 205

Val Ile Thr Leu Tyr Cys Lys Arg Gly Arg Lys Leu Leu Tyr Ile
210                 215                 220

Phe Lys Gln Pro Phe Met Arg Pro Val Gln Thr Thr Gln Glu Glu Asp
225                 230                 235                 240

Gly Cys Ser Cys Arg Phe Pro Glu Glu Glu Glu Gly Gly Cys Glu Leu
                245                 250                 255

Arg Val Lys Phe Ser Arg Ser Ala Asp Ala Pro Ala Tyr Lys Gln Gly
                260                 265                 270

Gln Asn Gln Leu Tyr Asn Glu Leu Asn Leu Gly Arg Arg Glu Glu Tyr
                275                 280                 285

Asp Val Leu Asp Lys Arg Arg Gly Arg Asp Pro Glu Met Gly Gly Lys
                290                 295                 300

Pro Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
                325                 330                 335

Arg Arg Gly Lys Gly His Asp Gly Leu Tyr Gln Gly Leu Ser Thr Ala
                340                 345                 350

Thr Lys Asp Thr Tyr Asp Ala Leu His Met Gln Ala Leu Pro Pro Arg
                355                 360                 365

<210> SEQ ID NO 183
<211> LENGTH: 753
<212> TYPE: PRT
<213> ORGANISM: Artificial Sequence
<220> FEATURE:
<223> OTHER INFORMATION: Synthetic Construct

<400> SEQUENCE: 183

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Asp Leu
                20                  25                  30

Val Arg Pro Gly Gly Ser Leu Arg Leu Ser Cys Ala Ala Ser Gly Phe
            35                  40                  45

Thr Phe Ser Ile Tyr Asp Met Asn Trp Val Arg Gln Ala Pro Gly Lys
        50                  55                  60

Gly Leu Glu Trp Val Ala Gly Ile Ser Gly Asn Gly Tyr Ser Thr Ser
65                  70                  75                  80

Tyr Ala Glu Ser Val Lys Gly Arg Phe Thr Ile Ser Arg Asp Asn Ala
                85                  90                  95

Lys Asn Thr Val Tyr Leu Gln Leu Ser Ser Leu Lys Phe Glu Asp Thr
            100                 105                 110

Ala Met Tyr Tyr Cys Val Arg Asp Ala Glu Arg Trp Asp Glu Asn Asp
        115                 120                 125

Leu Arg Arg Lys Gly Gln Gly Thr Gln Val Thr Val Ser Ser Ile Glu
    130                 135                 140

Val Met Tyr Pro Pro Tyr Leu Asp Asn Glu Lys Ser Asn Gly Thr
145                 150                 155                 160

Ile Ile His Val Lys Gly Lys His Leu Cys Pro Ser Pro Leu Phe Pro
                165                 170                 175

Gly Pro Ser Lys Pro Phe Trp Val Leu Val Val Val Gly Gly Val Leu
            180                 185                 190
```

```
Ala Cys Tyr Ser Leu Leu Val Thr Val Ala Phe Ile Ile Phe Trp Val
            195                 200                 205

Arg Ser Lys Arg Ser Arg Leu Leu His Ser Asp Tyr Met Asn Met Thr
210                 215                 220

Pro Arg Arg Pro Gly Pro Thr Arg Lys His Tyr Gln Pro Tyr Ala Pro
225                 230                 235                 240

Pro Arg Asp Phe Ala Ala Tyr Arg Ser Arg Val Lys Phe Ser Arg Ser
            245                 250                 255

Ala Asp Ala Pro Ala Tyr Lys Gln Gly Gln Asn Gln Leu Tyr Asn Glu
            260                 265                 270

Leu Asn Leu Gly Arg Arg Glu Tyr Asp Val Leu Asp Lys Arg Arg
            275                 280                 285

Gly Arg Asp Pro Glu Met Gly Gly Lys Pro Arg Arg Lys Asn Pro Gln
290                 295                 300

Glu Gly Leu Tyr Asn Glu Leu Gln Lys Asp Lys Met Ala Glu Ala Tyr
305                 310                 315                 320

Ser Glu Ile Gly Met Lys Gly Glu Arg Arg Arg Gly Lys Gly His Asp
            325                 330                 335

Gly Leu Tyr Gln Gly Leu Ser Thr Ala Thr Lys Asp Thr Tyr Asp Ala
            340                 345                 350

Leu His Met Gln Ala Leu Pro Pro Arg Gly Ser Gly Ala Thr Asn Phe
            355                 360                 365

Ser Leu Leu Lys Gln Ala Gly Asp Val Glu Glu Asn Pro Gly Pro Met
370                 375                 380

Ala Leu Pro Val Thr Ala Leu Leu Leu Pro Leu Ala Leu Leu Leu His
385                 390                 395                 400

Ala Ala Arg Pro Gln Ile Gln Leu Val Glu Ser Gly Gly Gly Ser Val
            405                 410                 415

Gln Ala Gly Gly Ser Leu Arg Leu Ser Cys Val Ala Ser Gly Tyr Ile
            420                 425                 430

Gly Gly His Tyr Tyr Met Gly Trp Phe Arg Gln Ala Pro Gly Lys Glu
            435                 440                 445

Arg Glu Gly Val Ala Ala Ile Asp Ile Asp Ser Asp Gly Arg Thr Arg
            450                 455                 460

Tyr Ala Gly Ser Val Gln Gly Arg Phe Thr Ile Ser Gln Asp Asn Ala
465                 470                 475                 480

Lys Asn Thr Leu His Leu Gln Met Ser Ser Leu Lys Pro Glu Asp Thr
            485                 490                 495

Gly Met Tyr Tyr Cys Ala Val Gly Val Gly Trp Val Pro Ala Arg Leu
            500                 505                 510

Thr Pro Gln Ala Val Ser Tyr Trp Gly Lys Gly Thr Leu Val Thr Val
            515                 520                 525

Ser Ser Thr Thr Thr Pro Ala Pro Arg Pro Pro Thr Pro Ala Pro Thr
530                 535                 540

Ile Ala Ser Gln Pro Leu Ser Leu Arg Pro Glu Ala Cys Arg Pro Ala
545                 550                 555                 560

Ala Gly Gly Ala Val His Thr Arg Gly Leu Asp Phe Ala Cys Asp Ile
            565                 570                 575

Tyr Ile Trp Ala Pro Leu Ala Gly Thr Cys Gly Val Leu Leu Leu Ser
            580                 585                 590

Leu Val Ile Thr Leu Tyr Cys Lys Arg Gly Arg Lys Lys Leu Leu Tyr
            595                 600                 605
```

```
Ile Phe Lys Gln Pro Phe Met Arg Pro Val Gln Thr Thr Gln Glu Glu
    610                 615                 620

Asp Gly Cys Ser Cys Arg Phe Pro Glu Glu Glu Gly Gly Cys Glu
625                 630                 635                 640

Leu Arg Val Lys Phe Ser Arg Ser Ala Asp Ala Pro Ala Tyr Lys Gln
                645                 650                 655

Gly Gln Asn Gln Leu Tyr Asn Glu Leu Asn Leu Gly Arg Arg Glu Glu
            660                 665                 670

Tyr Asp Val Leu Asp Lys Arg Gly Arg Asp Pro Glu Met Gly Gly
                675                 680                 685

Lys Pro Arg Arg Lys Asn Pro Gln Glu Gly Leu Tyr Asn Glu Leu Gln
690                 695                 700

Lys Asp Lys Met Ala Glu Ala Tyr Ser Glu Ile Gly Met Lys Gly Glu
705                 710                 715                 720

Arg Arg Arg Gly Lys Gly His Asp Gly Leu Tyr Gln Gly Leu Ser Thr
                725                 730                 735

Ala Thr Lys Asp Thr Tyr Asp Ala Leu His Met Gln Ala Leu Pro Pro
                740                 745                 750

Arg

<210> SEQ ID NO 184
<211> LENGTH: 753
<212> TYPE: PRT
<213> ORGANISM: Artificial Sequence
<220> FEATURE:
<223> OTHER INFORMATION: Synthetic Construct

<400> SEQUENCE: 184

Met Ala Leu Pro Val Thr Ala Leu Leu Pro Leu Ala Leu Leu Leu
1               5                   10                  15

His Ala Ala Arg Pro Gln Val Gln Leu Val Glu Ser Gly Gly Asp Leu
                20                  25                  30

Val Arg Pro Gly Gly Ser Leu Arg Leu Ser Cys Ala Ala Ser Gly Phe
            35                  40                  45

Thr Phe Ser Ile Tyr Asp Met Asn Trp Val Arg Gln Ala Pro Gly Lys
50                  55                  60

Gly Leu Glu Trp Val Ala Gly Ile Ser Gly Asn Gly Tyr Ser Thr Ser
65                  70                  75                  80

Tyr Ala Glu Ser Val Lys Gly Arg Phe Thr Ile Ser Arg Asp Asn Ala
                85                  90                  95

Lys Asn Thr Val Tyr Leu Gln Leu Ser Ser Leu Lys Phe Glu Asp Thr
                100                 105                 110

Ala Met Tyr Tyr Cys Val Arg Asp Ala Glu Arg Trp Asp Glu Asn Asp
            115                 120                 125

Leu Arg Arg Lys Gly Gln Gly Thr Gln Val Thr Val Ser Ser Ile Glu
130                 135                 140

Val Met Tyr Pro Pro Tyr Leu Asp Asn Glu Lys Ser Asn Gly Thr
145                 150                 155                 160

Ile Ile His Val Lys Gly Lys His Leu Cys Pro Ser Pro Leu Phe Pro
                165                 170                 175

Gly Pro Ser Lys Pro Phe Trp Val Leu Val Val Val Gly Gly Val Leu
            180                 185                 190

Ala Cys Tyr Ser Leu Leu Val Thr Val Ala Phe Ile Ile Phe Trp Val
            195                 200                 205

Arg Ser Lys Arg Ser Arg Leu Leu His Ser Asp Tyr Met Asn Met Thr
```

-continued

```
            210                 215                 220
Pro Arg Arg Pro Gly Pro Thr Arg Lys His Tyr Gln Pro Tyr Ala Pro
225                 230                 235                 240

Pro Arg Asp Phe Ala Ala Tyr Arg Ser Arg Val Lys Phe Ser Arg Ser
                245                 250                 255

Ala Asp Ala Pro Ala Tyr Lys Gln Gly Gln Asn Gln Leu Tyr Asn Glu
                260                 265                 270

Leu Asn Leu Gly Arg Arg Glu Glu Tyr Asp Val Leu Asp Lys Arg Arg
            275                 280                 285

Gly Arg Asp Pro Glu Met Gly Gly Lys Pro Arg Arg Lys Asn Pro Gln
        290                 295                 300

Glu Gly Leu Tyr Asn Glu Leu Gln Lys Asp Lys Met Ala Glu Ala Tyr
305                 310                 315                 320

Ser Glu Ile Gly Met Lys Gly Glu Arg Arg Arg Gly Lys Gly His Asp
                325                 330                 335

Gly Leu Tyr Gln Gly Leu Ser Thr Ala Thr Lys Asp Thr Tyr Asp Ala
                340                 345                 350

Leu His Met Gln Ala Leu Pro Pro Arg Gly Ser Gly Ala Thr Asn Phe
            355                 360                 365

Ser Leu Leu Lys Gln Ala Gly Asp Val Glu Glu Asn Pro Gly Pro Met
        370                 375                 380

Ala Leu Pro Val Thr Ala Leu Leu Leu Pro Leu Ala Leu Leu Leu His
385                 390                 395                 400

Ala Ala Arg Pro Gln Val Gln Leu Val Glu Ser Gly Gly Gly Leu Val
                405                 410                 415

Gln Ala Gly Gly Ser Leu Arg Leu Ser Cys Thr Ala Ser Gly Phe Thr
                420                 425                 430

Phe Asp Asn Tyr Val Met Gly Trp Phe Arg Gln Ala Pro Gly Lys Glu
            435                 440                 445

Arg Glu Gly Val Ser Cys Ile Gly Trp Ser Gly Gly Ser Thr Tyr Tyr
        450                 455                 460

Ala Asp Ser Val Lys Gly Arg Phe Thr Ile Ser Arg Asp Asn Ala Lys
465                 470                 475                 480

Asn Thr Leu Tyr Leu Gln Met Asn Ser Leu Lys Pro Glu Asp Thr Ala
                485                 490                 495

Met Tyr Tyr Cys Ala Ala Asp Gln Gly Lys Cys Ser Leu Gly Ser Ala
                500                 505                 510

Gly Ala Asp Asp Met Asp Tyr Trp Gly Arg Gly Thr Leu Val Thr Val
            515                 520                 525

Ser Ser Thr Thr Thr Pro Ala Pro Arg Pro Pro Thr Pro Ala Pro Thr
        530                 535                 540

Ile Ala Ser Gln Pro Leu Ser Leu Arg Pro Glu Ala Cys Arg Pro Ala
545                 550                 555                 560

Ala Gly Gly Ala Val His Thr Arg Gly Leu Asp Phe Ala Cys Asp Ile
                565                 570                 575

Tyr Ile Trp Ala Pro Leu Ala Gly Thr Cys Gly Val Leu Leu Leu Ser
                580                 585                 590

Leu Val Ile Thr Leu Tyr Cys Lys Arg Gly Arg Lys Lys Leu Leu Tyr
            595                 600                 605

Ile Phe Lys Gln Pro Phe Met Arg Pro Val Gln Thr Thr Gln Glu Glu
        610                 615                 620

Asp Gly Cys Ser Cys Arg Phe Pro Glu Glu Glu Glu Gly Gly Cys Glu
625                 630                 635                 640
```

```
Leu Arg Val Lys Phe Ser Arg Ser Ala Asp Ala Pro Ala Tyr Lys Gln
                645                 650                 655

Gly Gln Asn Gln Leu Tyr Asn Glu Leu Asn Leu Gly Arg Arg Glu Glu
            660                 665                 670

Tyr Asp Val Leu Asp Lys Arg Gly Arg Asp Pro Glu Met Gly Gly
        675                 680                 685

Lys Pro Arg Arg Lys Asn Pro Gln Glu Gly Leu Tyr Asn Glu Leu Gln
690                 695                 700

Lys Asp Lys Met Ala Glu Ala Tyr Ser Glu Ile Gly Met Lys Gly Glu
705                 710                 715                 720

Arg Arg Arg Gly Lys Gly His Asp Gly Leu Tyr Gln Gly Leu Ser Thr
                725                 730                 735

Ala Thr Lys Asp Thr Tyr Asp Ala Leu His Met Gln Ala Leu Pro Pro
            740                 745                 750

Arg
```

```
<210> SEQ ID NO 185
<211> LENGTH: 742
<212> TYPE: PRT
<213> ORGANISM: Artificial Sequence
<220> FEATURE:
<223> OTHER INFORMATION: Synthetic Construct

<400> SEQUENCE: 185

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Val Tyr Asp Met Asn Trp Phe Arg Gln Ala Pro Gly Lys
    50                  55                  60

Gly Leu Glu Trp Val Ser Gly Ile Thr Gly Asn Gly Tyr Thr Thr Ser
65                  70                  75                  80

Tyr Ala Asp Ser Val Lys Gly Arg Phe Thr Ile Ser Arg Asp Asn Ala
                85                  90                  95

Lys Asn Thr Leu Tyr Leu Gln Leu Asn Ser Leu Lys Ser Glu Asp Thr
            100                 105                 110

Ala Met Tyr Tyr Cys Ala Lys Glu Thr Asn Arg Gly Gln Gly Thr Gln
        115                 120                 125

Val Thr Val Ser Ser Ile Glu Val Met Tyr Pro Pro Pro Tyr Leu Asp
    130                 135                 140

Asn Glu Lys Ser Asn Gly Thr Ile Ile His Val Lys Gly Lys His Leu
145                 150                 155                 160

Cys Pro Ser Pro Leu Phe Pro Gly Pro Ser Lys Pro Phe Trp Val Leu
                165                 170                 175

Val Val Val Gly Gly Val Leu Ala Cys Tyr Ser Leu Leu Val Thr Val
            180                 185                 190

Ala Phe Ile Ile Phe Trp Val Arg Ser Lys Arg Ser Arg Leu Leu His
        195                 200                 205

Ser Asp Tyr Met Asn Met Thr Pro Arg Arg Pro Gly Pro Thr Arg Lys
    210                 215                 220

His Tyr Gln Pro Tyr Ala Pro Pro Arg Asp Phe Ala Ala Tyr Arg Ser
225                 230                 235                 240
```

```
Arg Val Lys Phe Ser Arg Ser Ala Asp Ala Pro Ala Tyr Lys Gln Gly
            245                 250                 255

Gln Asn Gln Leu Tyr Asn Glu Leu Asn Leu Gly Arg Arg Glu Glu Tyr
        260                 265                 270

Asp Val Leu Asp Lys Arg Arg Gly Arg Asp Pro Glu Met Gly Gly Lys
        275                 280                 285

Pro Arg Arg Lys Asn Pro Gln Glu Gly Leu Tyr Asn Glu Leu Gln Lys
        290                 295                 300

Asp Lys Met Ala Glu Ala Tyr Ser Glu Ile Gly Met Lys Gly Glu Arg
305                 310                 315                 320

Arg Arg Gly Lys Gly His Asp Gly Leu Tyr Gln Gly Leu Ser Thr Ala
                325                 330                 335

Thr Lys Asp Thr Tyr Asp Ala Leu His Met Gln Ala Leu Pro Pro Arg
            340                 345                 350

Gly Ser Gly Ala Thr Asn Phe Ser Leu Leu Lys Gln Ala Gly Asp Val
        355                 360                 365

Glu Glu Asn Pro Gly Pro Met Ala Leu Pro Val Thr Ala Leu Leu Leu
        370                 375                 380

Pro Leu Ala Leu Leu Leu His Ala Ala Arg Pro Gln Val Gln Leu Val
385                 390                 395                 400

Glu Ser Gly Gly Gly Leu Val Gln Ala Gly Gly Ser Leu Arg Leu Ser
                405                 410                 415

Cys Ala Ala Ser Gly Asn Val Phe Arg Phe Asn Ile Met Gly Trp Tyr
            420                 425                 430

Arg Gln Ala Pro Gly Asn Gln Arg Glu Leu Val Ala Ser Ile Asp Asp
        435                 440                 445

Gly Gly Asp Arg Ser Tyr Ala Asp Ser Val Glu Gly Arg Phe Thr Ile
    450                 455                 460

Ser Arg Glu Asn Gly Lys Lys Ile Met Tyr Leu Gln Met Asn Ser Leu
465                 470                 475                 480

Lys Pro Glu Asp Thr Ala Val Tyr Tyr Cys Ala Ala Gly Leu Gly Thr
                485                 490                 495

Tyr Leu Asn Gly Arg Val Ser Met Ala Thr Asn Tyr Trp Gly Gln Gly
            500                 505                 510

Thr Gln Val Thr Val Ser Ser Thr Thr Pro Ala Pro Arg Pro Pro
        515                 520                 525

Thr Pro Ala Pro Thr Ile Ala Ser Gln Pro Leu Ser Leu Arg Pro Glu
        530                 535                 540

Ala Cys Arg Pro Ala Ala Gly Gly Ala Val His Thr Arg Gly Leu Asp
545                 550                 555                 560

Phe Ala Cys Asp Ile Tyr Ile Trp Ala Pro Leu Ala Gly Thr Cys Gly
                565                 570                 575

Val Leu Leu Leu Ser Leu Val Ile Thr Leu Tyr Cys Lys Arg Gly Arg
            580                 585                 590

Lys Lys Leu Leu Tyr Ile Phe Lys Gln Pro Phe Met Arg Pro Val Gln
        595                 600                 605

Thr Thr Gln Glu Glu Asp Gly Cys Ser Cys Arg Phe Pro Glu Glu Glu
        610                 615                 620

Glu Gly Gly Cys Glu Leu Arg Val Lys Phe Ser Arg Ser Ala Asp Ala
625                 630                 635                 640

Pro Ala Tyr Lys Gln Gly Gln Asn Gln Leu Tyr Asn Glu Leu Asn Leu
                645                 650                 655

Gly Arg Arg Glu Glu Tyr Asp Val Leu Asp Lys Arg Arg Gly Arg Asp
```

```
              660                 665                 670
Pro Glu Met Gly Gly Lys Pro Arg Arg Lys Asn Pro Gln Glu Gly Leu
            675                 680                 685
Tyr Asn Glu Leu Gln Lys Asp Lys Met Ala Glu Ala Tyr Ser Glu Ile
            690                 695                 700
Gly Met Lys Gly Glu Arg Arg Gly Lys Gly His Asp Gly Leu Tyr
705                 710                 715                 720
Gln Gly Leu Ser Thr Ala Thr Lys Asp Thr Tyr Asp Ala Leu His Met
                725                 730                 735
Gln Ala Leu Pro Pro Arg
            740

<210> SEQ ID NO 186
<211> LENGTH: 361
<212> TYPE: PRT
<213> ORGANISM: Artificial Sequence
<220> FEATURE:
<223> OTHER INFORMATION: Synthetic Construct

<400> SEQUENCE: 186

Met Ala Leu Pro Val Thr Ala Leu Leu Leu Pro Leu Ala Leu Leu Leu
1               5                   10                  15
His Ala Ala Arg Pro Gln Val Gln Leu Val Glu Ser Gly Gly Asp Leu
            20                  25                  30
Val Arg Pro Gly Gly Ser Leu Arg Leu Ser Cys Ala Ala Ser Gly Phe
        35                  40                  45
Thr Phe Ser Ile Tyr Asp Met Asn Trp Val Arg Gln Ala Pro Gly Lys
    50                  55                  60
Gly Leu Glu Trp Val Ala Gly Ile Ser Gly Asn Gly Tyr Ser Thr Ser
65                  70                  75                  80
Tyr Ala Glu Ser Val Lys Gly Arg Phe Thr Ile Ser Arg Asp Asn Ala
                85                  90                  95
Lys Asn Thr Val Tyr Leu Gln Leu Ser Ser Leu Lys Phe Glu Asp Thr
            100                 105                 110
Ala Met Tyr Tyr Cys Val Arg Asp Ala Glu Arg Trp Asp Glu Asn Asp
        115                 120                 125
Leu Arg Arg Lys Gly Gln Gly Thr Gln Val Thr Val Ser Ser Ile Glu
    130                 135                 140
Val Met Tyr Pro Pro Pro Tyr Leu Asp Asn Glu Lys Ser Asn Gly Thr
145                 150                 155                 160
Ile Ile His Val Lys Gly Lys His Leu Cys Pro Ser Pro Leu Phe Pro
                165                 170                 175
Gly Pro Ser Lys Pro Phe Trp Val Leu Val Val Val Gly Gly Val Leu
            180                 185                 190
Ala Cys Tyr Ser Leu Leu Val Thr Val Ala Phe Ile Ile Phe Trp Val
        195                 200                 205
Arg Ser Lys Arg Ser Arg Leu Leu His Ser Asp Tyr Met Asn Met Thr
    210                 215                 220
Pro Arg Arg Pro Gly Pro Thr Arg Lys His Tyr Gln Pro Tyr Ala Pro
225                 230                 235                 240
Pro Arg Asp Phe Ala Ala Tyr Arg Ser Arg Val Lys Phe Ser Arg Ser
                245                 250                 255
Ala Asp Ala Pro Ala Tyr Lys Gln Gly Gln Asn Gln Leu Tyr Asn Glu
            260                 265                 270
Leu Asn Leu Gly Arg Arg Glu Glu Tyr Asp Val Leu Asp Lys Arg Arg
```

```
                275                 280                 285
Gly Arg Asp Pro Glu Met Gly Gly Lys Pro Arg Arg Lys Asn Pro Gln
    290                 295                 300
Glu Gly Leu Tyr Asn Glu Leu Gln Lys Asp Lys Met Ala Glu Ala Tyr
305                 310                 315                 320
Ser Glu Ile Gly Met Lys Gly Glu Arg Arg Arg Gly Lys Gly His Asp
                325                 330                 335
Gly Leu Tyr Gln Gly Leu Ser Thr Ala Thr Lys Asp Thr Tyr Asp Ala
            340                 345                 350
Leu His Met Gln Ala Leu Pro Pro Arg
            355                 360

<210> SEQ ID NO 187
<211> LENGTH: 352
<212> TYPE: PRT
<213> ORGANISM: Artificial Sequence
<220> FEATURE:
<223> OTHER INFORMATION: Synthetic Construct

<400> SEQUENCE: 187

Met Ala Leu Pro Val Thr Ala Leu Leu Leu Pro Leu Ala Leu Leu Leu
1               5                   10                  15
His Ala Ala Arg Pro Gln Val Gln Leu Val Glu Ser Gly Gly Gly Leu
            20                  25                  30
Val Gln Pro Gly Gly Ser Leu Arg Leu Ser Cys Ala Ala Ser Gly Phe
        35                  40                  45
Thr Phe Ser Val Tyr Asp Met Asn Trp Phe Arg Gln Ala Pro Gly Lys
    50                  55                  60
Gly Leu Glu Trp Val Ser Gly Ile Thr Gly Asn Gly Tyr Thr Thr Ser
65                  70                  75                  80
Tyr Ala Asp Ser Val Lys Gly Arg Phe Thr Ile Ser Arg Asp Asn Ala
                85                  90                  95
Lys Asn Thr Leu Tyr Leu Gln Leu Asn Ser Leu Lys Ser Glu Asp Thr
            100                 105                 110
Ala Met Tyr Tyr Cys Ala Lys Glu Thr Asn Arg Gly Gln Gly Thr Gln
        115                 120                 125
Val Thr Val Ser Ser Ile Glu Val Met Tyr Pro Pro Pro Tyr Leu Asp
    130                 135                 140
Asn Glu Lys Ser Asn Gly Thr Ile Ile His Val Lys Gly Lys His Leu
145                 150                 155                 160
Cys Pro Ser Pro Leu Phe Pro Gly Pro Ser Lys Pro Phe Trp Val Leu
                165                 170                 175
Val Val Val Gly Gly Val Leu Ala Cys Tyr Ser Leu Leu Val Thr Val
            180                 185                 190
Ala Phe Ile Ile Phe Trp Val Arg Ser Lys Arg Ser Arg Leu Leu His
        195                 200                 205
Ser Asp Tyr Met Asn Met Thr Pro Arg Arg Pro Gly Pro Thr Arg Lys
    210                 215                 220
His Tyr Gln Pro Tyr Ala Pro Pro Arg Asp Phe Ala Ala Tyr Arg Ser
225                 230                 235                 240
Arg Val Lys Phe Ser Arg Ser Ala Asp Ala Pro Ala Tyr Lys Gln Gly
                245                 250                 255
Gln Asn Gln Leu Tyr Asn Glu Leu Asn Leu Gly Arg Arg Glu Glu Tyr
            260                 265                 270
Asp Val Leu Asp Lys Arg Arg Gly Arg Asp Pro Glu Met Gly Gly Lys
```

```
                275                 280                 285
Pro Arg Arg Lys Asn Pro Gln Glu Gly Leu Tyr Asn Glu Leu Gln Lys
    290                 295                 300

Asp Lys Met Ala Glu Ala Tyr Ser Glu Ile Gly Met Lys Gly Glu Arg
305                 310                 315                 320

Arg Arg Gly Lys Gly His Asp Gly Leu Tyr Gln Gly Leu Ser Thr Ala
                325                 330                 335

Thr Lys Asp Thr Tyr Asp Ala Leu His Met Gln Ala Leu Pro Pro Arg
                340                 345                 350

<210> SEQ ID NO 188
<211> LENGTH: 25
<212> TYPE: PRT
<213> ORGANISM: Artificial Sequence
<220> FEATURE:
<223> OTHER INFORMATION: Synthetic Construct

<400> SEQUENCE: 188

Gln Val Gln Leu Val Glu Ser Gly Gly Gly Ser Val Gln Ala Gly Gly
1               5                   10                  15

Ala Leu Ser Leu Ser Cys Ala Ala Ser
            20                  25

<210> SEQ ID NO 189
<211> LENGTH: 10
<212> TYPE: PRT
<213> ORGANISM: Artificial Sequence
<220> FEATURE:
<223> OTHER INFORMATION: Synthetic Construct

<400> SEQUENCE: 189

Gly Tyr Thr Val Arg Ile Asp Tyr Met Gly
1               5                   10

<210> SEQ ID NO 190
<211> LENGTH: 14
<212> TYPE: PRT
<213> ORGANISM: Artificial Sequence
<220> FEATURE:
<223> OTHER INFORMATION: Synthetic Construct

<400> SEQUENCE: 190

Trp Tyr Arg Gln Thr Pro Gly Lys Gly Arg Glu Pro Val Ala
1               5                   10

<210> SEQ ID NO 191
<211> LENGTH: 16
<212> TYPE: PRT
<213> ORGANISM: Artificial Sequence
<220> FEATURE:
<223> OTHER INFORMATION: Synthetic Construct

<400> SEQUENCE: 191

Thr Ile Ala Ser Asn Gly Gly Thr Ala Tyr Ala Asp Ser Val Glu Gly
1               5                   10                  15

<210> SEQ ID NO 192
<211> LENGTH: 32
<212> TYPE: PRT
<213> ORGANISM: Artificial Sequence
<220> FEATURE:
<223> OTHER INFORMATION: Synthetic Construct

<400> SEQUENCE: 192
```

```
Arg Phe Thr Ile Ser Gln Asp Asn Ala Lys Asn Ser Val Tyr Leu Gln
1               5                   10                  15

Met Asn Thr Leu Lys Pro Gly Asp Thr Ala Met Tyr Tyr Cys Ala Ala
            20                  25                  30

<210> SEQ ID NO 193
<211> LENGTH: 8
<212> TYPE: PRT
<213> ORGANISM: Artificial Sequence
<220> FEATURE:
<223> OTHER INFORMATION: Synthetic Construct

<400> SEQUENCE: 193

Gly Thr Trp Pro Thr Leu Thr Tyr
1               5

<210> SEQ ID NO 194
<211> LENGTH: 11
<212> TYPE: PRT
<213> ORGANISM: Artificial Sequence
<220> FEATURE:
<223> OTHER INFORMATION: Synthetic Construct

<400> SEQUENCE: 194

Phe Gly Gln Gly Thr Gln Val Thr Val Ser Ser
1               5                   10

<210> SEQ ID NO 195
<211> LENGTH: 25
<212> TYPE: PRT
<213> ORGANISM: Artificial Sequence
<220> FEATURE:
<223> OTHER INFORMATION: Synthetic Construct

<400> SEQUENCE: 195

Gln Val Gln Leu Val Glu Ser Gly Gly Asp Leu Val Arg Pro Gly Gly
1               5                   10                  15

Ser Leu Arg Leu Ser Cys Ala Ala Ser
            20                  25

<210> SEQ ID NO 196
<211> LENGTH: 10
<212> TYPE: PRT
<213> ORGANISM: Artificial Sequence
<220> FEATURE:
<223> OTHER INFORMATION: Synthetic Construct

<400> SEQUENCE: 196

Gly Phe Thr Phe Ser Ile Tyr Asp Met Asn
1               5                   10

<210> SEQ ID NO 197
<211> LENGTH: 14
<212> TYPE: PRT
<213> ORGANISM: Artificial Sequence
<220> FEATURE:
<223> OTHER INFORMATION: Synthetic Construct

<400> SEQUENCE: 197

Trp Val Arg Gln Ala Pro Gly Lys Gly Leu Glu Trp Val Ala
1               5                   10

<210> SEQ ID NO 198
<211> LENGTH: 17
<212> TYPE: PRT
<213> ORGANISM: Artificial Sequence
```

-continued

```
<220> FEATURE:
<223> OTHER INFORMATION: Synthetic Construct

<400> SEQUENCE: 198

Gly Ile Ser Gly Asn Gly Tyr Ser Thr Ser Tyr Ala Glu Ser Val Lys
1               5                   10                  15

Gly

<210> SEQ ID NO 199
<211> LENGTH: 32
<212> TYPE: PRT
<213> ORGANISM: Artificial Sequence
<220> FEATURE:
<223> OTHER INFORMATION: Synthetic Construct

<400> SEQUENCE: 199

Arg Phe Thr Ile Ser Arg Asp Asn Ala Lys Asn Thr Val Tyr Leu Gln
1               5                   10                  15

Leu Ser Ser Leu Lys Phe Glu Asp Thr Ala Met Tyr Tyr Cys Val Arg
            20                  25                  30

<210> SEQ ID NO 200
<211> LENGTH: 12
<212> TYPE: PRT
<213> ORGANISM: Artificial Sequence
<220> FEATURE:
<223> OTHER INFORMATION: Synthetic Construct

<400> SEQUENCE: 200

Asp Ala Glu Arg Trp Asp Glu Asn Asp Leu Arg Arg
1               5                   10

<210> SEQ ID NO 201
<211> LENGTH: 11
<212> TYPE: PRT
<213> ORGANISM: Artificial Sequence
<220> FEATURE:
<223> OTHER INFORMATION: Synthetic Construct

<400> SEQUENCE: 201

Lys Gly Gln Gly Thr Gln Val Thr Val Ser Ser
1               5                   10

<210> SEQ ID NO 202
<211> LENGTH: 25
<212> TYPE: PRT
<213> ORGANISM: Artificial Sequence
<220> FEATURE:
<223> OTHER INFORMATION: Synthetic Construct

<400> SEQUENCE: 202

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 203
<211> LENGTH: 10
<212> TYPE: PRT
<213> ORGANISM: Artificial Sequence
<220> FEATURE:
<223> OTHER INFORMATION: Synthetic Construct

<400> SEQUENCE: 203

Gly Phe Thr Phe Ser Val Tyr Asp Met Asn
```

```
<210> SEQ ID NO 204
<211> LENGTH: 14
<212> TYPE: PRT
<213> ORGANISM: Artificial Sequence
<220> FEATURE:
<223> OTHER INFORMATION: Synthetic Construct

<400> SEQUENCE: 204

Trp Phe Arg Gln Ala Pro Gly Lys Gly Leu Glu Trp Val Ser
1               5                   10

<210> SEQ ID NO 205
<211> LENGTH: 17
<212> TYPE: PRT
<213> ORGANISM: Artificial Sequence
<220> FEATURE:
<223> OTHER INFORMATION: Synthetic Construct

<400> SEQUENCE: 205

Gly Ile Thr Gly Asn Gly Tyr Thr Thr Ser Tyr Ala Asp Ser Val Lys
1               5                   10                  15

Gly

<210> SEQ ID NO 206
<211> LENGTH: 32
<212> TYPE: PRT
<213> ORGANISM: Artificial Sequence
<220> FEATURE:
<223> OTHER INFORMATION: Synthetic Construct

<400> SEQUENCE: 206

Arg Phe Thr Ile Ser Arg Asp Asn Ala Lys Asn Thr Leu Tyr Leu Gln
1               5                   10                  15

Leu Asn Ser Leu Lys Ser Glu Asp Thr Ala Met Tyr Tyr Cys Ala Lys
            20                  25                  30

<210> SEQ ID NO 207
<211> LENGTH: 3
<212> TYPE: PRT
<213> ORGANISM: Artificial Sequence
<220> FEATURE:
<223> OTHER INFORMATION: Synthetic Construct

<400> SEQUENCE: 207

Glu Thr Asn
1

<210> SEQ ID NO 208
<211> LENGTH: 11
<212> TYPE: PRT
<213> ORGANISM: Artificial Sequence
<220> FEATURE:
<223> OTHER INFORMATION: Synthetic Construct

<400> SEQUENCE: 208

Arg Gly Gln Gly Thr Gln Val Thr Val Ser Ser
1               5                   10

<210> SEQ ID NO 209
<211> LENGTH: 116
<212> TYPE: PRT
<213> ORGANISM: Artificial Sequence
<220> FEATURE:
<223> OTHER INFORMATION: Synthetic Construct
```

<400> SEQUENCE: 209

Gln Val Gln Leu Val Glu Ser Gly Gly Ser Val Gln Ala Gly Gly
1               5                   10                  15

Ala Leu Ser Leu Ser Cys Ala Ala Ser Gly Tyr Thr Val Arg Ile Asp
            20                  25                  30

Tyr Met Gly Trp Tyr Arg Gln Thr Pro Gly Lys Gly Arg Glu Pro Val
        35                  40                  45

Ala Thr Ile Ala Ser Asn Gly Thr Ala Tyr Ala Asp Ser Val Glu
50                  55                  60

Gly Arg Phe Thr Ile Ser Gln Asp Asn Ala Lys Asn Ser Val Tyr Leu
65                  70                  75                  80

Gln Met Asn Thr Leu Lys Pro Gly Asp Thr Ala Met Tyr Tyr Cys Ala
                85                  90                  95

Ala Gly Thr Trp Pro Thr Leu Thr Tyr Phe Gly Gln Gly Thr Gln Val
            100                 105                 110

Thr Val Ser Ser
            115

<210> SEQ ID NO 210
<211> LENGTH: 121
<212> TYPE: PRT
<213> ORGANISM: Artificial Sequence
<220> FEATURE:
<223> OTHER INFORMATION: Synthetic Construct

<400> SEQUENCE: 210

Gln Val Gln Leu Val Glu Ser Gly Gly Asp Leu Val Arg Pro Gly Gly
1               5                   10                  15

Ser Leu Arg Leu Ser Cys Ala Ala Ser Gly Phe Thr Phe Ser Ile Tyr
            20                  25                  30

Asp Met Asn Trp Val Arg Gln Ala Pro Gly Lys Gly Leu Glu Trp Val
        35                  40                  45

Ala Gly Ile Ser Gly Asn Gly Tyr Ser Thr Ser Tyr Ala Glu Ser Val
50                  55                  60

Lys Gly Arg Phe Thr Ile Ser Arg Asp Asn Ala Lys Asn Thr Val Tyr
65                  70                  75                  80

Leu Gln Leu Ser Ser Leu Lys Phe Glu Asp Thr Ala Met Tyr Tyr Cys
                85                  90                  95

Val Arg Asp Ala Glu Arg Trp Asp Gly Asn Asp Leu Arg Arg Lys Gly
            100                 105                 110

Gln Gly Thr Gln Val Thr Val Ser Ser
            115                 120

<210> SEQ ID NO 211
<211> LENGTH: 112
<212> TYPE: PRT
<213> ORGANISM: Artificial Sequence
<220> FEATURE:
<223> OTHER INFORMATION: Synthetic Construct

<400> SEQUENCE: 211

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Asp Met Asn Trp Phe Arg Gln Ala Pro Gly Lys Gly Leu Glu Trp Val
        35                  40                  45

```
Ser Gly Ile Thr Gly Asn Gly Tyr Thr Thr Ser Tyr Ala Asp Ser Val
    50                  55                  60

Lys Gly Arg Phe Thr Ile Ser Arg Asp Asn Ala Lys Asn Thr Leu Tyr
 65                  70                  75                  80

Leu Gln Leu Asn Ser Leu Lys Ser Glu Asp Thr Ala Met Tyr Tyr Cys
                85                  90                  95

Ala Lys Glu Thr Asn Arg Gly Gln Gly Thr Gln Val Thr Val Ser Ser
            100                 105                 110
```

<210> SEQ ID NO 212
<211> LENGTH: 494
<212> TYPE: PRT
<213> ORGANISM: Artificial Sequence
<220> FEATURE:
<223> OTHER INFORMATION: Synthetic Construct

<400> SEQUENCE: 212

```
Met Ala Leu Pro Val Thr Ala Leu Leu Leu Pro Leu Ala Leu Leu Leu
 1               5                  10                  15

His Ala Ala Arg Pro Gln Val Gln Leu Val Gln Ser Gly Ala Glu Val
            20                  25                  30

Lys Lys Pro Gly Glu Ser Val Lys Val Ser Cys Lys Ala Ser Gly Tyr
        35                  40                  45

Thr Phe Thr Asn Tyr Gly Met Asn Trp Val Lys Gln Ala Pro Gly Gln
    50                  55                  60

Gly Leu Glu Trp Met Gly Trp Ile Asn Thr Tyr Thr Gly Glu Pro Thr
 65                  70                  75                  80

Tyr Ala Asp Lys Phe Gln Gly Arg Val Thr Met Thr Thr Asp Thr Ser
                85                  90                  95

Thr Ser Thr Ala Tyr Met Glu Ile Arg Asn Leu Gly Gly Asp Asp Thr
            100                 105                 110

Ala Val Tyr Tyr Cys Ala Arg Trp Ser Trp Ser Asp Gly Tyr Tyr Val
        115                 120                 125

Tyr Phe Asp Tyr Trp Gly Gln Gly Thr Ser Val Thr Val Ser Ser Gly
    130                 135                 140

Gly Gly Gly Ser Gly Gly Gly Gly Ser Gly Gly Gly Gly Ser Asp Ile
145                 150                 155                 160

Val Met Thr Gln Ser Pro Asp Ser Leu Thr Val Ser Leu Gly Glu Arg
                165                 170                 175

Thr Thr Ile Asn Cys Lys Ser Ser Gln Ser Val Leu Asp Ser Ser Thr
            180                 185                 190

Asn Lys Asn Ser Leu Ala Trp Tyr Gln Gln Lys Pro Gly Gln Pro Pro
        195                 200                 205

Lys Leu Leu Leu Ser Trp Ala Ser Thr Arg Glu Ser Gly Ile Pro Asp
    210                 215                 220

Arg Phe Ser Gly Ser Gly Ser Gly Thr Asp Phe Thr Leu Thr Ile Asp
225                 230                 235                 240

Ser Pro Gln Pro Glu Asp Ser Ala Thr Tyr Tyr Cys Gln Gln Ser Ala
                245                 250                 255

His Phe Pro Ile Thr Phe Gly Gln Gly Thr Arg Leu Glu Ile Lys Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300
```

```
Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Ser Leu Val Ile
            325                 330                 335

Thr Leu Tyr Cys Lys Arg Gly Arg Lys Leu Leu Tyr Ile Phe Lys
        340                 345                 350

Gln Pro Phe Met Arg Pro Val Gln Thr Thr Gln Glu Glu Asp Gly Cys
            355                 360                 365

Ser Cys Arg Phe Pro Glu Glu Glu Glu Gly Gly Cys Glu Leu Arg Val
370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
                435                 440                 445

Met Ala Glu Ala Tyr Ser Glu Ile Gly Met Lys Gly Glu Arg Arg Arg
450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490

<210> SEQ ID NO 213
<211> LENGTH: 1011
<212> TYPE: PRT
<213> ORGANISM: Artificial Sequence
<220> FEATURE:
<223> OTHER INFORMATION: Synthetic Construct

<400> SEQUENCE: 213

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
                20                  25                  30

Ser Ala Ser Val Gly Asp Arg Val Thr Ile Thr Cys Arg Ala Ser Gln
            35                  40                  45

Ser Val Ser Thr Ser Ser Tyr Asn Tyr Met His Trp Tyr Gln Gln Lys
        50                  55                  60

Pro Gly Lys Pro Pro Lys Leu Leu Ile Lys Tyr Ala Ser Asn Leu Glu
65                  70                  75                  80

Ser Gly Val Pro Ser Arg Phe Ser Gly Ser Gly Ser Gly Thr Asp Phe
                85                  90                  95

Thr Leu Thr Ile Ser Ser Leu Gln Pro Glu Asp Phe Ala Thr Tyr Tyr
            100                 105                 110

Cys Gln His Ser Trp Glu Ile Pro Leu Thr Phe Gly Gln Gly Thr Lys
        115                 120                 125

Val Glu Ile Lys Gly Gly Gly Gly Ser Gly Gly Gly Gly Ser Gly Gly
    130                 135                 140

Gly Gly Ser Glu Val Gln Leu Val Gln Ser Gly Ala Glu Val Lys Lys
145                 150                 155                 160

Pro Gly Ala Ser Val Lys Val Ser Cys Lys Ala Ser Gly Tyr Ser Phe
                165                 170                 175
```

-continued

```
Thr Asp Tyr Tyr Met His Trp Val Arg Gln Ala Pro Gly Gln Gly Leu
            180                 185                 190

Glu Trp Ile Gly Arg Ile Asn Pro Tyr Asn Gly Ala Ala Phe Tyr Ser
        195                 200                 205

Gln Asn Phe Lys Asp Arg Val Thr Leu Thr Val Asp Thr Ser Thr Ser
210                 215                 220

Thr Ala Tyr Leu Glu Leu Ser Ser Leu Arg Ser Glu Asp Thr Ala Val
225                 230                 235                 240

Tyr Tyr Cys Ala Ile Glu Arg Gly Ala Asp Leu Glu Gly Tyr Ala Met
                245                 250                 255

Asp Tyr Trp Gly Gln Gly Thr Leu Val Thr Val Ser Ser Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Arg Ser Lys Arg Ser Arg Leu Leu His Ser Asp Tyr Met Asn
            340                 345                 350

Met Thr Pro Arg Arg Pro Gly Pro Thr Arg Lys His Tyr Gln Pro Tyr
        355                 360                 365

Ala Pro Pro Arg Asp Phe Ala Ala Tyr Arg Ser Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Gln Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg Gly Ser Gly Ala
                485                 490                 495

Thr Asn Phe Ser Leu Leu Lys Gln Ala Gly Asp Val Glu Glu Asn Pro
            500                 505                 510

Gly Pro Met Ala Leu Pro Val Thr Ala Leu Leu Leu Pro Leu Ala Leu
        515                 520                 525

Leu Leu His Ala Ala Arg Pro Met Ala Asp Tyr Lys Asp Ile Val Met
    530                 535                 540

Thr Gln Ser His Lys Phe Leu Leu Val Ser Val Gly Asp Arg Val Ser
545                 550                 555                 560

Ile Thr Cys Lys Ala Ser Gln Asp Val Ser Thr Ala Val Ala Trp Tyr
                565                 570                 575

Gln Gln Lys Pro Gly Gln Ser Pro Lys Leu Leu Ile Tyr Ser Ala Ser
            580                 585                 590
```

```
Tyr Arg Tyr Thr Gly Val Pro Asp Arg Phe Ile Gly Ser Gly
            595                 600                 605

Thr Asp Phe Thr Leu Thr Ile Ser Ser Val Gln Ala Glu Asp Leu Ala
610                 615                 620

Asp Tyr Phe Cys Gln Gln His Tyr Ser Thr Pro Leu Thr Phe Gly Ala
625                 630                 635                 640

Gly Thr Lys Leu Glu Ile Lys Arg Gly Gly Gly Gly Ser Gly Gly Gly
                645                 650                 655

Gly Ser Gly Gly Gly Gly Ser Ser Gly Gly Ser Glu Val Gln Leu
            660                 665                 670

Lys Glu Ser Gly Pro Gly Leu Val Ala Pro Ser Gln Ser Leu Ser Ile
            675                 680                 685

Thr Cys Thr Val Ser Gly Phe Pro Leu Thr Ser Tyr Gly Val Ser Trp
            690                 695                 700

Val Arg Gln Pro Pro Gly Lys Gly Leu Glu Trp Leu Gly Val Ile Trp
705                 710                 715                 720

Gly Asp Gly Ser Thr Asn Tyr His Ser Ala Leu Ile Ser Arg Leu Ser
                725                 730                 735

Ile Ser Lys Asp Asn Ser Lys Ser Gln Val Phe Leu Lys Leu Asn Asn
                740                 745                 750

Leu Gln Thr Asp Asp Thr Ala Thr Tyr Tyr Cys Ala Arg Asp Thr Tyr
            755                 760                 765

Tyr Pro Tyr Tyr Ala Met Asp Tyr Trp Gly Gln Gly Thr Ser Val Thr
            770                 775                 780

Val Ser Ser Thr Thr Thr Pro Ala Pro Arg Pro Pro Thr Pro Ala Pro
785                 790                 795                 800

Thr Ile Ala Ser Gln Pro Leu Ser Leu Arg Pro Glu Ala Cys Arg Pro
                805                 810                 815

Ala Ala Gly Gly Ala Val His Thr Arg Gly Leu Asp Phe Ala Cys Asp
                820                 825                 830

Ile Tyr Ile Trp Ala Pro Leu Ala Gly Thr Cys Gly Val Leu Leu Leu
            835                 840                 845

Ser Leu Val Ile Thr Leu Tyr Cys Lys Arg Gly Arg Lys Lys Leu Leu
850                 855                 860

Tyr Ile Phe Lys Gln Pro Phe Met Arg Pro Val Gln Thr Thr Gln Glu
865                 870                 875                 880

Glu Asp Gly Cys Ser Cys Arg Phe Pro Glu Glu Glu Glu Gly Gly Cys
                885                 890                 895

Glu Leu Arg Val Lys Phe Ser Arg Ser Ala Asp Ala Pro Ala Tyr Gln
            900                 905                 910

Gln Gly Gln Asn Gln Leu Tyr Asn Glu Leu Asn Leu Gly Arg Arg Glu
            915                 920                 925

Glu Tyr Asp Val Leu Asp Lys Arg Arg Gly Arg Asp Pro Glu Met Gly
            930                 935                 940

Gly Lys Pro Gln Arg Arg Lys Asn Pro Gln Glu Gly Leu Tyr Asn Glu
945                 950                 955                 960

Leu Gln Lys Asp Lys Met Ala Glu Ala Tyr Ser Glu Ile Gly Met Lys
                965                 970                 975

Gly Glu Arg Arg Arg Gly Lys Gly His Asp Gly Leu Tyr Gln Gly Leu
            980                 985                 990

Ser Thr Ala Thr Lys Asp Thr Tyr Asp Ala Leu His Met Gln Ala Leu
            995                 1000                1005

Pro Pro Arg
```

-continued

```
            1010

<210> SEQ ID NO 214
<211> LENGTH: 497
<212> TYPE: PRT
<213> ORGANISM: Artificial Sequence
<220> FEATURE:
<223> OTHER INFORMATION: Synthetic Construct

<400> SEQUENCE: 214

Met Ala Leu Pro Val Thr Ala Leu Leu Leu Pro Leu Ala Leu Leu Leu
1               5                   10                  15

His Ala Ala Arg Pro Met Ala Asp Tyr Lys Asp Ile Val Met Thr Gln
            20                  25                  30

Ser His Lys Phe Leu Leu Val Ser Val Gly Asp Arg Val Ser Ile Thr
        35                  40                  45

Cys Lys Ala Ser Gln Asp Val Ser Thr Ala Val Ala Trp Tyr Gln Gln
    50                  55                  60

Lys Pro Gly Gln Ser Pro Lys Leu Leu Ile Tyr Ser Ala Ser Tyr Arg
65                  70                  75                  80

Tyr Thr Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Asp Tyr
            100                 105                 110

Phe Cys Gln Gln His Tyr Ser Thr Pro Leu Thr Phe Gly Ala Gly Thr
        115                 120                 125

Lys Leu Glu Ile Lys Arg Gly Gly Gly Ser Gly Gly Gly Gly Ser
    130                 135                 140

Gly Gly Gly Gly Ser Gly Gly Gly Ser Glu Val Gln Leu Lys Glu
145                 150                 155                 160

Ser Gly Pro Gly Leu Val Ala Pro Ser Gln Ser Leu Ser Ile Thr Cys
                165                 170                 175

Thr Val Ser Gly Phe Pro Leu Thr Ser Tyr Gly Val Ser Trp Val Arg
            180                 185                 190

Gln Pro Pro Gly Lys Gly Leu Glu Trp Leu Gly Val Ile Trp Gly Asp
        195                 200                 205

Gly Ser Thr Asn Tyr His Ser Ala Leu Ile Ser Arg Leu Ser Ile Ser
    210                 215                 220

Lys Asp Asn Ser Lys Ser Gln Val Phe Leu Lys Leu Asn Asn Leu Gln
225                 230                 235                 240

Thr Asp Asp Thr Ala Thr Tyr Tyr Cys Ala Arg Asp Thr Tyr Tyr Pro
                245                 250                 255

Tyr Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
```

```
                    355                 360                 365
Gly Cys Ser Cys Arg Phe Pro Glu Glu Glu Gly Cys Glu Leu
    370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                    405                 410                 415

Asp Val Leu Asp Lys Arg Arg Gly Arg Asp Pro Glu Met Gly Gly Lys
                420                 425                 430

Pro Gln Arg Arg Lys Asn Pro Gln Glu Gly Leu Tyr Asn Glu Leu Gln
                435                 440                 445

Lys Asp Lys Met Ala Glu Ala Tyr Ser Glu Ile Gly Met Lys Gly Glu
            450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 215
<211> LENGTH: 356
<212> TYPE: PRT
<213> ORGANISM: Artificial Sequence
<220> FEATURE:
<223> OTHER INFORMATION: Synthetic Construct

<400> SEQUENCE: 215

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Ser
                20                  25                  30

Val Gln Ala Gly Gly Ala Leu Ser Leu Ser Cys Ala Ala Ser Gly Tyr
            35                  40                  45

Thr Val Arg Ile Asp Tyr Met Gly Trp Tyr Arg Gln Thr Pro Gly Lys
        50                  55                  60

Gly Arg Glu Pro Val Ala Thr Ile Ala Ser Asn Gly Thr Ala Tyr
65                  70                  75                  80

Ala Asp Ser Val Glu Gly Arg Phe Thr Ile Ser Gln Asp Asn Ala Lys
                85                  90                  95

Asn Ser Val Tyr Leu Gln Met Asn Thr Leu Lys Pro Gly Asp Thr Ala
                100                 105                 110

Met Tyr Tyr Cys Ala Ala Gly Thr Trp Pro Thr Leu Thr Tyr Phe Gly
            115                 120                 125

Gln Gly Thr Gln Val Thr Val Ser Ser Ile Glu Val Met Tyr Pro Pro
        130                 135                 140

Pro Tyr Leu Asp Asn Glu Lys Ser Asn Gly Thr Ile Ile His Val Lys
145                 150                 155                 160

Gly Lys His Leu Cys Pro Ser Pro Leu Phe Pro Gly Pro Ser Lys Pro
                165                 170                 175

Phe Trp Val Leu Val Val Gly Gly Val Leu Ala Cys Tyr Ser Leu
                180                 185                 190

Leu Val Thr Val Ala Phe Ile Ile Phe Trp Val Arg Ser Lys Arg Ser
            195                 200                 205

Arg Leu Leu His Ser Asp Tyr Met Asn Met Thr Pro Arg Arg Pro Gly
        210                 215                 220
```

```
Pro Thr Arg Lys His Tyr Gln Pro Tyr Ala Pro Pro Arg Asp Phe Ala
225                 230                 235                 240

Ala Tyr Arg Ser Arg Val Lys Phe Ser Arg Ser Ala Asp Ala Pro Ala
                245                 250                 255

Tyr Lys Gln Gly Gln Asn Gln Leu Tyr Asn Glu Leu Asn Leu Gly Arg
            260                 265                 270

Arg Glu Glu Tyr Asp Val Leu Asp Lys Arg Arg Gly Arg Asp Pro Glu
            275                 280                 285

Met Gly Gly Lys Pro Arg Arg Lys Asn Pro Gln Glu Gly Leu Tyr Asn
    290                 295                 300

Glu Leu Gln Lys Asp Lys Met Ala Glu Ala Tyr Ser Glu Ile Gly Met
305                 310                 315                 320

Lys Gly Glu Arg Arg Arg Gly Lys Gly His Asp Gly Leu Tyr Gln Gly
                325                 330                 335

Leu Ser Thr Ala Thr Lys Asp Thr Tyr Asp Ala Leu His Met Gln Ala
                340                 345                 350

Leu Pro Pro Arg
        355

<210> SEQ ID NO 216
<211> LENGTH: 25
<212> TYPE: PRT
<213> ORGANISM: Artificial Sequence
<220> FEATURE:
<223> OTHER INFORMATION: Synthetic Construct

<400> SEQUENCE: 216

Gly Gly Gly Gly Ser Gly Gly Gly Gly Ser Gly Gly Gly Gly Ser Gly
1               5                   10                  15

Gly Gly Gly Ser Gly Gly Gly Gly Ser
                20                  25
```